US012605523B2

(12) United States Patent
Hitchcock et al.

(10) Patent No.: US 12,605,523 B2
(45) Date of Patent: Apr. 21, 2026

(54) INTERVENTIONAL DEVICE ASSEMBLY WITH ANTI-BUCKLING SYSTEM

(71) Applicant: Imperative Care, Inc., Campbell, CA (US)

(72) Inventors: Robert Hitchcock, Los Gatos, CA (US); Sean Totten, Kirkland, WA (US); Lilip Lau, Los Altos, CA (US); Craig Mar, Fremont, CA (US)

(73) Assignee: Imperative Care, Inc., Campbell, CA (US)

( * ) Notice: Subject to any disclaimer, the term of this patent is extended or adjusted under 35 U.S.C. 154(b) by 141 days.

(21) Appl. No.: 18/524,973

(22) Filed: Nov. 30, 2023

(65) Prior Publication Data

US 2024/0181209 A1 Jun. 6, 2024

Related U.S. Application Data

(60) Provisional application No. 63/455,893, filed on Mar. 30, 2023, provisional application No. 63/429,498, filed on Dec. 1, 2022.

(51) Int. Cl.
*A61M 25/00* (2006.01)
*A61B 34/30* (2016.01)
(Continued)

(52) U.S. Cl.
CPC ......... *A61M 25/0021* (2013.01); *A61B 34/30* (2016.02); *A61M 25/0023* (2013.01);
(Continued)

(58) Field of Classification Search
CPC .......... A61M 25/0021; A61M 25/0023; A61M 25/0043; A61M 25/0054; A61M 25/0097;
(Continued)

(56) References Cited

U.S. PATENT DOCUMENTS 1,286,033 A 11/1918 Lambeth
4,819,653 A 4/1989 Marks
(Continued)

FOREIGN PATENT DOCUMENTS

AU 2006268156 4/2012
CN 102462533 5/2012
(Continued)

OTHER PUBLICATIONS

US 12,076,032 B1, 09/2024, Teigen et al. (withdrawn)
(Continued)

*Primary Examiner* — Richard G Louis
(74) *Attorney, Agent, or Firm* — Knobbe, Martens Olson & Bear, LLP

(57) ABSTRACT

An interventional device assembly includes a first hub positioned along a drive table, the first hub having a proximal end and a distal end, an interventional device coupled to the first hub and extending distally therefrom, and a telescoping tube having a proximal end and a distal end. The proximal end of the telescoping tube is secured within an interior of the first hub between the proximal end of the first hub and the distal end of the first hub. The distal end of the telescoping tube is configured to secure to a second hub positioned along the drive table or a distal attachment coupled to the drive table. At least a portion of the interventional device extends through the telescoping tube.

20 Claims, 80 Drawing Sheets

(51) Int. Cl.

| | |
|---|---|
| *A61M 25/06* | (2006.01) |
| *A61M 25/09* | (2006.01) |
| *F16C 1/10* | (2006.01) |
| *F16C 1/14* | (2006.01) |
| *F16C 3/03* | (2006.01) |
| *A61M 25/01* | (2006.01) |
| *F16C 1/22* | (2006.01) |

(52) U.S. Cl.
CPC .... *A61M 25/0043* (2013.01); *A61M 25/0054* (2013.01); *A61M 25/0097* (2013.01); *A61M 25/0662* (2013.01); *A61M 25/09* (2013.01); *F16C 1/102* (2013.01); *F16C 1/145* (2013.01); *F16C 3/03* (2013.01); *A61B 2034/301* (2016.02); *A61B 2034/302* (2016.02); *A61M 2025/0059* (2013.01); *A61M 2025/0063* (2013.01); *A61M 25/0127* (2013.01); *A61M 25/09041* (2013.01); *A61M 2025/09183* (2013.01); *F16C 1/226* (2013.01); *F16C 2226/74* (2013.01)

(58) Field of Classification Search
CPC .............. A61M 25/0662; A61M 25/09; A61M 25/0127; A61M 25/09041; A61M 2025/0059; A61M 2025/0063; A61M 2025/09183; A61B 34/30; A61B 2034/301; A61B 2034/302; F16C 1/102; F16C 1/145; F16C 3/03; F16C 1/226; F16C 2226/74

See application file for complete search history.

(56) References Cited

U.S. PATENT DOCUMENTS

| | | | |
|---|---|---|---|
| 4,925,444 A | 5/1990 | Orkin | |
| 5,131,391 A | 7/1992 | Sakai et al. | |
| 5,380,268 A | 1/1995 | Wheeler | |
| 5,638,818 A | 6/1997 | Diab et al. | |
| 5,882,333 A | 3/1999 | Schaer et al. | |
| 5,989,208 A | 11/1999 | Nita | |
| 6,096,004 A | 8/2000 | Meglan et al. | |
| 6,400,971 B1 | 6/2002 | Firanov et al. | |
| 6,726,675 B1 | 4/2004 | Beyar | |
| 6,821,287 B1 | 11/2004 | Jang | |
| 7,192,433 B2 | 3/2007 | Osypka et al. | |
| 7,214,230 B2 | 5/2007 | Brock et al. | |
| 7,331,967 B2 | 2/2008 | Lee et al. | |
| 7,379,790 B2 | 5/2008 | Toth et al. | |
| 7,556,611 B2 | 7/2009 | Kolenbrander et al. | |
| 7,567,233 B2 | 7/2009 | Garibaldi et al. | |
| 7,608,083 B2 | 10/2009 | Lee et al. | |
| 7,615,042 B2 | 11/2009 | Beyar et al. | |
| 7,747,960 B2 | 6/2010 | Garibaldi et al. | |
| 7,756,308 B2 | 7/2010 | Viswanathan | |
| 7,761,133 B2 | 7/2010 | Viswanathan et al. | |
| 7,766,894 B2 | 8/2010 | Weitzner et al. | |
| 7,789,874 B2 | 9/2010 | Yu et al. | |
| D626,250 S | 10/2010 | Wenderow et al. | |
| 7,818,076 B2 | 10/2010 | Viswanathan | |
| 7,831,294 B2 | 11/2010 | Viswanathan | |
| 7,850,640 B2 | 12/2010 | Williams et al. | |
| 7,850,642 B2 | 12/2010 | Moll et al. | |
| 7,853,306 B2 | 12/2010 | Viswanathan et al. | |
| 7,884,727 B2 | 2/2011 | Tran | |
| 7,886,743 B2 | 2/2011 | Cooper et al. | |
| 7,887,549 B2 | 2/2011 | Wenderow et al. | |
| 7,909,798 B2 | 3/2011 | Osypka | |
| 7,951,243 B2 | 5/2011 | Boyle, Jr. et al. | |
| 7,955,316 B2 | 6/2011 | Weitzner et al. | |
| 7,963,288 B2 | 6/2011 | Rosenberg et al. | |
| 8,004,229 B2 | 8/2011 | Nowlin et al. | |
| 8,021,326 B2 | 9/2011 | Moll et al. | |
| RE42,804 E | 10/2011 | Dedig et al. | |
| 8,052,636 B2 | 11/2011 | Moll et al. | |
| 8,083,753 B2 | 12/2011 | Solar et al. | |
| 8,108,069 B2 | 1/2012 | Stahler et al. | |
| 8,114,032 B2 | 2/2012 | Ferry et al. | |
| 8,123,726 B2 | 2/2012 | Searfoss et al. | |
| 8,131,379 B2 | 3/2012 | Hauck | |
| 8,137,317 B2 | 3/2012 | Osypka | |
| 8,146,874 B2 | 4/2012 | Yu | |
| 8,165,684 B2 | 4/2012 | Putz et al. | |
| 8,190,238 B2 | 5/2012 | Moll et al. | |
| 8,220,468 B2 | 7/2012 | Cooper et al. | |
| 8,242,972 B2 | 8/2012 | Garibaldi et al. | |
| 8,244,824 B2 | 8/2012 | Garibaldi et al. | |
| 8,257,302 B2 | 9/2012 | Beyar et al. | |
| 8,262,671 B2 | 9/2012 | Osypka | |
| 8,281,807 B2 | 10/2012 | Trombley et al. | |
| 8,307,693 B2 | 11/2012 | Uram et al. | |
| D674,484 S | 1/2013 | Murphy et al. | |
| 8,343,096 B2 | 1/2013 | Kirschenman et al. | |
| 8,343,098 B2 | 1/2013 | Nystrom et al. | |
| 8,377,077 B2 | 2/2013 | Reis | |
| 8,390,438 B2 | 3/2013 | Olson et al. | |
| 8,399,871 B2 | 3/2013 | Beyar et al. | |
| 8,403,909 B2 | 3/2013 | Spohn et al. | |
| D680,645 S | 4/2013 | Murphy et al. | |
| 8,409,172 B2 | 4/2013 | Moll et al. | |
| 8,467,853 B2 | 6/2013 | Hunter et al. | |
| D685,468 S | 7/2013 | Murphy et al. | |
| 8,480,618 B2 | 7/2013 | Wenderow et al. | |
| 8,498,691 B2 | 7/2013 | Moll et al. | |
| 8,506,555 B2 | 8/2013 | Morales | |
| 8,521,331 B2 | 8/2013 | Itkowitz | |
| 8,529,582 B2 | 9/2013 | Devengenzo et al. | |
| 8,540,698 B2 | 9/2013 | Spohn et al. | |
| 8,551,084 B2 | 10/2013 | Hauck et al. | |
| 8,603,068 B2 | 12/2013 | Weitzner et al. | |
| 8,613,730 B2 | 12/2013 | Hieb et al. | |
| 8,617,102 B2 | 12/2013 | Moll et al. | |
| 8,620,473 B2 | 12/2013 | Diolaiti et al. | |
| 8,671,817 B1 | 3/2014 | Bogusky | |
| 8,672,880 B2 | 3/2014 | Cohen et al. | |
| 8,679,150 B1 | 3/2014 | Janardhan | |
| 8,684,953 B2 | 4/2014 | Cabiri | |
| 8,684,962 B2 | 4/2014 | Kirschenman et al. | |
| 8,694,157 B2 | 4/2014 | Wenderow et al. | |
| 8,740,840 B2 | 6/2014 | Foley et al. | |
| 8,747,358 B2 | 6/2014 | Trombley et al. | |
| 8,790,297 B2 | 7/2014 | Bromander et al. | |
| 8,799,792 B2 | 8/2014 | Garibaldi et al. | |
| 8,800,881 B2 | 8/2014 | Biset et al. | |
| 8,801,661 B2 | 8/2014 | Moll et al. | |
| 8,806,359 B2 | 8/2014 | Garibaldi et al. | |
| 8,827,948 B2 | 9/2014 | Romo | |
| 8,828,021 B2 | 9/2014 | Wenderow et al. | |
| 8,833,293 B2 | 9/2014 | Horn | |
| 8,840,628 B2 | 9/2014 | Green et al. | |
| 8,852,162 B2 | 10/2014 | Williams et al. | |
| 8,852,167 B2 | 10/2014 | Trombley et al. | |
| 8,852,184 B2 | 10/2014 | Kucklick | |
| 8,876,726 B2 | 11/2014 | Amit et al. | |
| 8,894,610 B2 | 11/2014 | Macnamara et al. | |
| 8,905,969 B2 | 12/2014 | Nystrom et al. | |
| 8,939,963 B2 | 1/2015 | Rogers et al. | |
| 8,961,491 B2 | 2/2015 | Uber et al. | |
| 8,968,333 B2 | 3/2015 | Yu et al. | |
| 8,974,408 B2 | 3/2015 | Wallace et al. | |
| 8,974,420 B2 | 3/2015 | Searfoss et al. | |
| 8,979,871 B2 | 3/2015 | Tye | |
| 8,986,246 B2 | 3/2015 | Foley et al. | |
| 9,005,271 B2 | 4/2015 | Ivancev | |
| 9,056,200 B2 | 6/2015 | Uber et al. | |
| 9,066,740 B2 | 6/2015 | Carlson et al. | |
| 9,070,486 B2 | 6/2015 | Guerrera et al. | |
| 9,095,681 B2 | 8/2015 | Wenderow et al. | |
| 9,101,379 B2 | 8/2015 | Au et al. | |
| 9,111,016 B2 | 8/2015 | Besson et al. | |
| 9,132,949 B2 | 9/2015 | Bidet et al. | |
| 9,138,566 B2 | 9/2015 | Cabiri | |

(56) References Cited

U.S. PATENT DOCUMENTS

| | | |
|---|---|---|
| 9,168,356 B2 | 10/2015 | Wenderow et al. |
| 9,186,046 B2 | 11/2015 | Ramamurthy et al. |
| 9,199,033 B1 | 12/2015 | Cowan et al. |
| 9,205,227 B2 | 12/2015 | Cohen et al. |
| 9,206,309 B2 | 12/2015 | Appleby |
| 9,220,568 B2 | 12/2015 | Bromander et al. |
| 9,233,225 B2 | 1/2016 | Hebert |
| 9,241,768 B2 | 1/2016 | Sandhu et al. |
| 9,242,252 B2 | 1/2016 | Eberle et al. |
| 9,259,526 B2 | 2/2016 | Barron et al. |
| 9,295,527 B2 | 3/2016 | Kirschenman et al. |
| 9,314,306 B2 | 4/2016 | Yu |
| 9,314,307 B2 | 4/2016 | Richmond et al. |
| 9,314,310 B2 | 4/2016 | Kirschenman et al. |
| 9,314,311 B2 | 4/2016 | Wenderow et al. |
| 9,314,594 B2 | 4/2016 | Kirschenman |
| 9,315,663 B2 | 4/2016 | Appleby |
| 9,320,479 B2 | 4/2016 | Wenderow et al. |
| 9,320,573 B2 | 4/2016 | Sandhu et al. |
| 9,333,324 B2 | 5/2016 | Cohen et al. |
| 9,345,859 B2 | 5/2016 | Blacker |
| 9,351,735 B2 | 5/2016 | Nagano et al. |
| 9,375,729 B2 | 6/2016 | Eberle et al. |
| 9,402,977 B2 | 8/2016 | Wenderow et al. |
| 9,408,669 B2 | 8/2016 | Kokish et al. |
| 9,427,515 B1 | 8/2016 | Nystrom |
| 9,427,562 B2 | 8/2016 | Blacker |
| 9,439,736 B2 | 9/2016 | Olson |
| 9,447,890 B2 | 9/2016 | Jennings et al. |
| 9,452,276 B2 | 9/2016 | Duindam et al. |
| 9,452,277 B2 | 9/2016 | Blacker |
| 9,474,857 B2 | 10/2016 | Riley et al. |
| 9,480,797 B1 | 11/2016 | Swantner et al. |
| 9,488,971 B2 | 11/2016 | Yip et al. |
| 9,498,291 B2 | 11/2016 | Gilbert et al. |
| 9,510,912 B2 | 12/2016 | Bencteux et al. |
| 9,517,305 B2 | 12/2016 | Uram et al. |
| 9,532,840 B2 | 1/2017 | Wong et al. |
| 9,533,121 B2 | 1/2017 | Pacheco et al. |
| 9,545,497 B2 | 1/2017 | Wenderow et al. |
| 9,549,783 B2 | 1/2017 | Zirps |
| 9,566,201 B2 | 2/2017 | Yu |
| 9,566,414 B2 | 2/2017 | Wong et al. |
| 9,572,481 B2 | 2/2017 | Duindam et al. |
| 9,585,806 B2 | 3/2017 | Herrig |
| 9,586,029 B2 | 3/2017 | Shekalim et al. |
| 9,603,573 B2 | 3/2017 | Leininger et al. |
| 9,623,209 B2 | 4/2017 | Wenderow et al. |
| 9,629,595 B2 | 4/2017 | Walker et al. |
| 9,636,479 B2 | 5/2017 | Bencteux et al. |
| 9,687,304 B2 | 6/2017 | Bencteux et al. |
| 9,700,698 B2 | 7/2017 | Pacheco et al. |
| 9,707,377 B2 | 7/2017 | Cohen et al. |
| 9,717,552 B2 | 8/2017 | Cosman |
| 9,744,305 B2 | 8/2017 | Cowan et al. |
| 9,750,576 B2 | 9/2017 | Murphy et al. |
| 9,750,953 B2 | 9/2017 | Kalafut |
| 9,764,114 B2 | 9/2017 | Murphy et al. |
| 9,770,301 B2 | 9/2017 | Bencteux et al. |
| 9,782,130 B2 | 10/2017 | Hauck et al. |
| 9,782,564 B2 | 10/2017 | Zirps et al. |
| 9,789,285 B1 | 10/2017 | Blacker |
| 9,814,534 B2 | 11/2017 | Wenderow et al. |
| 9,825,455 B2 | 11/2017 | Sandhu et al. |
| 9,827,410 B2 | 11/2017 | Cowan et al. |
| 9,828,157 B2 | 11/2017 | Roesler |
| 9,833,293 B2 | 12/2017 | Wenderow et al. |
| 9,839,481 B2 | 12/2017 | Blumenkranz et al. |
| 9,855,101 B2 | 1/2018 | Wenderow et al. |
| 9,943,321 B2 | 4/2018 | Nita |
| 9,943,958 B2 | 4/2018 | Blacker et al. |
| 9,949,799 B2 | 4/2018 | Hingwe et al. |
| 9,962,229 B2 | 5/2018 | Blacker et al. |
| 9,981,109 B2 | 5/2018 | Blacker et al. |
| 9,993,614 B2 | 6/2018 | Pacheco et al. |
| 9,993,615 B2 | 6/2018 | Blacker |
| 9,999,751 B2 | 6/2018 | Pacheco et al. |
| 10,010,699 B2 | 7/2018 | Cohen et al. |
| 10,029,072 B2 | 7/2018 | Hebert |
| 10,046,140 B2 | 8/2018 | Kokish et al. |
| 10,052,761 B2 | 8/2018 | Langenfeld et al. |
| 10,071,224 B2 | 9/2018 | Hebert |
| 10,071,225 B2 | 9/2018 | Hebert |
| 10,085,805 B1 | 10/2018 | Blacker |
| 10,086,167 B2 | 10/2018 | Hebert |
| 10,105,486 B2 | 10/2018 | Trombley et al. |
| 10,111,703 B2 | 10/2018 | Cosman, Jr |
| 10,123,843 B2 | 11/2018 | Wong et al. |
| 10,123,844 B2 | 11/2018 | Nowlin et al. |
| 10,124,149 B2 | 11/2018 | Hebert |
| 10,130,427 B2 | 11/2018 | Tanner et al. |
| 10,138,025 B2 | 11/2018 | Nakamura |
| 10,145,747 B1 | 12/2018 | Lin et al. |
| 10,149,698 B2 | 12/2018 | Wulfman et al. |
| 10,178,995 B2 | 1/2019 | Cragg |
| 10,201,314 B2 | 2/2019 | Frederick et al. |
| 10,207,315 B2 | 2/2019 | Appleby |
| 10,231,788 B2 | 3/2019 | Olson et al. |
| 10,238,456 B2 | 3/2019 | Murphy et al. |
| 10,245,112 B2 | 4/2019 | Kottenstette et al. |
| 10,258,285 B2 | 4/2019 | Hauck et al. |
| 10,271,910 B2 | 4/2019 | Wenderow et al. |
| 10,299,867 B2 | 5/2019 | Wenderow et al. |
| 10,307,061 B2 | 6/2019 | Cohen |
| 10,307,570 B2 | 6/2019 | Blacker |
| 10,322,277 B2 | 6/2019 | Nystrom |
| 10,342,606 B2 | 7/2019 | Cosman |
| 10,342,953 B2 | 7/2019 | Wenderow et al. |
| 10,363,062 B2 | 7/2019 | Spencer et al. |
| 10,363,109 B2 | 7/2019 | Dachs, II et al. |
| 10,368,951 B2 | 8/2019 | Moll et al. |
| 10,391,234 B2 | 8/2019 | Sams et al. |
| 10,420,537 B2 | 9/2019 | Salahieh et al. |
| 10,426,557 B2 | 10/2019 | Amiri et al. |
| 10,426,559 B2 | 10/2019 | Graetzel et al. |
| 10,426,926 B2 | 10/2019 | Blacker et al. |
| 10,449,007 B2 | 10/2019 | Deboeuf et al. |
| 10,456,556 B2 | 10/2019 | Cabiri |
| 10,512,514 B2 | 12/2019 | Nowlin et al. |
| 10,522,250 B2 | 12/2019 | Spohn et al. |
| 10,531,883 B1 | 1/2020 | Deville et al. |
| 10,531,929 B2 | 1/2020 | Widenhouse et al. |
| 10,537,400 B2 | 1/2020 | Dachs, II et al. |
| 10,539,478 B2 | 1/2020 | Lin et al. |
| 10,549,071 B2 | 2/2020 | Falb et al. |
| 10,549,084 B2 | 2/2020 | Sokolov et al. |
| 10,555,780 B2 | 2/2020 | Tanner et al. |
| 10,556,092 B2 | 2/2020 | Yu et al. |
| 10,561,821 B2 | 2/2020 | Wenderow et al. |
| 10,568,539 B2 | 2/2020 | Kowshik et al. |
| 10,568,700 B2 | 2/2020 | Donhowe et al. |
| 10,583,276 B2 | 3/2020 | Zirps |
| 10,588,656 B2 | 3/2020 | Trosper et al. |
| 10,589,018 B2 | 3/2020 | Uber et al. |
| D881,234 S | 4/2020 | Capela |
| 10,611,391 B1 | 4/2020 | Klem et al. |
| 10,639,098 B2 | 5/2020 | Cosman |
| 10,647,007 B2 | 5/2020 | Cordoba et al. |
| 10,653,863 B1 | 5/2020 | Blacker et al. |
| 10,660,814 B2 | 5/2020 | Soundararajan et al. |
| 10,661,453 B2 | 5/2020 | Koenig et al. |
| 10,687,903 B2 | 6/2020 | Lewis et al. |
| 10,695,140 B2 | 6/2020 | Overmyer et al. |
| 10,695,533 B2 | 6/2020 | Deboeuf et al. |
| 10,695,536 B2 | 6/2020 | Weitzner et al. |
| 10,709,510 B2 | 7/2020 | Kottenstette |
| 10,709,512 B2 | 7/2020 | Bajo et al. |
| 10,716,726 B2 | 7/2020 | Bergman et al. |
| 10,722,253 B2 | 7/2020 | Deville et al. |
| 10,729,825 B2 | 8/2020 | Boyle, Jr. et al. |
| 10,736,706 B2 | 8/2020 | Scheib |
| 10,737,061 B2 | 8/2020 | Parmar |
| 10,744,302 B2 | 8/2020 | Pacheco et al. |
| 10,765,303 B2 | 9/2020 | Graetzel et al. |

(56) References Cited

U.S. PATENT DOCUMENTS

| | | | |
|---|---|---|---|
| 10,765,486 B2 | 9/2020 | Bajo et al. |
| 10,779,775 B2 | 9/2020 | Bergman et al. |
| 10,779,895 B2 | 9/2020 | Wenderow et al. |
| 10,783,993 B2 | 9/2020 | Spohn et al. |
| 10,799,305 B2 | 10/2020 | Murphy et al. |
| 10,806,905 B2 | 10/2020 | Asmus |
| 10,813,713 B2 | 10/2020 | Koch et al. |
| 10,814,102 B2 | 10/2020 | Laby et al. |
| 10,820,951 B2 | 11/2020 | Soundararajan et al. |
| 10,820,954 B2 | 11/2020 | Marsot et al. |
| 10,827,913 B2 | 11/2020 | Ummalaneni et al. |
| 10,828,463 B2 | 11/2020 | Blacker |
| 10,835,153 B2 | 11/2020 | Rafil-Tari et al. |
| 10,835,329 B2 | 11/2020 | Wenderow et al. |
| 10,835,668 B2 | 11/2020 | Novickoff et al. |
| 10,849,702 B2 | 12/2020 | Hsu et al. |
| 10,864,629 B2 | 12/2020 | Guerrera et al. |
| 10,874,468 B2 | 12/2020 | Wallace et al. |
| 10,881,472 B2 | 1/2021 | Sen et al. |
| 10,881,474 B2 | 1/2021 | Blacker et al. |
| 10,881,765 B2 | 1/2021 | Igarashi |
| 10,898,082 B2 | 1/2021 | Sandgaard |
| 10,898,288 B2 | 1/2021 | Dachs, II et al. |
| 10,900,771 B2 | 1/2021 | Kottenstette et al. |
| 10,912,624 B2 | 2/2021 | Prentakis et al. |
| 10,912,924 B2 | 2/2021 | Park et al. |
| 10,945,904 B2 | 3/2021 | de Jesus Ruiz et al. |
| 10,953,206 B2 | 3/2021 | Blacker |
| 10,959,789 B2 | 3/2021 | Yi et al. |
| 10,959,792 B1 | 3/2021 | Huang et al. |
| 10,987,179 B2 | 4/2021 | Ummalaneni et al. |
| 10,987,491 B2 | 4/2021 | Wenderow et al. |
| 10,994,102 B2 | 5/2021 | Blacker |
| 11,007,118 B2 | 5/2021 | Cowan et al. |
| 11,007,348 B2 | 5/2021 | Blacker |
| 11,040,147 B2 | 6/2021 | Wagner |
| 11,045,274 B2 | 6/2021 | Dachs, II et al. |
| 11,052,226 B2 | 7/2021 | Salahieh et al. |
| 11,058,508 B2 | 7/2021 | Scheib et al. |
| 11,076,924 B2 | 8/2021 | Kim et al. |
| 11,078,945 B2 | 8/2021 | Grout et al. |
| 11,083,842 B2 | 8/2021 | Chassot |
| 11,083,873 B2 | 8/2021 | Hebert |
| 11,083,882 B2 | 8/2021 | Schrauder et al. |
| 11,096,712 B2 | 8/2021 | Teigen et al. |
| 11,104,012 B2 | 8/2021 | Cordoba et al. |
| 11,109,919 B2 | 9/2021 | Murphy et al. |
| 11,109,920 B2 | 9/2021 | Al-Jadda et al. |
| 11,109,921 B2 | 9/2021 | Kottenstette et al. |
| 11,110,217 B2 | 9/2021 | O'Brien et al. |
| 11,114,918 B2 | 9/2021 | Zirps |
| 11,129,602 B2 | 9/2021 | Wong et al. |
| 11,141,566 B2 | 10/2021 | Cabiri |
| 11,147,950 B2 | 10/2021 | Destrebecq et al. |
| 11,179,213 B2 | 11/2021 | Huang et al. |
| 11,179,546 B2 | 11/2021 | Martin |
| 11,185,455 B2 | 11/2021 | Cagle et al. |
| 11,191,893 B2 | 12/2021 | Capone et al. |
| 11,197,683 B1 | 12/2021 | Teigen et al. |
| 11,207,147 B2 | 12/2021 | Diamond et al. |
| 11,209,300 B2 | 12/2021 | Johnson |
| 11,213,356 B2 | 1/2022 | Tanner et al. |
| 11,213,362 B2 | 1/2022 | Sharon et al. |
| 11,213,654 B2 | 1/2022 | Murphy et al. |
| 11,234,779 B2 | 2/2022 | Fuerst et al. |
| 11,234,781 B2 | 2/2022 | Penny et al. |
| 11,234,784 B2 | 2/2022 | Alden |
| 11,241,291 B2 | 2/2022 | Sharon et al. |
| 11,259,881 B2 | 3/2022 | Garcia Kilroy et al. |
| 11,266,424 B2 | 3/2022 | Hofmann et al. |
| 11,291,515 B2 | 4/2022 | Sharon et al. |
| 11,298,198 B2 | 4/2022 | Fournier et al. |
| 11,304,668 B2 | 4/2022 | Wenderow et al. |
| 11,318,618 B2 | 5/2022 | Desai |
| 11,331,157 B2 | 5/2022 | Russell et al. |
| 11,337,712 B2 | 5/2022 | Teigen et al. |
| 11,337,764 B2 | 5/2022 | Deboeuf et al. |
| 11,357,586 B2 | 6/2022 | Huang et al. |
| 11,357,597 B2 | 6/2022 | Jhaveri et al. |
| 11,359,156 B2 | 6/2022 | Long et al. |
| 11,376,086 B2 | 7/2022 | McGrogan et al. |
| 11,389,360 B2 | 7/2022 | Koenig et al. |
| 11,400,214 B2 | 8/2022 | Porter |
| 11,406,402 B2 | 8/2022 | Deville et al. |
| 11,413,101 B2 | 8/2022 | Sen et al. |
| 11,413,431 B2 | 8/2022 | Blacker |
| 11,419,977 B2 | 8/2022 | Cowan et al. |
| 11,426,246 B2 | 8/2022 | Asadian et al. |
| 11,432,835 B2 | 9/2022 | Shaffer et al. |
| 11,432,840 B2 | 9/2022 | Grothe et al. |
| 11,448,327 B2 | 9/2022 | Heffner et al. |
| 11,464,587 B2 | 10/2022 | Yu et al. |
| 11,464,589 B1 | 10/2022 | Roh et al. |
| 11,472,030 B2 | 10/2022 | Ho et al. |
| 11,478,329 B2 | 10/2022 | Gee et al. |
| 11,490,911 B2 | 11/2022 | Panian |
| 11,491,313 B2 | 11/2022 | Fischell |
| 11,497,481 B2 | 11/2022 | Penny et al. |
| 11,497,523 B2 | 11/2022 | Trosper et al. |
| 11,497,568 B2 | 11/2022 | Ho et al. |
| 11,510,736 B2 | 11/2022 | Rafii-Tari et al. |
| D976,399 S | 1/2023 | Carmi |
| 11,547,426 B2 | 1/2023 | Deville et al. |
| 11,547,511 B2 | 1/2023 | Asadian et al. |
| 11,564,649 B2 | 1/2023 | Kedmi-Shahar et al. |
| 11,571,267 B2 | 2/2023 | Gonenc et al. |
| 11,576,743 B2 | 2/2023 | Venkataraman et al. |
| 11,577,382 B2 | 2/2023 | Cagle et al. |
| 11,589,931 B2 | 2/2023 | Desal et al. |
| 11,607,108 B2 | 3/2023 | Yu et al. |
| 11,628,024 B2 | 4/2023 | Kapadia |
| 11,633,247 B2 | 4/2023 | Johnson et al. |
| 11,642,181 B2 | 5/2023 | Nobles et al. |
| 11,653,905 B2 | 5/2023 | Wong et al. |
| 11,660,151 B2 | 5/2023 | Schena |
| 11,660,437 B2 | 5/2023 | Verma |
| 11,672,602 B2 | 6/2023 | Monteverde et al. |
| 11,678,943 B2 | 6/2023 | Zhou et al. |
| 11,678,948 B2 | 6/2023 | Vargas et al. |
| 11,684,759 B2 | 6/2023 | Hayzelden |
| 11,690,985 B2 | 7/2023 | Calhoun et al. |
| 11,696,808 B2 | 7/2023 | Blacker et al. |
| 11,696,810 B2 | 7/2023 | Asadian et al. |
| 11,701,196 B2 | 7/2023 | Scheib et al. |
| 11,703,604 B2 | 7/2023 | Dissertori et al. |
| 11,712,805 B2 | 8/2023 | Zhou et al. |
| 11,713,376 B2 | 8/2023 | Leroux et al. |
| 11,717,356 B2 | 8/2023 | Amiri et al. |
| 11,717,640 B2 | 8/2023 | Fantuzzi et al. |
| 11,723,739 B2 | 8/2023 | Asadian et al. |
| 11,723,744 B2 | 8/2023 | Ergueta Tejerina et al. |
| 11,730,499 B1 | 8/2023 | Thio et al. |
| 11,737,821 B2 | 8/2023 | Algawi et al. |
| 11,744,989 B2 | 9/2023 | Blacker |
| 11,759,269 B2 | 9/2023 | Zhou et al. |
| 11,764,873 B2 | 9/2023 | Burla et al. |
| 11,765,360 B2 | 9/2023 | Schroers et al. |
| 11,766,786 B2 | 9/2023 | Cordoba et al. |
| 11,780,092 B2 | 10/2023 | Desal et al. |
| 11,785,938 B2 | 10/2023 | Clavien et al. |
| 11,786,329 B2 | 10/2023 | Fuerst et al. |
| 11,789,315 B1 | 10/2023 | Yu et al. |
| 11,793,500 B2 | 10/2023 | Vargas |
| 11,793,597 B2 | 10/2023 | Vargas et al. |
| 11,801,365 B2 | 10/2023 | Blacker et al. |
| 11,813,203 B2 | 11/2023 | Timm et al. |
| 11,819,295 B2 | 11/2023 | Wenderow et al. |
| 11,832,904 B2 | 12/2023 | Wenderow et al. |
| 11,844,580 B2 | 12/2023 | Sen et al. |
| 11,844,732 B2 | 12/2023 | Klem et al. |
| 11,883,119 B2 | 1/2024 | Sen et al. |
| 11,883,245 B2 | 1/2024 | Fathollahi Ghezelghieh et al. |
| 11,890,024 B2 | 2/2024 | Panian |
| 11,890,432 B2 | 2/2024 | Awad et al. |

(56) References Cited

U.S. PATENT DOCUMENTS

| | | | |
|---|---|---|---|
| 11,896,325 | B2 | 2/2024 | Clark et al. |
| 11,903,669 | B2 | 2/2024 | Cope et al. |
| 11,906,009 | B2 | 2/2024 | Klem |
| 11,910,997 | B2 | 2/2024 | Fuerst et al. |
| 11,911,120 | B2 | 2/2024 | Freiin von Kapri et al. |
| 11,911,910 | B2 | 2/2024 | Gonenc et al. |
| 11,918,240 | B2 | 3/2024 | Deville et al. |
| 11,918,312 | B2 | 3/2024 | Yu |
| 11,918,423 | B2 | 3/2024 | Kottenstette et al. |
| 11,931,901 | B2 | 3/2024 | Murphy et al. |
| 11,998,290 | B2 | 6/2024 | Murphy et al. |
| 12,004,829 | B2 | 6/2024 | Searfoss et al. |
| 12,005,589 | B2 | 6/2024 | Rea et al. |
| 12,035,989 | B2 | 7/2024 | Clark et al. |
| 12,046,363 | B2 | 7/2024 | Shrivastava et al. |
| D1,038,990 | S | 8/2024 | Inwood |
| 12,059,161 | B2 | 8/2024 | Deville et al. |
| 12,059,225 | B2 | 8/2024 | Zhou et al. |
| D1,043,739 | S | 9/2024 | Hernandez |
| 12,076,036 | B2 | 9/2024 | Baron et al. |
| 12,076,099 | B2 | 9/2024 | Shrivastava et al. |
| 12,076,497 | B2 | 9/2024 | Fantuzzi et al. |
| 12,076,505 | B2 | 9/2024 | Haubert |
| 12,082,982 | B2 | 9/2024 | Jhaveri et al. |
| 12,087,024 | B2 | 9/2024 | Djelouah et al. |
| 12,102,290 | B2 | 10/2024 | Sharon et al. |
| 12,114,940 | B2 | 10/2024 | Garcia Kilroy et al. |
| 12,117,624 | B2 | 10/2024 | Fuerst et al. |
| 12,133,700 | B2 | 11/2024 | Miller et al. |
| 12,133,702 | B2 | 11/2024 | Nowlin et al. |
| 12,133,965 | B2 | 11/2024 | Chassot et al. |
| 12,137,990 | B2 | 11/2024 | Walker et al. |
| 12,138,004 | B2 | 11/2024 | Cone et al. |
| 12,138,130 | B2 | 11/2024 | Garbus et al. |
| 12,144,564 | B2 | 11/2024 | Barbagli et al. |
| 12,144,569 | B2 | 11/2024 | Cone et al. |
| 12,144,575 | B2 | 11/2024 | Torabi |
| 12,150,660 | B1 | 11/2024 | Teigen et al. |
| 12,150,796 | B2 | 11/2024 | Wenderow et al. |
| 12,156,666 | B2 | 12/2024 | Trosper et al. |
| 12,156,667 | B2 | 12/2024 | Trosper et al. |
| 12,156,711 | B2 | 12/2024 | Liao et al. |
| 12,157,238 | B2 | 12/2024 | Fredrickson et al. |
| 12,161,419 | B2 | 12/2024 | Fuerst et al. |
| 12,171,505 | B2 | 12/2024 | Barbagli et al. |
| 12,171,543 | B2 | 12/2024 | Duindam et al. |
| 12,177,411 | B2 | 12/2024 | Culman |
| 12,178,387 | B2 | 12/2024 | McDowall et al. |
| 12,178,399 | B2 | 12/2024 | Itkowitz et al. |
| 12,178,526 | B2 | 12/2024 | McKenney et al. |
| 12,178,534 | B2 | 12/2024 | Asadian et al. |
| 12,185,947 | B2 | 1/2025 | Hart |
| 12,191,031 | B2 | 1/2025 | Azizian et al. |
| 12,201,484 | B2 | 1/2025 | Itkowitz et al. |
| 12,201,485 | B2 | 1/2025 | McDowall et al. |
| 12,212,240 | B2 | 1/2025 | Schulz |
| 12,350,415 | B2 | 7/2025 | Kumar et al. |
| 12,377,206 | B2 | 8/2025 | Bartholomew et al. |
| 12,383,668 | B2 | 8/2025 | Batarilo et al. |
| 12,396,741 | B2 | 8/2025 | Blacker |
| 12,397,099 | B2 | 8/2025 | Aaron et al. |
| 12,419,501 | B2 | 9/2025 | Canale et al. |
| D1,102,447 | S | 11/2025 | Bartholomew et al. |
| 2002/0091372 | A1 | 7/2002 | Cragg et al. |
| 2002/0113501 | A1 | 8/2002 | Doi |
| 2002/0192113 | A1 | 12/2002 | Uffenheimer et al. |
| 2003/0071285 | A1 | 4/2003 | Tsukernik |
| 2003/0100849 | A1 | 5/2003 | Jang |
| 2003/0105451 | A1 | 6/2003 | Westlund et al. |
| 2003/0114739 | A1 | 6/2003 | Fuimaono et al. |
| 2003/0125673 | A1 | 7/2003 | Houde et al. |
| 2004/0068248 | A1 | 4/2004 | Mooney et al. |
| 2004/0097805 | A1 | 5/2004 | Verard et al. |
| 2004/0143225 | A1 | 7/2004 | Callan |
| 2005/0077225 | A1 | 4/2005 | Usher et al. |
| 2005/0107667 | A1 | 5/2005 | Danitz |
| 2005/0165276 | A1 | 7/2005 | Belson et al. |
| 2005/0277912 | A1 | 12/2005 | John |
| 2006/0011501 | A1 | 1/2006 | Itou et al. |
| 2006/0095022 | A1 | 5/2006 | Moll et al. |
| 2006/0146010 | A1 | 7/2006 | Schneider |
| 2006/0200026 | A1 | 9/2006 | Wallace et al. |
| 2006/0200191 | A1 | 9/2006 | Zadno-Azizi |
| 2007/0060879 | A1 | 3/2007 | Weitzner |
| 2007/0060915 | A1 | 3/2007 | Kucklick |
| 2007/0106208 | A1 | 5/2007 | Uber et al. |
| 2007/0142824 | A1 | 6/2007 | Devengenzo |
| 2007/0179473 | A1 | 8/2007 | Masters et al. |
| 2007/0270639 | A1 | 11/2007 | Long |
| 2008/0027464 | A1 | 1/2008 | Moll et al. |
| 2008/0086051 | A1 | 4/2008 | Voegele |
| 2008/0234631 | A1 | 9/2008 | Reis |
| 2008/0255505 | A1 | 10/2008 | Carlson et al. |
| 2008/0262513 | A1 | 10/2008 | Stahler et al. |
| 2008/0319387 | A1 | 12/2008 | Amisar et al. |
| 2009/0012464 | A1 | 1/2009 | Martin |
| 2009/0076445 | A1 | 3/2009 | Furnish |
| 2009/0082722 | A1 | 3/2009 | Munger et al. |
| 2009/0131955 | A1 | 5/2009 | Wenderow et al. |
| 2009/0153374 | A1 | 6/2009 | Maw et al. |
| 2009/0171332 | A1 | 7/2009 | Bonneau |
| 2009/0204078 | A1 | 8/2009 | Mitchell et al. |
| 2009/0247943 | A1 | 10/2009 | Kirschenman et al. |
| 2009/0247993 | A1 | 10/2009 | Kirschenman et al. |
| 2009/0254083 | A1 | 10/2009 | Wallace et al. |
| 2009/0259200 | A1 | 10/2009 | Lampropoulos |
| 2009/0264785 | A1 | 10/2009 | Causevic et al. |
| 2010/0069833 | A1 | 3/2010 | Wenderow et al. |
| 2010/0175701 | A1 | 7/2010 | Reis et al. |
| 2010/0204712 | A1 | 8/2010 | Mallaby |
| 2010/0204713 | A1 | 8/2010 | Ruiz Morales |
| 2010/0280363 | A1 | 11/2010 | Skarda et al. |
| 2010/0286756 | A1 | 11/2010 | Dorn |
| 2010/0305502 | A1 | 12/2010 | Ferry et al. |
| 2011/0004223 | A1 | 1/2011 | Leeflang |
| 2011/0015484 | A1 | 1/2011 | Alvarez et al. |
| 2011/0028894 | A1 | 2/2011 | Foley et al. |
| 2011/0144658 | A1 | 6/2011 | Wenderow et al. |
| 2011/0166447 | A1 | 7/2011 | Windolf |
| 2011/0238010 | A1 | 9/2011 | Kirschenman |
| 2011/0288544 | A1 | 11/2011 | Verin et al. |
| 2011/0313318 | A1 | 12/2011 | Rule et al. |
| 2012/0071822 | A1 | 3/2012 | Romo |
| 2012/0071895 | A1 | 3/2012 | Stahler et al. |
| 2012/0172798 | A1 | 7/2012 | Miller et al. |
| 2012/0179032 | A1 | 7/2012 | Bromander et al. |
| 2012/0245595 | A1 | 9/2012 | Kesavadas et al. |
| 2012/0316458 | A1 | 12/2012 | Rahman |
| 2013/0030408 | A1 | 1/2013 | Piferi |
| 2013/0035537 | A1 | 2/2013 | Wallace |
| 2013/0053704 | A1 | 2/2013 | Bernak et al. |
| 2013/0096551 | A1 | 4/2013 | Govari et al. |
| 2013/0131499 | A1 | 5/2013 | Chan et al. |
| 2013/0214912 | A1 | 8/2013 | Beyar et al. |
| 2013/0231678 | A1 | 9/2013 | Wenderow |
| 2014/0058321 | A1 | 2/2014 | Wenderow et al. |
| 2014/0066900 | A1 | 3/2014 | Blacker |
| 2014/0150782 | A1 | 6/2014 | Vazales |
| 2014/0163364 | A1 | 6/2014 | Perers |
| 2014/0216250 | A1 | 8/2014 | Meyer |
| 2014/0228762 | A1 | 8/2014 | Capone |
| 2014/0243742 | A1 | 8/2014 | Pacheco et al. |
| 2014/0276016 | A1 | 9/2014 | Stigall |
| 2014/0276233 | A1 | 9/2014 | Murphy |
| 2014/0276389 | A1 | 9/2014 | Walker |
| 2014/0276948 | A1 | 9/2014 | Zirps |
| 2014/0318702 | A1 | 10/2014 | Tegg |
| 2015/0005738 | A1 | 1/2015 | Blacker |
| 2015/0005745 | A1 | 1/2015 | Bergman et al. |
| 2015/0073391 | A1 | 3/2015 | Hutchins et al. |
| 2015/0088002 | A1 | 3/2015 | Podhajsky |
| 2015/0157252 | A1 | 6/2015 | Sabesan |
| 2015/0272683 | A1 | 10/2015 | Yang et al. |
| 2015/0314105 | A1 | 11/2015 | Gasparyan |

(56) References Cited

U.S. PATENT DOCUMENTS

| | | |
|---|---|---|
| 2015/0320478 A1 | 11/2015 | Cosman, Jr. |
| 2015/0320479 A1 | 11/2015 | Cosman, Jr. |
| 2015/0320480 A1 | 11/2015 | Cosman, Jr. |
| 2015/0320481 A1 | 11/2015 | Cosman, Jr. |
| 2015/0327875 A1 | 11/2015 | Look |
| 2015/0374483 A1 | 12/2015 | Janardhan |
| 2016/0058513 A1 | 3/2016 | Giorgi |
| 2016/0067448 A1 | 3/2016 | Blacker et al. |
| 2016/0074057 A1 | 3/2016 | Jezierski et al. |
| 2016/0082502 A1 | 3/2016 | Appleby |
| 2016/0184032 A1 | 6/2016 | Romo |
| 2016/0310702 A1 | 10/2016 | Cabiri |
| 2016/0374590 A1 | 12/2016 | Wong et al. |
| 2017/0000576 A1 | 1/2017 | Zirps |
| 2017/0014998 A1 | 1/2017 | Langenfeld et al. |
| 2017/0020627 A1 | 1/2017 | Tesar et al. |
| 2017/0027653 A1 | 2/2017 | Kirschenman |
| 2017/0135773 A1 | 5/2017 | Lohmeier et al. |
| 2017/0143416 A1 | 5/2017 | Guler et al. |
| 2017/0224224 A1 | 8/2017 | Yu |
| 2017/0252025 A1 | 9/2017 | Cabiri et al. |
| 2017/0281054 A1 | 10/2017 | Stever et al. |
| 2017/0281288 A1 | 10/2017 | Au |
| 2017/0317937 A1 | 11/2017 | Dillon |
| 2017/0333000 A1 | 11/2017 | Nystrom et al. |
| 2017/0348060 A1 | 12/2017 | Blacker |
| 2018/0126122 A1 | 5/2018 | Cabiri |
| 2018/0153477 A1 | 6/2018 | Nagale et al. |
| 2018/0161001 A1 | 6/2018 | Seip |
| 2018/0168751 A1* | 6/2018 | Yi ................ A61M 25/0116 |
| 2018/0185104 A1 | 7/2018 | Olson et al. |
| 2018/0199916 A1 | 7/2018 | Sugihara et al. |
| 2018/0250086 A1 | 9/2018 | Grubbs |
| 2018/0360398 A1 | 12/2018 | Wenderow et al. |
| 2019/0008360 A1 | 1/2019 | Peh et al. |
| 2019/0008591 A1 | 1/2019 | Desai |
| 2019/0030324 A1 | 1/2019 | Grace et al. |
| 2019/0076640 A1 | 3/2019 | Bhatnagar et al. |
| 2019/0111237 A1 | 4/2019 | Cabiri et al. |
| 2019/0133666 A1 | 5/2019 | Johnson |
| 2019/0209026 A1 | 7/2019 | Han et al. |
| 2019/0231373 A1 | 8/2019 | Quick |
| 2019/0254690 A1 | 8/2019 | Cabiri et al. |
| 2019/0254754 A1 | 8/2019 | Johnson |
| 2019/0255297 A1 | 8/2019 | Fischell et al. |
| 2019/0269368 A1 | 9/2019 | Hauck et al. |
| 2019/0274809 A1 | 9/2019 | Kapec |
| 2019/0301913 A1 | 10/2019 | Johnson |
| 2019/0304108 A1 | 10/2019 | Carrell et al. |
| 2019/0336227 A1 | 11/2019 | Murphy et al. |
| 2019/0336674 A1 | 11/2019 | Schermeier |
| 2019/0365485 A1 | 12/2019 | Kottenstette et al. |
| 2019/0380825 A1 | 12/2019 | Perkins et al. |
| 2020/0008891 A1 | 1/2020 | Wenderow et al. |
| 2020/0008896 A1 | 1/2020 | Cone et al. |
| 2020/0009354 A1 | 1/2020 | Wenderow et al. |
| 2020/0016371 A1 | 1/2020 | Blacker |
| 2020/0028181 A1 | 1/2020 | Arugula et al. |
| 2020/0054399 A1 | 2/2020 | Duindam |
| 2020/0054403 A1 | 2/2020 | Zhou et al. |
| 2020/0085528 A1 | 3/2020 | Olson et al. |
| 2020/0129740 A1 | 4/2020 | Kottenstette et al. |
| 2020/0163726 A1 | 5/2020 | Tanner et al. |
| 2020/0170630 A1 | 6/2020 | Wong et al. |
| 2020/0242767 A1 | 7/2020 | Zhao et al. |
| 2020/0282186 A1 | 9/2020 | Blacker et al. |
| 2020/0289219 A1 | 9/2020 | Denlinger et al. |
| 2020/0297444 A1 | 9/2020 | Camarillo et al. |
| 2020/0297973 A1 | 9/2020 | Blacker et al. |
| 2020/0306064 A1 | 10/2020 | Perkins et al. |
| 2020/0316340 A1 | 10/2020 | Wenderow et al. |
| 2020/0324084 A1 | 10/2020 | Falb et al. |
| 2020/0338308 A1 | 10/2020 | Saber et al. |
| 2020/0345979 A1 | 11/2020 | Loh et al. |
| 2020/0352494 A1 | 11/2020 | Gable et al. |
| 2020/0368494 A1 | 11/2020 | Parmar |
| 2020/0375671 A1 | 12/2020 | Wenderow et al. |
| 2020/0376249 A1 | 12/2020 | Lockhart |
| 2020/0390503 A1 | 12/2020 | Casas et al. |
| 2020/0397451 A1 | 12/2020 | Feltyberger et al. |
| 2020/0405408 A1 | 12/2020 | Shelton, IV et al. |
| 2020/0405410 A1 | 12/2020 | Shelton, IV et al. |
| 2020/0405950 A1 | 12/2020 | Burren |
| 2021/0007816 A1 | 1/2021 | Huang et al. |
| 2021/0022816 A1 | 1/2021 | DeBuys et al. |
| 2021/0030492 A1 | 2/2021 | Wenderow et al. |
| 2021/0045622 A1 | 2/2021 | Petroff et al. |
| 2021/0046284 A1 | 2/2021 | Mauch |
| 2021/0060767 A1 | 3/2021 | Guerrera et al. |
| 2021/0068852 A1 | 3/2021 | Spence |
| 2021/0077211 A1 | 3/2021 | Blacker et al. |
| 2021/0093406 A1 | 4/2021 | Blacker et al. |
| 2021/0100980 A1 | 4/2021 | Blacker |
| 2021/0106393 A1 | 4/2021 | Simi et al. |
| 2021/0145532 A1 | 5/2021 | Tucker et al. |
| 2021/0178032 A1 | 6/2021 | Hsu et al. |
| 2021/0178036 A1 | 6/2021 | Nazarifar et al. |
| 2021/0186534 A1 | 6/2021 | Hunt et al. |
| 2021/0192759 A1 | 6/2021 | Lang |
| 2021/0196242 A1 | 7/2021 | Perez |
| 2021/0196413 A1 | 7/2021 | Inoue |
| 2021/0212792 A1 | 7/2021 | Shelton et al. |
| 2021/0220064 A1 | 7/2021 | Kottenstette et al. |
| 2021/0228841 A1 | 7/2021 | Falb et al. |
| 2021/0244434 A1 | 8/2021 | Popa et al. |
| 2021/0247396 A9 | 8/2021 | Penny |
| 2021/0251472 A1 | 8/2021 | Baez |
| 2021/0259884 A1 | 8/2021 | Heeren et al. |
| 2021/0282863 A1 | 9/2021 | Rafii-Tari et al. |
| 2021/0282867 A1 | 9/2021 | Tegg et al. |
| 2021/0282875 A1 | 9/2021 | Sharon et al. |
| 2021/0282893 A1 | 9/2021 | Leo et al. |
| 2021/0290310 A1 | 9/2021 | Laby et al. |
| 2021/0290320 A1 | 9/2021 | Mao et al. |
| 2021/0290324 A1 | 9/2021 | Mintz et al. |
| 2021/0290327 A1 | 9/2021 | Yates et al. |
| 2021/0298847 A1 | 9/2021 | Mao et al. |
| 2021/0298850 A1 | 9/2021 | Huang et al. |
| 2021/0298857 A1 | 9/2021 | Zheng et al. |
| 2021/0298954 A1 | 9/2021 | Alvarez et al. |
| 2021/0305639 A1 | 9/2021 | Ho et al. |
| 2021/0315596 A1 | 10/2021 | Buck et al. |
| 2021/0353129 A1 | 11/2021 | Roelle et al. |
| 2021/0361366 A1 | 11/2021 | Murphy et al. |
| 2021/0369370 A1 | 12/2021 | Malanoski |
| 2021/0378696 A1 | 12/2021 | Yang et al. |
| 2021/0393338 A1 | 12/2021 | Graetzel et al. |
| 2021/0401527 A1 | 12/2021 | Hassan |
| 2022/0031415 A1 | 2/2022 | Vargas et al. |
| 2022/0040450 A1 | 2/2022 | Haubert |
| 2022/0047344 A1 | 2/2022 | Stepanauskas |
| 2022/0096120 A1 | 3/2022 | Bajo et al. |
| 2022/0167984 A1 | 6/2022 | Shelton, IV |
| 2022/0168000 A1 | 6/2022 | Naglretter et al. |
| 2022/0168001 A1 | 6/2022 | Naglretter et al. |
| 2022/0168002 A1 | 6/2022 | Naglretter et al. |
| 2022/0168049 A1 | 6/2022 | Tanner et al. |
| 2022/0211452 A1 | 7/2022 | Clark et al. |
| 2022/0233263 A1 | 7/2022 | Canale et al. |
| 2022/0233264 A1 | 7/2022 | Klem |
| 2022/0233820 A1 | 7/2022 | Clark et al. |
| 2022/0241490 A1 | 8/2022 | Marass |
| 2022/0313375 A1 | 10/2022 | Zhang et al. |
| 2022/0323096 A1 | 10/2022 | Naglretter et al. |
| 2022/0331509 A1 | 10/2022 | Buck et al. |
| 2022/0370161 A1 | 11/2022 | Yu |
| 2022/0370706 A1 | 11/2022 | Meganck |
| 2022/0378522 A1 | 12/2022 | Zemlok et al. |
| 2023/0000563 A1 | 1/2023 | Bell et al. |
| 2023/0035508 A1 | 2/2023 | Clark et al. |
| 2023/0035946 A1 | 2/2023 | Kapadia |
| 2023/0043432 A1 | 2/2023 | Kapadia |
| 2023/0046468 A1 | 2/2023 | Lau et al. |
| 2023/0047098 A1 | 2/2023 | Lau et al. |

(56) References Cited

U.S. PATENT DOCUMENTS

| | | |
|---|---|---|
| 2023/0048055 A1 | 2/2023 | Lau et al. |
| 2023/0048388 A1 | 2/2023 | Lau et al. |
| 2023/0052862 A1 | 2/2023 | Lau et al. |
| 2023/0107693 A1 | 4/2023 | Walker et al. |
| 2023/0116327 A1 | 4/2023 | Walker et al. |
| 2023/0116700 A1 | 4/2023 | Yu et al. |
| 2023/0117715 A1 | 4/2023 | Ho et al. |
| 2023/0126545 A1 | 4/2023 | Liu et al. |
| 2023/0202040 A1 | 6/2023 | Lin et al. |
| 2023/0209018 A1 | 6/2023 | Alexanderson et al. |
| 2023/0218816 A1 | 7/2023 | Germain et al. |
| 2023/0310100 A1 | 10/2023 | Wenderow et al. |
| 2023/0347110 A1 | 11/2023 | Wenderow et al. |
| 2023/0355299 A1 | 11/2023 | Cosman |
| 2023/0380914 A1 | 11/2023 | Meglan et al. |
| 2023/0380915 A1 | 11/2023 | Hundertmark |
| 2024/0001101 A1 | 1/2024 | Wallin et al. |
| 2024/0016560 A1 | 1/2024 | Canale et al. |
| 2024/0019042 A1 | 1/2024 | Lim |
| 2024/0032949 A1 | 2/2024 | Yang et al. |
| 2024/0033016 A1 | 2/2024 | Yang et al. |
| 2024/0033017 A1 | 2/2024 | Yang et al. |
| 2024/0033018 A1 | 2/2024 | Yang et al. |
| 2024/0033019 A1 | 2/2024 | Lau et al. |
| 2024/0033486 A1 | 2/2024 | Lau et al. |
| 2024/0041480 A1 | 2/2024 | Bartholomew |
| 2024/0042124 A1 | 2/2024 | Bartholomew |
| 2024/0042142 A1 | 2/2024 | Bartholomew |
| 2024/0122612 A1 | 4/2024 | Bartholomew |
| 2024/0130809 A1 | 4/2024 | Scheunert et al. |
| 2024/0138862 A1 | 5/2024 | Beach |
| 2024/0165415 A1 | 5/2024 | Grosskopf et al. |
| 2024/0180635 A1 | 6/2024 | Lau et al. |
| 2024/0180640 A1 | 6/2024 | Lau et al. |
| 2024/0180641 A1 | 6/2024 | Lau et al. |
| 2024/0180642 A1 | 6/2024 | Lau et al. |
| 2024/0180643 A1 | 6/2024 | Lau et al. |
| 2024/0180650 A1 | 6/2024 | Lau et al. |
| 2024/0180651 A1 | 6/2024 | Lau et al. |
| 2024/0180652 A1 | 6/2024 | Lau et al. |
| 2024/0180653 A1 | 6/2024 | Lau et al. |
| 2024/0180654 A1 | 6/2024 | Lau et al. |
| 2024/0180658 A1 | 6/2024 | Lau et al. |
| 2024/0180659 A1 | 6/2024 | Lau et al. |
| 2024/0181207 A1 | 6/2024 | Lau et al. |
| 2024/0181208 A1 | 6/2024 | Lau et al. |
| 2024/0181213 A1 | 6/2024 | Lau et al. |
| 2024/0181214 A1 | 6/2024 | Lau et al. |
| 2024/0181224 A1 | 6/2024 | Lau et al. |
| 2024/0183382 A1 | 6/2024 | Lau et al. |
| 2024/0197416 A1 | 6/2024 | Gonzalez |
| 2024/0197418 A1 | 6/2024 | Jourdan |
| 2024/0198039 A1 | 6/2024 | Wainwright et al. |
| 2024/0198051 A1 | 6/2024 | Jourdan |
| 2024/0207570 A1 | 6/2024 | Mar |
| 2024/0398495 A1 | 12/2024 | Lee et al. |
| 2025/0032201 A1 | 1/2025 | Bartholomew et al. |
| 2025/0195835 A1 | 6/2025 | Totten |
| 2025/0319243 A1 | 10/2025 | Mar |

FOREIGN PATENT DOCUMENTS

| | | |
|---|---|---|
| CN | 103976766 | 8/2014 |
| CN | 104042259 | 9/2014 |
| CN | 203935213 | 11/2014 |
| CN | 204428157 | 7/2015 |
| CN | 105534599 | 5/2016 |
| CN | 105616008 | 6/2016 |
| CN | 105640648 | 6/2016 |
| CN | 105662586 | 6/2016 |
| CN | 105662588 | 6/2016 |
| CN | 105662589 | 6/2016 |
| CN | 105796179 | 7/2016 |
| CN | 205598007 | 9/2016 |
| CN | 106691414 | 5/2017 |
| CN | 107307909 | 11/2017 |
| CN | 107349514 | 11/2017 |
| CN | 107374737 | 11/2017 |
| CN | 107374738 | 11/2017 |
| CN | 107374739 | 11/2017 |
| CN | 107374740 | 11/2017 |
| CN | 107374741 | 11/2017 |
| CN | 107550570 | 1/2018 |
| CN | 107684459 | 2/2018 |
| CN | 107744405 | 3/2018 |
| CN | 107744406 | 3/2018 |
| CN | 107744616 | 3/2018 |
| CN | 107811624 | 3/2018 |
| CN | 108158656 | 6/2018 |
| CN | 108175504 | 6/2018 |
| CN | 207970143 | 10/2018 |
| CN | 207979770 | 10/2018 |
| CN | 207979771 | 10/2018 |
| CN | 207980153 | 10/2018 |
| CN | 109567947 | 4/2019 |
| CN | 208693445 | 4/2019 |
| CN | 109730779 A | 5/2019 |
| CN | 109821137 A | 5/2019 |
| CN | 208989133 | 6/2019 |
| CN | 209136865 | 7/2019 |
| CN | 209137698 | 7/2019 |
| CN | 110151310 A | 8/2019 |
| CN | 110236679 | 9/2019 |
| CN | 209713130 | 12/2019 |
| CN | 211271130 | 12/2019 |
| CN | 210056225 | 2/2020 |
| CN | 111035453 | 4/2020 |
| CN | 111110353 | 5/2020 |
| CN | 111110354 | 5/2020 |
| CN | 111407416 | 7/2020 |
| CN | 111437033 | 7/2020 |
| CN | 111449752 | 7/2020 |
| CN | 210962301 | 7/2020 |
| CN | 111658154 | 9/2020 |
| CN | 111772801 | 10/2020 |
| CN | 211610046 | 10/2020 |
| CN | 211723416 U | 10/2020 |
| CN | 111916214 | 11/2020 |
| CN | 111931626 | 11/2020 |
| CN | 111933268 | 11/2020 |
| CN | 112017516 | 12/2020 |
| CN | 212089719 | 12/2020 |
| CN | 212089720 | 12/2020 |
| CN | 112546396 | 3/2021 |
| CN | 112546397 | 3/2021 |
| CN | 112587241 | 4/2021 |
| CN | 213465314 | 6/2021 |
| CN | 113303913 | 8/2021 |
| CN | 113304393 | 8/2021 |
| CN | 113693733 | 11/2021 |
| EP | 1 776 057 | 11/2009 |
| EP | 2 124 705 | 5/2019 |
| FR | 3118406 | 7/2022 |
| WO | WO 2000/18290 | 4/2000 |
| WO | WO 2007/102134 | 9/2007 |
| WO | WO 2008/057887 | 10/2008 |
| WO | WO 2013/103885 | 7/2013 |
| WO | WO 2016/191307 | 12/2016 |
| WO | WO 2017/220010 | 12/2017 |
| WO | WO 2019/222641 | 11/2019 |
| WO | WO 2020/031147 | 2/2020 |
| WO | WO 2020/061240 | 3/2020 |
| WO | WO 2020/123671 | 6/2020 |
| WO | WO 2020/130924 | 6/2020 |
| WO | WO 2021/004255 | 6/2020 |
| WO | WO 2020/142340 | 7/2020 |
| WO | WO 2021/011551 | 7/2020 |
| WO | WO 2020/167749 | 8/2020 |
| WO | WO 2020/263630 | 12/2020 |
| WO | WO 2021/011533 | 1/2021 |
| WO | WO 2021/011554 | 1/2021 |
| WO | WO 2021/015990 | 1/2021 |
| WO | WO 2021/126698 | 6/2021 |
| WO | WO 2021/127426 | 6/2021 |

(56)         References Cited

FOREIGN PATENT DOCUMENTS

| WO | WO 2021/183444 | 9/2021 |
|---|---|---|
| WO | WO 2021/184444 | 9/2021 |
| WO | WO 2022/048984 | 3/2022 |
| WO | WO 2022/115717 | 6/2022 |
| WO | WO 2022/154979 | 7/2022 |
| WO | WO 2023/110598 | 6/2023 |

OTHER PUBLICATIONS

US 12,108,960 B1, 10/2024, Teigen et al. (withdrawn)

Bao et al., Apr. 2018, Operation evaluation in-human of a novel remote-controlled vascular interventional robot, Biomedical Microdevices, 20(2):34.

Bao et al., Feb. 2018, A cooperation of catheters and guidewires-based novel remote-controlled vascular interventional robot, Biomedical Microdevices, 20(1):20.

Bell, Apr. 4, 2019, Coding for Empathy, https://www.youtube.com/watch?v=13tzbxofDVc, screenshot of video.

Bency et al., Apr. 25, 2019, Neural Path Planning: Fixed Time, Near-Optimal Path Generation via Oracle Imitation, arXiv:1904. 11102v1 [cs.RO], 8 pp.

Bergman et al., 2020, Robotic-assisted percutaneous coronary intervention, Handbook of Robotic and Image-Guided Surgery, doi: https://doi.org/10.1016/B978-0-12-814245-5.00020-7.

Chen et al., Feb. 14, 2020, Deep learning robotic guidance for autonomous vascular access, Nature Machine Intelligence, https://doi.org/10.1038/s42256-020-0148-7, 12 pp.

Das et al., Feb. 21, 2019, Learning-Based Proxy Collision Detection for Robot Motion Planning Applications, arXiv:1902.08164v1 [cs. RO], 19 pp.

Das et al., May 29, 2020, Stochastic Modeling of Distance to Collision for Robot Manipulators, arXiv:2005. 14391v1 [cs.RO], 8 pp.

Evard, Jun. 2018, Catheter localization utilizing a sensor-enabled guidewire design of a proof-of-concept system, Masters Thesis, California Polytechnic State University, San Luis Obispo, 186 pp.

Fagogenis et al., Apr. 2019, Autonomous Robotic Intracardiac Catheter Navigation Using Haptic Vision, Science Robotics, 4(29):1-12.

Guo et al., Apr. 13, 2018, Study on real-time force feedback for a master-slave interventional surgical robotic system, Biomedical Microdevices, 20(2):37, 12 pp.

Guo et al., May 20, 2020, Machine learning-based operation skills assessment with vascular difficultyindex for vascular intervention surgery, Medical & Biological Engineering & Computing, https://doi.org/10.1007/s11517-020-02195-9, 15 pp.

Guo et al., Oct. 16, 2020, An Improved Visual Auxiliary Algorithm for the Vascular Interventional Surgical Robot based on Neural Network, Proceedings of 2020 IEEE International Conference on Mechatronics and Automation, http://www.guolab.org/Papers/2020/ICMA2020-329.pdf, pp. 1923-1928.

Jiang et al., 2018, Initial clinical trial of robot of endovascular treatment with force feedback and cooperating of catheter and guidewire, Applied Bionics and Biomechanics, vol. 2018, Article ID 9735979, 10 pp.

Johnson et al., Aug. 12, 2020, Dynamically Constrained Motion Planning Networks for Non-Holonomic Robots, arXiv:2008. 05112v1 [cs.RO}, 7 pp.

Kagiyama et al., Jul. 31, 2019, First experience of robotic-assisted percutaneous coronary intervention in Japan, Intern Med Advance Publication, doi: 10/2016/internalmedicine.3272-19.

Kuang et al., Apr. 2020, Vibration-Based Multi-Axis Force Sensing: Design, Characterization, and Modeling, IEEE Robotics and Automation Letters, 5(2):3082-3089.

Li et al., 2022, An endovascular catheterization robotic system using collaborative operation with magnetically controlled haptic force feedback, Micromachines, 13:505.

Li et al., Jan. 17, 2021, MPC-MPNet: Model-Predictive Motion Planning Networks for Fast, Near-Optimal Planning Under Kinodynamic Constraints, arXiv:2101.06798v1 [cs.RO], 8 pp.

Liu et al., 2021, Animal experiment of a novel neurointerventional surgical robotic system with master-slave mode, Applied Bionics and Biomechanics, vol. 2021, Article ID 8836268, 8 pp.

Qureshi et al., Feb. 2021, Motion Planning Networks: Bridging the Gap Between Learning-Based and Classical Motion Planners, IEEE Transactions on Robotics, 37(1), 19 pp.

Qureshi et al., Jul. 3, 2021, Constrained Motion Planning Networks X, arXiv:2010.08702v2 [cs.RO), 20 pp.

Qureshi et al., Oct. 25-29, 2020, Neural Manipulation Planning on Constraint Manifolds, IEEE Robotics and Automation Letters, 5(4), 8 pp.

Richter et al., Apr. 2021, Autonomous Robotic Suction to Clear the Surgical Field for Hemostasis Using Image-Based Blood Flow Detection, IEEE Robotics and Automation Letters, 6(2), 8 pp.

Sapsalev et al., 2016, Structural model of a magnetic coupling, 17th International Conference of Young Specialists on Micro/Nanotechnologies and Electron Devices EDM 2016, pp. 555-558.

Schreiber et al., Sep. 15, 2020, ARCSnake: An Archimedes Screw-Propelled, Reconfigurable Serpentine Robot for Complex Environments, 2020 IEEE International Conference on Robotics and Automation (ICRA), 6 pp.

Sganga et al., Sep. 15, 2018, OffsetNet: Deep Learning for Localization in the Lung using Rendered Images, arXiv:1809.05645v1 [cs.CV], 7 pp.

Sganga, May 22, 2020, Webinar: Autonomous Surgical Robots, https://www.youtube.com/watch?v=QRO2KnfGlgo, screenshot of video.

Wang et al., Feb. 3, 2018, Online measuring and evaluation of guidewire inserting resistance for robotic interventional surgery systems, Microsystem Technologies, https://doi/org/10.1007/s00542-018-03750-4.

Wilcox et al., Jan. 2020, SOLAR-GP: Sparse Online Locally Adaptive Regression Using Gaussian Processes for Bayesian Robot Model Learning and Control, EEE Robotics and Automation Letters, 5(2), 8 pp.

Yip et al., 2017, Autonomous Control of Continuum Robot Manipulators for Complex Cardiac Ablation Tasks, Journal of Medical Robotics Research, 2(1),:1750002-1 - 1750002-13.

Yip et al., Jul. 10, 2017, Robot Autonomy for Surgery, https://arxiv.org/pdf/1707.03080.pdf, 33 pp.

Zhao et al., Apr. 2, 2018, Operating force information on-line acquisition of a novel slave manipulator for vascular interventional surgery, Biomedical Microdevices, 20(2):33, 13 pp.

Zhou et al., 2021, ADRC-based control method for the vascular intervention master-slave surgical robotic system, Micromachines, 12:1439.

International Search Report and Written Opinion dated May 6, 2024 in application No. PCT/US2023/081825.

Bergam et al., 2020, Robotic assisted percutaneous coronary interventions, in Handbook of Robotic and Image Guided Surgery, Elsevier Inc., pp. 341-362.

* cited by examiner

142

Side View of Puck and Carriage

Equivalent System

Constant Pressure

2102

2104

2106

2108

Move Devices Relative to Each Other.

2100

31,2906

501

502

Proximal end of Catheter

Rigid Hypo
Tube

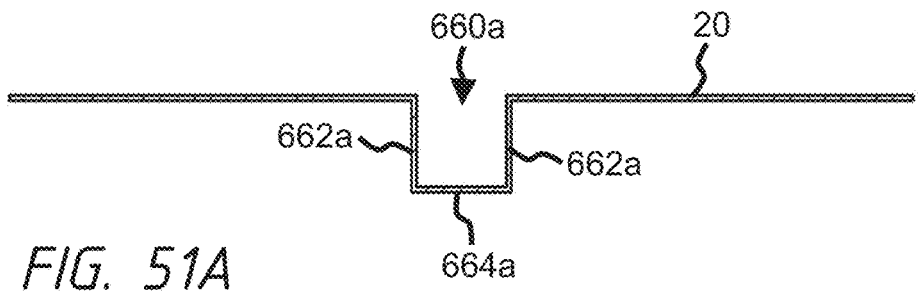
*FIG. 51A*
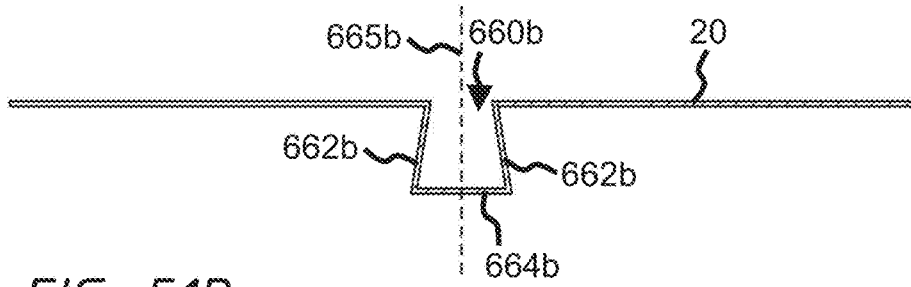
*FIG. 51B*
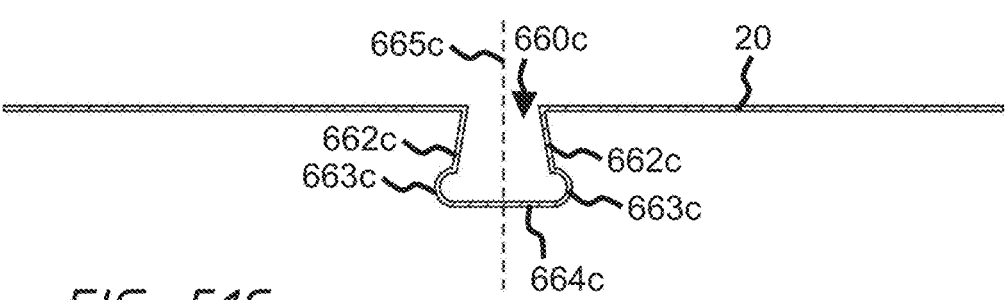
*FIG. 51C*
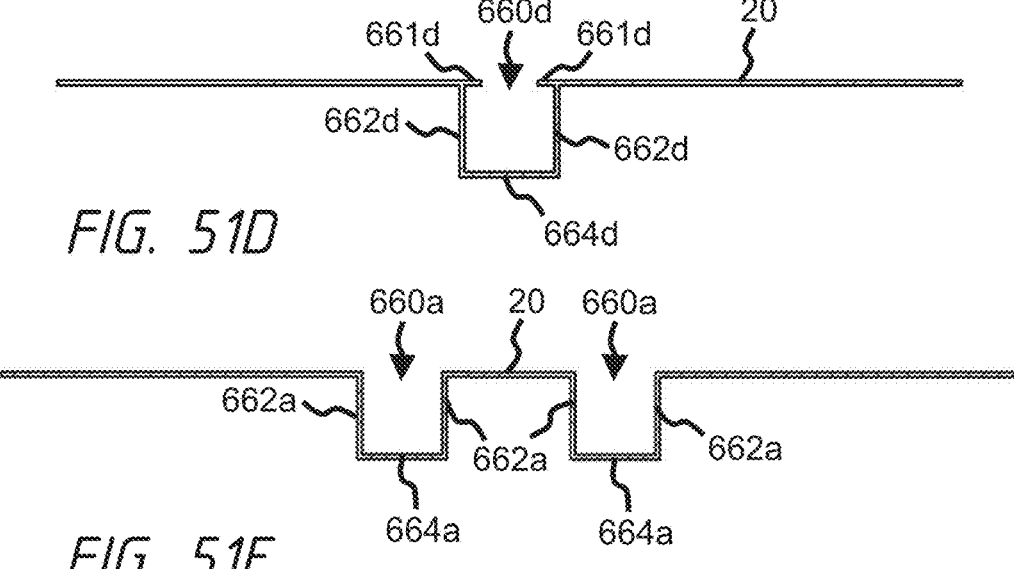
*FIG. 51D*
*FIG. 51E*

INTERVENTIONAL DEVICE ASSEMBLY WITH ANTI-BUCKLING SYSTEM

INCORPORATION BY REFERENCE TO ANY PRIORITY APPLICATIONS

This application claims the benefit of priority under 35 U.S.C. § 119(e) to U.S. Provisional Patent Application No. 63/429,498, filed Dec. 1, 2022, and U.S. Provisional Patent Application No. 63/455,893, filed Mar. 30, 2023. All of the above-mentioned applications are hereby incorporated by reference herein in their entireties and for all purposes. Any and all applications for which a foreign or domestic priority claim is identified in the Application Data Sheet as filed with the present application are hereby incorporated by reference under 37 CFR 1.57.

TECHNICAL FIELD

The present application relates to neurovascular procedures, and more particularly, to catheter assemblies and robotic control systems for neurovascular site access.

BACKGROUND

A variety of neurovascular procedures can be accomplished via a transvascular access, including thrombectomy, diagnostic angiography, embolic coil deployment and stent placement. However, the delivery of neurovascular care is limited or delayed by a variety of challenges. For example, there are not enough trained interventionalists and centers to meet the current demand for neuro interventions. Neuro interventions are difficult, with complex set up requirements and demands on the surgeon's dexterity. With two hands, the surgeon must exert precise control over 3-4 coaxial catheters plus manage the fluoroscopy system and patient position. Long, tortuous anatomy, requires delicate, precise maneuvers. Inadvertent catheter motion can occur due to energy storage and release caused by frictional interplay between coaxial shafts and the patient's vasculature. Supra-aortic access necessary to reach the neurovasculature is challenging to achieve, especially Type III arches. Once supra-aortic access is achieved, adapting the system for neurovascular treatments is time consuming and requires guidewire and access catheter removal and addition of a procedure catheter (and possibly one or more additional catheters) to the stack.

Thus, there remains a need for a supra-aortic access and neurovascular site access system that addresses some or all these challenges and increases the availability of neurovascular procedures. Preferably, the system is additionally capable of driving devices further distally through the supra-aortic access to accomplish procedures in the intracranial vessels.

SUMMARY

There is provided in accordance with one aspect of the present disclosure a supra-aortic access robotic control system. The system comprises a guidewire hub configured to adjust each of an axial position and a rotational position of a guidewire; a guide catheter hub configured to adjust a guide catheter in an axial direction; and an access catheter hub configured to adjust each of an axial position and a rotational position of an access catheter. The access catheter hub may also laterally deflect a distal deflection zone of the access catheter. The guidewire hub may additionally be configured to laterally deflect a distal portion of the guidewire.

There may also be provided a procedure catheter hub configured to manipulate a procedure catheter. Following robotic placement of the guidewire, access catheter and guide catheter such that the guide catheter achieves supra aortic access, the guidewire and access catheter may be proximally withdrawn and the procedure catheter advanced through and beyond the guide catheter, with or without guidewire support (said guidewire may be smaller in diameter and/or more flexible than the guidewire used to gain supra aortic access), to reach a more distal neurovascular treatment site. The procedure catheter may be an aspiration catheter; an embolic deployment catheter; a stent deployment catheter; a flow diverter deployment catheter, an access catheter; a diagnostic angiographic catheter; a guiding catheter, an imaging catheter, a physiological sensing/measuring catheter, an infusion or injection catheter, an ablation catheter, an RF ablation catheter or guidewire, a balloon catheter, or a microcatheter used to deliver a stent retriever, a balloon catheter or a stent retriever.

The control system may further comprise a driven magnet on each of a guidewire hub, an access catheter hub and a guide catheter hub, configured to cooperate with corresponding drive magnets such that the driven magnet moves in response to movement of the corresponding drive magnet. The drive magnets may each be independently axially movably carried by a support table. The drive magnets may be located outside of the sterile field, separated from the driven magnets by a barrier, and the driven magnets may within the sterile field. The barrier may comprise a tray made from a thin polymer membrane, or any membrane of non-ferromagnetic material.

The control system may further comprise a control console which may be connected to the support table or may be located remotely from the support table. The position of each driven magnet and corresponding hub is movable in response to manual manipulation of a guidewire drive control, access catheter drive control, or procedure catheter drive control on the console or on a particular controller not associated with the console.

The control system may further comprise a processor for controlling the position of the drive magnets. The processor may be in wired communication with the control console, or in wireless communication with the control console. The driven magnets may be configured to remain engaged with the corresponding drive magnets until application of an axial disruption force of at least about 300 grams.

There is also provided a robotically driven interventional device. The device comprises an elongate, flexible body, having a proximal end and a distal end. A hub is provided on the proximal end. At least one rotatable roller is provided on a first surface of the hub; and at least one magnet is provided on the first surface of the hub. The roller may extend further away from the first surface than the magnet. The hub may be further provided with at least a second roller.

Any of the guidewire hub, access catheter hub and procedure catheter hub may be further provided with a rotational drive, for rotating the corresponding interventional device with respect to the hub. The hub may be further provided with an axial drive mechanism to distally advance or proximally retract a control element extending axially through the interventional device, to adjust a characteristic such as shape or flexibility of the interventional device. In some embodiments, at least one control element may be an axially movable tubular body or fiber, ribbon, or wire such as a pull wire extending through the interventional device to, for example, a distal deflection zone. In some embodiments, any number of control elements may be advanced, retracted, or otherwise moved in a similar manner.

There is also provided a control system for controlling movement of interventional devices. In one configuration, the control system comprises a guidewire control, configured to control axial travel and rotation of a guidewire; an access catheter control, configured to control axial and rotational movement of an access catheter; and a guide catheter control, configured to control axial movement and/or rotation of a guide catheter.

The control system may further comprise a deflection control, configured to control deflection of the access catheter or procedure catheter, and may be configured for wired or wireless communication with a robotic catheter drive system.

The control system may be configured to independently control the three or more hubs in a variety of modes. For example, two or more hubs may be selectively ganged together so that they drive the respective devices simultaneously and with the same motion. Alternatively, the control system may be configured to drive respective devices simultaneously but with different motions.

The control system may further comprise a physician interface for operating the control system. The physician interface may be carried by a support table having a robotic interventional device drive system. Alternatively, the physician interface for operating the control system may be carried on a portable, handheld device or desktop computer, and may be located in the same room as the patient, the same facility as the patient, or in a remote facility.

The control system may further comprise a graphical user interface with at least one display for indicating the status of at least one device parameter, and/or indicating the status of at least one patient parameter.

There is also provided a sterile packaging assembly for transporting interventional devices to a robotic surgery site. The packaging assembly may comprise a base and a sterile barrier configured to enclose a sterile volume. At least one interventional device may be provided within the sterile volume, the device including a hub and an elongate flexible body. The hub may include at least one magnet and at least one roller configured to roll on the base.

In one implementation, the sterile barrier is removably attached to the base to define the enclosed volume between the sterile barrier and the base. In another implementation, the sterile barrier is in the form of a tubular enclosure for enclosing the sterile volume. The tubular enclosure may surround the base and the at least one interventional device, which are within the sterile volume.

The hub may be oriented within the packaging such that the roller and the magnet face the base. Alternatively, the base may be in the form of a tray having an elongate central axis. An upper, sterile field side of the tray may have an elongate support surface for supporting and permitting sliding movement of one or more hubs. At least one and optionally two elongate trays may be provided, extending parallel to the central axis. At least one hub and interventional device may be provided in the tray, and the sterile tray with sterile hub and interventional device may be positioned in a sterile volume defined by a sterile barrier.

The base may be configured to reside on a support table adjacent a patient, with an upper surface of the base within a sterile field and a lower surface of the base outside of the sterile field.

Any of the hubs disclosed herein may further comprise a fluid injection port and/or a wireless RF transceiver for communications and/or power transfer. The hub may comprise a visual indicator, for indicating the presence of a clot. In some embodiments, the hub may also comprise wired electrical communications and power port. The visual indicator may comprise a clot chamber having a transparent window. A filter may be provided in the clot chamber.

Any of the hubs disclosed herein may further comprise a sensor for detecting a parameter of interest such as the presence of a clot. The sensor, in some instances, may be positioned on a flexible body. The sensor may comprise a pressure sensor or an optical sensor. In some embodiments, the sensor may comprise one or more of a force sensor, a positioning sensor, a temperature sensor, and/or an oxygen sensor. In some embodiments, the sensor may comprise a Fiber Bragg grating sensor. For example, a Fiber Bragg grating sensor (e.g., an optical fiber) may detect strain locally that can facilitate the detection and/or determination of force being applied. The device may further include a plurality of sensors. The plurality of sensors may each comprise one or more of any type of sensor disclosed herein. In some embodiments, a plurality (e.g., 3 or more) of sensors (e.g., Fiber Bragg grating sensors) may be distributed around a perimeter to facilitate the detection and/or determination of shape. The position of the device, in some instance, may be determined through the use of one or more sensors to detect and/or determine the position. For example, one or more optical encoders may be located in or proximate to one or more the motors that drive linear motion such that the optical encoders may determine a position.

There is also provided a method of performing a neurovascular procedure, in which a first phase includes robotically achieving supra-aortic access, and a second phase includes manually or robotically performing a neurovascular procedure via the supra-aortic access. The method comprises the steps of providing an access catheter having an access catheter hub; coupling the access catheter hub to a hub adapter movably carried by a support table; driving the access catheter in response to movement of the hub adapter along the table until the access catheter is positioned to achieve supra-aortic access. The access catheter and access catheter hub may then be decoupled from the hub adapter; and a procedure catheter hub having a procedure catheter may then be coupled to the hub adapter.

The method may additionally comprise advancing the procedure catheter hub to position a distal end of the procedure catheter at a neurovascular treatment site. The driving the access catheter step may comprise driving the access catheter distally through a guide catheter. The driving the access catheter step may include the step of laterally deflecting a distal region of the access catheter to achieve supra-aortic access. In some embodiments, the driving the access catheter step may also include rotating the access catheter.

There is also provided a method of performing a neurovascular procedure, comprising the steps of providing an access assembly comprising a guidewire, access catheter and guide catheter. The access assembly may be releasably coupled to a robotic drive system. The access assembly may be driven by the robotic drive system to achieve access to a desired point, such as to achieve supra-aortic access. The guidewire and the access catheter may then be decoupled from the access assembly, leaving the guide catheter in place. A procedure assembly may be provided, comprising at least a guidewire and a first procedure catheter. The procedure assembly may be releasably coupled to the robotic drive system; and a neurovascular procedure may be accomplished using the procedure assembly. A second procedure catheter may also be provided, for extending through the first procedure catheter to a treatment site.

The coupling the access assembly step may comprise magnetically coupling a hub on each of the guidewire, access catheter and guide catheter, to separate corresponding couplers carrying corresponding drive magnets independently movably carried by the drive table. The procedure assembly may comprise a guidewire, a first catheter and a second catheter. The guidewire and first catheter may be positioned concentrically within the second catheter. The procedure assembly may be advanced as a unit through at least a portion of the length of the guide catheter, and the procedure may comprise a neurovascular thrombectomy.

There is also provided a method of performing a neurovascular procedure. The method includes the steps of providing a multi-catheter assembly including an access catheter, a guide catheter, and a procedure catheter, coupling the assembly to a robotic drive system, driving the assembly to achieve supra-aortic access, driving a subset of the assembly to a neurovascular site, wherein the subset includes the guide catheter and the procedure catheter, proximally removing the access catheter, and performing a neurovascular procedure using the procedure catheter.

The neurovascular procedure can include a neurovascular thrombectomy. The assembly may further include a guidewire, wherein each of the guidewire, the access catheter, the guide catheter, and the procedure catheter are configured to be adjusted by a respective hub. Coupling the assembly to the robotic drive system can include magnetically coupling a first hub of the guidewire to a first drive magnet, magnetically coupling a second hub of the access catheter to a second drive magnet, magnetically coupling a third hub of the guide catheter to a third drive magnet, and magnetically coupling a fourth hub of the procedure catheter to a fourth drive magnet. The first drive magnet, the second drive magnet, the third drive magnet, and the fourth drive magnet can each be independently movably carried by a drive table. The procedure catheter can be an aspiration catheter. The procedure catheter can be an embolic deployment catheter. The procedure catheter can be a stent deployment catheter. The procedure catheter can be a flow diverter deployment catheter. The procedure catheter can be a diagnostic angiographic catheter. The procedure catheter can be a stent retriever catheter. The procedure catheter can be a clot retriever. The procedure catheter can be a balloon catheter. The procedure catheter can be a catheter to facilitate percutaneous valve repair or replacement. The procedure catheter can be an ablation catheter.

There is also provided a method of performing a neurovascular procedure. The method includes the steps of providing an assembly including a guidewire, an access catheter, a guide catheter, and a procedure catheter coaxially moveably assembled into a single multi-catheter assembly, coupling the assembly to a drive system, driving the assembly to achieve supra-aortic access, driving a subset of the assembly to an intracranial site, wherein the subset includes the guidewire, the guide catheter, and the procedure catheter, and performing a neurovascular procedure using the subset of the assembly.

Each of the guidewire, the access catheter, the guide catheter, and the procedure catheter can be configured to be adjusted by a respective hub. Coupling the assembly to the drive system can include magnetically coupling a first hub of the guidewire to a first drive magnet, magnetically coupling a second hub of the access catheter to a second drive magnet, magnetically coupling a third hub of the guide catheter to a third drive magnet, and magnetically coupling a fourth hub of the procedure catheter to a fourth drive magnet. The drive system can be a robotic drive system, and the first drive magnet, the second drive magnet, the third drive magnet, and the fourth drive magnet can each be independently movably carried by a drive table associated with the robotic drive system. The first drive magnet, the second drive magnet, the third drive magnet, and the fourth drive magnet can each be independently movably carried by a drive table.

There is also provided a method of performing a neurovascular procedure. The method includes providing an assembly including a guidewire having a guidewire hub, an access catheter having an access catheter hub, and a guide catheter having a guide catheter hub. The method also includes coupling the guidewire hub to a first hub adapter, the access catheter hub to a second hub adapter, and the guide catheter hub to a third hub adapter, wherein each of the first hub adapter, the second hub adapter and the third hub adapter is movably carried by a support table. The method also includes driving the assembly in response to movement of each of the first hub adapter, the second hub adapter and the third hub adapter along the support table until the assembly is positioned to achieve supra-aortic vessel access.

The method can include the step of driving a subset of the assembly along the support table until the subset of the assembly is positioned to perform a neurovascular procedure at a neurovascular treatment site, wherein the subset of the assembly includes the guidewire, the guide catheter, and a procedure catheter. The neurovascular procedure can include a thrombectomy. Coupling the guidewire hub to the first hub adapter can include magnetically coupling the guidewire hub to a first drive magnet. Coupling the access catheter hub to the second hub adapter can include magnetically coupling the access catheter hub to a second drive magnet. Coupling the guide catheter hub to the third hub adapter can include magnetically coupling the guide catheter hub to a third drive magnet. The first drive magnet, the second drive magnet and the third drive magnets can be independently movably carried by the support table. The first drive magnet can be coupled to a first driven magnet across a sterile field barrier. The second drive magnet can be coupled to a second driven magnet across the sterile field barrier. The third drive magnet can be coupled to a third driven magnet across the sterile field barrier. Coupling the guidewire hub to the first hub adapter can include mechanically coupling the guidewire hub to a first drive. Coupling the access catheter hub to the second hub adapter can include mechanically coupling the access catheter hub to a second drive. Coupling the guide catheter hub to the third hub adapter can include mechanically coupling the guide catheter hub to a third drive. The guidewire and the guide catheter can be advanced as a unit along at least a portion of a length of the access catheter after supra-aortic access is achieved. The guidewire hub can be configured to adjust an axial position and a rotational position of the guidewire. The assembly can further include a procedure catheter having a procedure catheter hub. The procedure catheter hub can be configured to adjust an axial position and a rotational position of the procedure catheter. The procedure catheter hub can be further configured to laterally deflect a distal deflection zone of the procedure catheter. The guidewire hub can be configured to adjust an axial position and a rotational position of the guidewire. The procedure catheter hub can be configured to adjust an axial position and a rotational position of the procedure catheter. The guide catheter hub can be configured to adjust an axial position and a rotational position of the guide catheter. The access catheter hub can be configured to adjust an axial position and a rotational position of the access catheter. The procedure catheter hub can be further configured to laterally deflect a distal deflection zone of the procedure catheter. The access catheter hub can be further configured to laterally deflect a distal deflection zone of the access catheter. The guide catheter hub can be configured to adjust an axial position and a rotational position of the guide catheter. The access catheter hub can be configured to adjust an axial position and a rotational position of the access catheter. The access catheter hub can be further configured to laterally deflect a distal deflection zone of the access catheter.

There is also provided a drive system for achieving supra-aortic access and neurovascular treatment site access. The system includes a guidewire hub configured to adjust an axial position and a rotational position of a guidewire, a procedure catheter hub configured to adjust an axial position and a rotational position of a procedure catheter, a guide catheter hub configured to adjust an axial position and a rotational position of a guide catheter, and an access catheter hub configured to adjust an axial position and a rotational position of an access catheter, the access catheter further configured to laterally deflect a distal deflection zone of the access catheter.

The procedure catheter hub can be further configured to laterally deflect a distal deflection zone of the procedure catheter. The guidewire hub can be configured to couple to a guidewire hub adapter by magnetically coupling the guidewire hub to a first drive magnet. The access catheter hub can be configured to couple to an access catheter hub adapter by magnetically coupling the access catheter hub to a second drive magnet. The guide catheter hub can be configured to couple to a guide catheter hub adapter by magnetically coupling the guide catheter hub to a third drive magnet. The procedure catheter hub can be configured to couple to a procedure catheter hub adapter by magnetically coupling the procedure catheter hub to a fourth drive magnet. The first drive magnet, the second drive magnet, the third drive magnet, and the fourth drive magnet can be independently movably carried by a drive table. The system can include first driven magnet on the guidewire hub configured to cooperate with the first drive magnet such that the first driven magnet moves in response to movement of the first drive magnet. The first drive magnet can be configured to move outside of a sterile field while separated from the first driven magnet by a sterile field barrier while the first driven magnet is within the sterile field. A position of the first drive magnet can be movable in response to manipulation of a procedure drive control on a control console in electrical communication with the drive table. The system can include a second driven magnet on the access catheter hub configured to cooperate with the second drive magnet such that the second driven magnet is configured to move in response to movement of the second drive magnet, wherein the second drive magnet is configured to move outside of the sterile field while separated from the second driven magnet by the barrier while the second driven magnet is within the sterile field. The system can include a third driven magnet on the guide catheter hub configured to cooperate with the third drive magnet such that the third driven magnet is configured to move in response to movement of the third drive magnet, wherein the third drive magnet is configured to move outside of the sterile field while separated from the third driven magnet by the barrier while the third driven magnet is within the sterile field. The system can include a fourth driven magnet on the procedure catheter hub configured to cooperate with the fourth drive magnet such that the fourth driven magnet is configured to move in response to movement of the fourth drive magnet, wherein the fourth drive magnet is configured to move outside of the sterile field while separated from the fourth driven magnet by the barrier while the fourth driven magnet is within the sterile field. The procedure catheter can be an aspiration catheter. The procedure catheter can be an embolic deployment catheter. The procedure catheter can be a stent deployment catheter. The procedure catheter can be a flow diverter deployment catheter. The procedure catheter can be a diagnostic angiographic catheter. The procedure catheter can be a stent retriever catheter. The procedure catheter can be a balloon catheter. The procedure catheter can be a catheter to facilitate percutaneous valve repair or replacement. The procedure catheter can be an ablation catheter.

There is also provided method of achieving supra-aortic access and neurovascular treatment site access. The method includes the steps of providing a drive system including a guidewire hub configured to adjust an axial position and a rotational position of a guidewire, a procedure catheter hub configured to adjust an axial position and a rotational position of a procedure catheter; a guide catheter hub configured to adjust an axial position and a rotational position of a guide catheter, and an access catheter hub configured to adjust an axial position and a rotational position of an access catheter, the access catheter further configured to laterally deflect a distal deflection zone of the access catheter, and moving at least one of the guidewire hub, the procedure catheter hub, the guide catheter hub, and the access catheter hub to drive movement of at least one of the guidewire, the procedure catheter, the guide catheter, and the access catheter. The method can further include controlling the procedure catheter hub to laterally deflect a distal deflection zone of the procedure catheter.

There is also provided a method of achieving supra aortic access. The method includes the steps of providing an assembly including a guidewire, an access catheter and a guide catheter, coaxially moveably assembled into a single multi-catheter assembly, coupling the assembly to a drive system, driving the assembly to an aortic arch, and advancing the access catheter to achieve supra-aortic access to a branch vessel off of the aortic arch.

The method can further include driving a subset of the assembly to an intracranial site, and performing a neurovascular procedure using the subset of the assembly. The subset can include the guidewire, the guide catheter, and a procedure catheter. The procedure catheter can be an aspiration catheter. The procedure catheter can be an embolic deployment catheter. The procedure catheter can be a stent deployment catheter. The procedure catheter can be a flow diverter deployment catheter. The procedure catheter can be a diagnostic angiographic catheter. The procedure catheter can be a stent retriever catheter. The procedure catheter can be a clot retriever. The procedure catheter can be a balloon catheter. The procedure catheter can be a catheter to facilitate percutaneous valve repair or replacement. The procedure catheter can be an ablation catheter. The intracranial procedure can include an intracranial thrombectomy. The neurovascular procedure can include a neurovascular thrombectomy. At least one of the guidewire, the access catheter, and the guide catheter can include a hub configured to couple to a robotic drive system. Coupling the assembly to the drive system can include magnetically coupling a guide catheter hub to the drive system. Coupling the assembly to the drive system can include mechanically coupling a guide catheter hub to the drive system. The drive system can be a robotic drive system, and at least a first drive magnet, a second drive magnet, and a third drive magnet are each independently movably carried by a drive table associated with the robotic drive system.

There is also provided a method of priming an interventional device assembly. The method includes providing the interventional device assembly, the interventional device assembly including a first interventional device coupled to a first hub and a second interventional device coupled to a second hub arranged in a concentric stack, the second interventional device being positioned within a lumen of the first interventional device. The method includes coupling the interventional device assembly to a drive system while arranged in the concentric stack, axially advancing the first interventional device and the first hub relative to the second hub to decrease a depth of insertion of the second interventional device within the lumen of the first interventional device while maintaining a distal end of the second interventional device within the lumen of the first interventional device, and flushing the first interventional device with fluid after decreasing the depth of insertion of the second interventional device within the lumen of the first interventional device.

The drive system can be a robotic drive system. Axially advancing the first interventional device and the first hub relative to the second hub can include axially moving a first robotic drive coupled to the first hub relative to a second robotic drive coupled to the second hub. Axially advancing the first interventional device and the first hub relative to the second hub can include axially advancing the first interventional device and the first hub relative to the second hub in response to a control signal. The first interventional device can be a first catheter and the second interventional device can be a second catheter. The first catheter can be a guide catheter, the first hub can be a guide catheter hub, the second catheter can be a procedure catheter, and the second hub can be a procedure catheter hub. The interventional device assembly can include an access catheter coupled to an access catheter hub arranged in the concentric stack, the access catheter being positioned within a lumen of the procedure catheter. The method can include returning the guide catheter to an initial position relative to the procedure catheter after flushing the guide catheter with fluid, axially advancing the guide catheter, the guide catheter hub, the procedure catheter, and the procedure catheter hub relative to the access catheter hub to decrease a depth of insertion of the access catheter within the lumen of the procedure catheter while maintaining a distal end of the access catheter within the lumen of the procedure catheter and substantially maintaining a relative position between the guide catheter and the procedure catheter, and flushing the procedure catheter with fluid after decreasing the depth of insertion of the access catheter within the lumen of the procedure catheter. The interventional device assembly can include a guidewire coupled to a guidewire hub arranged in the concentric catheter stack, the guidewire being positioned within a lumen of the access catheter. The method can include returning the guide catheter and the procedure catheter to an initial position relative to the access catheter after flushing the procedure catheter with fluid, axially advancing the guide catheter, the guide catheter hub, the procedure catheter, the procedure catheter hub, the access catheter, and the access catheter hub relative to the guidewire hub to decrease a depth of insertion of the guidewire within the lumen of the access catheter while maintaining a distal end of the guidewire within the lumen of the access catheter and substantially maintaining relative positions between the guide catheter, the procedure catheter, and the access catheter, and flushing the access catheter with fluid after decreasing the depth of insertion of the guidewire within the lumen of the access catheter. The method can include flushing the second catheter with fluid, wherein the steps of flushing the first catheter and flushing the second catheter are performed simultaneously. The fluid can be saline, contrast media, or a combination of saline and contrast media. The first interventional device can be a catheter and the second interventional device can be a guidewire. The method can include reciprocally moving at least one of the first interventional device and the second interventional device relative to the other of the first interventional device and the second interventional device while flushing the first interventional device with fluid after decreasing the depth of insertion of the second interventional device within the lumen of the first interventional device.

There is also provided a method of priming a multi catheter assembly. The method includes providing the multi catheter assembly, the multi catheter assembly including a guidewire, an access catheter, a procedure catheter, and a guide catheter in a concentric stacked configuration, coupling the multi catheter assembly to a drive system, translating the guide catheter distally relative to the guidewire, the access catheter, and the procedure catheter, flushing the guide catheter with fluid, and translating the guide catheter proximally towards the guidewire, the access catheter, and the procedure catheter.

The drive system can be a robotic drive system. The method can include translating the procedure catheter and the guide catheter distally relative to the guidewire and the access catheter, flushing the procedure catheter with fluid, and translating the procedure catheter and the guide catheter proximally towards the guidewire and the access catheter. The method can include translating the access catheter, the procedure catheter, and the guide catheter distally relative to the guidewire, flushing the access catheter with fluid, and translating the access catheter, the procedure catheter, and the guide catheter proximally towards the guidewire. The fluid can be saline contrast media, or a combination of saline and contrast media. The drive system can be a robotic drive system. The guidewire can be coupled to a guidewire hub. The access catheter can be coupled to an access catheter hub. The procedure catheter can be coupled to a procedure catheter hub. The guide catheter can be coupled to a guide catheter hub. In the concentric stacked configuration, the procedure catheter is positioned within a lumen of the guide catheter, the access catheter is positioned within a lumen of the procedure catheter, and the guidewire is positioned within a lumen of the access catheter. The method can include reciprocally moving at least one of the guide catheter and the procedure catheter relative to the other of the guide catheter and the procedure catheter while flushing the guide catheter with fluid. The method can include rotating the guide catheter relative to the guidewire, access catheter, and procedure catheter.

There is also provided a method of priming an interventional device assembly. The method includes providing the interventional device assembly, the interventional device assembly comprising a first interventional device and a second interventional device, the second interventional device being positioned within the first interventional device, and reciprocally moving at least one of the first interventional device and the second interventional device relative to the other of the first interventional device and the second interventional device while flushing a lumen between the first interventional device and the second interventional device with fluid to remove microbubbles from the lumen.

Reciprocally moving at least one of the first interventional device and the second interventional device relative to the other of the first interventional device and the second interventional device can include reciprocally moving at least one of the first interventional device and the second interventional device relative to the other of the first interventional device and the second interventional device in response to a control signal. Reciprocally moving at least one of the first interventional device and the second interventional device relative to the other of the first interventional device and the second interventional device can include reciprocally moving at least one of a first robotic drive coupled to the first interventional device and a second robotic drive coupled to the second interventional device relative to the other of the first robotic drive and the second robotic drive. Reciprocally moving at least one of the first interventional device and the second interventional device relative to the other of the first interventional device and the second interventional device can include axially reciprocally moving at least one of the first interventional device and the second interventional device relative to the other of the first interventional device and the second interventional device. Reciprocally moving at least one of the first interventional device and the second interventional device relative to the other of the first interventional device and the second interventional device can further include rotationally reciprocally moving at least one of the first interventional device and the second interventional device relative to the other of the first interventional device and the second interventional device. Axially reciprocally moving at least one of the first interventional device and the second interventional device relative to the other of the first interventional device and the second interventional device can include axially reciprocally moving at least one of the first interventional device and the second interventional device relative to the other of the first interventional device and the second interventional device over a stroke length between about 10 mm and about 250 mm. Axially reciprocally moving at least one of the first interventional device and the second interventional device relative to the other of the first interventional device and the second interventional device can include axially reciprocally moving at least one of the first interventional device and the second interventional device relative to the other of the first interventional device and the second interventional device over a stroke length between about 25 mm and about 125 mm. Axially reciprocally moving at least one of the first interventional device and the second interventional device relative to the other of the first interventional device and the second interventional device can include axially reciprocally moving at least one of the first interventional device and the second interventional device relative to the other of the first interventional device and the second interventional device over a stroke length greater than 20 mm. Axially reciprocally moving at least one of the first interventional device and the second interventional device relative to the other of the first interventional device and the second interventional device can include axially reciprocally moving at least one of the first interventional device and the second interventional device relative to the other of the first interventional device and the second interventional device at a reciprocation frequency of no more than about 5 Hz. The reciprocation frequency can be no more than about 1 Hz. Reciprocally moving at least one of the first interventional device and the second interventional device relative to the other of the first interventional device and the second interventional device can include rotationally reciprocally moving at least one of the first interventional device and the second interventional device relative to the other of the first interventional device and the second interventional device. Reciprocally moving at least one of the first interventional device and the second interventional device relative to the other of the first interventional device and the second interventional device can include reciprocally moving both the first interventional device and the second interventional device relative to one another. Reciprocally moving at least one of the first interventional device and the second interventional device relative to the other of the first interventional device and the second interventional device can be performed by a robotic drive table. The first interventional device can be a first catheter and the second interventional device can be a second catheter. The first interventional device can be a catheter and the second interventional device can be a guidewire.

There is also provided a method of priming a multi catheter assembly. The method includes providing the multi catheter assembly, the multi catheter assembly including a guidewire, an access catheter, a procedure catheter, and a guide catheter arranged in a concentric catheter stack, wherein the guidewire is positioned within a lumen of the access catheter, the access catheter is positioned within a lumen of the procedure catheter, and the procedure catheter is positioned within a lumen of the guide catheter, and flushing the guide catheter with saline while reciprocally and/or rotationally moving at least one of the guide catheter and the procedure catheter relative to the other of the guide catheter and the procedure catheter.

Flushing the guide catheter with saline while reciprocally moving at least one of the guide catheter and the procedure catheter relative to the other of the guide catheter and the procedure catheter can include reciprocally moving at least one of the guide catheter and the procedure catheter relative to the other of the guide catheter and the procedure catheter in response to a control signal. Flushing the guide catheter with saline while reciprocally moving at least one of the guide catheter and the procedure catheter relative to the other of the guide catheter and the procedure catheter can include reciprocally moving at least one of a first robotic drive coupled to the guide catheter and a second robotic drive coupled to the procedure catheter relative to the other of the first robotic drive and the second robotic drive. Flushing the guide catheter with saline while reciprocally moving at least one of the guide catheter and the procedure catheter relative to the other of the guide catheter and the procedure catheter can include axially reciprocally moving, rotationally reciprocally moving, or both axially and rotationally reciprocally moving at least one of the guide catheter and the procedure catheter relative to the other of the guide catheter and the procedure catheter. The method can include flushing the procedure catheter with saline while reciprocally moving at least one of the procedure catheter and the access catheter relative to the other of the procedure catheter and the access catheter. Flushing the procedure catheter with saline while reciprocally moving at least one of the procedure catheter and the access catheter relative to the other of the procedure catheter and the access catheter can include axially reciprocally moving, rotationally reciprocally moving, or both axially and rotationally reciprocally moving at least one of the procedure catheter and the access catheter relative to the other of the procedure catheter and the access catheter. The method can include flushing the access catheter with saline while reciprocally moving at least one of the access catheter and the guidewire relative to the other of the access catheter and the guidewire. Flushing the access catheter with saline while reciprocally moving at least one of the access catheter and the guidewire can include axially reciprocally moving, rotationally recipro- cally moving, or both axially and rotationally reciprocally moving at least one of the access catheter and the guidewire relative to the other of the access catheter and the guidewire. The steps of flushing the guide catheter with saline while reciprocally moving at least one of the guide catheter and the procedure catheter relative to the other of the guide catheter and the procedure catheter, flushing the procedure catheter with saline while reciprocally moving at least one of the procedure catheter and the access catheter relative to the other of the procedure catheter and the access catheter, and flushing the access catheter with saline while reciprocally moving at least one of the access catheter and the guidewire relative to the other of the access catheter and the guidewire can be performed simultaneously.

There is also provided features and/or devices for pre- venting or reducing buckling of any of the interventional devices (e.g., catheters, guidewires, etc.) described herein. In some embodiments, the features and/or devices described herein can prevent any of the interventional devices described herein from significantly buckling during use. In some embodi- ments, significant buckling of a catheter, guidewire, and/or interventional device can be defined as buckling such that a position of a distal end of such device is more than about 1 mm away (e.g., longitudinally) from the position the distal end would be in if no buckling were present. In some embodiments, significant buckling of the catheter, guidewire, and/or interventional device can be defined as buckling such that a position of a distal end of such device is more than about 2 mm away or more than about 1 cm away (e.g., longitudinally) from the position the distal end would be in if no buckling were present. In a manually performed procedure, a physician may choose to grip such devices at different positions to ensure they are advanced inside a patient's body as expected, for example, as close to where they enter the patient as possible. In a robotically performed procedure, such devices may be pushed/advanced from their proximal end. This can potentially lead to such devices buckling and/or kinking between their proximal end and their distal end (e.g., between the proximal end of the interventional device and the entry point of the interven- tional device into the patient's body, between the proximal end of the interventional device and a distal hub/interven- tional device in a robotic interventional device assembly, or between a proximal end of the interventional device and a portion of the interventional device within the body). The anti-buckling features and/or devices disclosed herein can include, without limitation: a reinforced proximal end or region of such interventional devices; an increased stiffness of a proximal end or region of such interventional devices; an increased inner and/or outer diameter of a proximal end or region of such interventional devices; an increased inner and/or outer diameter and an increased wall thickness of a proximal end or region of such interventional devices; a telescoping tube through which at least a portion of such interventional devices extend therethrough; a telescoping spring through which at least a portion of such interventional devices extend therethrough; a spring through which at least a portion of such interventional devices extend therethrough; a scissor mechanism through which at least a portion of such interventional devices extend therethrough; a support rod- based split tube through which at least a portion of such interventional devices extend therethrough; a reel-based split tube through which at least a portion of such interven- tional devices extend therethrough; a sprocket-based split tube through which at least a portion of such interventional devices extend therethrough; a split tube through which at least a portion of such interventional devices extend there- through; a storable extendible support through which at least a portion of such interventional devices extend therethrough; supports through which at least a portion of such interven- tional devices extend therethrough; magnet-based supports along which at least a portion of such interventional devices extend therealong and/or therethrough; feed rollers that contact and feed at least a portion of such interventional devices therethrough; grippers that contact and feed at least a portion of such interventional devices therethrough; one or more channels through which at least a portion of such interventional devices extend therethrough; one or more channels with retention features through which at least a portion of such interventional devices extend therethrough; and one or more channels with magnet(s) through which at least a portion of such interventional devices extend there- through. In some implementations, the anti-buckling fea- tures and/or devices herein can be configured to accommo- date misalignment between interventional devices, their hubs, and/or components of an interventional device assem- bly. In some implementations, the anti-buckling features and/or devices herein can be configured to attach to and/or integrate with or within one or more hubs of an interven- tional device assembly. In some implementations, the anti- buckling features and/or devices herein can be configured to integrate with an interventional device. Any of the features or elements of any one of the anti-buckling solutions described herein can be combined or substituted with others, particularly when implemented in combination with an interventional device assembly.

Disclosed herein is an interventional device assembly comprising a first interventional device coupled to a first hub, a second interventional device coupled to a second hub, and an anti-buckling system configured to provide support to the first interventional device between the first hub and the second hub. The first interventional device and the second interventional device can be arranged in a concentric stack, with the first interventional device being positioned within a lumen of the second interventional device.

In the above interventional device assembly or in other implementations as described herein, one or more of the following features can also be provided. In some implemen- tations, the anti-buckling system is coupled to the first hub. In some implementations, a proximal end of the anti- buckling system is coupled to the first hub. In some imple- mentations, a distal end of the anti-buckling system is coupled to the second hub. In some implementations, the anti-buckling system comprises a telescoping tube through which at least a portion of the first interventional device extends. In some implementations, the telescoping tube comprises a plurality of concentric telescopically axially extendable and collapsible tube segments. In some imple- mentations, a proximal end of the telescoping tube is coupled to the first hub and a distal end of the telescoping tube is coupled to the second hub. In some implementations, the anti-buckling system comprises a spring extending between the first hub and the second hub. In some imple- mentations, the spring comprises a telescoping spring. In some implementations, the anti-buckling system comprises a scissor mechanism extending between the first hub and the second hub. In some implementations, the anti-buckling system comprises a split tube extending between the first hub and the second hub. In some implementations, the split tube comprises a split positioned at least partially within the first hub to receive the first interventional device therethrough. In some implementations, the anti-buckling system further comprises a reel coupled with the split tube and configured to exert tension on the split tube. In some implementations, the anti-buckling system further comprises a sprocket coupled with the split tube and configured to exert tension on the split tube. In some implementations, the anti-buckling system comprises a storable extendible support extending between the first hub and the second hub. In some implementations, the storable extendible support comprises a shape memory material or a zipper. In some implementations, the anti-buckling system comprises a plurality of supports movably coupled to a support rod, wherein adjacent supports are separated by springs. In some implementations, each of the plurality of supports comprises a magnet configured to apply a magnetic force on the first interventional device. In some implementations, the anti-buckling system comprises one or more feed rollers. In some implementations, the anti-buckling system comprises one or more grippers. In some implementations, the anti-buckling system comprises a channel configured to receive the first interventional device and being shaped to retain the first interventional device therein. In some implementations, the anti-buckling system comprises a channel configured to receive the first interventional device and comprising one or more magnets configured to apply a magnetic force on the first interventional device.

Disclosed herein is an interventional device assembly, comprising: a first hub positioned along a drive table, the first hub comprising a proximal end and a distal end; an interventional device coupled to the first hub and extending distally therefrom; and a telescoping tube comprising a proximal end and a distal end, the proximal end of the telescoping tube being secured within an interior of the first hub between the proximal end of the first hub and the distal end of the first hub, the distal end of the telescoping tube being configured to secure to a second hub positioned along the drive table or a distal attachment coupled to the drive table; wherein at least a portion of the interventional device extends through the telescoping tube.

In the above interventional device assembly or in other implementations as described herein, one or more of the following features can also be provided. In some implementations, the telescoping tube comprises a plurality of concentric telescopically axially extendable and collapsible tube segments. In some implementations, the plurality of tube segments comprise an outermost tube segment attached to a distal retainer and an innermost tube segment attached to a proximal retainer. In some implementations, the distal retainer is configured to releasably attach to the second hub or the distal attachment and the proximal retainer is configured to attach within the interior of the first hub. In some implementations, the distal retainer is further configured to releasably attach to the first hub when the telescoping tube is detached from the second hub and is fully axially collapsed. In some implementations, the distal retainer comprises a body with one or more tabs extending radially outward therefrom; and the second hub comprises a proximal hub attachment comprising a recess and one or more slots configured to receive the body and one or more tabs of the distal retainer, respectively; wherein the distal retainer is configured to be rotated relative to the proximal hub attachment when received within the proximal hub attachment to releasably attach the distal retainer to the proximal hub attachment. In some implementations, the distal retainer comprises a body with one or more tabs extending radially outward therefrom; and the distal attachment comprises a recess and one or more slots configured to receive the body and one or more tabs of the distal retainer, respectively; wherein the distal retainer is configured to be rotated relative to the distal attachment when received within the distal attachment to releasably attach the distal retainer to the distal attachment. In some implementations, the interventional device assembly further comprises an anti-buckling tubular attachment comprising a proximal end and a distal end and a tubular body extending therebetween, the proximal end attached to and extending distally from the distal retainer and the distal end configured to releasably attach to an insertion sheath. In some implementations, the tubular body of the anti-buckling tubular attachment comprises a plurality of circumferential cuts to provide the tubular attachment with flexibility. In some implementations, the plurality of tube segments comprises an innermost tube segment and one or more outer tube segments, wherein each of the one or more outer tube segments is coupled to a cap at its proximal end, the cap having a through hole configured to receive the interventional device therethrough. In some implementations, the cap has an outer diameter greater than an outer diameter of the tube segment to which the cap is coupled. In some implementations, the through hole of the cap has a diameter smaller than an inner diameter of the tube segment to which the cap is coupled. In some implementations, the plurality of tube segments comprises an outermost tube segment and one or more inner tube segments, wherein each of the one or more inner tube segments comprises a shim attached around a portion of its outer diameter. In some implementations, the plurality of tube segments comprises an outermost tube segment and one or more inner tube segments, wherein each of the one or more inner tube segments comprises a first tube section having a first outer diameter and a second tube section having a second outer diameter. In some implementations, each of the plurality of tube segments comprises an inner diameter reducing feature configured to reduce the unsupported free length of the interventional device when the interventional device extends through the telescoping tube. In some implementations, a clearance between adjacent concentric tube segments of the plurality of concentrically adjacent tube segments is between about 0.001 inches and about 0.010 inches. In some implementations, each of the plurality of tube segments has a wall thickness that is substantially the same. In some implementations, an innermost tube segment of the plurality of tube segments is attached to the interventional device. In some implementations, the innermost tube segment of the plurality of tube segments is bonded to the interventional device. In some implementations, the telescoping tube is contained by the first hub when detached from the second hub or the distal attachment and fully axially collapsed.

Disclosed herein is an anti-buckling device for an interventional device assembly, comprising: a telescoping tube comprising a proximal end and a distal end, the proximal end of the telescoping tube being coupled to a first hub of an interventional device assembly; and a distal retainer coupled to the distal end of the telescoping tube, the distal retainer being configured to releasably couple to a distal hub attachment at a distal end of the first hub in a first configuration and releasably couple to a second hub of the interventional device assembly positioned distal to the first hub in a second configuration.

In the above anti-buckling device or in other implementations as described herein, one or more of the following features can also be provided. In some implementations, the second hub comprises a proximal hub attachment configured to receive the distal retainer, wherein the distal retainer is configured to be rotated relative to the proximal hub attachment when received within the proximal hub attachment to releasably attach the distal retainer to the proximal hub attachment. In some implementations, the distal retainer comprises a body with one or more tabs extending radially outward therefrom; and the proximal hub attachment comprises a recess and one or more slots configured to receive the body and one or more tabs of the distal retainer, respectively. In some implementations, each of the one or more tabs of the distal retainer comprises a tapered leading edge. In some implementations, each of the one or more slots of the proximal hub attachment comprises an internal taper. In some implementations, the distal retainer comprises an arm extending from the body and configured to be manipulated by a user to rotate the distal retainer. In some implementations, the distal hub attachment of the first hub is configured to receive the distal retainer, wherein the distal retainer is configured to be rotated relative to the distal hub attachment when received within the distal hub attachment to releasably attach the distal retainer to the distal hub attachment. In some implementations, the distal retainer comprises a body with one or more tabs extending radially outward therefrom; and the distal hub attachment of the first hub comprises a recess and one or more slots configured to receive the body and one or more tabs of the distal retainer, respectively. In some implementations, each of the one or more tabs of the distal retainer comprises a tapered leading edge. In some implementations, each of the one or more slots of the distal hub attachment comprises an internal taper. In some implementations, the distal retainer comprises an arm extending from the body and configured to be manipulated by a user to rotate the distal retainer. In some implementations, the telescoping tube comprises a plurality of concentric telescopically axially extendable and collapsible tube segments. In some implementations, the plurality of tube segments comprise an outermost tube segment attached to the distal retainer and an innermost tube segment attached to a proximal retainer. In some implementations, the proximal retainer is secured within an interior of the first hub between a proximal end of the first hub and the distal end of the first hub. In some implementations, the plurality of tube segments comprises an innermost tube segment and one or more outer tube segments, wherein each of the one or more outer tube segments is coupled to a cap at its proximal end, the cap having a through hole configured to receive an interventional device therethrough. In some implementations, the cap has an outer diameter greater than an outer diameter of the tube segment to which the cap is coupled. In some implementations, the plurality of tube segments comprises an outermost tube segment and one or more inner tube segments, wherein each of the one or more inner tube segments comprises a first tube section having a first outer diameter and a second tube section having a second outer diameter. In some implementations, each of the plurality of tube segments comprises an inner diameter reducing feature configured to reduce the unsupported free length of an interventional device when the interventional device extends through the telescoping tube. In some implementations, the cap is attached to a distal end of each of the plurality of tube segments. In some implementations, the telescoping tube is contained by the first hub when in the first configuration.

Disclosed herein is an anti-buckling device for an interventional device assembly, comprising: a telescoping tube comprising a plurality of concentric telescopically axially extendable and collapsible tube segments each having a proximal end and a distal end, the plurality of tube segments comprising an innermost tube segment and one or more outer tube segments, the innermost tube being configured to couple to a hub of an interventional device assembly, the telescoping tube being configured to extend distally from the hub; wherein each of the one or more outer tube segments is coupled to a cap at its proximal end, the cap having a through hole configured to receive an interventional device of the interventional device assembly therethrough and an outer diameter greater than an outer diameter of the outer tube segment to which the cap is coupled.

In the above anti-buckling device or in other implementations as described herein, one or more of the following features can also be provided. In some implementations, the through hole of the cap has a diameter smaller than an inner diameter of the tube segment to which the cap is coupled. In some implementations, an inner diameter portion of a cap of an outer tube segment of the one or more outer tube segments can be dimensioned to act as a stop for an outer diameter portion of a cap of an inner tube segment that is concentrically adjacent to the outer tube segment. In some implementations, the cap is ring-shaped. In some implementations, the cap is concentrically attached to the tube segment to which the cap is coupled. In some implementations, the cap of an outer tube segment can be configured to prevent hyper-extension of an inner tube segment that is concentrically adjacent to the outer tube segment. In some implementations, the innermost tube segment and all but an outermost tube segment of the one or more outer tube segments comprises a shim attached around a portion of its outer diameter, wherein the cap of the each of the one or more outer tube segments is configured to act as a stop for an inner tube segment that is concentrically adjacent to the outer tube segment to which the cap is coupled. In some implementations, the shim is attached adjacent the distal end of its corresponding tube segment. In some implementations, a cap of an outer tube segment can be configured to prevent hyper-collapse of an inner tube segment that is concentrically adjacent to the outer tube segment. In some implementations, the proximal end of the innermost tube segment is attached to a proximal retainer, the proximal retainer being configured to secure within an interior of the hub between a proximal end of the hub and a distal end of the hub. In some implementations, an outermost tube segment of the one or more outer tube segments is attached to a distal retainer, the distal retainer being configured to releasably attach to the distal end of the hub or a proximal end of a second hub. In some implementations, the innermost tube segment and all but an outermost tube segment of the one or more outer tube segments comprises a first tube section having a first outer diameter and a second tube section having a second outer diameter. In some implementations, the first outer diameter of the first tube section is greater than the second outer diameter of the second tube section and the first tube section is disposed adjacent the distal end of its corresponding tube segment. In some implementations, each of the plurality of tube segments comprises an inner diameter reducing feature configured to reduce the unsupported free length of the interventional device when the interventional device extends through the telescoping tube. In some implementations, the cap is attached to the distal end of each of the plurality of tube segments. In some implementations, a clearance between adjacent concentric tube segments of the plurality of concentrically adjacent tube segments is between about 0.001 inches and about 0.010 inches. In some implementations, an outer tube segment of the plurality of tube segments is shorter in length than an inner tube segment that is concentrically adjacent thereto. In some implementations, each of the plurality of tube segments has a wall thickness that is substantially the same. In some implementations, the telescoping tube is contained by the first hub when fully axially collapsed. In some implementations, the innermost tube segment is bonded to the interventional device.

Disclosed herein is an anti-buckling device for an interventional device assembly, comprising: a telescoping tube comprising a plurality of concentric telescopically axially extendable and collapsible tube segments each with a proximal end and a distal end; wherein one or more of the plurality of tube segments comprises: an inner diameter reducing feature configured to reduce an unsupported free length of an interventional device of the interventional device assembly when the interventional device extends through the telescoping tube, the inner diameter reducing feature attached to the distal end of its associated tube segment having a through hole configured to receive the interventional device therethrough.

In the above anti-buckling device or in other implementations as described herein, one or more of the following features can also be provided. In some implementations, the through hole of the inner diameter reducing feature is centered relative to the inner diameter of the tube segment to which the inner diameter reducing feature is attached. In some implementations, the through hole of the inner diameter reducing feature is off-centered relative to the inner diameter of the tube segment to which the inner diameter reducing feature is attached. In some implementations, the inner diameter reducing feature comprises a cap. In some implementations, the cap is concentrically attached to the tube segment to which the cap is coupled. In some implementations, the cap is a disc-shaped cap. In some implementations, the cap is a cup-shaped cap. In some implementations, the plurality of tube segments comprises an innermost tube segment and one or more outer tube segments, wherein each of the one or more outer tube segments is coupled to a second cap at its proximal end, the second cap having a second through hole configured to receive the interventional device therethrough. In some implementations, the second cap has an outer diameter greater than an outer diameter of the tube segment to which the second cap is coupled. In some implementations, the second through hole of the second cap has a diameter smaller than an inner diameter of the tube segment to which the second cap is coupled. In some implementations, the plurality of tube segments comprises an outermost tube segment and one or more inner tube segments, wherein each of the one or more inner tube segments comprises a shim attached around a portion of its outer diameter. In some implementations, the shim is attached adjacent the distal end of its corresponding tube segment. In some implementations, the plurality of tube segments comprises an outermost tube segment and one or more inner tube segments, wherein each of the one or more inner tube segments comprises a first tube section having a first outer diameter and a second tube section having a second outer diameter. In some implementations, the first outer diameter of the first tube section is greater than the second outer diameter of the second tube section and the first tube section is disposed adjacent the distal end of its corresponding tube segment. In some implementations, the proximal end of an innermost tube segment of the plurality of tube segments is attached to a proximal retainer, the proximal retainer being configured to secure within an interior of a hub of the interventional device assembly between a proximal end of the hub and a distal end of the hub. In some implementations, the distal end of an outermost tube segment of the plurality of tube segments is attached to a distal retainer, the distal retainer being configured to releasably attach to the distal end of the hub or a proximal end of a second hub. In some implementations, a clearance between adjacent concentric tube segments of the plurality of concentrically adjacent tube segments is between about 0.001 inches and about 0.010 inches. In some implementations, each of the plurality of tube segments has a wall thickness that is substantially the same. In some implementations, an innermost tube segment of the plurality of tube segments is bonded to an interventional device of the interventional device assembly. In some implementations, the interventional device comprises a guidewire.

Disclosed herein is an anti-buckling device for an interventional device assembly, comprising: a telescoping tube comprising a plurality of concentric telescopically axially extendable and collapsible tube segments, the plurality of tube segments comprising an outermost tube segment and one or more inner tube segments; wherein each of the one or more inner tube segments comprises a first tube section having a first outer diameter and a second tube section having a second outer diameter.

In the above anti-buckling device or in other implementations as described herein, one or more of the following features can also be provided. In some implementations, each of the one or more inner tube segments has a uniform inner diameter. In some implementations, the first tube section is disposed adjacent a distal end of its corresponding tube segment. In some implementations, the first outer diameter of the first tube section is greater than the second outer diameter of the second tube section. In some implementations, each of the one or more inner tube segments further comprises a tapered section between the first tube section and the second tube section, the tapered section having a diameter that tapers between the first outer diameter and the second outer diameter. In some implementations, each of the one or more inner tube segments further comprises a shoulder of between about 0.002 inches and about 0.0045 inches between the first tube section and the second tube section. In some implementations, the first tube section has a wall thickness of between about 0.005 inches and about 0.020 inches and the second tube section has a wall thickness of between about 0.003 inches and about 0.014 inches. In some implementations, the first tube section comprises a shim attached around a portion of the tube segment. In some implementations, the shim comprises a tape or a heat shrink. In some implementations, the shim has a thickness of between about 0.002 inches and about 0.0045 inches. In some implementations, the one or more inner tube segments of the plurality of tube segments comprises an innermost tube segment, wherein each of the plurality of tube segments except for the innermost tube segment is coupled to a cap at a proximal end thereof, the cap having a through hole configured to receive an interventional device of the interventional device assembly therethrough. In some implementations, the cap has an outer diameter greater than the second outer diameter of the second tube section. In some implementations, the through hole of the cap has a diameter smaller than an inner diameter of the tube segment to which the cap is coupled. In some implementations, the one or more inner tube segments of the plurality of tube segments comprises an innermost tube segment and a proximal end of the innermost tube segment is attached to a proximal retainer, the proximal retainer being configured to secure within an interior of a hub of the interventional device assembly between a proximal end of the hub and a distal end of the hub. In some implementations, the telescoping tube is contained by the hub when fully axially collapsed. In some implementations, a distal end of the outermost tube segment of the plurality of tube segments is attached to a distal retainer, the distal retainer being configured to releasably attach to the distal end of the hub or a proximal end of a second hub. In some implementations, the distal retainer comprises a body with one or more tabs extending radially outward therefrom; and the second hub comprises a proximal hub attachment comprising a recess and one or more slots configured to receive the body and one or more tabs of the distal retainer, respectively; wherein the distal retainer is configured to be rotated relative to the proximal hub attachment when received within the proximal hub attachment to releasably attach the distal retainer to the proximal hub attachment. In some implementations, a clearance between adjacent concentric tube segments of the plurality of concentrically adjacent tube segments is between about 0.001 inches and about 0.010 inches. In some implementations, an outer tube segment of the plurality of tube segments is shorter in length than an inner tube segment that is concentrically adjacent thereto. In some implementations, the one or more inner tube segments of the plurality of tube segments comprises an innermost tube segment, and wherein the innermost tube segment is bonded to an interventional device of the interventional device assembly.

Disclosed herein is an anti-buckling device for an interventional device assembly, comprising: a telescoping tube comprising a proximal end and a distal end, the proximal end of the telescoping tube being coupled to a first hub of an interventional device assembly; and a distal retainer coupled to the distal end of the telescoping tube, the distal retainer being configured to releasably couple to a distal hub attachment at a distal end of the first hub in a first configuration and releasably couple to a second hub or a distal retainer of the interventional device assembly positioned distal to the first hub in a second configuration.

Disclosed herein is an interventional device assembly, comprising: a first interventional device coupled to a first hub; a second interventional device coupled to a second hub, wherein the first interventional device and the second interventional device are arranged in a concentric stack, the first interventional device being positioned within a lumen of the second interventional device; and a telescoping tube having a proximal end and a distal end, the proximal end coupled to the first hub and the distal end coupled to the second hub, the telescoping tube configured to provide anti-buckling support to the first interventional device between the first hub and the second hub; wherein at least a portion of the first interventional device extends through the telescoping tube.

Disclosed herein is a system for performing an interventional procedure, comprising: an interventional device assembly comprising: a guidewire having a guidewire hub, an access catheter having an access catheter hub, and a guide catheter having a guide catheter hub, wherein the access catheter hub is positioned distal of the guidewire hub and the guide catheter hub is positioned distal of the access catheter hub, and wherein the guidewire, the access catheter, and the guide catheter are arranged in a concentric stack with the guidewire being positioned within a lumen of the access catheter and the guidewire and access catheter being positioned within a lumen of the guide catheter; a first telescoping tube with a proximal end and a distal end, the proximal end coupled to the guidewire hub and the distal end coupled to the access catheter hub, the first telescoping tube configured to provide anti-buckling support to the guidewire between the guidewire hub and the access catheter hub; and a second telescoping tube with a proximal end and a distal end, the proximal end coupled to the access catheter hub and the distal end being coupled to the guide catheter hub, the second telescoping tube configured to provide anti-buckling support to at least the access catheter between the access catheter hub and the guide catheter hub.

Disclosed herein is an anti-buckling device for an interventional device assembly, comprising: a telescoping tube with a proximal end and a distal end, the telescoping tube comprising a plurality of concentric telescopically axially extendable and collapsible tube segments; a proximal retainer coupled to a proximal end of an outermost tube segment of the telescoping tube; and a distal retainer coupled to a distal end of an innermost tube segment of the telescoping tube; wherein the proximal retainer is configured to couple the proximal end of the telescoping tube to a first hub of the interventional device assembly; and wherein the distal retainer is configured to releasably couple the distal end of the telescoping tube to a second hub of the interventional device assembly positioned distal to the first hub.

Disclosed herein is a method of preparing an interventional assembly for an interventional procedure, comprising the steps of: providing an interventional assembly comprising: a guidewire having a guidewire hub coupled to a proximal end of a first telescoping tube, an access catheter having an access catheter hub coupled to a proximal end of a second telescoping tube, and a guide catheter having a guide catheter hub; and coupling: the guidewire hub to a first hub adapter, the access catheter hub to a second hub adapter positioned distal of the first hub adapter, the guide catheter hub to a third hub adapter positioned distal of the second hub adapter, a distal end of the first telescoping tube to the access catheter hub, and a distal end of the second telescoping tube to the guide catheter hub, wherein each of the first hub adapter, the second hub adapter and the third hub adapter is movably carried by a support table.

Disclosed herein is a method of performing a neurovascular procedure, comprising the steps of: providing an interventional assembly comprising: a guidewire having a guidewire hub coupled to a proximal end of a first telescoping tube, an access catheter having an access catheter hub coupled to a proximal end of a second telescoping tube, and a guide catheter having a guide catheter hub; and coupling: the guidewire hub to a first hub adapter, the access catheter hub to a second hub adapter positioned distal of the first hub adapter, the guide catheter hub to a third hub adapter positioned distal of the second hub adapter, a distal end of the first telescoping tube to the access catheter hub, and a distal end of the second telescoping tube to the guide catheter hub, wherein each of the first hub adapter, the second hub adapter and the third hub adapter is movably carried by a support table; and driving the interventional assembly in response to movement of each of the first hub adapter, the second hub adapter and the third hub adapter along the support table until the interventional assembly is positioned to achieve supra-aortic vessel access; wherein the first telescoping tube is configured to provide anti-buckling support to the guidewire between the guidewire hub and the access catheter hub and the second telescoping tube is configured to provide anti-buckling support to at least the access catheter between the access catheter hub and the guide catheter hub.

BRIEF DESCRIPTION OF THE DRAWINGS

FIGS. 23D-23F illustrate the example catheter assembly of FIGS. 23A-23C.

FIGS. 51A-51E depict examples of anti-buckling channel(s).

25

Figures 59A, 59B, 59C:
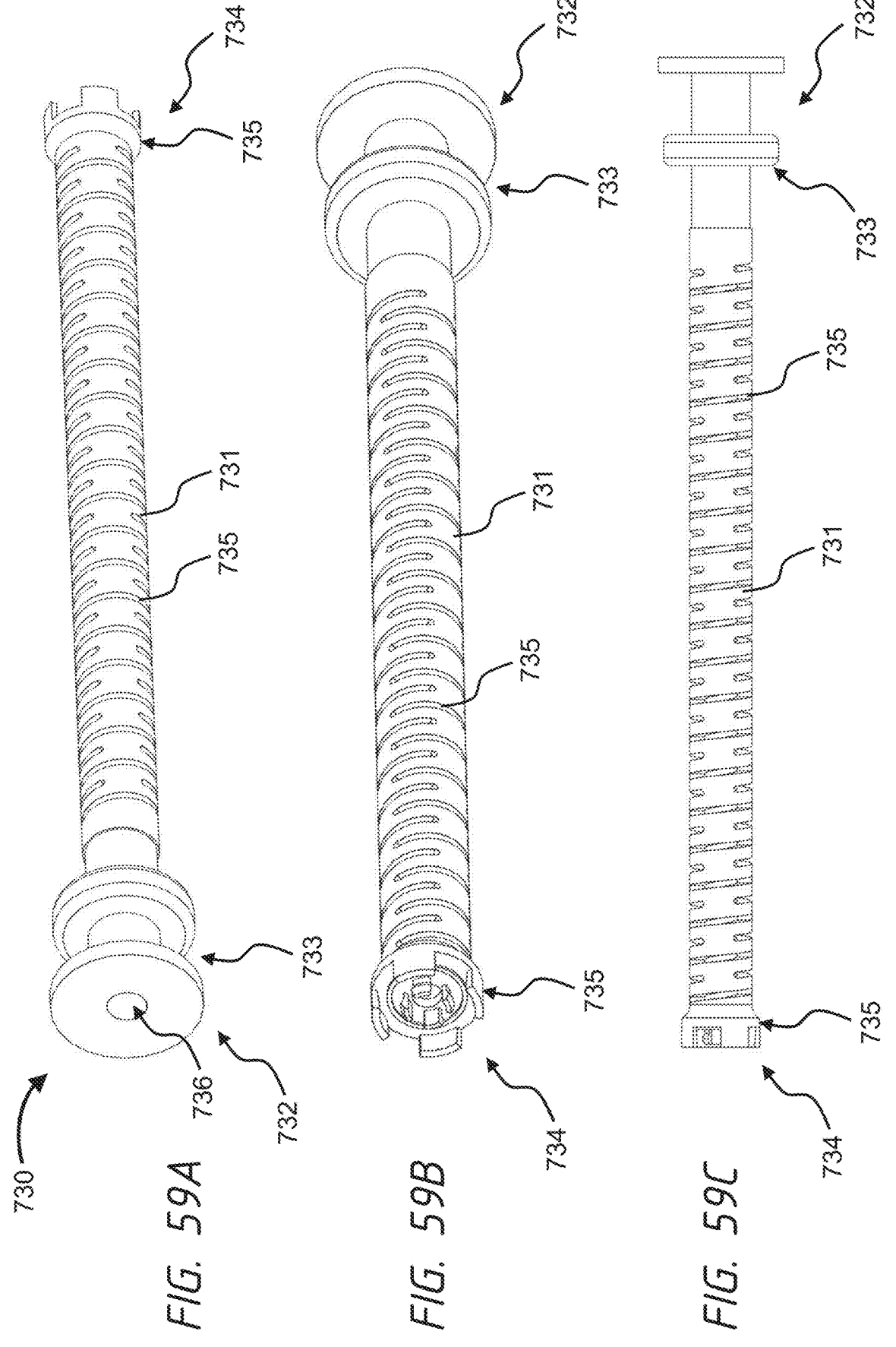

FIGS. 59A-59C depict an example of an anti-buckling tubular attachment.

FIGS. 60A-60G depict another example of an anti-buckling telescoping tube.

Figure 60A:
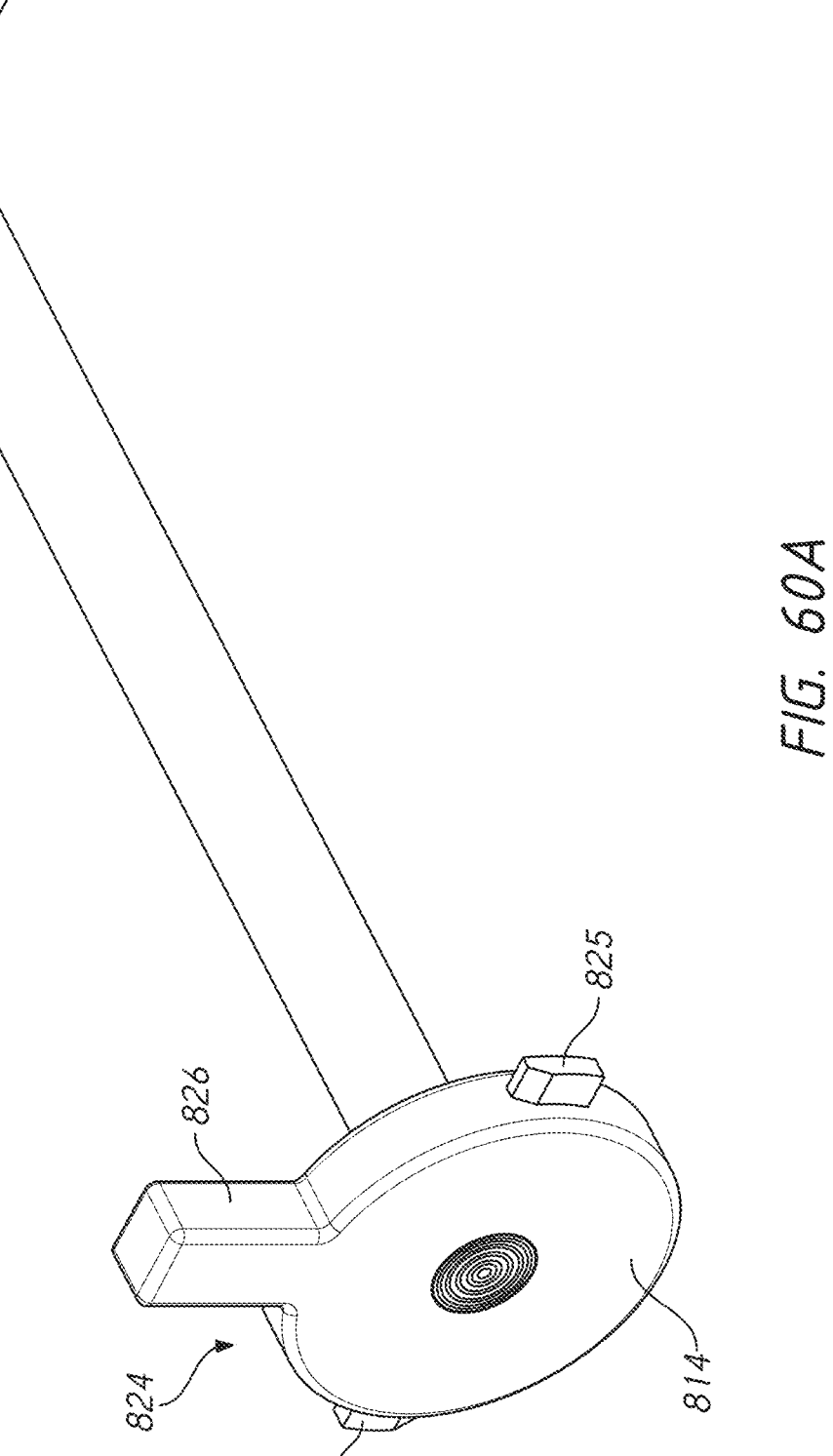
Figure 60B:
Figures 60C, 60D, 60E:
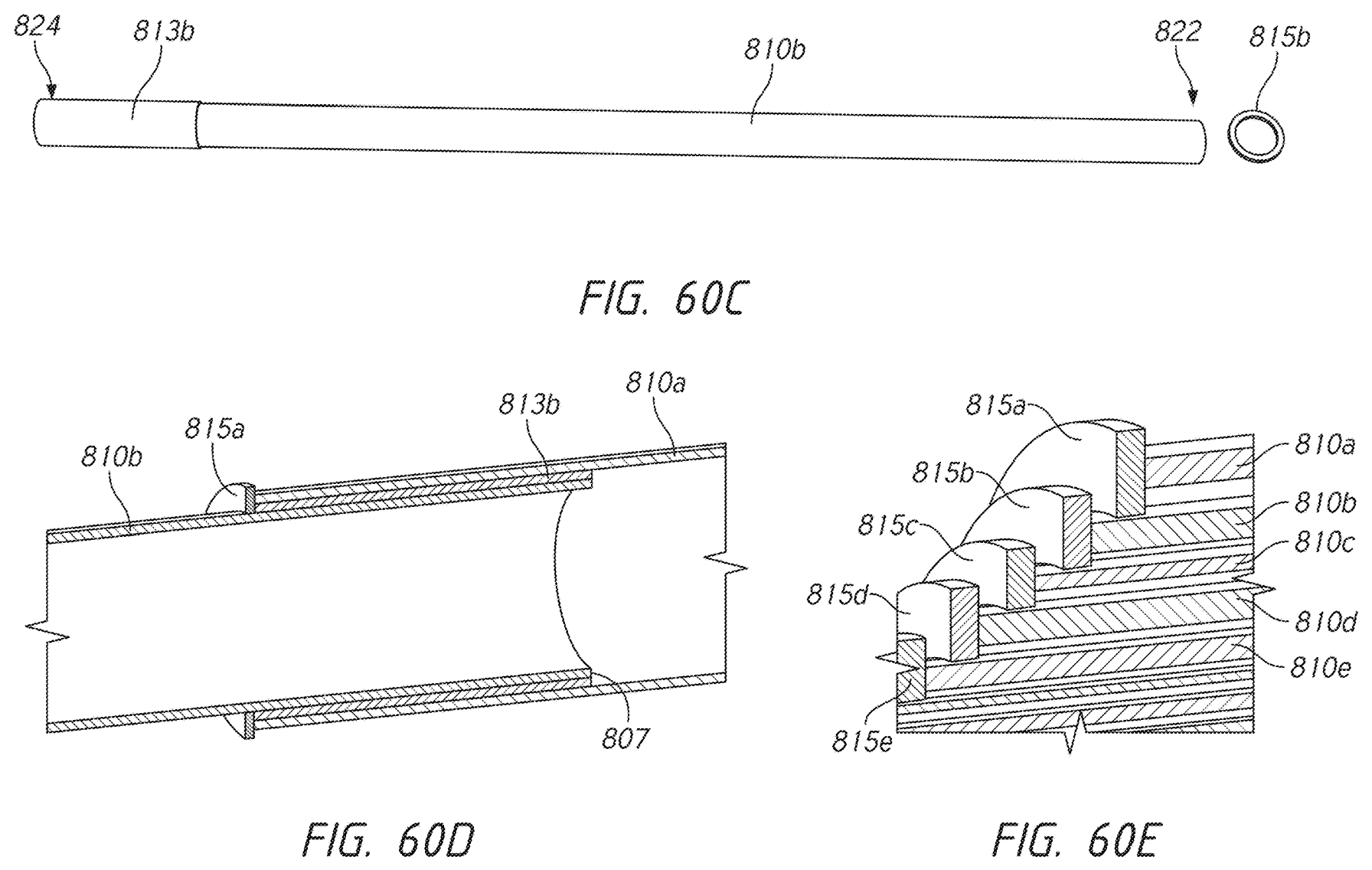
Figures 60F, 60G:
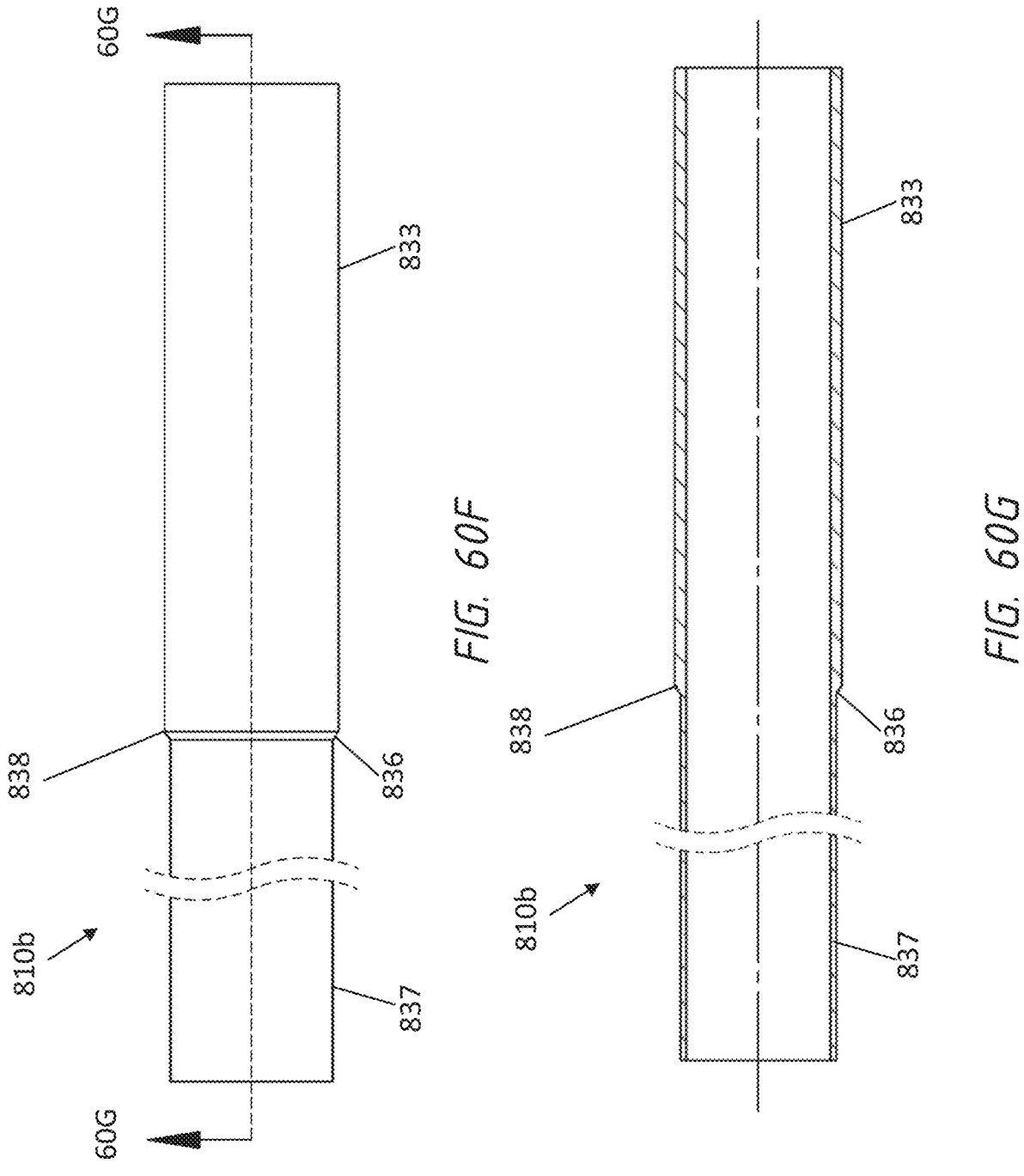
Figure 60H:
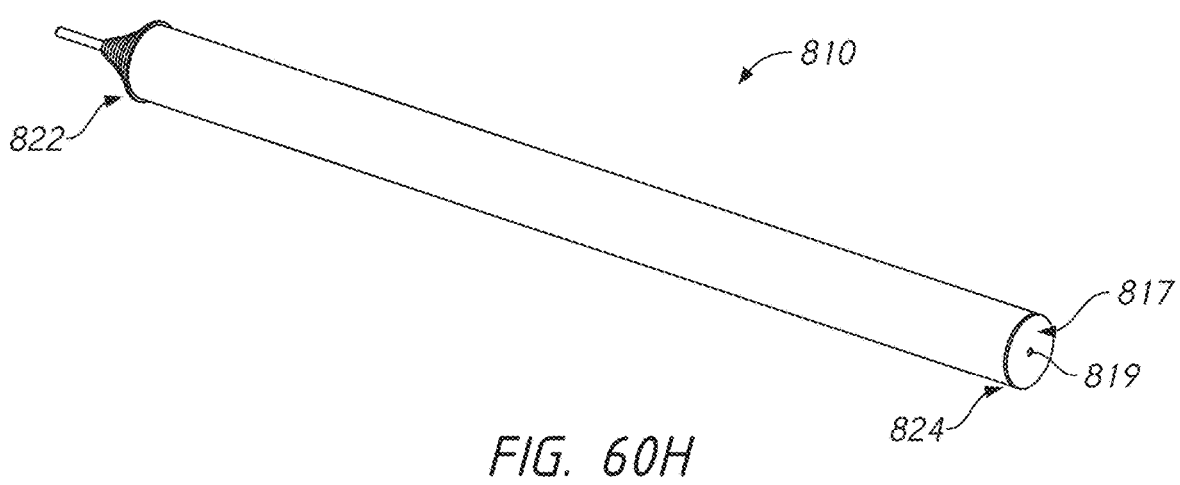
Figure 60I:
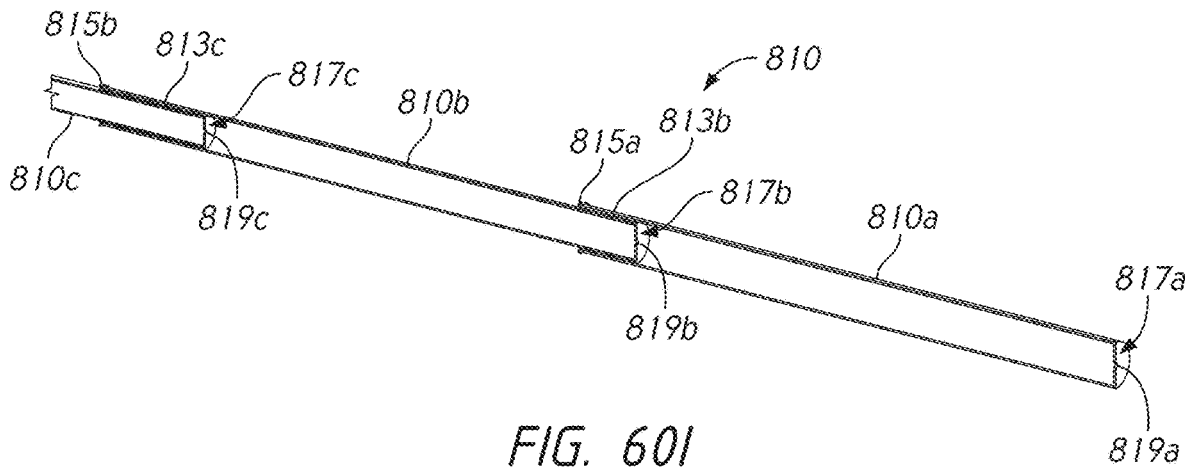
Figure 60J:
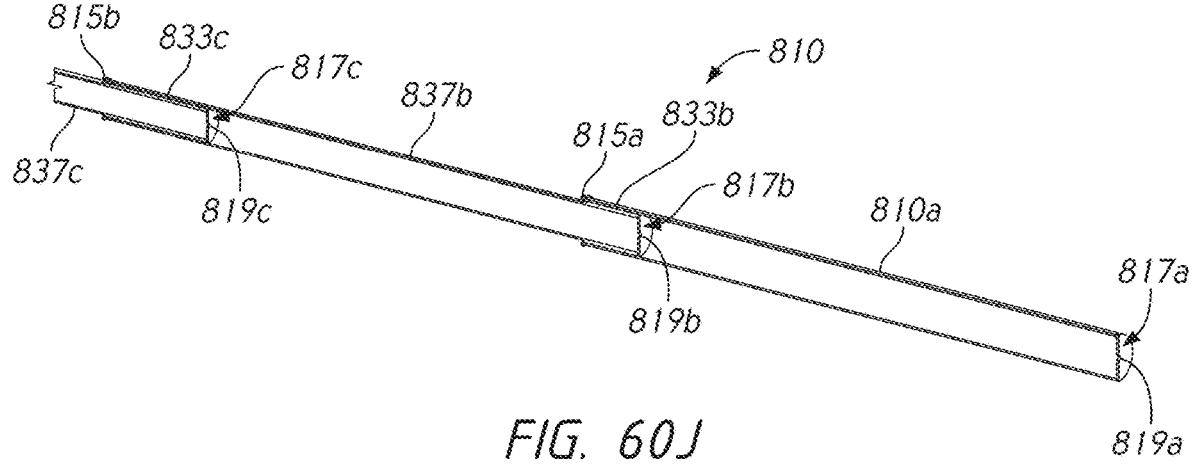

FIGS. 60H-60J depict alternative embodiments of the anti-buckling telescoping tubes of FIGS. 60A-60G.

FIGS. 61A-61E depict an example of an interventional device assembly utilizing an anti-buckling telescoping tube according to FIGS. 60A-60E.

Figures 62A, 62B:
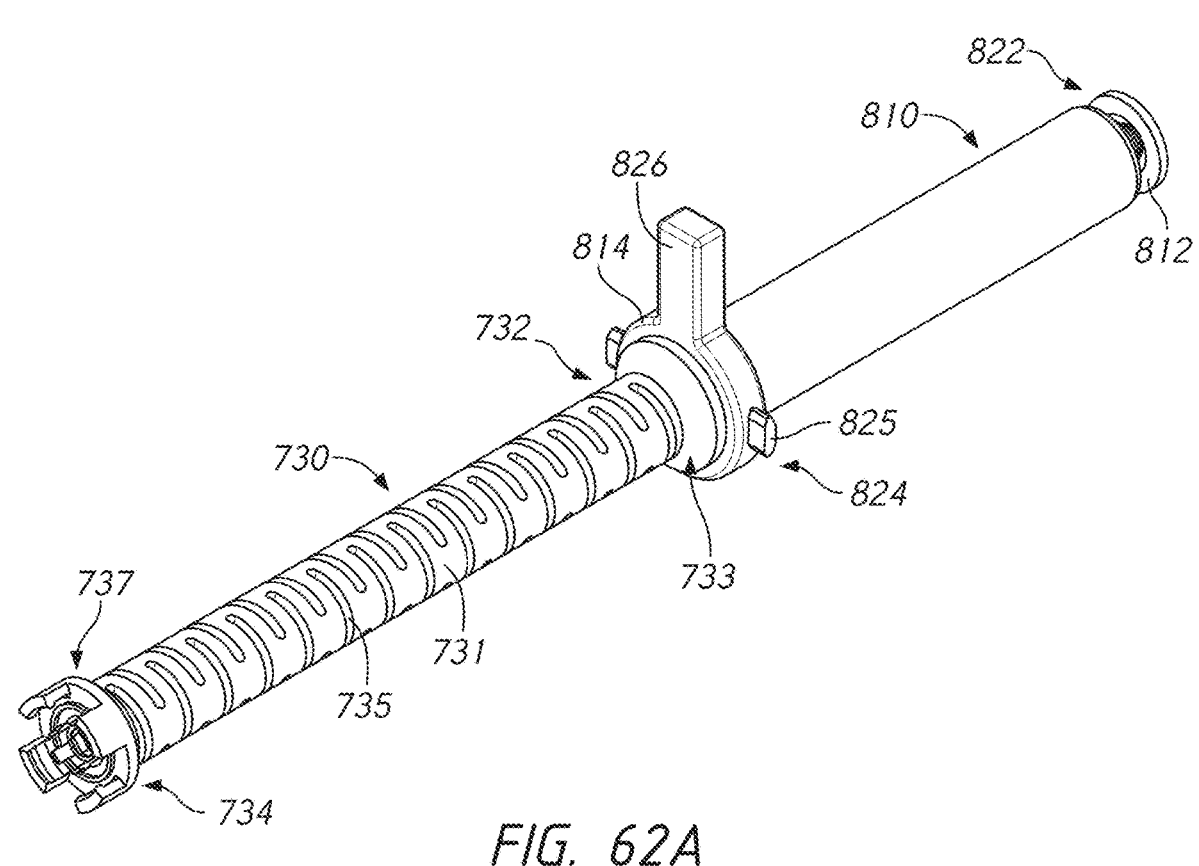

FIGS. 62A-62B depict an example of an interventional device assembly utilizing an anti-buckling telescoping tube according to FIGS. 60A-60E with an anti-buckling tubular attachment.

Figures 63A, 63B, 64A, 64B:
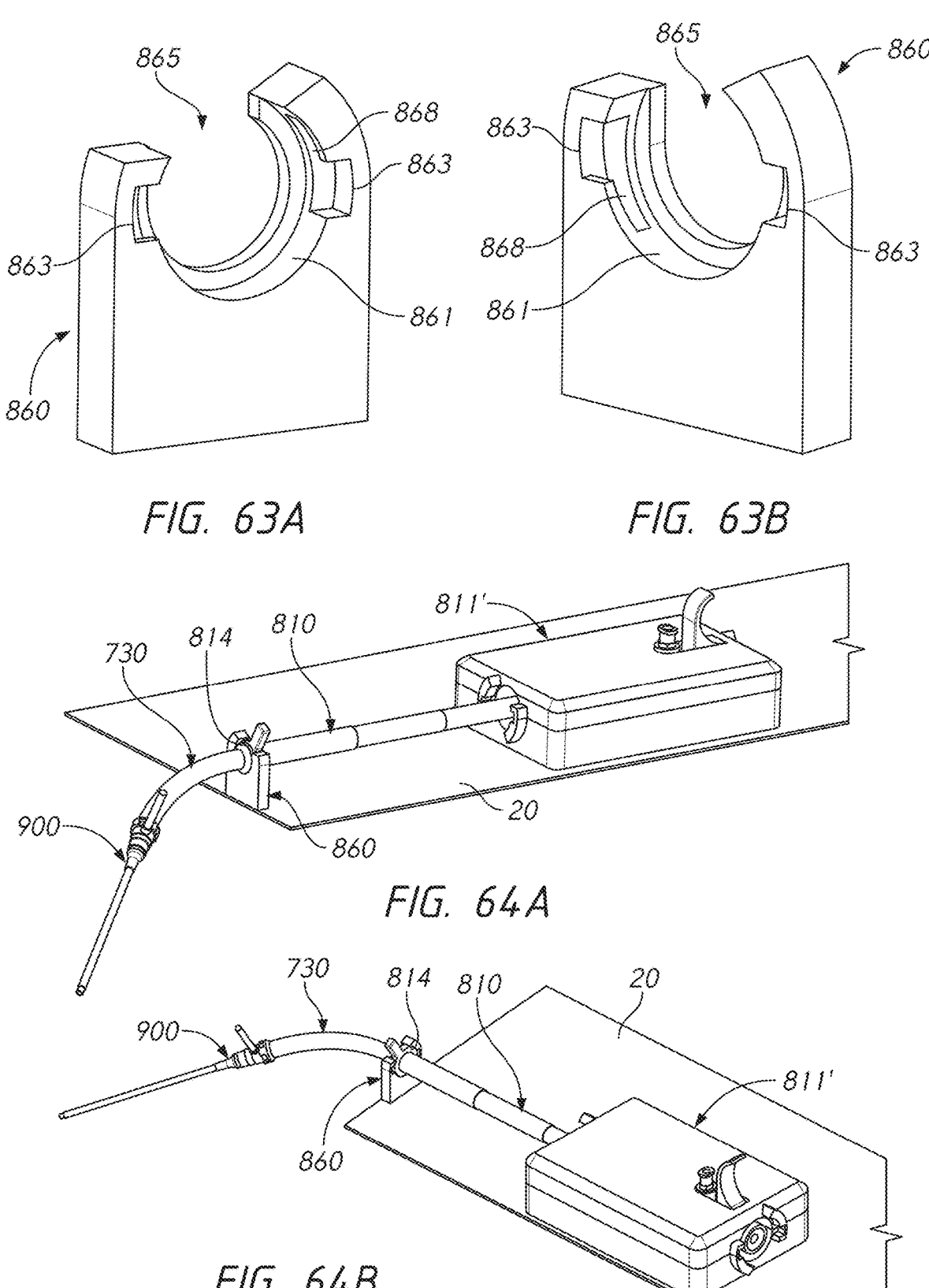

FIGS. 63A-63B depict an example of a distal attachment for an interventional device assembly having an anti-buckling telescoping tube.

FIGS. 64A-64B depict the interventional device assembly utilizing an anti-buckling telescoping tube with an anti-buckling tubular attachment according to FIGS. 62A-62B coupled to a distal attachment according to FIGS. 63A-63B and an insertion sheath.

FIGS. 65A-65F depict an example of an attachment between a telescoping tube and an interventional device.

Figure 66B:
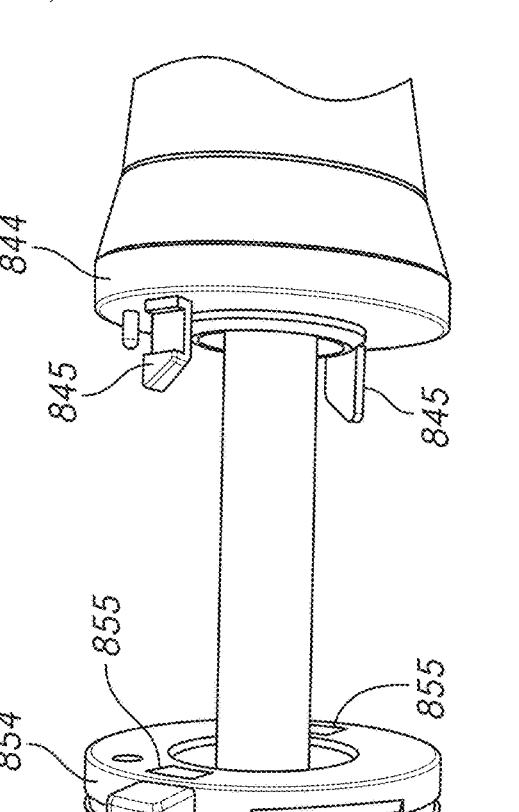
Figure 66A:
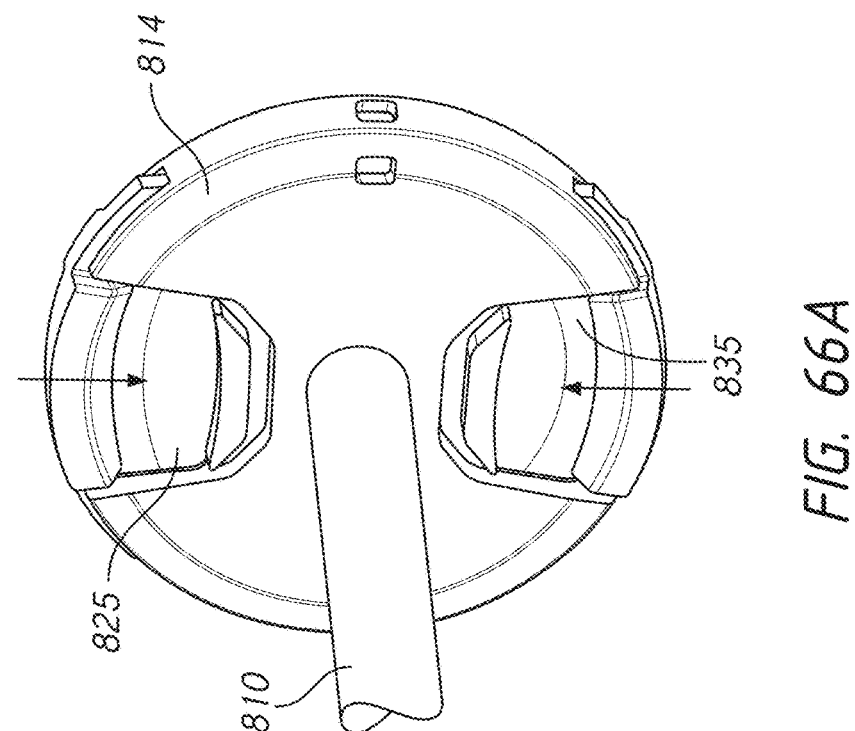

FIGS. 66A-66B depict variants of attachment portions of anti-buckling telescoping tubes.

Figure 67:
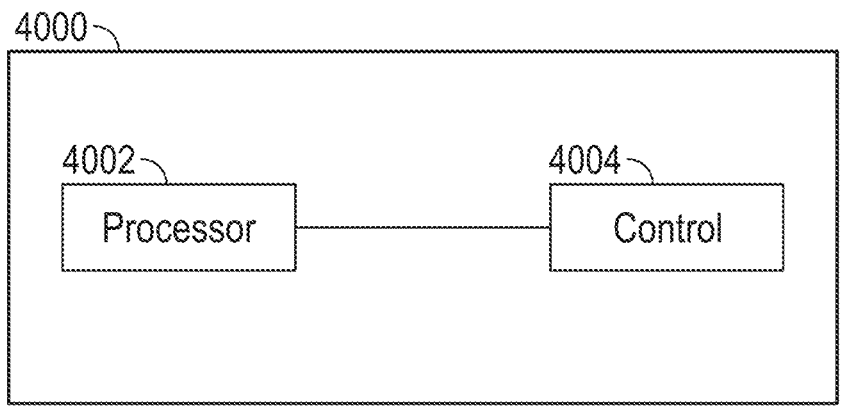

FIG. 67 depicts a schematic of a control system.

DETAILED DESCRIPTION

In certain embodiments, a system is provided for advancing a guide catheter from a femoral artery or radial artery access into the ostium of one of the great vessels at the top of the aortic arch, thereby achieving supra-aortic access. A surgeon can then take over and advance interventional devices into the cerebral vasculature via the robotically placed guide catheter.

In some implementations, the system may additionally be configured to robotically gain intra-cranial vascular access and to perform an aspiration thrombectomy or other neuro vascular procedure.

A drive table can be positioned over or alongside the patient, and configured to axially advance, retract, and in some cases rotate and/or laterally deflect two or three or more different (e.g., concentrically or side by side oriented) intravascular devices. The hub is moveable along a path along the surface of the drive table to advance or retract the interventional device as desired. Each hub may also contain mechanisms to rotate or deflect the device as desired, and is connected to fluid delivery tubes (not shown) of the type conventionally attached to a catheter hub. Each hub can be in electrical communication with an electronic control system, either via hard wired connection, RF wireless connection or a combination of both. Each hub may have or be coupled to a valve mechanism that can control the supply of one or more fluids (e.g., saline, contrast media) and/or the application of vacuum to the hub and corresponding catheter.

Each hub is independently movable across the surface of a sterile field barrier membrane carried by the drive table. Each hub is releasably magnetically coupled to a unique drive carriage on the table side of the sterile field barrier. The drive system independently moves each hub in a proximal or distal direction across the surface of the barrier, to move the corresponding interventional device proximally or distally within the patient's vasculature.

The carriages on the drive table, which magnetically couple with the hubs to provide linear motion actuation, are universal. Functionality of the catheters/guidewire are provided based on what is contained in the hub and the shaft designs. This allows flexibility to configure the system to do a wide range of procedures using a wide variety of interventional devices on the same drive table. Additionally, the interventional devices and methods disclosed herein can be readily adapted for use with any of a wide variety of other drive systems (e.g., any of a wide variety of robotic surgery drive systems).

Figure 1:
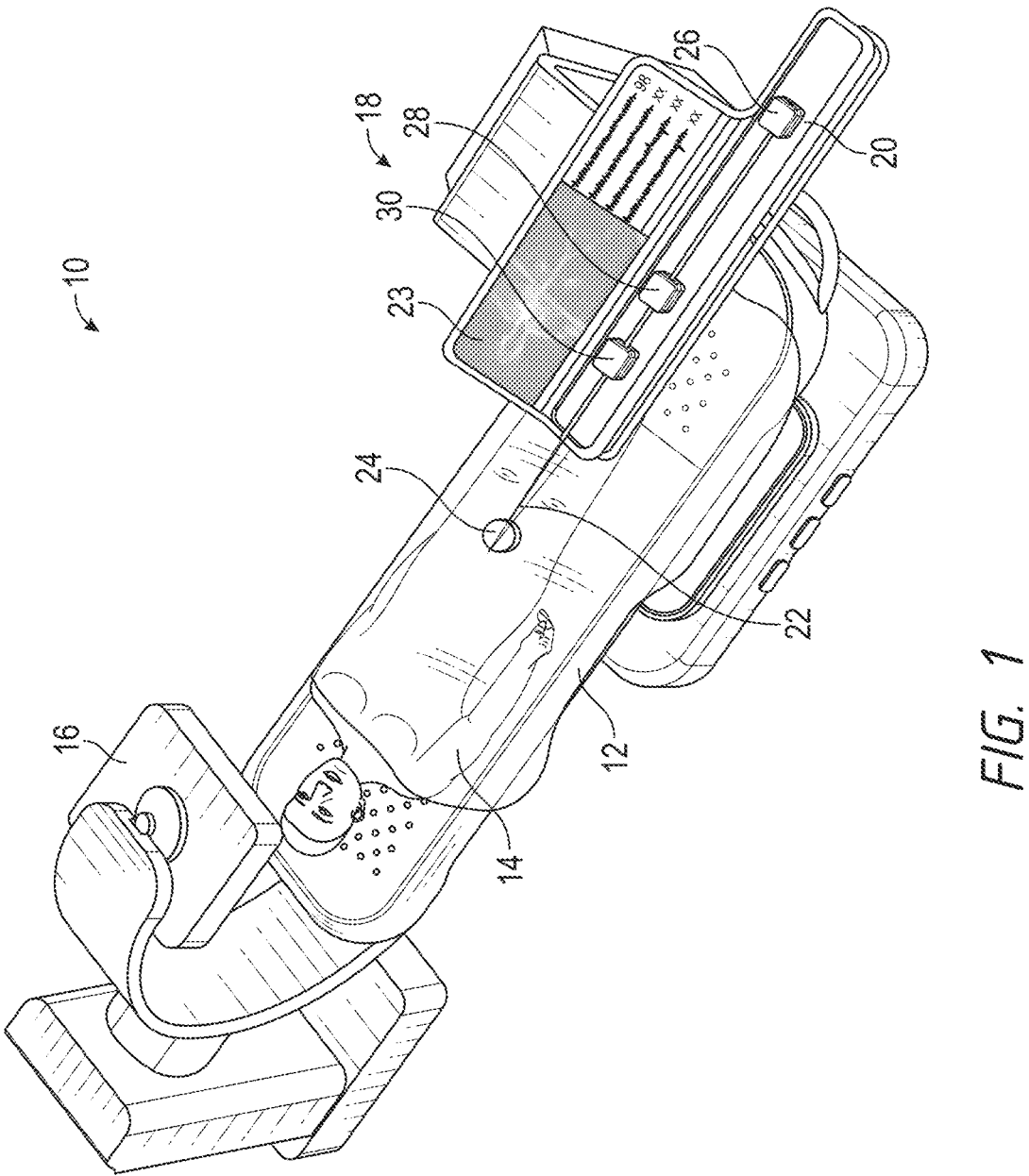
FIG. 1 is a schematic perspective view of an interventional setup having an imaging system, a patient support table, and a robotic drive system in accordance with the present disclosure.

FIG. 1 is a schematic perspective view of an interventional setup 10 having a patient support table 12 for supporting a patient 14. An imaging system 16 may be provided, along with a robotic interventional device drive system 18 in accordance with the present disclosure.

The drive system 18 may include a support table 20 for supporting, for example, a guidewire hub 26, an access catheter hub 28 and a guide catheter hub 30. In the present context, the term 'access' catheter can be any catheter having a lumen with at least one distally facing or laterally facing distal opening, that may be utilized to aspirate thrombus, provide access for an additional device to be advanced therethrough or therealong, or to inject saline or contrast media or therapeutic agents.

More or fewer interventional device hubs may be provided depending upon the desired clinical procedure. For example, in certain embodiments, a diagnostic angiogram procedure may be performed using only a guidewire hub 26 and an access catheter hub 28 for driving a guidewire and an access catheter (in the form of a diagnostic angiographic catheter), respectively. Multiple interventional devices 22 extend between the support table 20 and (in the illustrated example) a femoral access point 24 on the patient 14. Depending upon the desired procedure, access may be achieved by percutaneous or cut down access to any of a variety of arteries or veins, such as the femoral artery or radial artery. Although disclosed herein primarily in the context of neuro vascular access and procedures, the robotic drive system and associated interventional devices can readily be configured for use in a wide variety of additional medical interventions, in the peripheral and coronary arterial and venous vasculature, gastrointestinal system, lymphatic system, cerebral spinal fluid lumens or spaces (such as the spinal canal, ventricles, and subarachnoid space), pulmonary airways, treatment sites reached via trans ureteral or urethral or fallopian tube navigation, or other hollow organs or structures in the body (for example, in intra-cardiac or structural heart applications, such as valve repair or replacement, or in any endoluminal procedures).

A display 23 such as for viewing fluoroscopic images, catheter data (e.g., fiber Bragg grating fiber optics sensor data or other force or shape sensing data) or other patient data may be carried by the support table 20 and or patient support 12. Alternatively, the physician input/output interface including display 23 may be remote from the patient, such as behind radiation shielding, in a different room from the patient, or in a different facility than the patient.

In the illustrated example, a guidewire hub 26 is carried by the support table 20 and is moveable along the table to advance a guidewire into and out of the patient 14. An access catheter hub 28 is also carried by the support table 20 and is movable along the table to advance the access catheter into and out of the patient 14. The access catheter hub may also be configured to rotate the access catheter in response to manipulation of a rotation control and may also be configured to laterally deflect a deflectable portion of the access catheter-in response to manipulation of a deflection control.

Figure 2:
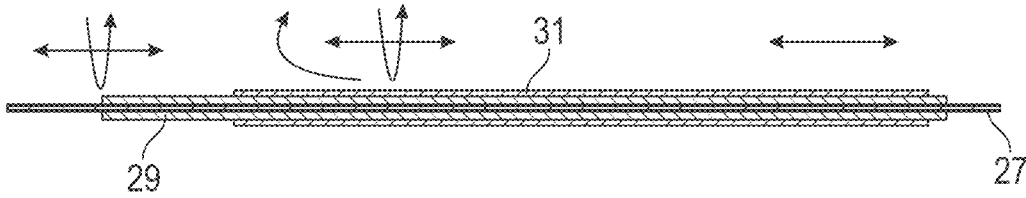
FIG. 2 is a longitudinal cross section showing the concentric relationship between a guidewire having two degrees of freedom, an access catheter having 3 degrees of freedom and a guide catheter having one degree of freedom.

FIG. 2 is a longitudinal cross section schematically showing the motion relationship between a guidewire 27 having two degrees of freedom (axial and rotation), an access catheter 29 having three degrees of freedom (axial, rotational and lateral deflection) and a guide catheter 31, having one degree of freedom (axial).

Figure 3A:
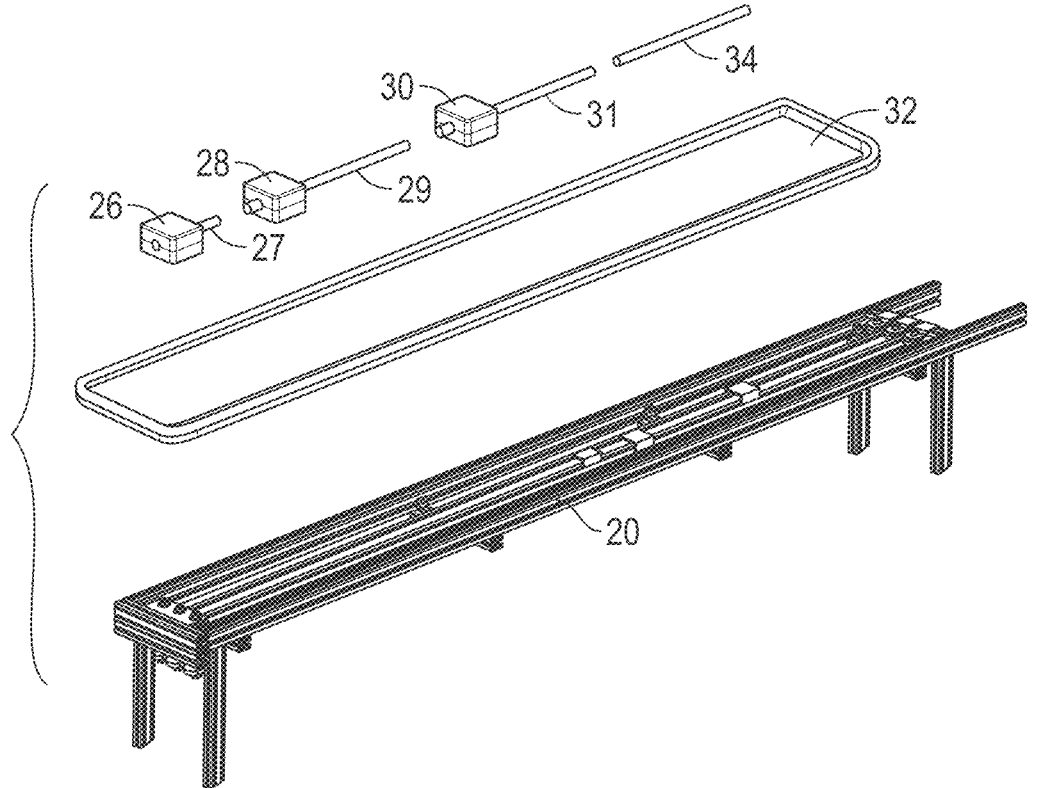
FIG. 3A is an exploded schematic view of interventional device hubs separated from a support table by a sterile barrier.

Referring to FIG. 3A, the support table 20 includes a drive mechanism described in greater detail below, to independently drive the guidewire hub 26, access catheter hub 28, and guide catheter hub 30. An anti-buckling device 34 may be provided in a proximal anti-buckling zone for resisting buckling of the portion of the interventional devices spanning the distance between the support table 20 and the femoral artery access point 24. The anti-buckling device 34 may comprise a plurality of concentric telescopically axially extendable and collapsible tubes through which the interventional devices extend. In some implementations, such an anti-buckling device 34 can comprise any one or more of the anti-buckling devices and/or features described herein.

Alternatively, or in addition, a proximal segment of one or more of the device shafts may be configured with enhanced stiffness to reduce buckling under compression. For example, a proximal reinforced segment may extend distally from the hub through a distance of at least about 5 centimeters or 10 centimeters but typically no more than about 120 centimeters or 100 centimeters to support the device between the hub and the access point 24 on the patient. Reinforcement may be accomplished by using metal or polymer tubing or embedding at least one or two or more axially extending elements into the wall of the device shafts, such as elongate wires or ribbons. In some implementations, the extending element may be hollow and protect from abrasion, buckling, or damage at the inputs and outputs of the hubs. In some embodiments, the hollow extending element may be a hollow and flexible coating attached to a hub. The hollow, extending element (e.g., a hollow and flexible coating) may cover a portion of the device shaft when threaded through the hubs. In some embodiments in which the hollow extending element is a coating, the coating may be attached to a portion of a hub such that threading the catheter device through the hub 26, 28, or 30 threads the catheter device through the coating as well. In some implementations, an anti-buckling device may be installed on or about or surrounding a device shaft to avoid misalignment or insertion angle errors between hubs or between a hub and an insertion point. The anti-buckling device may be a laser cut hypo tube, a spring, telescoping tubes, tensioned split tubing, or any of the anti-buckling devices described herein.

In some implementations, a number of deflection sensors may be placed along a catheter length to identify buckling. Identifying buckling may be performed by sensing that a hub is advancing distally, while the distal tip of the catheter or interventional device has not moved. In some implementations, the buckling may be detected by sensing that an energy load (e.g., due to friction) has occurred between catheter shafts. Alternatively, or in addition, identifying buckling can be performed by detecting displacement of the distal end/tip of the catheter or interventional device and/or the shape thereof (e.g., shape of the shaft thereof). Such identification can be performed using sensors, sensing fibers, and/or image processing of a fluoroscopic image. For example, the shape of the device may be analyzed using shape sensing fibers or fluoroscopic image processing. In some implementations, various methods of identifying buckling can be compared to one another for determining that buckling or shaft compression has occurred.

Alternatively, thin tubular stiffening structures can be embedded within or carried over the outside of the device wall, such as a tubular polymeric extrusion or length of hypo-tube. Alternatively, a removable stiffening mandrel may be placed within a lumen in the proximal segment of the device, and proximally removed following distal advance of the hub towards the patient access site, to prevent buckling of the proximal shafts during distal advance of the hub. Alternatively, a proximal segment of one or more of the device shafts may be constructed as a tubular hypo tube, which may be machined (e.g., with a laser) so that its mechanical properties vary along its length. This proximal segment may be formed of stainless steel, nitinol, and/or cobalt chrome alloys, optionally in combination with polymer components which may provide for lubricity and hydraulic sealing. In some embodiments, this proximal segment may be formed of a polymer, such as polyether ether ketone (PEEK). Alternatively, the wall thickness or diameter of the interventional device can be increased in the anti-buckling zone.

In certain embodiments, a device shaft having advanced stiffness (e.g., axially and torsionally) may provide improved transmission of motion from the proximal end of the device shaft to the distal end of the device shaft. For example, the device shafts may be more responsive to motion applied at the proximal end. Such embodiments may be advantageous for robotic driving in the absence of haptic feedback to a user.

In some embodiments, a flexible coating can be applied to a device shaft and/or hub to reduce frictional forces between the device shaft and/or hub and a second device shaft when the second device shaft passes therethrough. Such a coating can be a hydrophilic coating or a hydrophobic coating. In some implementations wherein the coating is hydrophilic, the system can be configured to wet such coating, for example, with saline, to maintain a wet state of the coating and/or prevent it from drying out. Furthermore, the system can be configured to wet such coating robotically/remotely and/or manually. For example, the system can be configured to have a tubular support disposed at least partially around the device shafts and/or hubs to contain fluid (e.g., fluid used in an initial flushing of such tubular support and the coated device shafts/hubs therein and/or fluid added during a procedure). In some embodiments, the tubular support can use fluid from a catheter lumen priming sequence. In some embodiments, the tubular support can act as a humidity chamber during a procedure to prevent the coating from drying out and/or losing its lubricity. In some implementations, the system can be configured to have an enclosure disposed at least partially around the device shafts and/or hubs to similarly contain fluid and/or maintain a humid environment therearound.

The interventional device hubs may be separated from the support table 20 by sterile barrier 32. Sterile barrier 32 may comprise a thin plastic membrane such as polyethylene terephthalate (PET), polyethylene terephthalate glycol (PETG), polyethylene terephthalate (PETE), high-density polyethylene (HDPE), polyvinyl chloride (PVC), low-density polyethylene (LDPE), polypropylene (PP), polystyrene (PS), or styrene. This allows the support table 20 and associated drive system to reside on a non-sterile (lower) side of sterile barrier 32. The guidewire hub 26, access catheter hub 28, guide catheter hub 30 and the associated interventional devices are all on a sterile (top) side of the sterile barrier 32. The sterile barrier is preferably waterproof and can also serve as a tray used in the packaging of the interventional devices, discussed further below. The interventional devices can be provided individually or as a coaxially preassembled kit that is shipped and stored in the tray and enclosed within a sterile packaging. Hubs of the interventional device assembly can be configured to minimize their mass and/or dimensions. Such configuration of the hubs can facilitate their handling during setup, during a procedure, and/or during teardown and minimize dead length(s) of an interventional device assembly as described herein. For example, hubs can have a length of about 10 cm or less.

FIGS. 3B-3F schematically illustrate an alternate sterile barrier in the form of a dual function sterile barrier for placement on the support table during the interventional procedure, and shipping tray, having one or more storage channels for carrying sterile interventional devices. The sterile barrier may also act as a sterile work surface for preparation of catheters or other devices during a procedure.

Figure 3B:
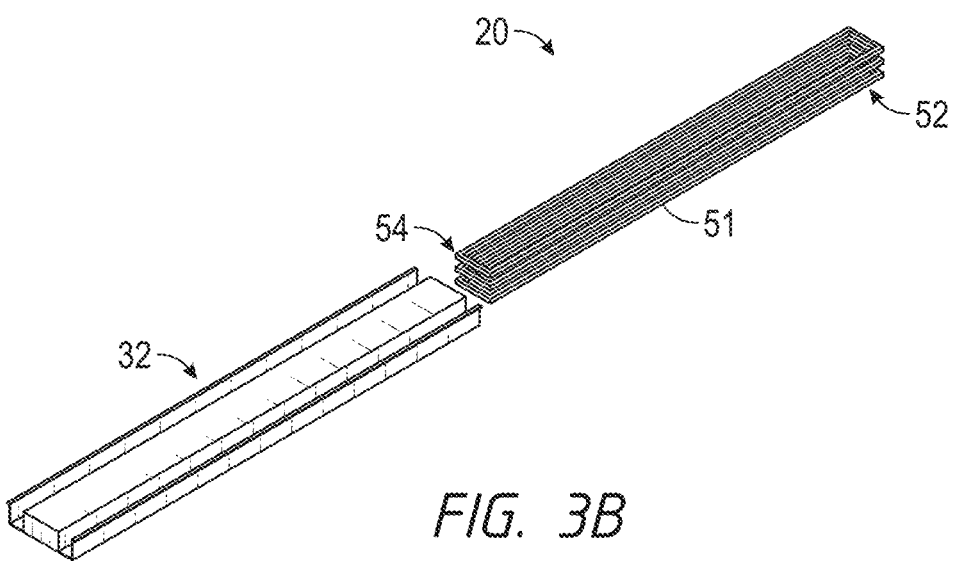
FIGS. 3B-3F show an alternate sterile barrier in the form of a shipping tray having one or more storage channels for carrying interventional devices.
Figure 3C:
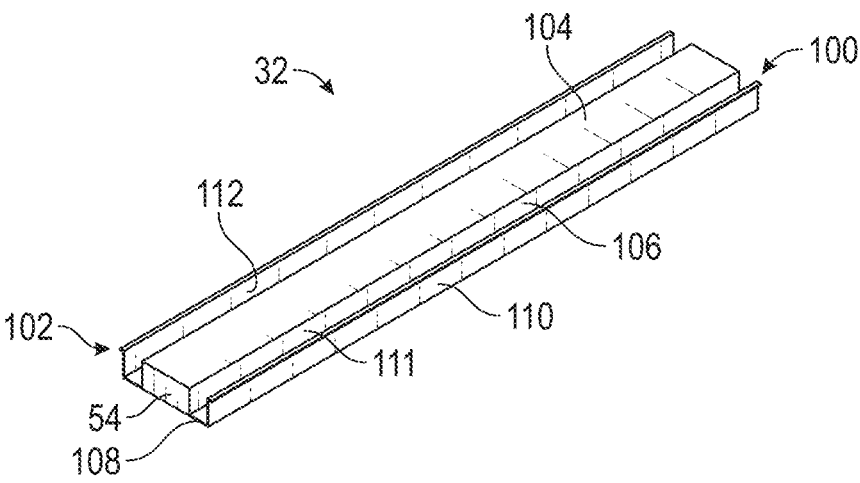

Referring to FIGS. 3B and 3C, there is illustrated a sterile barrier 32 in the form of a pre-shaped tray, for fitting over an elongate support table 20. In use, the elongate support table 20 would be positioned below the sterile barrier 32. The sterile barrier 32 extends between a proximal end 100 and a distal end 102 and includes an upper support surface 104 for supporting the interventional device hubs. In one implementation, the support surface 104 has an axial length greater than the length of the intended interventional devices, in a linear drive configuration.

The length of support surface 104 will typically be at least about 100 centimeters and within the range of from about 100 centimeters to about 2.7 meters. Shorter lengths may be utilized in a system configured to advance the drive couplers along an arcuate path. In some embodiments, two or more support surfaces may be used instead of a single support surface 104. The two or more support surfaces may have a combined length between 100 centimeters to about 2.7 meters. The width of the linear drive table is preferably no more than about 30 to about 80 centimeters.

At least a first channel 106 may be provided, extending axially at least a portion of the length of the support table 20. In the illustrated implementation, first channel 106 extends the entire length of the support table 20. Preferably, the first channel 106 has a sufficient length to hold the interventional devices, and sufficient width and depth to hold the corresponding hubs (for example, by providing lateral support to prevent dislodgment of the hubs when forces are applied to the hubs). First channel 106 is defined within a floor 108, outer side wall 110 and inner side wall 111, forming an upwardly facing concavity. Optionally, a second channel 112 may be provided. Second channel 112 may be located on the same side or the opposite side of the upper support surface 104 from the first channel 106. Two or three or more additional recesses such as additional channels or wells may be provided, to hold additional medical devices or supplies that may be useful during the interventional procedure as well as to collect fluids and function as wash basins for catheters and related devices.

Figure 3D:
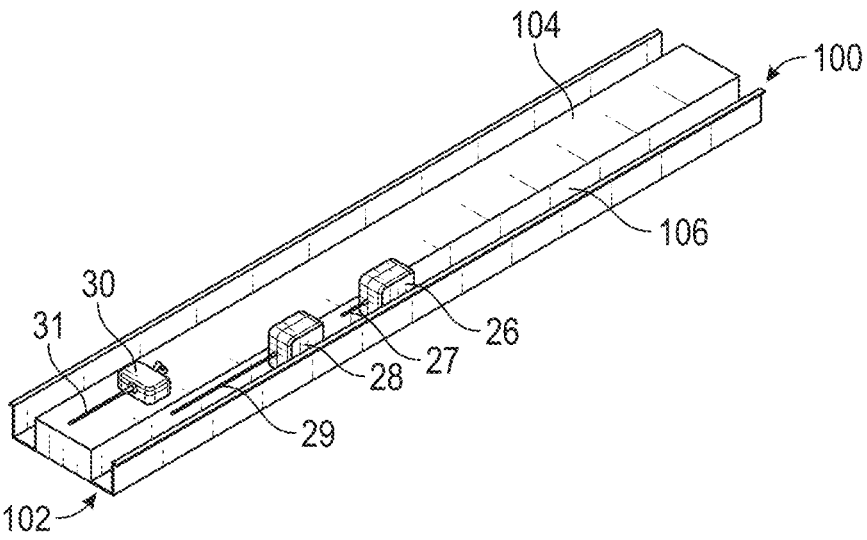

Referring to FIG. 3D, the guide catheter hub 30 is shown positioned on the upper support surface 104, and magnetically coupled to the corresponding coupler holding the drive magnets, positioned beneath the sterile barrier 32. The access catheter hub 28 and access catheter 29, and guidewire hub 26 and guidewire 27 are illustrated residing within the first channel 106 such as before introduction through the guide catheter 31 or following removal from the guide catheter 31.

The interventional devices may be positioned within the channel 106 and enclosed in a sterile barrier for shipping. At the clinical site, an upper panel of the sterile barrier may be removed, or a tubular sterile barrier packaging may be opened and axially removed from the support table 20 and sterile barrier 32 assembly, exposing the sterile top side of the sterile barrier tray and any included interventional devices. The interventional devices may be separately carried in the channel, or preassembled into an access assembly or procedure assembly, discussed in additional detail below.

Figure 3E:
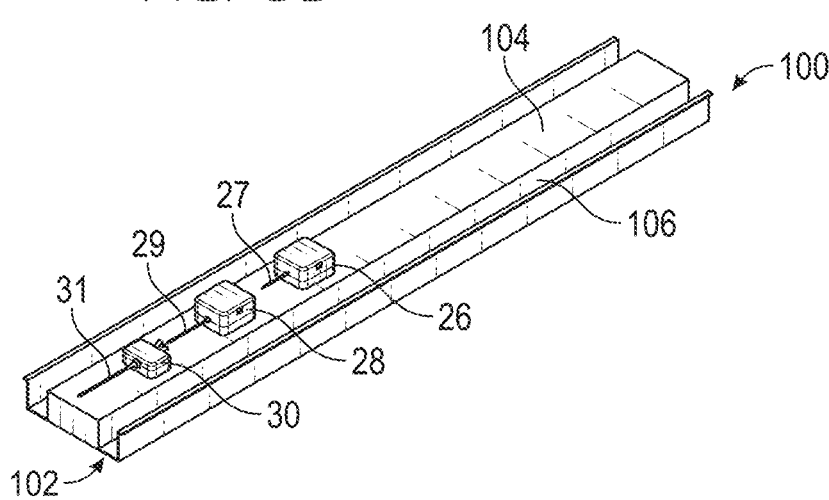
Figure 3F:
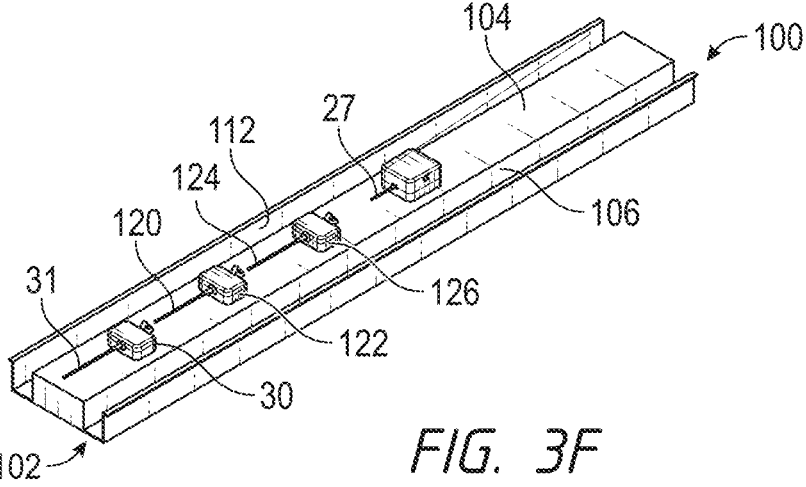

FIGS. 3D-3F illustrate the support table with sterile barrier in place, and in FIG. 3E, the interventional devices configured in an access assembly for aortic access, following coupling of the access assembly to the corresponding carriages beneath the sterile barrier. The access assembly may be preassembled with the guidewire fully advanced through the access catheter which is in turn fully advanced through the guide catheter. In embodiments in which the access catheter or other catheters are pre-shaped (i.e., pre-curved or not straight), the guidewire and/or outer catheters may be positioned so that relatively stiff sections are not superimposed with curved stiffer sections of the pre-shaped catheter, for example, to avoid creep or straightening of the pre-shaped catheter and/or introduction of a curve into an otherwise straight catheter. This access assembly may be lifted out of the channel 106 and positioned on the support surface 104 for coupling to the respective drive magnets and introduction into the patient. The guide catheter hub 30 is the distal most hub. Access catheter hub 28 is positioned proximally of the guide catheter hub, so that the access catheter 29 can extend distally through the guide catheter. The guidewire hub 26 is positioned most proximally, in order to allow the guidewire 27 to advance through the access catheter 29 and guide catheter 31.

A procedure assembly is illustrated in FIG. 3F following introduction of the procedure assembly through the guide catheter 31 that was used to achieve supra-aortic access. In this implementation, guide catheter 31 remains the distal most of the interventional devices. A first procedure catheter 120 and corresponding hub 122 is illustrated extending through the guide catheter 31. An optional second procedure catheter 124 and corresponding hub 126 is illustrated extending through the first procedure catheter 120. The guidewire 27 extends through at least a portion of the second procedure catheter 124 in a rapid exchange version of second procedure catheter 124, or the entire length of second procedure catheter 124 in an over the wire implementation.

As is discussed in greater detail in connection with FIG. 17, the multi catheter stack may be utilized to achieve both access and the intravascular procedure without the need for catheter exchange. This may be accomplished in either a manual or a robotically driven procedure. In one example, the guide catheter 31 may comprise a catheter having an inner diameter of at least about 0.08 inches and in one implementation about 0.088 inches. The first procedure catheter 120 may comprise a catheter having an inner diameter within the range of from about 0.065 inches to about 0.075 inches and in one implementation catheter 120 has an inner diameter of about 0.071 inches. The second procedure catheter 124 may be an access catheter having an OD sized to permit advance through the first procedure catheter 120. The second procedure catheter may be steerable, having a deflection control 2908 configured to laterally deflect a distal end of the catheter. The second procedure (access) catheter may also have an inner lumen sized to allow an appropriately sized guidewire to remain inside the second procedure catheter while performing contrast injections through the second procedure catheter.

In certain embodiments, the catheter 31 may be a 'large bore' access catheter or guide catheter having an inner diameter of at least about 0.075 or at least about 0.080 inches in diameter. The catheter 120 may be an aspiration catheter having an inner diameter within the range of from about 0.060 to about 0.075 inches. The catheter 124 may be a steerable catheter with a deflectable distal tip, having an inner diameter within the range of from about 0.025 to about 0.050 inches. The guidewire 27 may have an outer diameter within the range of from about 0.014 to about 0.020 inches. In one example, the catheter 31 may have an inner diameter of about 0.088 inches, the catheter 120 may have an inner diameter of about 0.071 inches, the catheter 124 may have an inner diameter of about 0.035 inches, and the guidewire 27 may have an outer diameter of about 0.018 inches.

In one commercial execution, a preassembled access assembly (guide catheter, access catheter and guidewire) may be carried within a first channel on the sterile barrier tray and a preassembled procedure assembly (one or two procedure catheters and a guidewire) may be carried within the same or a different, second channel on the sterile barrier tray. One or two or more additional catheters or interventional tools may also be provided, depending upon potential needs during the interventional procedure.

Figures 3G, 3H, 3I, 3J, 3K, 3L, 3M:
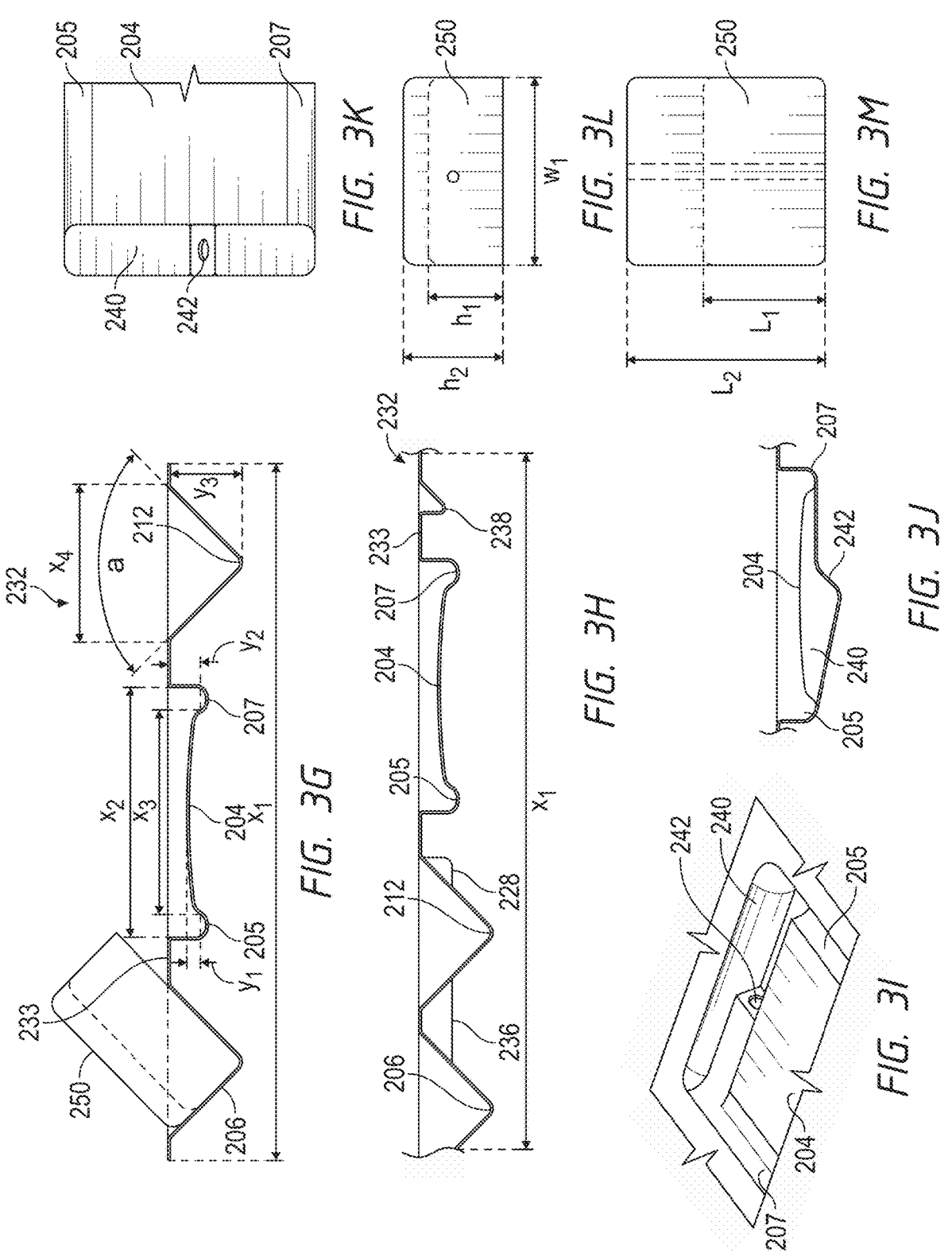
FIGS. 3G-3K show embodiments of an alternate sterile barrier having a convex drive surface.
FIGS. 3L and 3M depict an example of a hub that may be used with the sterile barriers of FIGS. 3G-3K.

FIGS. 3G-3K illustrate embodiments of an alternate sterile barrier having a convex drive surface (e.g., a convex, crowned road like drive surface). FIG. 3G is a cross-sectional view of a sterile barrier 232. The sterile barrier 232 includes a convex upper support surface 204. Fluid channels 205 and 207 are positioned laterally of and below the support surface 204 for self-clearing or draining of fluids from the support surface 204 (for example, during an interventional procedure). The fluid channels 205 and 207 may extend axially at least a portion of the length of the sterile barrier.

FIGS. 3I, 3J, and 3K illustrate a sectional perspective view, a cross-sectional view, and a top sectional view, respectively, of a proximal end of the sterile barrier 232. As shown, in FIGS. 3I-3K, the sterile barrier 232 can include a trough 240 in communication with the fluid channels 205 and 207. The trough 240 can receive fluids from the channels 205 and 207 (for example, during an interventional procedure). The trough 240 may be positioned at least partially below the fluid channels 205 and 207 so that fluid within the channels 205 and 207 flows into the trough 240. In certain embodiments, the fluid channels 205 and 207 may be angled relative to a horizontal plane (for example, may decline from an end of the channel furthest from the trough 240 to the trough 240) so that fluid within the channels 205 and 207 is directed to the trough 240. For example, the channels 205 and 207 may increase in depth from an end of the channels furthest from the trough 240 to the trough 240. Alternatively, the sterile barrier 232 and/or support table may be positioned at an angle relative to a horizontal plane, during part of or an entirety of an interventional procedure, such that the end of the channels 205 and 207 furthest from the trough 240 is positioned higher than the trough 240. For example, the sterile barrier 232 and/or support table may be constructed or arranged in an angled arrangement so that an end of the sterile barrier 232 and/or support table opposite the trough 240 is positioned higher than the trough 240. Alternatively or additionally, a drive mechanism may temporarily tilt the sterile barrier 232 and/or support table so that an end of the sterile barrier 232 and/or support table opposite the trough 240 is positioned higher than the trough 240 (for example, by lifting an end of the sterile barrier and/or support table opposite the trough 240 or lowering an end of the sterile barrier 232 and/or support table at which the trough 240 is positioned) so that fluids within the channels 205 and 207 flow into the trough 240.

The trough 240 can include a drain hole 242. The trough 240 can be shaped, dimensioned, and/or otherwise configured so that fluid within the trough 240 empties to the drain hole 242. The drain hole 242 can include tubing, a barb fitting, and/or an on-off valve for removal of fluids from the trough 240. As shown in FIGS. 3I-3K, the trough 240 can be positioned at the proximal end of the sterile barrier 232. In alternate embodiments, the trough 240 may be positioned at a distal end of the sterile barrier 232. In some embodiments, the sterile barrier 232 can include a first trough 240 at the proximal end and a second trough 240 at the distal end. In some embodiments, the trough 240 can also be used as a wash basin.

A first channel 206 may extend axially at least a portion of the length of the sterile barrier 232. The channel 206 can have a sufficient length to hold the interventional devices, and sufficient width and depth to hold the corresponding hubs (for example, by providing support to prevent dislodgement of the hubs when forces are applied to the hubs). Optionally, a second channel 212 may be provided. The second channel 212 may be located on the same side or the opposite side of the upper support surface 204 from the first channel 206. FIG. 3G illustrates the channel 212 located on the opposite side of the support surface 204 from the channel 206. FIG. 3H is a cross-sectional view illustrating an alternate embodiment of the sterile barrier 232 in which the channel 212 is on the same side of the support surface 204 as the channel 206.

As shown in FIGS. 3G and 3H, the channels 206 and 212 can have generally triangular, wedge-shaped, or otherwise angled cross-sections, so as to hold the hubs at an angle relative to a horizontal plane. Holding the hubs at an angle relative to the horizontal plane can allow for smaller width of the sterile barrier 232.

Two or three or more additional recesses such as additional channels or wells may be provided, to hold additional medical devices or supplies that may be useful during the interventional procedure as well as to collect fluids and function as wash basins for catheters and related devices.

In some embodiments, the sterile barrier 232 can include one or more structural ribs 236. The sterile barrier 232 can further include one or more frame support bosses 228 and 238.

In the embodiment of the sterile barrier 232 shown in FIG. 3G, a width $x_1$ can be 14 in, about 14 in, between 12 in and 16 in, between 10 in and 18 in, or any other suitable width. In the embodiment of the sterile barrier 232 shown in FIG. 3H, the width $x_1$ can be 15 in, about 15 in, between 13 in and 17 in, between 11 in and 19 in, or any other suitable width. A height $y_1$ of the support surface 204 can be 0.125 in, about 0.125 in, between 0.1 and 0.15 in, or any other suitable height. In some embodiments, the support surface 204 can be recessed from a top surface 233 of the sterile barrier 232. A height $y_2$ between a bottom of the support surface 204 and the top surface 233 can be 0.5 in, about 0.5 in, between 0.25 in and 0.75 in, or any other suitable height. A width $x_2$ from a lateral edge of the channel 205 to a lateral edge of the channel 207 can be 5 in, about 5 in, between 4 in and 6 in, or any other suitable width. A width $x_3$ of the support surface 204 can be 4 in, about 4 in, between 3 in and 5 in, or any other suitable width. A height $y_3$ of the channel 206 and/or channel 212 can be 1.5 in, about 1.5 in, between 1 in and 2 in, or any other suitable height. A width $x_4$ of the channel 206 and/or channel 212 can be 3 in, about 3 in, between 2 in and 4 in, or any other suitable width. The channel 206 and/or channel 212 can be defined by an arc angle α of 90°, about 90°, between 80° and 100°, or any other suitable angle, and a radius of curvature of 0.125 in, about 0.125 in, between 0.1 and 0.15 in, or any other suitable radius of curvature. In certain embodiments, an arc angle α of 90° or about 90° may be used to hold a hub having a rectangular or generally rectangular cross-section. The support surface 204 can be defined by a radius of curvature of 13 in, about 13 in, between 11 in and 15 in, or any other suitable radius of curvature. The channel 205 and/or channel 207 can be defined by a radius of curvature of 0.25 in, about 0.25 in, between 0.15 in and 0.35 in, or any other suitable radius of curvature.

FIGS. 3L and 3M depict example dimensions of a hub 250 that may be used with the sterile barrier 232 as shown in FIGS. 3G-3K. The hub 250 may be any of the hubs described herein. In certain embodiments, the hub 250 can have a width $w_1$ of 3.75 in, about 3.75 in, between 3.25 in and 4.25 in, or any other suitable width. The hub 250 can have a height h1 of 1.5 in, about 1.5 in, between 1.25 in and 1.75 in, or any other suitable height. Alternatively, the hub 250 can have a height $h_2$ of 2 in, about 2 in, between 1.75 in and 2.25 in, or any other suitable height. In some embodiments, the hub 250 can have a length $L_1$ of 2.5 in, about 2.5 in, between 2 in and 3 in or any other suitable length. Alternatively, the hub 250 can have a length $L_2$ of 4 in, about 4 in, between 3.25 in and 4.75 in, or any other suitable length.

In some embodiments, a top surface of the support table can include surface features that generally correspond to those of the sterile barrier 232. For example, the support table can include a convex surface configured to correspond to the shape, size, and location of the support surface 204 and/or one or more recesses configured to correspond to the shape, size, and location of the channels 205 and 207.

In alternate embodiments, a planar support surface (for example, support surface 104 of sterile barrier 32) can be positioned at an angle to a horizontal plane to facilitate the draining of fluids. In some embodiments, the sterile barrier and/or support table may be positioned, during part of or the entirety of an interventional procedure, at an angle to a horizontal plane to facilitate the draining of fluids. For example, the sterile barrier and/or support table may be constructed or arranged in an angled arrangement (for example, so that one lateral side of the planar support surface is positioned higher than the other lateral side of the planar support surface, the proximal end is higher than the distal end, or the distal end is higher than the proximal end) to facilitate the drainage of fluids. Alternatively or addition- ally, a drive mechanism may temporarily tilt the sterile barrier and/or support table (for example, so that one lateral side of the planar support surface is positioned higher than the other lateral side of the planar support surface, the proximal end is higher than the distal end, or the distal end is higher than the proximal end) to facilitate the drainage of fluids. For example, the drive mechanism may raise or lower one lateral side of the sterile barrier and/or support table, the proximal end of the sterile barrier and/or support table, and/or the distal end of the sterile barrier and/or support table.

In certain embodiments, a support surface (for example, support surface 104 of sterile barrier 32) can be positioned in a vertical configuration instead in the horizontal configu- ration shown, for example, in FIGS. 3A-3F. For example, the support surface 104 can be positioned at about 90 degrees (or any other suitable angle) from a horizontal plane (e.g., rotated 90 degrees about a long axis of the support surface 104 relative to the embodiment shown in of FIGS. 3A-3F). A vertical configuration may provide for easier interaction with the drive system 18 by a physician. A vertical configuration may also provide for a lower axis of catheter travel closer to a patient without adding standoff height to the drive system 18.

In some embodiments, the drive system 18 may be positioned, during part of or the entirety of an interventional procedure, at an angle to a horizontal plane to facilitate the draining of fluids. For example, the drive system 18 may be constructed or arranged in an angled arrangement (for example, so that one lateral side of the planar support surface is positioned higher than the other lateral side of the planar support surface, the proximal end is higher than the distal end, or the distal end is higher than the proximal end) to facilitate the drainage of fluids. Alternatively or addition- ally, a drive mechanism may temporarily tilt the drive system 18 (for example, so that one lateral side of the drive system 18 is positioned higher than the other lateral side of the drive system 18, the proximal end is higher than the distal end, or the distal end is higher than the proximal end) to facilitate the drainage of fluids. For example, the drive mechanism may raise or lower one lateral side of the system 18, the proximal end of the drive system 18, and/or the distal end of the drive system 18. In some embodiments, the drive system 18 may be angled so that it extends at an angle away from axis point 24 (for example, so that the proximal end is higher than the distal end), for example, to allow for clearance of a patient's feet.

Figures 4, 5A, 5B:
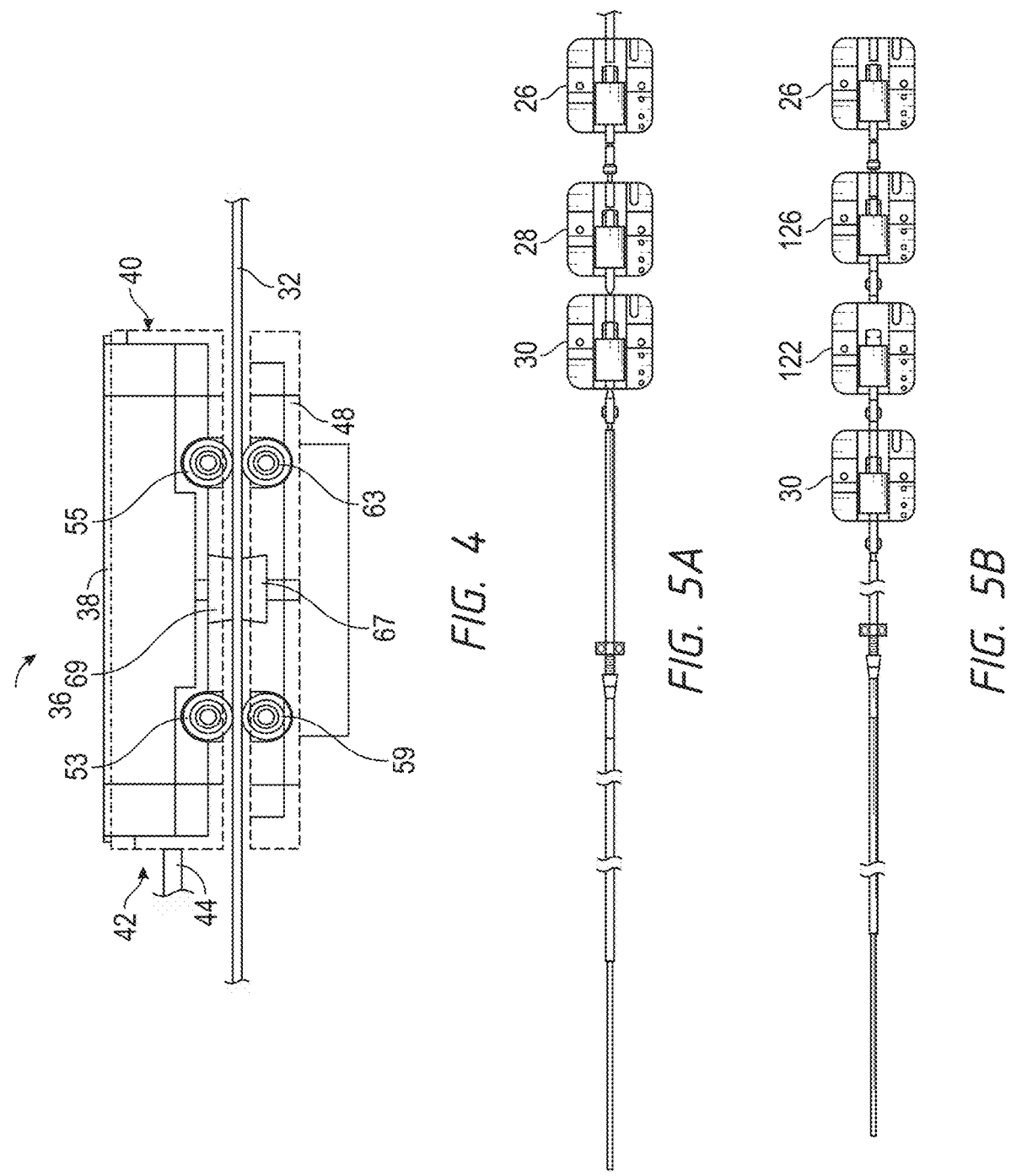
FIG. 4 is a schematic elevational cross section through a hub adapter having a drive magnet separated from an interventional device hub and driven magnet by a sterile barrier.
FIGS. 5A and 5B schematically illustrate a three interventional device and a four interventional device assembly.

Referring to FIG. 4, hub 36 may represent any of the hubs previously described. Hub 36 includes a housing 38 which extends between a proximal end 40 and a distal end 42. An interventional device 44, which could be any of the inter- ventional devices disclosed herein, extends distally from the hub 36 and into the patient 14 (not illustrated). A hub adapter 48 or carriage acts as a shuttle by advancing proximally or distally along a track in response to operator instructions or controller manipulations. The hub adapter 48 includes at least one drive magnet 67 configured to couple with a driven magnet 69 carried by the hub 36. This provides a magnetic coupling between the drive magnet 67 and driven magnet 69 through the sterile barrier such that the hub 36 is moved across the top of the sterile barrier 32 in response to movement of the hub adapter 48 outside of the sterile field. Movement of the hub adapter is driven by a drive system carried by the support table and described in additional detail below. The hub adapter may act as a robotic drive for an interventional device coupled thereto.

To reduce friction in the system, the hub 36 may be provided with at least a first roller 53 and a second roller 55 which may be in the form of wheels or rotatable balls or drums. The rollers space the sterile barrier apart from the surface of the driven magnet 69 by at least about 0.02 centimeters (about 0.008 inches) and generally no more than about 0.08 centimeters (about 0.03 inches). In some imple- mentations, the space is within the range of from about 0.03 centimeters (about 0.010 inches) and about 0.041 centime- ters (about 0.016 inches). The space between the drive magnet 67 and driven magnet 69 is generally no more than about 0.38 centimeters (about 0.15 inches) and in some implementations is no more than about 0.254 centimeters (about 0.10 inches) such as within the range of from about 0.216 centimeters (about 0.085 inches) to about 0.229 cen- timeters (about 0.090 inches). The hub adapter 48 may similarly be provided with at least a first hub adapter roller 59 and the second hub adapter roller 63, which may be positioned opposite the respective first roller 53 and second roller 55 as illustrated in FIG. 4.

Figure 6:
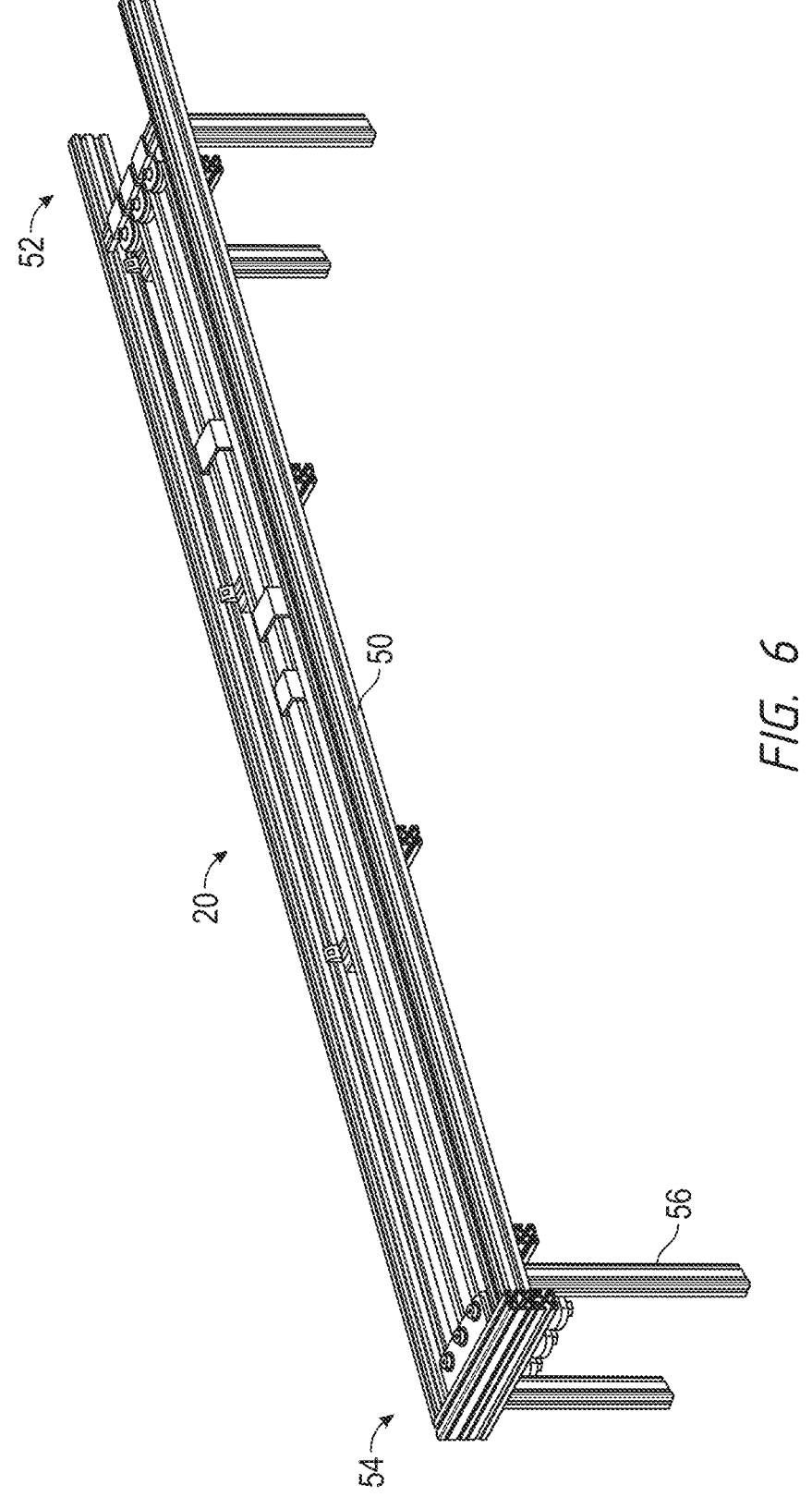
FIG. 6 is a perspective view of a support table.

Referring to FIG. 6, there is schematically illustrated one example of a low-profile linear drive support table 20. Support table 20 comprises an elongated frame 51 extending between a proximal end 52 and a distal end 54. At least one support table support 56 is provided to stabilize the support table 20 with respect to the patient (not illustrated). Support 56 may comprise one or more legs or preferably an articulating arm configured to allow movement and positioning of the frame 51 over or adjacent to the patient.

Figure 7:
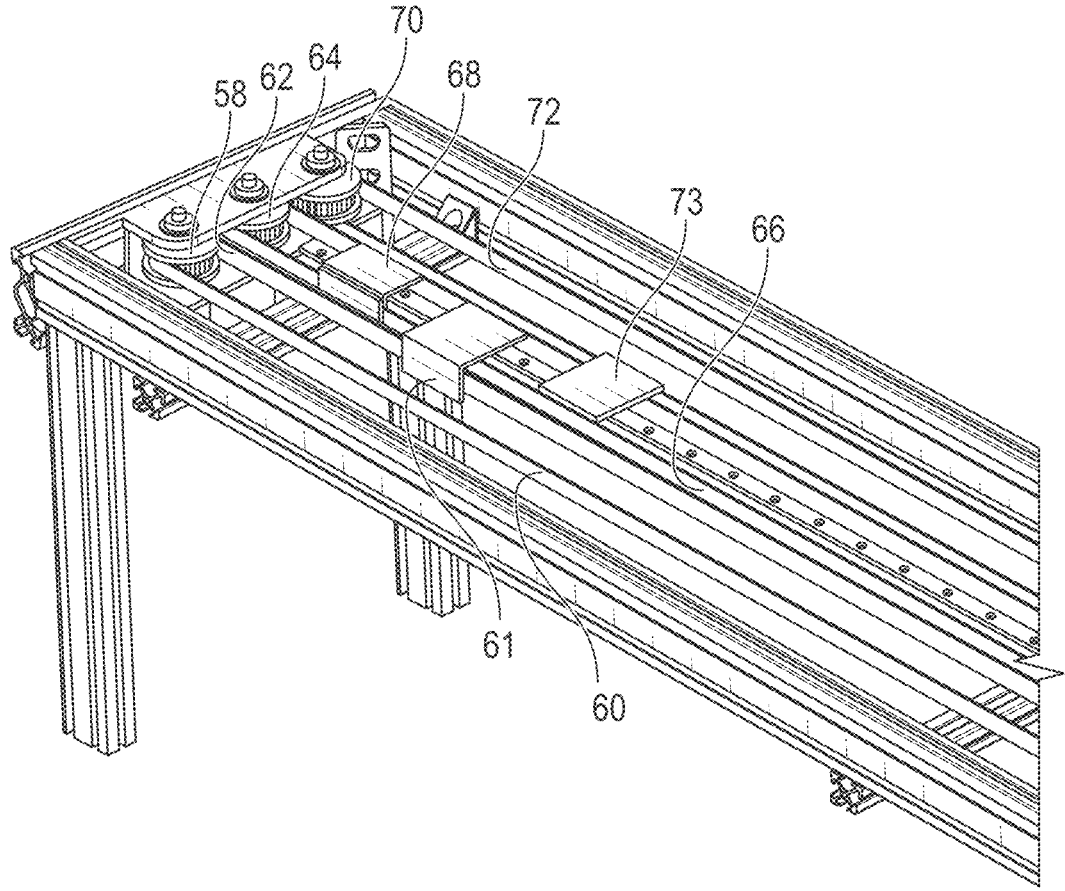
FIG. 7 is a close-up view of the motor drive end of a support table.

One example of a linear drive table 20 illustrated in FIG. 7 includes three distinct drives. However, two drives or four or more drives (e.g., up to eight drives) may be included depending upon the desired clinical performance. A first drive pulley 58 engages a first drive belt 60. A first carriage bracket 61 is secured to the first drive belt 60 such that rotation of the first drive pulley 58 causes rotation of the first drive belt 60 through an elongate closed loop path. The first carriage bracket 61 may be advanced in a proximal or distal direction along the longitudinal axis of the support table 20 depending upon the direction of rotation of the drive pully 58. In the illustrated implementation, the drive pulley 58 is provided with surface structures such as a plurality of drive pulley teeth 62 for engaging complementary teeth on the first drive belt 60.

A second drive pulley 64 may engage a second drive belt 66 configured to axially move a second carriage bracket 68 along an axial path on the support table 20. A third drive pulley 70 may be configured to drive a third drive belt 72, to advance a third carriage bracket 73 axially along the support table 20. Each of the carriage brackets may be provided with a drive magnet assembly discussed previously but not illustrated in FIG. 7, to form couplers for magnetically coupling to a corresponding driven magnet within the hub of an interventional device as has been discussed.

Figure 8:
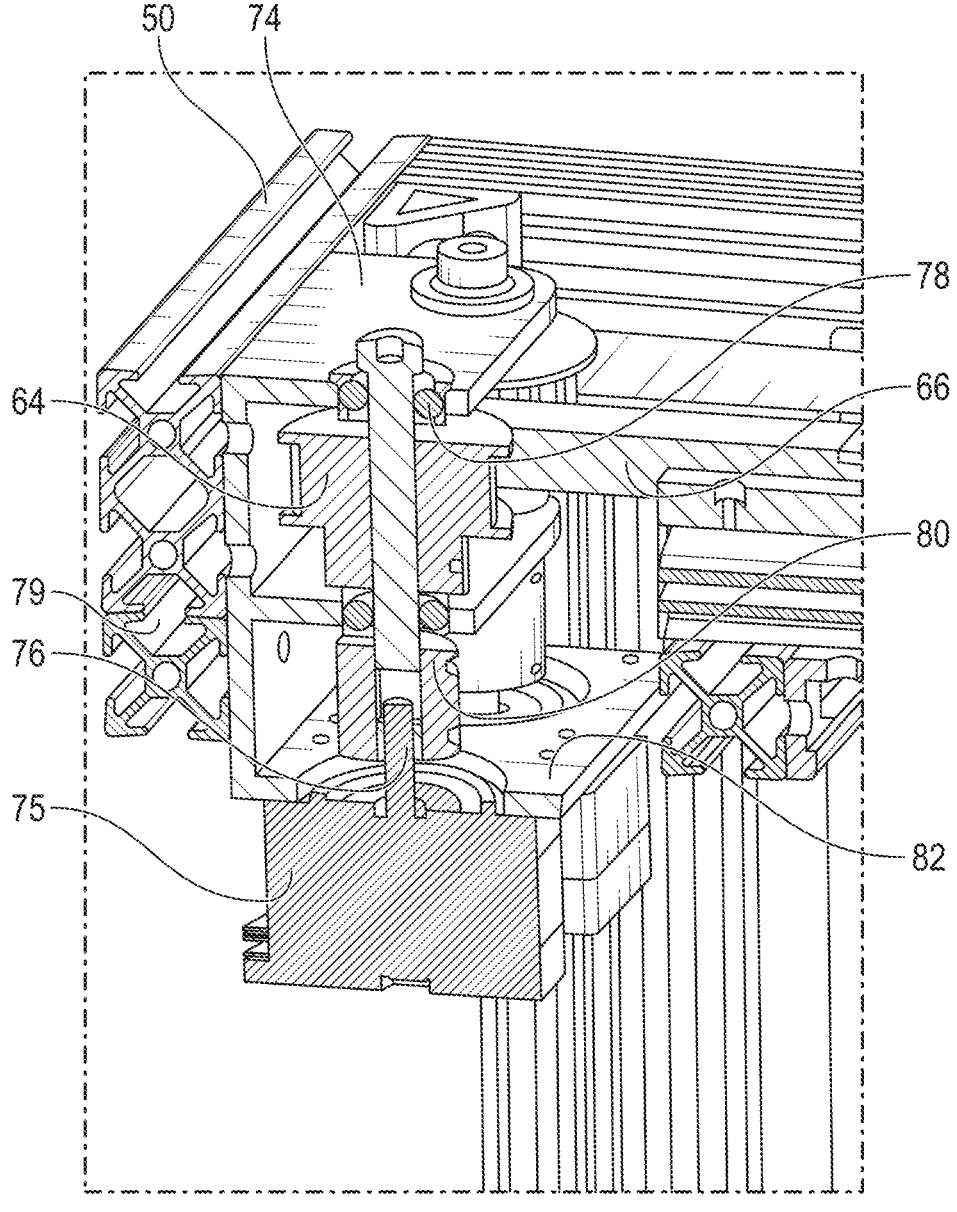
FIG. 8 is an elevational cross section through a motor and belt drive assembly.

A detailed view of a drive system is shown schematically in FIG. 8. A drive support 74 may be carried by the frame 51 for supporting the drive assembly. The second drive pulley 64 is shown in elevational cross section as rotationally driven by a motor 75 via a rotatable shaft 76. The rotatable shaft 76 may be rotatably carried by the support 74 via a first bearing 78, a shaft coupling 80 and second bearing 79. Motor 75 may be stabilized by a motor bracket 82 connected to the drive support 74 and or the frame 51. The belt drive assemblies for the first drive belt 60 and third drive belt 72 may be similarly constructed and are not further detailed herein. In some embodiments, the drive systems described herein may be a rack and pinion drive table system that is foldable. In such embodiments, motors 75 may be attached to and move with the carriages.

Figure 9:
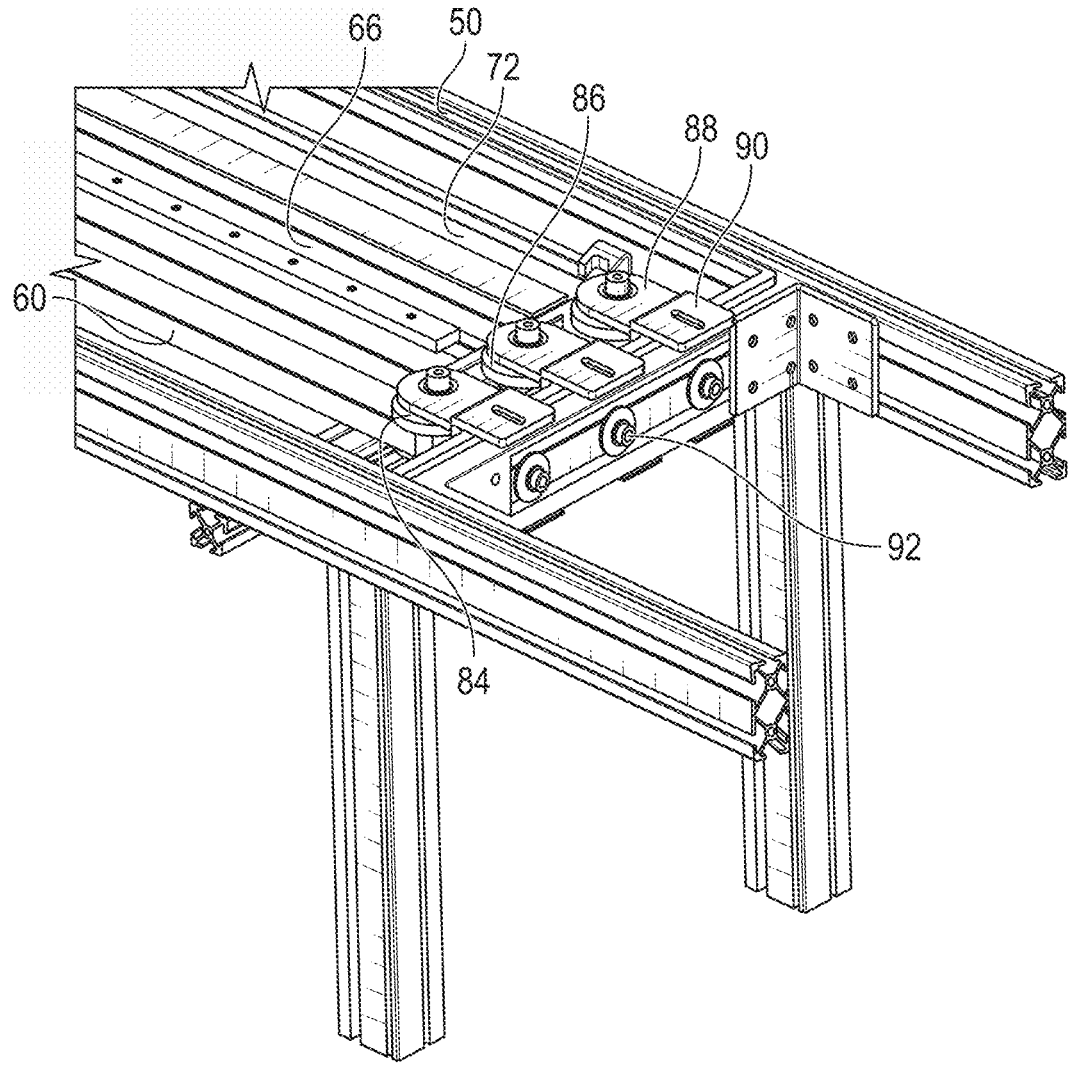
FIG. 9 is a close-up view of a pulley end of the support table.
Figure 10:
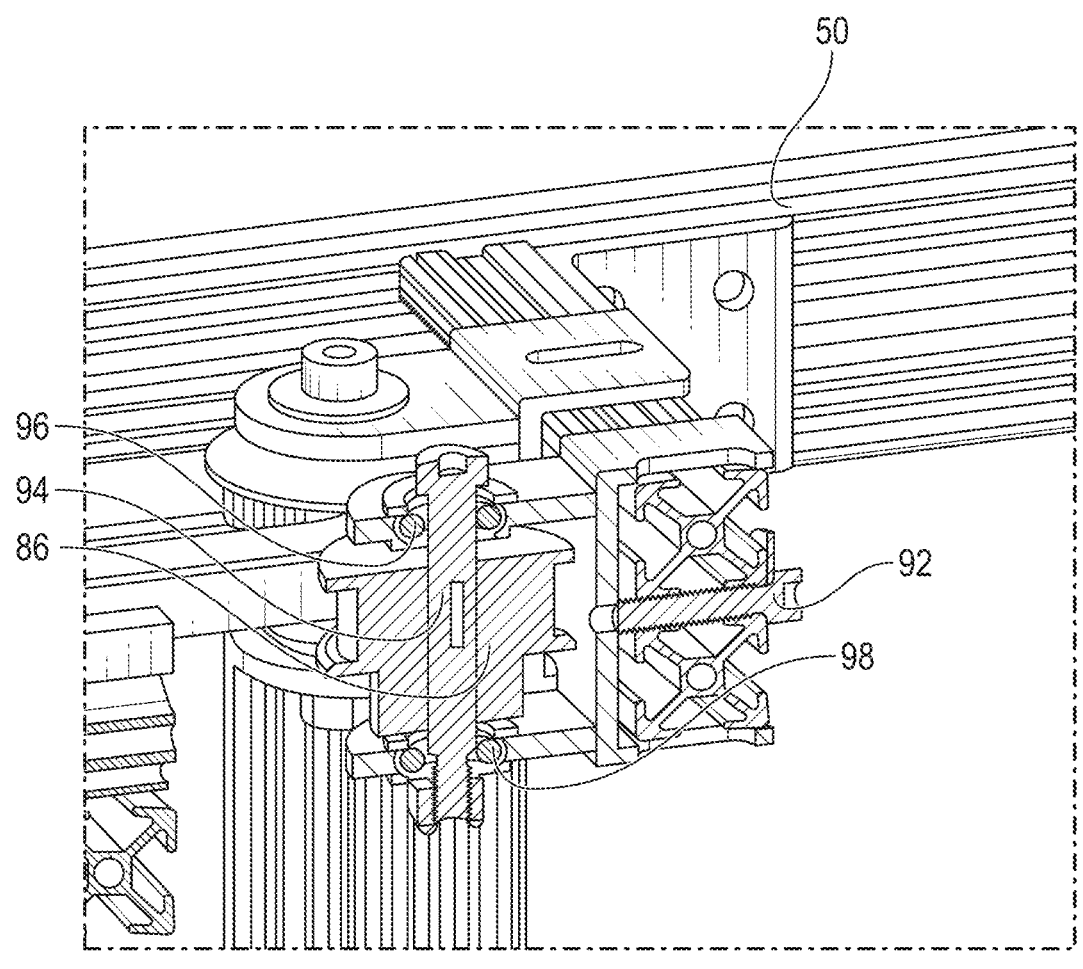
FIG. 10 is an elevational cross section through a belt pully.

Referring to FIGS. 9 and 10, each of the first second and third drive belts extends around a corresponding first idler pulley 84 second idler pulley 86 and third idler pulley 88. Each idler pulley may be provided with a corresponding tensioning bracket 90, configured to adjust the idler pulleys in a proximal or distal direction in order to adjust the tension of the respective belt. Each tensioning bracket 90 is therefore provided with a tensioning adjustment 92 such as a rotatable screw.

As seen in FIG. 10, the second idler pulley 86, for example, may be carried by a rotatable shaft 94, rotatably secured with respect to the mounting bracket by a first bearing 96 and second bearing 98.

Figure 11:
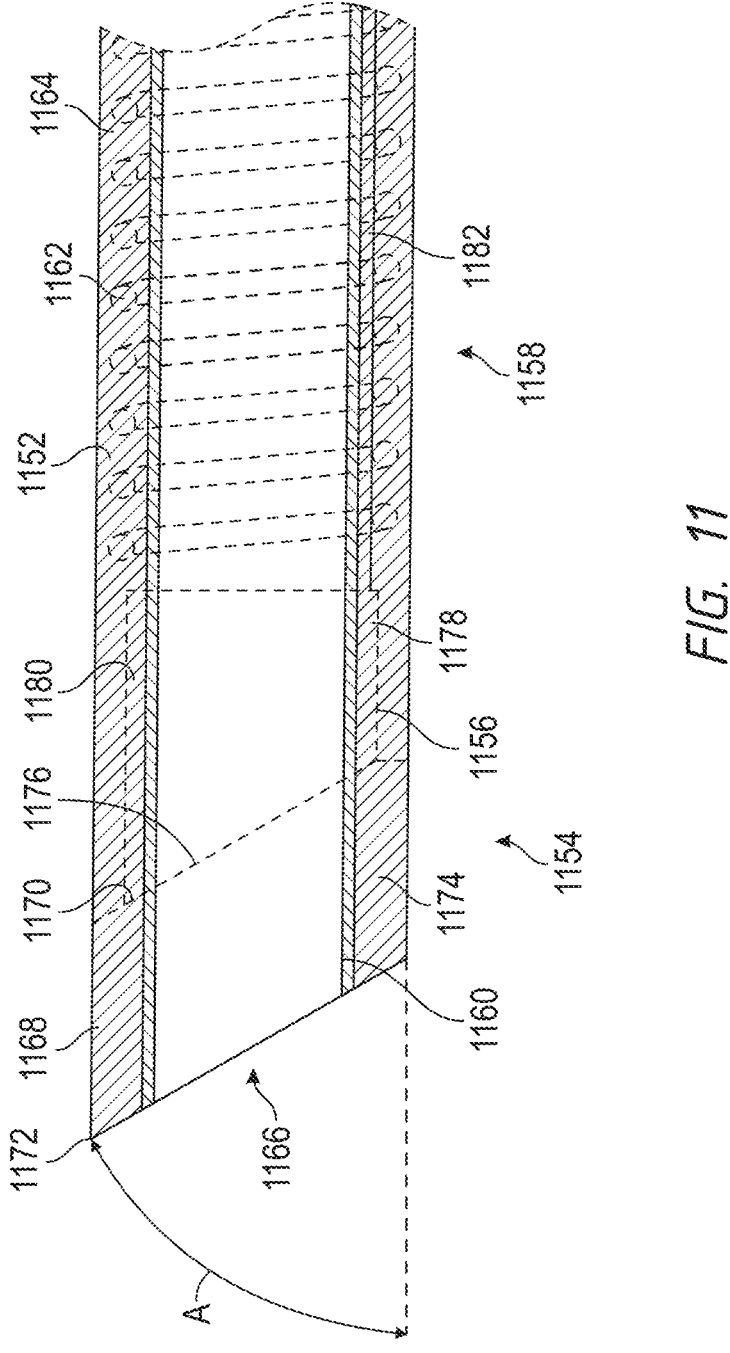
FIG. 11 is a side elevational cross-section through a distal portion of a catheter such as any of those shown in FIGS. 5A and 5B.

Any of the catheters illustrated, for example, in FIG. 5A, 5B or 11 generally comprise an elongate tubular body extending between a proximal end and a distal functional end. The length and diameter of the tubular body depends upon the desired application. For example, lengths in the area of from about 90 centimeters to about 195 centimeters or more are typical for use in femoral access percutaneous transluminal coronary applications. Intracranial or other applications may call for a different catheter shaft length depending upon the vascular access site.

Any of the catheters disclosed herein may be provided with an inclined distal tip. Referring to FIG. 11, distal catheter tip 1150 comprises a tubular body 1152 which includes an advance segment 1154, a marker band 1156 and a proximal segment 1158. An inner tubular liner 1160 may extend throughout the length of the distal catheter tip 1150, and may comprise dip coated or extruded PTFE or other lubricious material.

A reinforcing element 1162 such as a braid and/or spring coil is embedded in an outer jacket 1164 which may extend the entire length of the catheter.

The advance segment 1154 terminates distally in an angled face 1166, to provide a leading side wall portion 1168 having a length measured between the distal end 130 of the marker band 1156 and a distal tip 1172. In some embodiments, the entire distal tip may be shaped to avoid snagging the tip in areas of arterial bifurcation. A trailing side wall portion 1174 of the advance segment 1154, has an axial length in the illustrated embodiment of approximately equal to the axial length of the leading side wall portion 1168 as measured at approximately 180 degrees around the catheter from the leading side wall portion 1168. The leading side wall portion 1168 may have an axial length within the range of from about 0.1 millimeters to about 5 millimeters and generally within the range of from about 1 to 3 millimeters. The trailing side wall portion 1174 may be equal to or at least about 0.1 or 0.5 or 1 millimeter or 2 millimeters or more shorter than the axial length of the leading side wall portion 1168, depending upon the desired performance.

The angled face 1166 inclines at an angle A within the range of from about 45 degrees to about 80 degrees from the longitudinal axis of the catheter. For certain implementations, the angle is within the range of from about 55 degrees to about 65 degrees from the longitudinal axis of the catheter. In one implementation, the angle A is about 60 degrees. One consequence of an angle A of less than 90 degrees is an elongation of a major axis of the area of the distal port which increases the surface area of the port and may enhance clot aspiration or retention. Compared to the surface area of the circular port (angle A is 90 degrees), the area of the angled port is generally at least about 105 percent, and no more than about 130 percent, in some implementations within the range of from about 110 percent and about 125 percent, and in one example is about 115 percent of the area of the corresponding circular port (angle A is 90 degrees).

In the illustrated embodiment, the axial length of the advance segment is substantially constant around the circumference of the catheter, so that the angled face 1166 is approximately parallel to the distal surface 1176 of the marker band 1156. The marker band 1156 has a proximal surface approximately transverse to the longitudinal axis of the catheter, producing a marker band 1156 having a right trapezoid configuration inside elevational view. A short sidewall 1178 is rotationally aligned with the trailing side wall portion 1174, and has an axial length within the range of from about 0.2 millimeters to about 4 millimeters, and typically from about 0.5 millimeters to about 2 millimeters. An opposing long sidewall 1180 is rotationally aligned with the leading side wall portion 1168. Long sidewall 1180 of the marker band 1156 is generally at least about 10 percent or 20 percent longer than short sidewall 1178 and may be at least about 50 percent or 70 percent or 90 percent or more longer than short sidewall 1178, depending upon desired performance. Generally, the long sidewall 1180 will have a length of at least about 0.5 millimeters or 1 millimeter and less than about 5 millimeters or 4 millimeters.

The marker band may be a continuous annular structure, or may have at least one and optionally two or three or more axially extending slits throughout its length. The slit may be located on the short sidewall 1178 or the long sidewall 1180 or in between, depending upon desired bending characteristics. The marker band may comprise any of a variety of radiopaque materials, such as a platinum/iridium alloy, with a wall thickness preferably no more than about 0.003 inches and in one implementation is about 0.001 inches.

The fluoroscopic appearance of the marker bands may be unique or distinct for each catheter size or type when a plurality of catheters is utilized so that the marker bands can be distinguishable from one another by a software algorithm. Distinguishing the marker bands of a plurality of catheters may be advantageous when the multiple catheters are used together, for example, in a multi catheter assembly or stack as described herein. In some embodiments, the marker band of a catheter may be configured so that a software algorithm can detect motion of the catheter tip.

The marker band zone of the assembled catheter may have a relatively high bending stiffness and high crush strength, such as at least about 50 percent or at least about 100 percent less than proximal segment 18 but generally no more than about 200 percent less than proximal segment 1158. The high crush strength may provide radial support to the adjacent advance segment 1154 and particularly to the leading side wall portion 1168, to facilitate the functioning of distal tip 1172 as an atraumatic bumper during transluminal advance and to resist collapse under vacuum. The proximal segment 1158 preferably has a lower bending stiffness than the marker band zone, and the advance segment 1154 preferably has even a lower bending stiffness and crush strength than the proximal segment 1158.

The advance segment 1154 may comprise a distal extension of the outer tubular jacket 1164 and optionally the inner liner 1160, without other internal supporting structures distally of the marker band 1156. Outer jacket 1164 may comprise extruded polyurethane, such as Tecothane®. The advance segment 1154 may have a bending stiffness and radial crush stiffness that is no more than about 50 percent, and in some implementations no more than about 25 percent or 15 percent or 5 percent or less than the corresponding value for the proximal segment 1158.

The catheter may further comprise an axial tension element or support such as a ribbon or one or more filaments or fibers for increasing the tension resistance and/or influencing the bending characteristics in the distal zone. The tension support may comprise one or more axially extending mono strand or multi strand filaments. The one or more tension element 1182 may be axially placed inside the catheter wall near the distal end of the catheter. The one or more tension element 1182 may serve as a tension support and resist tip detachment or elongation of the catheter wall under tension (e.g., when the catheter is being proximally retracted through a kinked outer catheter or tortuous or narrowed vasculature).

At least one of the one or more tension element 1182 may proximally extend along the length of the catheter wall from within about 1.0 centimeters from the distal end of the catheter to less than about 10 centimeters from the distal end of the catheter, less than about 20 centimeters from the distal end of the catheter, less than about 30 centimeters from the distal end of the catheter, less than about 40 centimeters from the distal end of the catheter, or less than about 50 centimeters from the distal end of the catheter.

The one or more tension element 1182 may have a length greater than or equal to about 40 centimeters, greater than or equal to about 30 centimeters, greater than or equal to about 20 centimeters, greater than or equal to about 10 centimeters, or greater than or equal to about 5 centimeters.

At least one of the one or more tension element 1182 may extend at least about the most distal 50 centimeters of the length of the catheter, at least about the most distal 40 centimeters of the length of the catheter, at least about the most distal 30 centimeters or 20 centimeters or 10 centimeters of the length of the catheter.

In some implementations, the tension element extends proximally from the distal end of the catheter along the length of the coil 24 and ends proximally within about 5 centimeters or 2 centimeters or less either side of a transition between a distal coil and a proximal braid. The tension element may end at the transition without overlapping with the braid.

The one or more tension element 1182 may be placed near or radially outside the inner liner 1160. The one or more tension element 1182 may be placed near or radially inside the braid and/or the coil. The one or more tension element 1182 may be carried between the inner liner 1160 and the helical coil, and may be secured to the inner liner or other underlying surface by an adhesive prior to addition of the next outer adjacent layer such as the coil. Preferably, the tension element 1182 is secured to the marker band 1156 such as by adhesives or by mechanical interference. In one implementation, the tension element 1182 extends distally beyond the marker band on a first (e.g., inside) surface of the marker band, then wraps around the distal end of the marker band and extends along a second (e.g., outside) surface in either or both a proximal inclined or circumferential direction to wrap completely around the marker band.

When more than one tension element 1182 or filament bundles are spaced circumferentially apart in the catheter wall, the tension elements 1182 may be placed in a radially symmetrical manner. For example, the angle between two tension elements 1182 with respect to the radial center of the catheter may be about 180 degrees. Alternatively, depending on desired clinical performances (e.g., flexibility, trackability), the tension elements 1182 may be placed in a radially asymmetrical manner. The angle between any two tension elements 1182 with respect to the radial center of the catheter may be less than about 180 degrees, less than or equal to about 165 degrees, less than or equal to about 135 degrees, less than or equal to about 120 degrees, less than or equal to about 90 degrees, less than or equal to about 45 degrees or, less than or equal to about 15 degrees.

The one or more tension element 1182 may comprise materials such as Vectran®, Kevlar®, Polyester®, Spectra®, Dyneema®, Meta-Para-Aramide®, or any combinations thereof. At least one of the one or more tension element 1182 may comprise a single fiber or a multi-fiber bundle, and the fiber or bundle may have a round or rectangular (e.g., ribbon) cross section. The terms fiber or filament do not convey composition, and they may comprise any of a variety of high tensile strength polymers, metals or alloys depending upon design considerations such as the desired tensile failure limit and wall thickness. The cross-sectional dimension of the one or more tension element 1182, as measured in the radial direction, may be no more than about 2 percent, 5 percent, 8 percent, 15 percent, or 20 percent of that of the catheter 10.

The cross-sectional dimension of the one or more tension element 1182, as measured in the radial direction, may be no more than about 0.03 millimeters (about 0.001 inches), no more than about 0.0508 millimeters (about 0.002 inches), no more than about 0.1 millimeters (about 0.004 inches), no more than about 0.15 millimeters (about 0.006 inches), no more than about 0.2 millimeters (about 0.008 inches), or about 0.38 millimeters (about 0.015 inches).

The one or more tension element 1182 may increase the tensile strength of the distal zone of the catheter before failure under tension (e.g., marker band detachment) to at least about 1 pound, at least about 2 pounds, at least about 3 pounds, at least about 4 pounds, at least about 5 pounds, at least about 6 pounds, at least about 7 pounds, at least about 8 pounds, or at least about 10 pounds or more.

Figure 12A:
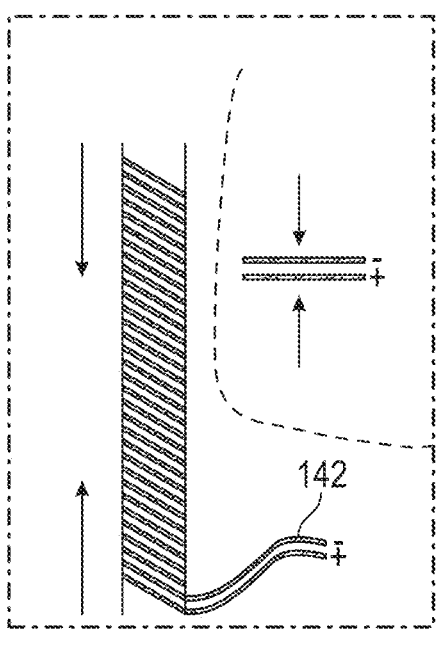
FIGS. 12A and 12B schematically illustrate a force sensor integrated into the sidewall of the catheter.

Any of a variety of sensors may be provided on any of the catheters, hubs, carriages, or table, depending upon the desired data. For example, in some implementations, it may be desirable to measure axial tension or compression force applied to the catheter such as along a force sensing zone. The distal end of the catheter would be built with a similar construction as illustrated in FIG. 11, with a helical coil distal section. But instead of using a single helical coil of nitinol wire, a first conductor 140 and second conductor 142 are wrapped into intertwined helical coils and electrically isolated from each other such as by the plastic/resin of the tubular body. See FIG. 12A. Each coil is in electrical communication with the proximal hub by a unique electrical conductor such as a conductive trace or proximal extension of the wire.

Figure 12B:
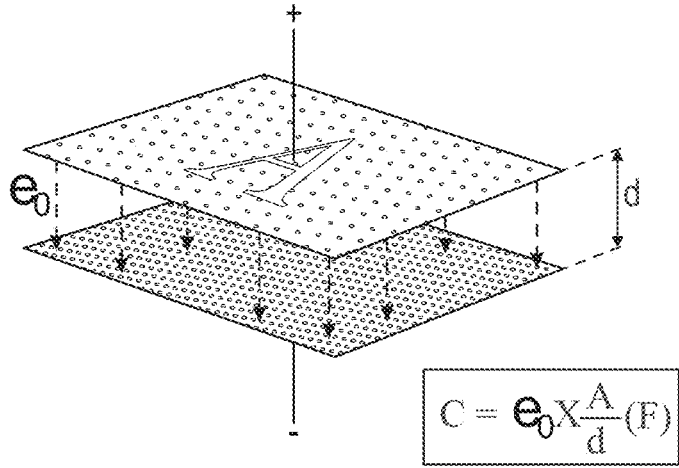

This construction of double, electrically isolated helical coils creates a capacitor. This is roughly equivalent to two plates of nitinol with a plastic layer between them, illustrated in FIG. 12B. The capacitance is inversely proportional to the distance between wires. The only variable that would be changing would be d, the distance between the plates. If an axial compressive force is applied to the catheter, the wires (e.g., conductor 140 and conductor 142) will move closer together, thus increasing the capacitance. If an axial tensile force is applied, the wires will get further apart, decreasing the capacitance. This capacitance can be measured at the proximal end of the catheter, giving a measurement of the force at the helical capacitor. Although referred to as a capacitor, this sensor is measuring the electrical interaction between the two coils of wire. There may be a measurable change in inductance or other resulting change due to applied axial forces.

At least a first helical capacitor may have at least one or five or ten or more complete revolutions of each wire. A capacitor may be located within the distal most 5 or 10 or 20 centimeters of the catheter body to sense forces experienced at the distal end. At least a second capacitor may be provided within the proximal most 5 or 10 or 20 centimeters of the catheter body, to sense forces experienced at the proximal end of the catheter.

Figure 13A:
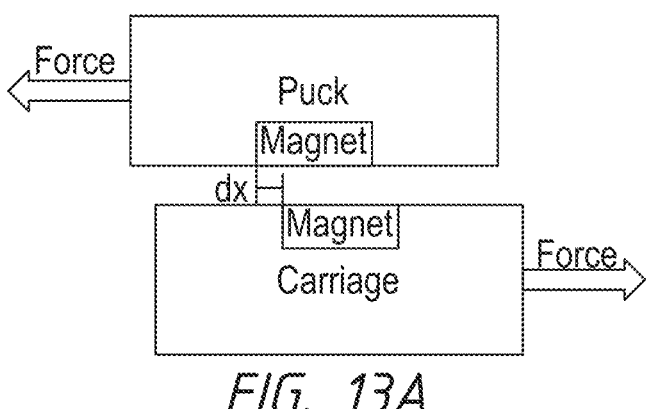
FIGS. 13A and 13B schematically illustrate a sensor for measuring elastic forces at the magnetic coupling between the hub and corresponding carriage.
Figure 13B:

It may also be desirable to measure elastic forces across the magnetic coupling between the hub and corresponding carriage, using the natural springiness (compliance) of the magnetic coupling to measure the force applied to the hub. The magnetic coupling between the hubs and carriages creates a spring. When a force is applied to the hub, the hub will move a small amount relative to the carriage. See FIG. 13A. In robotics, this is called a series elastic actuator. This property can be used to measure the force applied from the carriage to the hub. To measure the force, the relative distance between the hub and the carriage (dx shown in FIG. 13A) is determined and characterize some effective spring constant k between the two components. See FIG. 13B.

The relative distance could be measured in multiple different ways. One method for measuring the relative distance between the hub and carriage is a magnetic sensor (e.g., a Hall effect Sensor between hub and carriage). A magnet is mounted to either the hub or carriage, and a corresponding magnetic sensor is mounted on the other device (carriage or hub). The magnetic sensor might be a hall effect sensor, a magnetoresistive sensor, or another type of magnetic field sensor. Generally, multiple sensors may be used to increase the reliability of the measurement. This reduces noise and reduces interference from external magnetic fields.

Other non-contact distance sensors can also be used. These include optical sensors, inductance sensors, and capacitance sensors. Optical sensors would preferably be configured in a manner that avoids accumulation of blood or other fluid in the interface between the hubs carriages. In some implementations, wireless (i.e., inductive) power may be used to translate movement and/or transfer information across the sterile barrier between a drive carriage and a hub, for example.

The magnetic coupling between the hub and the carriage has a shear or axial break away threshold which may be about 300 grams or 1000 grams or more. The processor can be configured to compare the axial force applied to the catheter to a preset axial trigger force which if applied to the catheter is perceived to create a risk to the patient. If the trigger force is reached, the processor may be configured to generate a response such as a visual, auditory or tactile feedback to the physician, and/or intervene and shut down further advance of the catheter until a reset is accomplished. An override feature may be provided so the physician can elect to continue to advance the catheter at forces higher than the trigger force, in a situation where the physician believes the incremental force is warranted.

Force and or torque sensing fiber optics (e.g., Fiber Bragg Grating (FBG) sensors) may be built into the catheter side wall to measure the force and/or torque at various locations along the shaft of a catheter or alternatively may be integrated into a guidewire. The fiber measures axial strain, which can be converted into axial force or torque (when wound helically). At least a first FBG sensor can be integrated into a distal sensing zone, proximal sensing zone and/or intermediate sensing zone on the catheter or guidewire, to measure force and or torque in the vicinity of the sensor.

It may also be desirable to understand the three-dimensional configuration of the catheter or guidewire during and/or following transvascular placement. Shape sensing fiber optics such as an array of FBG fibers to sense the shape of catheters and guidewires. By using multiple force sensing fibers that are a known distance from each other, the shape along the length of the catheter/guidewire can be determined.

A resistive strain gauge may be integrated into the body of the catheter or guidewire to measure force or torque. Such as at the distal tip and/or proximal end of the device.

Measurements of force and/or torque applied to the catheter or guidewire shafts can be used to determine applied force and/or torque above a safety threshold. When an applied force and/or torque exceeds a safety threshold, a warning may be provided to a user. Applied force and/or torque measurements may also be used to provide feedback related to better catheter manipulation and control. Applied force and/or torque measurements may also be used with processed fluoroscopic imaging information to determine or characterize distal tip motion.

Absolute position of the hubs (and corresponding catheters) along the length of the table may be determined in a variety of ways. For example, a non-contact magnetic sensor may be configured to directly measure the position of the hubs through the sterile barrier. The same type of sensor can also be configured to measure the position of the carriages. Each hub may have at least one magnet attached to it. The robotic table would have a linear array of corresponding magnetic sensors going the entire length of the table. A processor can be configured to determine the location of the magnet along the length of the linear sensor array, and display axial position information to the physician.

The foregoing may alternatively be accomplished using a non-contact inductive sensor to directly measure the position of the hubs through the sterile barrier. Each hub or carriage may be provided with an inductive "target" in it. The robotic table may be provided with an inductive sensing array over the entire working length of the table. As a further alternative, an absolute linear encoder may be used to directly measure the linear position of the hubs or carriages. The encoder could use any of a variety of different technologies, including optical, magnetic, inductive, and capacitive methods.

In one implementation, a passive (no electrical connections) target coil may be carried by each hub. A linear printed circuit board (PCB) may run the entire working length of the table (e.g., at least about 1.5 meters to about 1.9 meters) configured to ping an interrogator signal which stimulates a return signal from the passive coil. The PCB is configured to identify the return signal and its location.

Axial position of the carriages may be determined using a multi-turn rotary encoder to measure the rotational position of the pulley, which directly correlates to the linear position of the carriage. Direct measurement of the location of the carriage may alternatively be accomplished by recording the number of steps commanded to the stepper motor to measure the rotational position of the pulley, which directly correlates to the linear position of the carriage.

The location of the catheters and guidewires within the anatomy may also be determined by processing the fluoroscopic image with machine vision, such as to determine the distal tip position, distal tip orientation, and/or guidewire shape. Comparing distal tip position or movement or lack thereof to commanded or actual proximal catheter or guidewire movement at the hub, may be used to detect a loss of relative motion, which may be indicative of a device shaft buckling, prolapse, kinking, or a similar outcome (for example, along the device shaft length inside the body (e.g., in the aorta) or outside the body between hubs. The processing may be done in real time to provide position/ orientation data at up to 30 Hertz, although this technique would only provide data while the fluoroscopic imaging is turned on. In some embodiments, machine vision algorithms can be used to generate and suggest optimal catheter manipulations to access or reach anatomical landmarks, similar to driver assist. The machine vision algorithms may utilize data to automatically drive the catheters depending on the anatomy presented by fluoroscopy.

Figure 14:
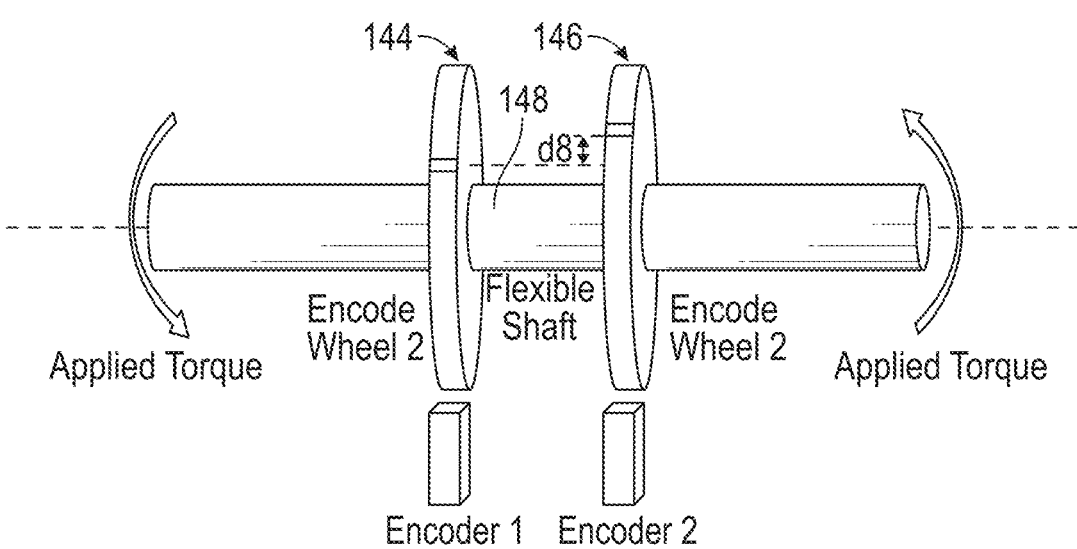
FIG. 14 schematically illustrates a dual encoder torque sensor for use with a catheter of the present disclosure.

Proximal torque applied to the catheter or guidewire shaft may be determined using a dual encoder torque sensor. Referring to FIG. 14, a first encoder 144 and a second encoder 146 may be spaced axially apart along the shaft 148, for measuring the difference in angle over a length of flexible catheter/tube. The difference in angle is interpolated as a torque, since the catheter/tube has a known torsional stiffness. As torque is applied to the shaft, the slightly flexible portion of the shaft will twist. The difference between the angles measured by the encoders (dθ) tells us the torque. $T=k*d\theta$, where k is the torsional stiffness.

Confirming the absence of bubbles in fluid lines may also be accomplished using bubble sensors, particularly where the physician is remote from the patient. This may be accomplished using a non-contact ultrasonic sensor that measures the intensity and doppler shift of the reflected ultrasound through the sidewall of fluid tubing to detect bubbles and measure fluid flow rate or fluid level. An ultrasonic or optical sensor may be positioned adjacent an incoming fluid flow path within the hub, or in a supply line leading to the hub. To detect the presence of air bubbles in the infusion line (that is formed of ultrasonically or optically transmissive material) the sensor may include a signal source on a first side of the flow path and a receiver on a second side of the flow path to measure transmission through the liquid passing through the tube to detect bubbles. Alternatively, a reflected ultrasound signal may be detected from the same side of the flow path as the source due to the relatively high echogenicity of bubbles.

Preferably, a bubble removal system is automatically activated upon detection of in line bubbles. A processor may be configured to activate a valve positioned in the flow path downstream of the bubble detector, upon the detection of bubbles. The valve diverts a column of fluid out of the flow path to the patient and into a reservoir. Once bubbles are no longer detected in the flow path and after the volume of fluid in the flow path between the detector and the valve has passed through the valve, the valve may be activated to reconnect the source of fluid with the patient through the flow path. In other embodiments, the bubble removal system can include a pump and control system upstream of the bubble detector for removal of in line bubbles. A processor may be configured to activate the pump upon detection of bubbles to reverse the fluid flow and clear the bubbles into a waste reservoir before reestablishing bubble free forward flow.

Figure 15:
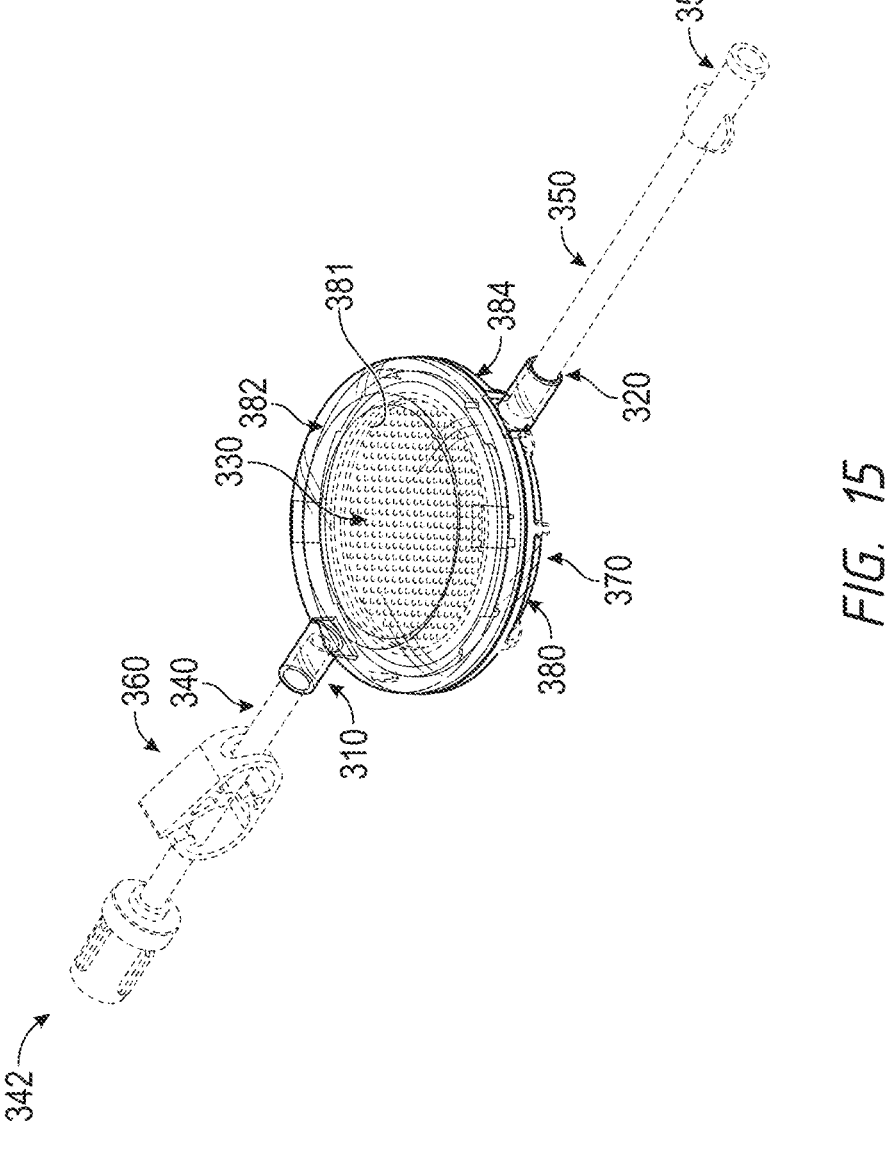
FIG. 15 illustrates a clot capture and visualization device that can be integrated into a hub and/or connected to an aspiration line.

It may additionally be desirable for the physician to be able to view aspirated clot at a location within the sterile field and preferably as close to the patient as practical for fluid management purposes. This may be accomplished by providing a clot retrieval device mounted on the hub, or in an aspiration line leading away from the hub in the direction of the pump. Referring to FIG. 15, one example of a clot retrieval device 370 can include a body 380 enclosing a chamber 381 which communicates with a first port 310 and a second port 320.

In some embodiments, the body 380 includes a housing having a top portion 382 and a bottom portion 384. The body 380 may include a filter 330 positioned in the chamber 381 between the top portion 382, and the bottom portion 384. In some examples, the first port 310 is configured to connect to a first end of a first tube 340 that is fluidly connected to a proximal end of an aspiration catheter.

In an embodiment that is configured to be connected downstream from the hub, the first tube 340 includes a connector 342 positioned at a second end of the first tube 340 that is configured to engage or mate with a corresponding connector on or in communication with the hub. The first port 310 directly communicates with the chamber on the upstream (e.g., top side) of the filter, and the second port 320 directly communicates with the chamber on the downstream (e.g., bottom side) of the filter to facilitate direct visualization of material caught on the upstream side of the filter.

In an implementation configured for remote operation, any of a variety of sensors may be provided to detect clot passing through the aspiration line and/or trapped in the filter, such as an optical sensor, pressure sensor, flow rate sensor, ultrasound sensor or others known in the art.

In some embodiments, the second port 320 is configured to connect to a first end of a second tube 350 that is fluidly connected to an aspiration source (e.g., a pump). In some embodiments, the second tube 350 includes a connector 352 positioned at a second end of the second tube 350 that is configured to engage or mate with a corresponding connector on the pump.

In some examples, the system 300 can include an on-off valve 360 such as a clamp 360. The clamp 360 can be positioned in between the filter 330 and the patient, such as over the first tube 340 to allow the user to engage the clamp and provide flow control by isolating the patient from the clot retrieval device 370. Closing the valve 360 and operating the remote vacuum pump (not illustrated) causes the canister associated with the vacuum pump and the chamber 381 to reach the same low pressure. Due to the short distance and small line volume of the lumen between the chamber 381 end the distal end of the catheter, a sharp negative pressure spike is experienced at the distal end of the catheter rapidly following opening of the valve 360. Additional details are disclosed in U.S. Pat. No. 11,259,821 issued Mar. 1, 2022 to Buck et al., entitled Aspiration System with Accelerated Response, the entirety of which is hereby expressly incorporated by reference herein. In some embodiments, a vacuum may be cycled against a clot to retrieve the clot. The vacuum may be automatically and robotically controlled to remove the clot.

The body 380 can have a top surface spaced apart from a bottom surface by a tubular side wall. In the illustrated implementation, the top and bottom surfaces are substantially circular, and spaced apart by a cylindrical side wall. The top surface may have a diameter that is at least about three times, or five times or more than the axial length (transverse to the top and bottom surfaces) of the side wall, to produce a generally disc shaped housing. Preferably at least a portion of the top wall is optically transparent to improve clot visualization once it is trapped in the clot retrieval device 370. Additional details may be found in U.S. Patent Application No. 63/256,743, the entirety of which is hereby incorporated by reference herein.

In some examples, the body 380 can include a flush port (not illustrated) that is configured to allow the injection of an optically transparent media such as air, saline or other fluid into the chamber 381 to clear an optical path between the window and the filter to improve clot visualization once it is trapped in the filter 330.

The foregoing represents certain specific implementations of a drive table and associated components and catheters. A wide variety of different drive table constructions can be made, for supporting and axially advancing and retracting two or three or four or more drive magnet assemblies to robotically drive interventional devices, fluid elements, and electrical umbilical elements for communicating electrical signals and fluids to the catheter hubs, as will be appreciated by those of skill in the art in view of the disclosure herein. Additional details may be found in U.S. patent application Ser. No. 17/527,393, the entirety of which is hereby incorporated by reference herein.

While the foregoing describes robotically driven interventional devices and manually driven interventional devices, the devices may be manually driven, robotically driven, or a combination of both manually and robotically driven interventional devices, as will be appreciated by those of skill in the art in view of the disclosure herein.

Figure 16A:
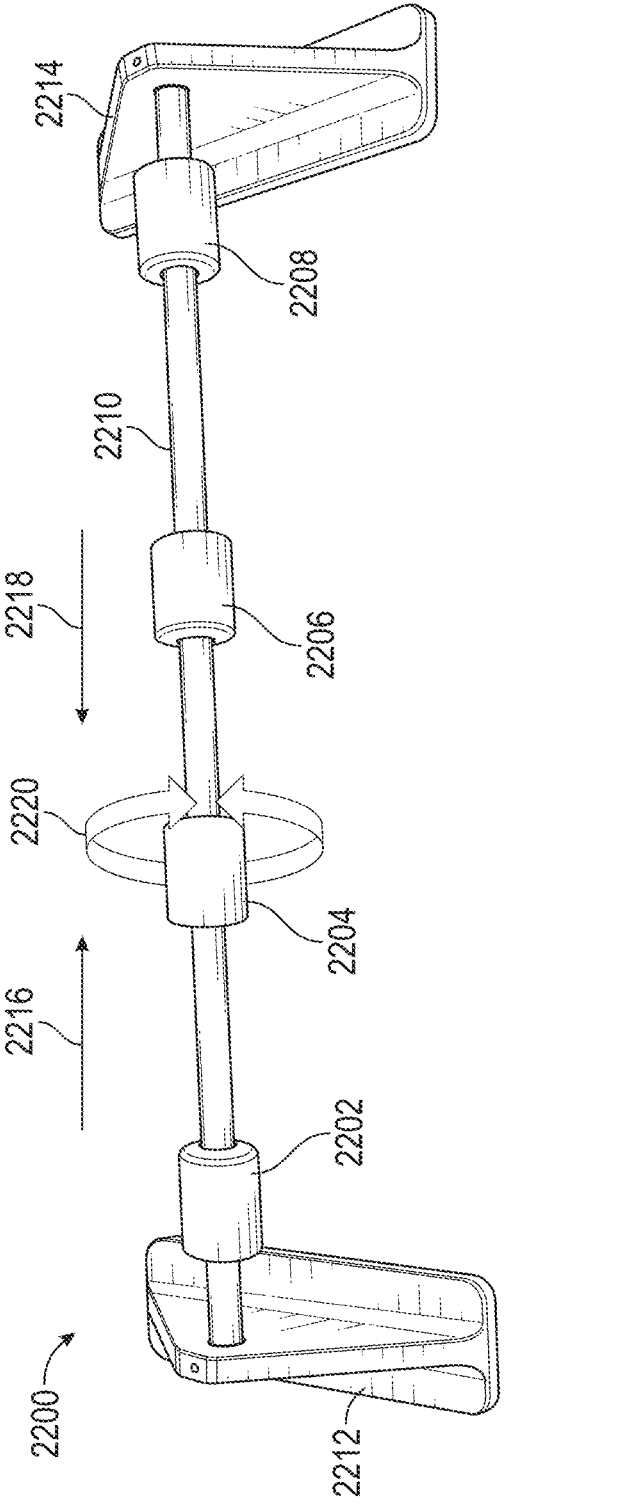
FIGS. 16A-16C illustrate an example control mechanism for manipulating interventional devices driven by respective hubs.
Figure 16B:
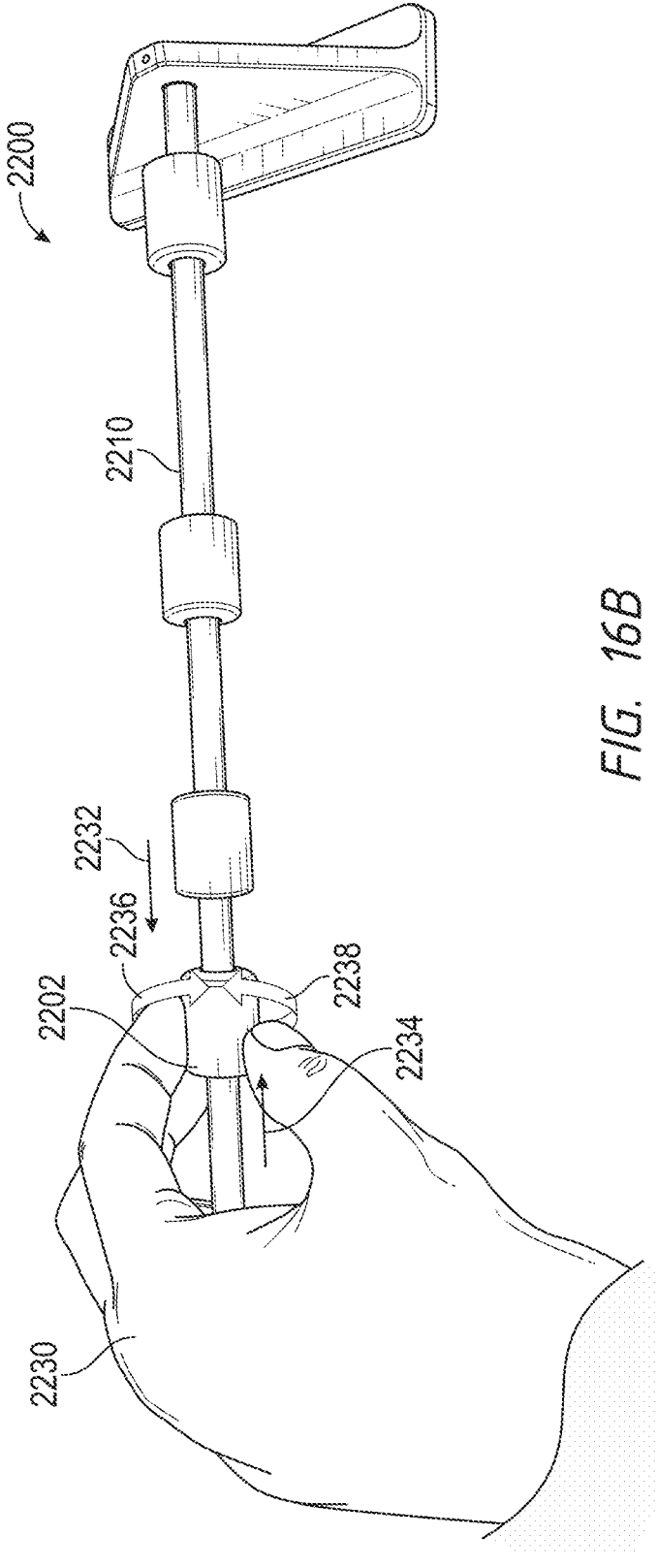
Figure 16C:
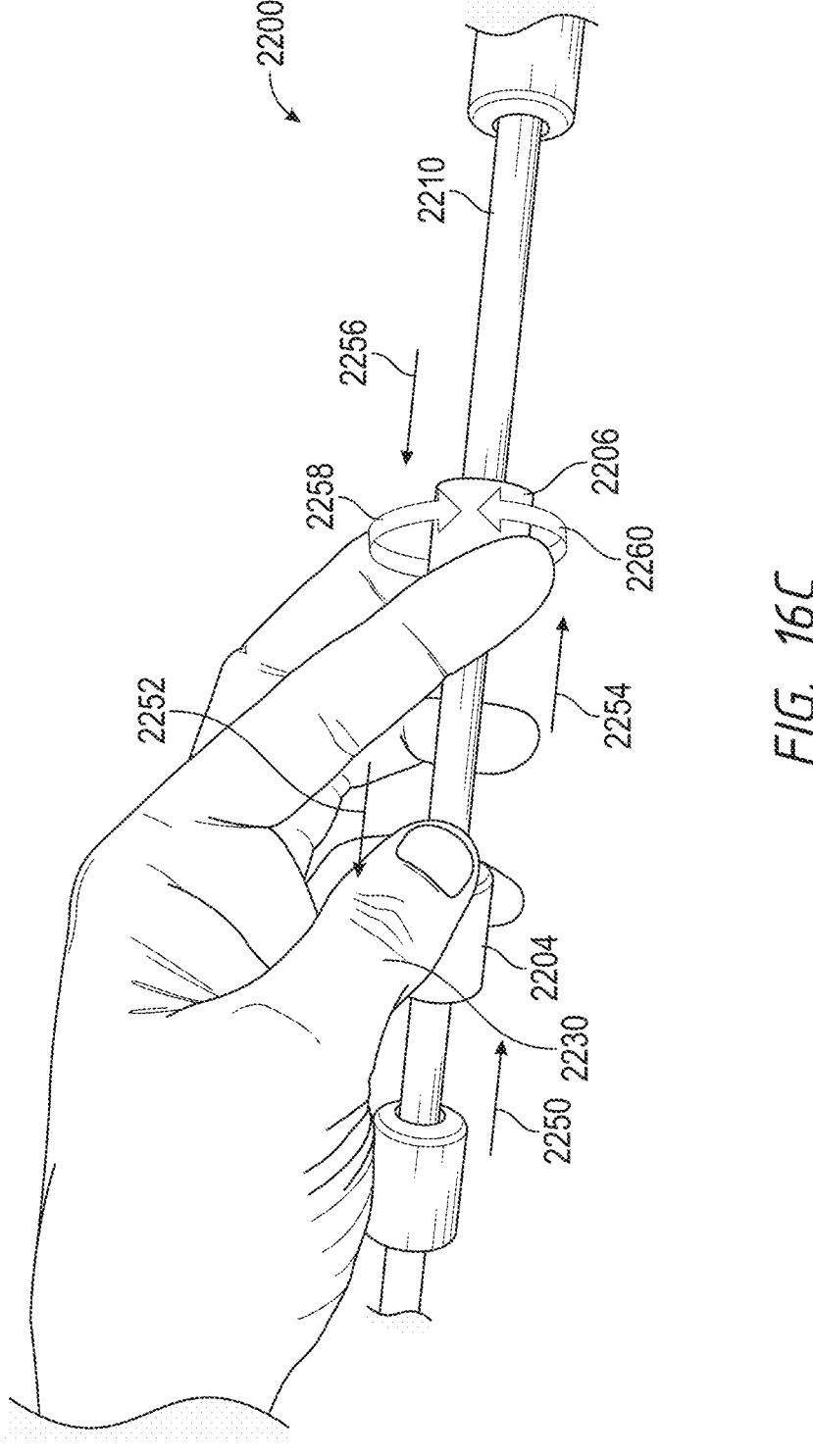

FIGS. 16A-16C illustrate an example control mechanism 2200 for manipulating interventional devices driven by (or otherwise associated with) respective hubs. For example, each hub may be manipulated and/or otherwise moved using at least one control installed in control mechanism 2200. Each control may be adapted to move a unique hub and associated interventional device during an interventional procedure.

As shown in FIG. 16A, the control mechanism 2200 include a first control 2202, a second control 2204, a third control 2206, and a fourth control 2208. More or fewer controls may be provided, depending upon the intended interventional devices configuration. Each control 2202-2208 is movably carried on a shaft 2210 that is coupled to a distal bracket 2212 and to a proximal bracket 2214. The controls 2202-2208 may advance distally or retract proximally on the shaft 2210, as indicated by arrow 2218 and arrow 2216. In addition, each control 2202-2208 may also be rotated about the shaft 2210, as indicated by arrow 2220. Each control movement may trigger a responsive movement in a corresponding carriage on the support table, which may in turn drive movement of a corresponding hub as has been discussed.

The control mechanism 2200 may be positioned on or near to a patient support table having a set of hubs and catheters/interventional devices. In some implementations, the control mechanism 2200 may be positioned remote from the support table such as behind a radiation shield or in a different room or different geographical location in a telemedicine implementation.

Each control 2202-2208 may correspond to and drive movement of a hub and/or a hub and interventional device combination. For example, the control 2202 may be configured to drive hub 30 (FIG. 3F) to move an interventional device such as an 0.088 inch guide catheter corresponding to the hub 30. Similarly, the control 2204 may be configured to drive hub 28 (122) to move an interventional device such as an 0.071 inch procedure catheter. The control 2206 may be configured to drive hub 126 to move an interventional device such as a steerable access catheter. The control 2208 may be configured to drive hub 26 to axially and rotationally move an interventional device such as a guidewire.

FIG. 16B illustrates an example of manually manipulating the control 2202 on control mechanism 2200. In operation, if the user 2230 moves the control 2202 axially along shaft 2210 and distally, as shown by arrow 2232, a corresponding coupled hub and/or interventional device may move responsively in the same direction by a same or scaled amount. If the user 2230 rotates the control 2202 about the shaft 2210 and advances the control proximally, as shown by arrow 2234, a corresponding coupled interventional device will responsively move rotationally and proximally by a same or scaled amount. If the user 2230 moves the control 2202 rotationally about the shaft 2210, as shown by arrow 2236 or arrow 2238, a corresponding coupled hub will drive the corresponding interventional device rotationally in the same direction and/or by a same or scaled amount.

Other axes and degrees of freedom may be defined to enable control 2202 to perform movements that may be translated to movement of hubs and/or interventional devices. For example, the control mechanism may be provided with one or more deflection controls configured to initiate a lateral deflection in a deflection zone on the corresponding interventional device.

Axial movement of a control may be configured to move the coupled hub on a 1:1 basis, or on a non 1:1 scaled basis. For example, if the user 2230 advances the control 2022 about 5 millimeters distally along the shaft 2210, then the corresponding hub may responsively move 5 millimeters in the distal direction.

If the user 2230 rotates the control 2022 about its rotational axis by 5 degrees, the coupled hub will cause the corresponding interventional device to rotate on a 1:1 basis or on a non 1:1 scaled basis. The scaled amount may be selected to reduce or increase the amount of distance and rotation that a hub and/or interventional device moves in accordance with the control movement.

In some implementations, the scaled amount described herein may be determined using a scale factor. The scale factor may apply to one or both translational and rotational movement. In some implementations, a first scale factor is selected for translational movement and a second scale factor, different than the first scale factor, is selected for rotational movement. The axial scaling factor may drive proximal catheter movement at a faster speed than distal catheter movement for a given proximal or distal manipulation of the control.

The rotational scale factor may be 1:1 while the axial scale factor may move the hub by a greater distance than movement of the control such that hub travel to control travel is at least about 2:1 or 5:1 or 10:1 or more depending upon the desired axial length of the control assembly.

The control mechanism 2200 may be configured to enable the clinician to adjust the scale factor for different parts of the procedure. For example, distal advance of the procedure catheter and access catheter through the guide catheter and up to the selected ostium may desirably be accomplished in a 'fast' mode. But more distal travel into the neuro vasculature may desirably be accomplished in a relatively slow mode by actuation of a speed control.

In another implementation, one or more controls may be configured to progressively drive advance or retraction speeds of the corresponding hub and associated catheter. For example, distal control 2202 may drive the guide catheter. A slight distal movement of the control 2202 may advance the guide catheter distally at a slow speed, while advancing the control 2202 by a greater distance distally increases the rate of distal travel of the guide catheter.

Controlling the speed of the corresponding hubs either axially or both axially and rotationally may enhance the overall speed of the procedure. For example, advance of the various devices from the femoral access point up to the aortic arch may desirably be accomplished at a faster rate than more distal navigation closer to the treatment site. Also proximal retraction of the various devices, particularly the guidewire, access catheter and procedure catheter may be desirably accomplished at a relatively higher speeds than distal advance.

FIG. 16C illustrates another example of manually manipulating a control on the control mechanism 2200 to move hubs and/or other interventional devices. In some implementations, two or more controls 2202-2208 may be moved in combination to trigger movement of one or more hubs and/or related interventional devices. In the depicted example, the user 2230 moves control 2204 and control 2206 in combination (e.g., sequentially, simultaneously) such as to simultaneously move the 0.088 guide catheter and the 0.071 aspiration catheter as a unit. Example movement of control 2204 may include axial proximal movement in the directions shown by arrows 2250. Sequentially or simultaneously, the user 2230 may move control 2206 axially in either of the directions shown by arrows 2254 and 2256 while also moving control 2206 rotationally in either of the directions shown by arrows 2258 and 2260.

In some implementations, each control mechanism and/or additional controls (not shown) may be color coded, shaped coded, tactile coded, or other coding to indicate to the user 2230 which color is configured to move which hub or interventional device. In some implementations, the control color coding may also be applied to the hubs and/or interventional devices such that a user may visually match a particular hub/device with a particular control.

In some implementations, other control operations beyond translational movement and rotational movement may be carried out using controls 2202-2208. For example, controls 2202-2208 may be configured to drive a shape change and/or stiffness change of a corresponding interventional device. Controls 2202-2208 may be toggled between different operating modes. For example, controls 2202-2208 may be toggled between movement driven by acceleration and velocity to movement that reflects actual linear displacement or rotation.

In some implementations, the control mechanism 2200 may be provided with a visual display or other indicator of the relative positions of the controls which may correspond the relative positions of the interventional devices. Such displays may depict any or all movement directions, instructions, percentage of movements performed, and/or hub and/or catheter indicators to indicate which device is controlled by a particular control. In some implementations, the display may depict applied force or resistance encountered by the catheter or other measurement being detected or observed by a particular hub or interventional component.

In some implementations, the control mechanism 2200 may include haptic components to provide haptic feedback to a user operating the controls. For example, if the control 2202 is triggering movement of a catheter and the catheter detects a large force at the tip, the control 2202 may generate haptic feedback to indicate to the user to stop or reverse a performed movement. In some implementations, haptic feedback may be generated at the control to indicate to the user to slow or speed a movement using the control. In some implementations, haptics may provide feedback on a large torsional strain buildup that might precede an abrupt rotation, or a large axial force buildup that may be a prelude to buckling of the catheter.

The systems described herein may compare an actual fluoroscopic image position to an input displacement from the controller. A static fluoroscopic image of the patient may be captured in which the patient's vasculature is indexed relative to bony landmarks or one or more implanted soft tissue fiducial markers. Then a real time fluoroscopic image may be displayed as an overlay, aligned with the static image by registration of the fiducial markers. Visual observation of conformance of the real time movement with the static image, assisted by detected force data can help confirm proper navigation of the associated catheter or guidewire. The systems described herein can also display a comparison of an input proximal mechanical translation of a catheter or guidewire and a resulting distal tip output motion or lack thereof. A loss of relative motion at the distal tip may indicate shaft buckling, prolapse, kinking, or a similar outcome, either inside or outside the body. Such a comparison may be beneficial when the shaft buckling, prolapse, kinking, or similar outcome occurs outside of a current fluoroscopic view.

Figure 17:
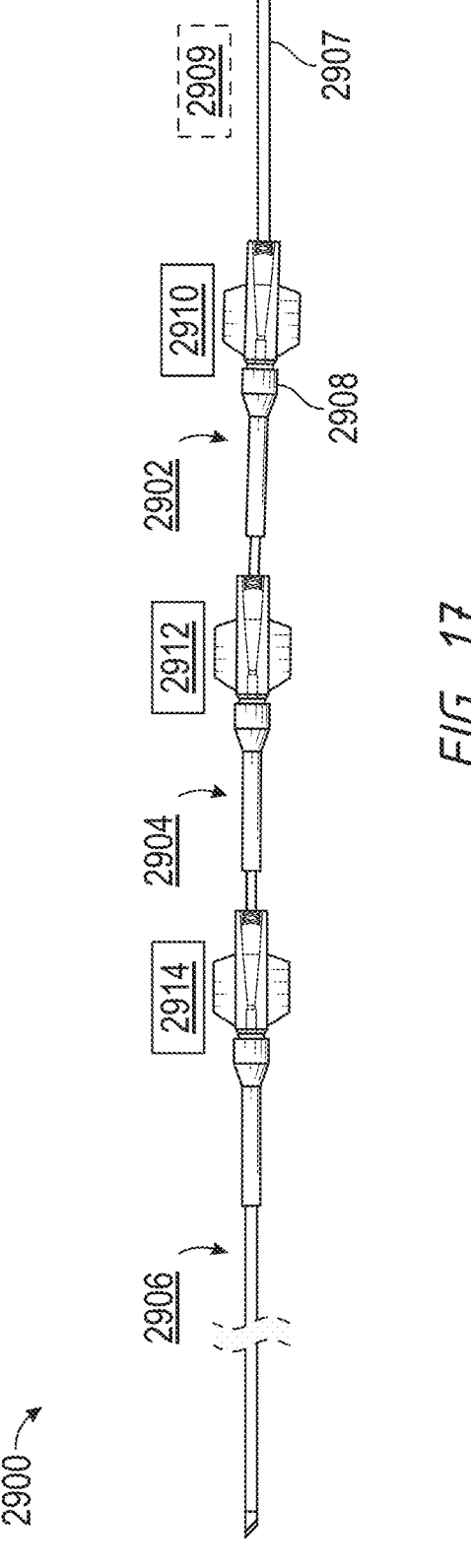
FIG. 17 illustrates a side elevational schematic view of an interventional device assembly for supra-aortic access and neuro-interventional procedures.

FIG. 17 illustrates a side elevational schematic view of a multi catheter interventional device assembly 2900 for combined supra-aortic access and/or neurovascular site access and procedure (e.g., aspiration), as described herein. The multi catheter assembly 2900 may be configured for either a manual or a robotic procedure.

The interventional device assembly 2900 includes an insert or access catheter 2902, a procedure catheter 2904, and a guide catheter 2906. Other components are possible including, but not limited to, one or more guidewires (e.g., optional guidewire 2907), one or more guide catheters, an access sheath and/or one or more other procedure catheters and/or associated catheter (control) hubs. In some embodiments, the assembly 2900 may also be configured with an optional deflection control 2908 for controlling deflection of one or more catheters of assembly 2900.

In operation, the multi-catheter assembly 2900 may be used without having to exchange hub components. For example, in the two stage procedure disclosed previously, a first stage for achieving supra-aortic access includes mounting an access catheter, guide catheter and guidewire to the support table. Upon gaining supra aortic access, the access catheter and guidewire were typically removed from the guide catheter. Then, a second catheter assembly is introduced through the guide catheter after attaching a new guidewire hub and a procedure catheter hub to the corresponding drive carriage on the support table.

The single multi catheter assembly 2900 of FIG. 17 is configured to be operated without having to remove hubs and catheters and without the addition of additional assemblies and/or hubs. Thus, the multicomponent access and procedure configuration of assembly 2900 may utilize a guidewire 2907 manufactured to function as an access guidewire and a navigation guidewire to allow for sufficient access and support, and navigation to the particular distal treatment site. In a non-limiting example configured for robotic implementation, a catheter assembly may include a guidewire hub (e.g., guidewire hub 2909 or guidewire hub 26 positioned on a drive table and to the right of catheter 2902), an insert or access catheter hub 2910, a procedure catheter hub 2912, a guide catheter hub 2914 and corresponding catheters. In certain embodiments, one or more of the hubs may include or be coupled to a hemostasis valve (e.g., a rotating hemostasis valve) to accommodate introduction of interventional devices therethrough. Additional details regarding hemostasis valves are included in U.S. patent application Ser. No. 17/879,614, entitled Multi Catheter System With Integrated Fluidics Management, filed Aug. 2, 2022, which is hereby expressly incorporated by reference in its entirety herein.

Once access above the aortic arch has been achieved, the insert or access catheter 2902 (associated with insert catheter hub 2910) may be parked in the vicinity of a carotid artery ostia and the remainder or a subset of the catheter assembly may be guided more distally toward a particular site (e.g., a clot site, a surgical site, a procedure site, etc.).

In some embodiments, other smaller procedure catheters may also be added and used at the site. As used herein for catheter assembly 2900, in a robotic configuration of assembly 2900, the catheter 2906 may function as a guide catheter. The catheter 2904 may function as a procedure (e.g., aspiration) catheter. In some embodiments, the catheter 2906 may function to perform aspiration in addition to functioning as a guide catheter, either instead of or in addition to the catheter 2904. The access catheter 2902 may have a distal deflection zone and can function to access a desired ostium. One of skill in the art will appreciate from FIGS. 18A-18E that either manual manipulation or robotic manipulation of the multi catheter stack are contemplated herein.

In some embodiments, the catheter assembly 2900 (or other combined catheter assemblies described herein) may be driven as a unit to a location. However, each catheter (or guidewire) component may instead be operated and driven independent of one another to the same or different locations.

In a non-limiting example, the catheter assembly 2900 may be used for a diagnostic angiogram procedure. In some embodiments, the assembly 2900 may include only the guidewire 2907 and access catheter 2902 (in the form of a diagnostic angiographic catheter) for performing the diagnostic angiogram procedure or only the guidewire 2907 and the access catheter 2902 may be utilized during the procedure. Alternatively, the guide catheter 2906 and procedure catheter 2904 may be retracted proximally to expose the distal end of the access catheter 2902 (e.g., a few centimeters of the distal end of the access catheter) to perform the diagnostic angiography.

As shown in FIG. 17, the guide catheter 2906, procedure catheter 2904, access catheter 2902, and guidewire 2907 can be arranged concentrically. In certain embodiments, the guide catheter 2906 may be a 'large bore' guide catheter or access catheter having an inner diameter of at least about 0.075 or at least about 0.080 inches in diameter. The procedure catheter 2904 may be an aspiration catheter having an inner diameter within the range of from about 0.060 to about 0.075 inches. The access catheter 2902 may be a steerable catheter with a deflectable distal tip, having an inner diameter within the range of from about 0.025 to about 0.050 inches. The guidewire 2907 may have an outer diameter within the range of from about 0.014 to about 0.020 inches. In one example, the guide catheter 2906 may have an inner diameter of about 0.088 inches, the procedure catheter 2904 may have an inner diameter of about 0.071 inches, the access catheter 2902 may have an inner diameter of about 0.035 inches, and the guidewire 2907 may have an outer diameter of about 0.018 inches.

FIGS. 18A-18E depict an example sequence of steps of introducing a multi-catheter assembly configured to achieve access all the way to the clot, either manually or robotically. FIGS. 18A-18E may be described using the interventional device assembly of FIG. 17. Other combinations of catheters may be substituted for the interventional device assembly, as will be appreciated by those of skill in the art in view of the disclosure herein.

Figures 18A, 18B, 18C:
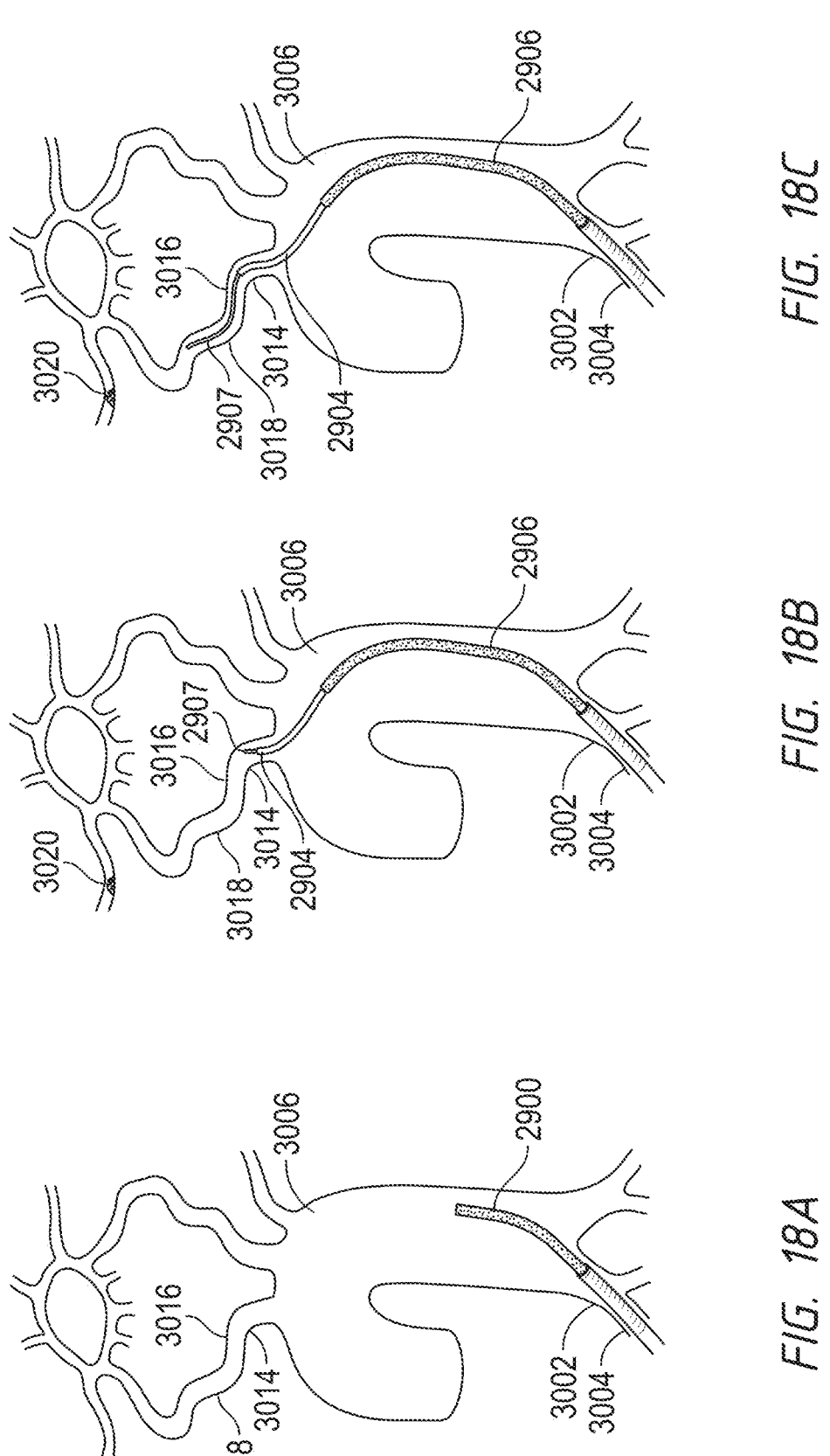
FIGS. 18A-18E depict an example sequence of steps of introducing a catheter assembly configured to achieve supra-aortic access and neurovascular site access.

Referring to FIG. 18A, the three catheter interventional device assembly 2900 is shown driven through an introducer sheath 3002, up through the iliac artery 3004 and into the descending aorta. Next, the access catheter 2902, the procedure catheter 2904 (e.g., 0.071 inch) and the guide catheter 2906 (e.g., 0.088 inch) are tracked up to the aortic arch 3006, as shown in FIG. 18B. Here, the distal end of the guide catheter 2906 may be parked below the aortic arch 3006 and the procedure catheter 2904, access catheter 2902 (positioned within the procedure catheter 2904 and not visible in FIG. 18B), and a guidewire 2907 can be driven into the ostium (e.g., simultaneously or separately). In some embodiments, the access catheter 2902 is advanced out of the procedure catheter 2904 and the guide catheter 2906 to engage the ostium first. After the distal end of the access catheter 2902 is positioned within the desired ostium, the guidewire 2907 can be advanced distally into the ostium to secure access. After the access catheter 2902 and guidewire 2907 are positioned within the desired ostium, the procedure catheter 2904 and/or guide catheter 2906 can be advanced into the ostium (and, in some embodiments, beyond), while using the support of the access catheter 2902 and/or guidewire 2907 to maneuver through the aorta and into the ostium. In the embodiment shown in FIG. 18B, the procedure catheter 2904 has been advanced into the ostium while the guide catheter 2906 has remained parked below the aortic arch 3006.

Referring to FIG. 18C, the guidewire 2907 may be distally advanced and the radiopacity of the guidewire 2907 may be used to confirm under fluoroscopic imaging that access through the desired ostia has been attained. The guidewire 2907 engages the origin of the brachiocephalic artery 3014. The guidewire 2907 is then advanced up to the petrous segment 3018 of the internal carotid artery 3016.

Figure 18E:
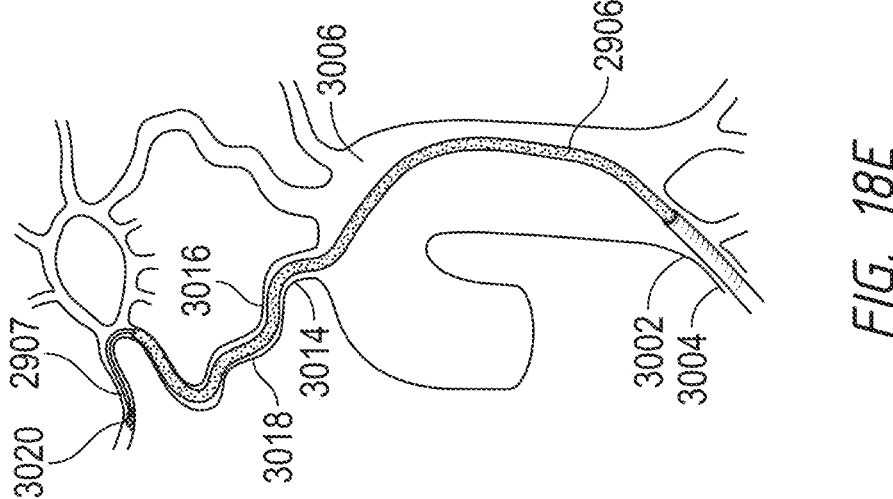
Figure 18D:
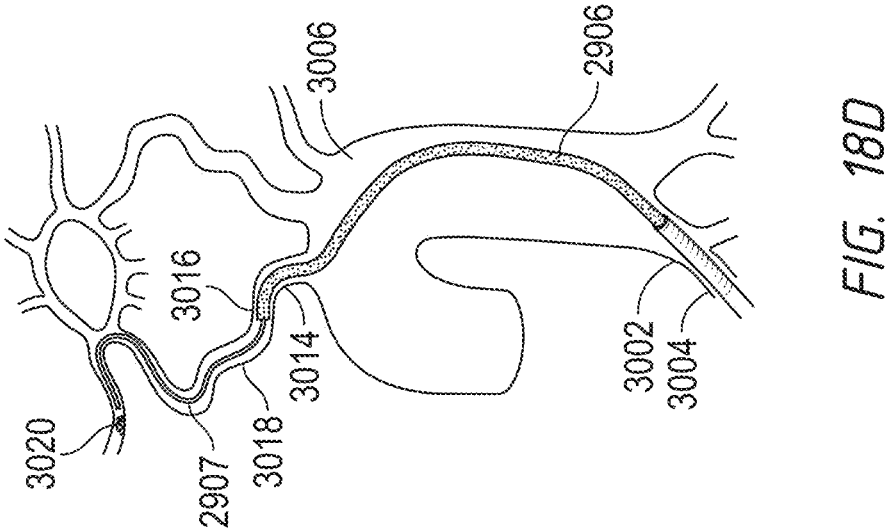

Referring to FIG. 18D, the guide catheter 2906 and the procedure catheter 2904 (positioned within the guide catheter 2906 and not visible in FIG. 18D) are both advanced (e.g., simultaneously or sequentially) over the guidewire 2907 and over the insert or access catheter 2902 (positioned within the procedure catheter 2904 and not visible in FIG. 18D) while the access catheter 2902 remains at the ostium for support. The guidewire 2907 may be further advanced past the petrous segment 3018 to the site of the clot 3020, such as the Ml segment.

Referring to FIG. 18E, the guide catheter 2906 and the procedure catheter 2904 (positioned within the guide catheter 2906 and not visible in FIG. 18E) are advanced (e.g., simultaneously or sequentially) to position the distal tip of the procedure catheter 2904 at the procedure site, for example on the face of the clot 3020. The guidewire 2907 and access catheter 2902 (positioned within the procedure catheter 2904 and not visible in FIG. 18E) are removed, and aspiration of the clot 3020 commences through the procedure catheter 2904. That is, the guidewire 2907 and the access catheter 2902 are proximally retracted to allow aspiration through the procedure catheter 2904. After aspiration of the clot, the procedure catheter 2904 and guide catheter 2906 can be removed (e.g., simultaneously or sequentially). For example, in some embodiments, the procure catheter 2904 may be removed before removing the guide catheter 2906.

The catheter assembly 2900 may be used to perform a neurovascular procedure, as described in FIGS. 18A-18E. For example, the neurovascular procedure may be a neurovascular thrombectomy. The steps of the procedure may include providing an assembly that includes at least a guidewire, an access catheter, a guide catheter, and a procedure catheter. For example, the catheter assembly 2900 includes a guidewire 2907, an access (e.g., insert) catheter 2902, a guide catheter 2906, and at least one procedure catheter 2904. The procedure catheter 2904 may include an aspiration catheter, an embolic deployment catheter, a stent deployment catheter, a flow diverter deployment catheter, a diagnostic angiographic catheter, a stent retriever catheter, a clot retriever catheter, a balloon catheter, a catheter to facilitate percutaneous valve repair or replacement, an ablation catheter, and/or an RF ablation catheter or guidewire.

The neurovascular procedure may further include steps of coupling the assembly to a non-robotic or a robotic drive system, and driving the assembly to achieve supra-aortic access. The steps may further include driving a subset of the assembly to a neurovascular site, and performing the neurovascular procedure using a subset of the assembly. The subset of the assembly may include the guidewire, the guide catheter, and the procedure catheter.

Each of the guidewire 2907, the access catheter 2902, the guide catheter 2906, and the procedure catheter 2904 is configured to be adjusted by a respective hub. For example, the guidewire 2907 may include (or be coupled to) a hub installed on one of the tray assemblies described herein. Similarly, the access catheter 2902 may be coupled to catheter hub 2910. The guide catheter 2906 may be coupled to the guide catheter hub 2914. The procedure catheter 2904 may be coupled to the procedure catheter hub 2912.

In general coupling of the assembly may include magnetically coupling a first hub 2909 on the guidewire 2907 to a first drive magnet, magnetically coupling a second hub 2910 on the access catheter 2902 to a second drive magnet, magnetically coupling a third hub 2912 on the procedure catheter 2904 to a third drive magnet, and magnetically coupling a fourth hub 2914 on the guide catheter 2906 to a fourth drive magnet. In general, the first drive magnet, the second drive magnet, the third drive magnet, and the fourth drive magnet are each independently movably carried by a drive table, as described with respect to tray assemblies and controls described herein. In some embodiments, the first drive magnet, the second drive magnet, the third drive magnet, and the fourth drive magnet are coupled (e.g., to their respective catheter hubs) through a sterile barrier (e.g., a sterile and fluid barrier) and independently movably carried by a drive table having a plurality of driven magnets. In some embodiments, two or more drive magnets can be tethered or otherwise coupled together to move as a unit in response to commands from a single controller tethered or otherwise coupled to one of the drive magnets.

In some implementations, the steps of performing the neurovascular procedure may include driving the assembly in response to movement of each of the hub adapters along a support table until the assembly is positioned to achieve supra-aortic vessel access. The hub adapters may include, for example, a coupler/carriage that acts as a shuttle by advancing proximally or distally along a track in response to operator instructions. The hub adapters described herein may each include at least one drive magnet configured to couple with a driven magnet carried by the respective hub. This provides a magnetic coupling between the drive magnet and driven magnet through the sterile barrier such that the respective hub is moved across the top of the sterile barrier in response to movement of the hub adapter outside of the sterile field (as described in detail in FIG. 4). Movement of the hub adapter is driven by a drive system carried by the support table in which the guidewire hub 2909, the guide catheter hub 2914, the procedure catheter hub 2912, and the access catheter hub 2910 are installed upon.

The steps may further include driving a subset of the assembly in response to movement of each of the hub adapters along the support table until the subset of the assembly is positioned to perform a neurovascular procedure at a neurovascular treatment site. The subset of the assembly may include the guidewire 2907, the guide catheter 2906, and the procedure catheter 2904.

In some embodiments, the guidewire 2907, the guide catheter 2906 and the procedure catheter 2904 are advanced as a unit through (with respect to the guidewire 2907) and over (with respect to the guide catheter 2906 and the procedure catheter 2904) at least a portion of a length of the access (e.g., insert) catheter 2902 after supra-aortic access is achieved.

In some embodiments, the catheter assembly 2900 may be part of a robotic control system for achieving supra-aortic access and neurovascular treatment site access, as described in FIGS. 18A-18E. In some embodiments, the catheter assembly 2900 may be part of a manual control system for achieving supra-aortic access and neurovascular treatment site access. In some embodiments, the catheter assembly 2900 may be part of a hybrid control system (with manual and robotic components) for achieving supra-aortic access and neurovascular treatment site access. For example, in such hybrid systems, supra-aortic access may be robotically driven while neurovascular site access and embolectomy or other procedures may be manual. Alternatively, in such hybrid systems, supra-aortic access may be manual while neurovascular site access may be robotically achieved. Still further, in such hybrid systems, any one or more of: the guidewire, access catheter, guide catheter, or procedure catheter may be robotically driven or manually manipulated.

An example robotic control system may include at least a guidewire hub (e.g., guidewire hub 2909) configured to adjust each of an axial position and a rotational position of a guidewire 2907. The robotic control system may also include an access catheter hub 2910 configured to adjust axial and rotational movement of an access catheter 2902. The robotic control system may also include a guide catheter hub 2914 configured to control axial movement of a guide catheter 2906. The robotic control system may also include a procedure catheter hub 2912 configured to adjust an axial position and a rotational position of a procedure catheter 2904.

In some embodiments, the procedure catheter hub 2912 is further configured to laterally deflect a distal deflection zone of the procedure catheter 2904.

In some embodiments, the guidewire hub 2909 is configured to couple to a guidewire hub adapter by magnetically coupling the guidewire hub to a first drive magnet. The access catheter hub 2910 is configured to couple to an access catheter hub adapter by magnetically coupling the access catheter hub 2910 to a second drive magnet. The procedure catheter hub 2912 is configured to couple to a procedure catheter hub adapter by magnetically coupling the procedure catheter hub 2912 to a third drive magnet. The guide catheter hub 2914 is configured to couple to a guide catheter hub adapter by magnetically coupling the guide catheter hub 2914 to a fourth drive magnet. In some embodiments, the first drive magnet, the second drive magnet, the third drive magnet, and the fourth drive magnet are independently movably carried by a drive table.

In some embodiments, the robotic control system includes a first driven magnet on the guidewire hub 2909. The first driven magnet may be configured to cooperate with the first drive magnet such that the first driven magnet is configured to move in response to movement of the first drive magnet. In some embodiments, the first drive magnet is configured to move outside of a sterile field separated from the first driven magnet by a barrier while the first driven magnet is within the sterile field. In some embodiments, a position of the first driven magnet is movable in response to manipulation of a procedure drive control on a control console associated with the drive table. Drive magnets and driven magnet interactions are described in detail with respect to FIG. 4 above.

In some embodiments, the robotic control system includes a second driven magnet on the access catheter hub 2910. The second driven magnet may be configured to cooperate with the second drive magnet such that the second driven magnet is configured to move in response to movement of the second drive magnet. In some embodiments, the second drive magnet is configured to move outside of a sterile field separated from the second driven magnet by a barrier while the second driven magnet is within the sterile field.

In some embodiments, the robotic control system includes a third driven magnet on the procedure catheter hub 2912. The third driven magnet may be configured to cooperate with the third drive magnet such that the third driven magnet is configured to move in response to movement of the third drive magnet. In some embodiments, the third drive magnet is configured to move outside of a sterile field separated from the third driven magnet by a barrier while the third driven magnet is within the sterile field.

In some embodiments, the robotic control system includes a fourth driven magnet on the guide catheter hub 2914. The fourth driven magnet may be configured to cooperate with the fourth drive magnet such that the fourth driven magnet is configured to move in response to movement of the fourth drive magnet. In some embodiments, the fourth drive magnet is configured to move outside of a sterile field separated from the fourth driven magnet by a barrier while the fourth driven magnet is within the sterile field. In some embodiments, there may be more than four driven magnets and corresponding catheter hubs for control of additional catheters.

In some embodiments, devices (e.g., hubs, hub adapters, interventional devices, and/or trays) described herein may be used during a robotically driven procedure. For example, in a robotically driven procedure, one or more of the interventional devices may be driven through vasculature and to a procedure site. Robotically driving such devices may include engaging electromechanical components that are controlled by user input. In some implementations, users may provide the input at a control system that interfaces with one or more hubs and hub adapters.

In some embodiments, the hubs, hub adapters, interventional devices, and trays described herein may be used during a non-robotic (e.g., manually driven) procedure. Manually driving such devices may include engaging manually with the hubs to affect movement of the interventional devices.

In some embodiments, the devices described herein may be used to carry out a method of performing an intracranial procedure at an intracranial site. The method of performing the intracranial procedure may include any of the same steps as described herein for performing a neurovascular procedure. The procedure may be robotically performed, manually performed, or a hybridized combination of both.

While the foregoing describes magnetic coupling of hubs to drive magnets, in other embodiments, any of the interventional devices and/or hubs may be mechanically coupled to a drive system. Any of the methods described herein may include steps of mechanically coupling one or more interventional devices (e.g., the guidewire 2907, the access catheter 2902, the procedure catheter 2904, and/or the guide catheter 2906) and/or one or more hubs (e.g., the guidewire hub 2909, the access catheter hub 2910, the procedure catheter hub 2912, and/or the guide catheter hub 2914) with one or more drive mechanisms.

Figure 19:
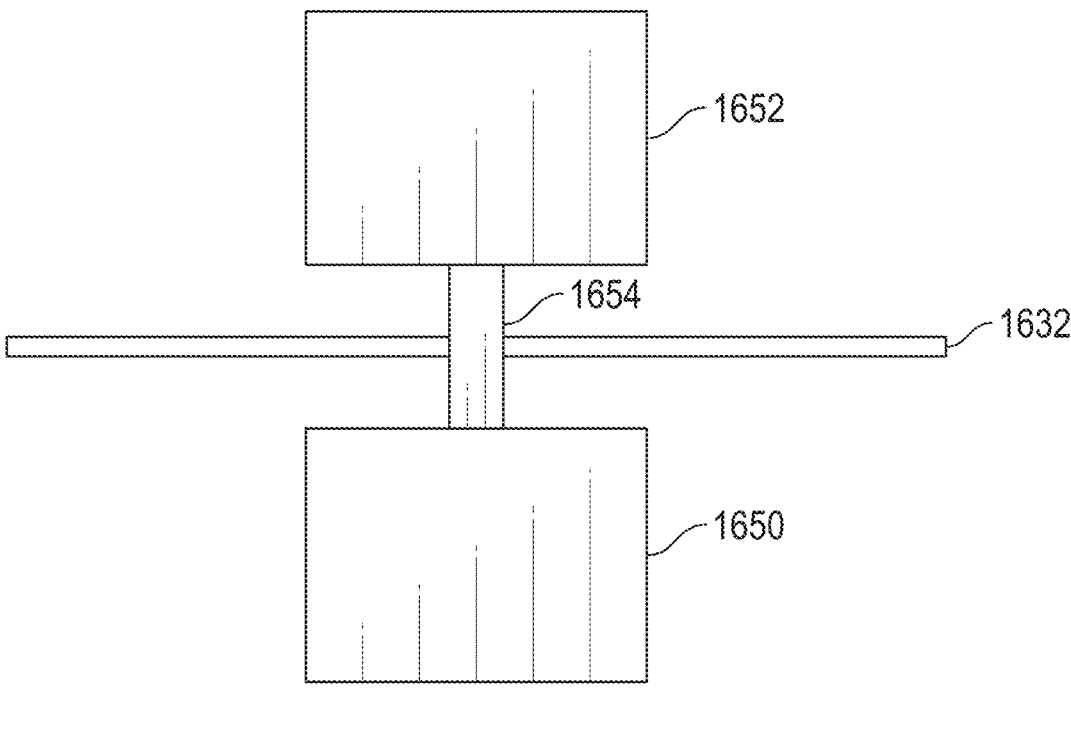
FIG. 19 schematically illustrates an embodiment of a mechanical coupling between a drive mechanism and a driven mechanism.

FIG. 19 illustrates a mechanical coupling mechanism 1654 between a drive mechanism 1650 and a driven mechanism 1652. Drive mechanism 1650 and driven mechanism 1652 may have any of the same or similar features or functions as the drive magnet 67 and driven magnet 69, respectively, except as otherwise described herein. The drive mechanism 1650 may be part of or coupled to a hub adapter (e.g., the hub adapter 48). The driven mechanism 1652 may be part of or coupled to a hub (e.g., the hub 36, the guidewire hub 2909, the access catheter hub 2910, the procedure catheter hub 2912, or the guide catheter hub 2914). In some instances, the mechanical coupling mechanism 1654 may comprise a structural support (e.g., a support rod or support strut) extending transversely through a seal in a sterile barrier 1632. The seal may permit the structural support to be advanced along a length of the sterile barrier 1632, while still maintaining a seal with the structural support to maintain the sterile field, as the drive mechanism 1650 and driven mechanism 1652 are advanced and/or retracted as described herein. For example, the seal may comprise a tongue and groove closure mechanism along the sterile barrier 1632 that is configured to close on either side of the structural support while permitting passage of the structural support through the sterile barrier 1632 and maintaining a seal against the structural support as the structural support is advanced along the length of the sterile barrier 1632.

In some embodiments, the structural support can extend through an elongate self closing seal between two adjacent coaptive edges of flexible material (e.g., similar in shape to a duckbill valve) that extends along an axis. As the structural support advances along the axis between the coaptive edges, the coaptive edges may permit the structural support to advance, and then may be biased back into a sealing engagement with each other as the structural support passes any given point along the axis.

In some embodiments, the drive mechanism may be a splined drive shaft (e.g., a non-sterile splined drive shaft). The mechanical coupling 1654 can include a pulley within a plate that serves as the sterile barrier 1632 and a sterile splined shaft configured to couple to the driven mechanism 1652. The driven mechanism 1652 can be a sterile pulley that receives the sterile splined shaft from the sterile barrier. In some embodiments, one or more splined drive shafts can engage and turn corresponding pulleys in the plate that serves as the sterile barrier. Each hub can have a sterile pulley that is configured to receive a sterile splined shaft from the sterile barrier plate. Rotation of the splined drive shaft can turn the pulley in the sterile barrier plate which can in turn the sterile pulley in the hub via the sterile splined shaft.

It will be understood by one having skill in the art that any embodiment as described herein may be modified to incorporate a mechanical coupling mechanism, for example, as shown in FIG. 19.

The interventional devices described herein may be provided individually or at least some of the interventional devices can be provided in a preassembled (e.g., nested or stacked) configuration. For example, the interventional devices may be provided in the form of an interventional device assembly, such as interventional device assembly 2900, in a concentric nested or stacked configuration. If provided individually, each catheter (and in some embodiments, each corresponding catheter hub) can be unpackaged and primed to remove air from its inner lumen, for example, by flushing the catheter (and in some embodiments, the corresponding catheter hub) to remove air by displacing it with a fluid, such as saline contrast media, or a mixture of saline and contrast media. After priming, the interventional devices can be manually assembled into a stacked configuration so that they are ready for introduction into the body for a surgical procedure, for example, via an introducer sheath.

Assembling the devices into a stacked configuration can include individually inserting interventional devices into one another by order of size. For example, an interventional device having a second largest diameter can be inserted into the lumen of an interventional device having a largest diameter. An interventional device having a third largest diameter can then be inserted into the interventional device having the second largest diameter and so on.

For example, with respect to FIG. 17, assembly can be performed by first inserting a distal end of the catheter 2904 through the hub 2914 and into the catheter 2906. The catheter 2904 can be advanced through the catheter 2906 until the distal tip of the catheter 2904 is flush with or extends beyond the distal tip of the catheter 2906, and/or until the catheter 2904 cannot be inserted any further. Then, the distal end of the catheter 2902 can be inserted through the hub 2912 and into the catheter 2904. The catheter 2902 can be advanced through the catheter 2904 until the distal tip of the catheter 2902 is flush with or extends beyond the distal tip of the catheter 2904, and/or until the catheter 2902 cannot be inserted any further. Then, the distal end of the guidewire 2907 can be inserted through the hub 2910 and into the catheter 2902. The guidewire 2907 can be advanced through the catheter 2902 until the distal tip of the guidewire 2907 is flush with or extends beyond the distal tip of the catheter 2902, and/or until the guidewire 2907 cannot be inserted any further.

Embodiments in which two or more of the interventional devices are packaged together as a single unit in an assembled (e.g., nested or stacked) configuration may provide efficient unpackaging and preparation prior to use and efficient assembly within a robotic control system. The interventional devices may be pre-mounted to their respective hubs prior to packaging. In certain embodiments, two or three or more interventional devices may be packaged in a fully nested (i.e., fully axially inserted) configuration or nearly fully nested configuration. In a fully nested configuration, each interventional device is inserted as far as possible into an adjacent distal hub and interventional device. Such a fully nested configuration may minimize a total length of the interventional device assembly and minimize the size of the packaging required to house the interventional device assembly.

In some embodiments, the interventional devices may also be sterilized prior to packaging while in the assembled configuration, for example, using ethylene oxide gas. In some embodiments, the interventional devices may be packaged while in the assembled configuration before sterilization with ethylene oxide gas. For interventional devices in a nested or stacked configuration, ethylene oxide gas can be provided in a space between adjacent interventional devices (for example, an annular lumen between an outer diameter of a first interventional device nested within a second interventional device and the inner diameter of the second interventional device) for sterilization. In some embodiments, the interventional device assembly can be packaged in a thermoformed tray and sealed with an HDPE (e.g., Tyvek®) lid. The interventional device assembly can be unpackaged by removal (e.g., opening or peeling off) of the lid by a user in a non-sterile field. A user in the sterile field can then remove the interventional device assembly and place it on the sterile work surface, for example, of a robotic drive table, as described herein.

Packaging the interventional devices in an assembled configuration and sterilized state can reduce the time associated with unpackaging and assembly of individual interventional devices and facilitate efficient connection to a robotic drive system. Each interventional device and hub combination may further be packaged with a fluidics connection for coupling to a fluid source and/or a vacuum source. In some embodiments, each hub or a hemostasis valve coupled to the hub may include the fluidics connection.

After the interventional device assembly is unpackaged (e.g., after the interventional device assembly is positioned on the robotic drive table), priming can be performed while the devices are concentrically nested or stacked. This is preferably accomplished in each fluid lumen, such as, for example, the annular lumen between the catheter 2906 and the catheter 2904 and in between each of the additional concentric interventional devices in the concentric stack. In certain embodiments, the fluid lumen can include a lumen between a distal hub and a proximal interventional device, such as, for example, the lumen between the hub 2914 and the catheter 2904. In certain embodiments, priming can be performed while the devices are still in the sterile packaging.

The fluidics connections can be connected to a fluidics system for delivering saline and contrast media to the catheters and providing aspiration. In some embodiments, the fluidics connections may be passed outside the sterile field for connection to the fluidics system. Once connected, the fluidics system can perform a priming sequence to flush each catheter of the interventional device assembly with fluid (e.g., saline, contrast media, or a mixture of saline and contrast media). The priming sequence may also include flushing each corresponding catheter hub with fluid. The fluid may be de-aired or de-gassed by the fluidics system prior to priming. In some embodiments, a vacuum source of the fluidics system can also be used to evacuate air from each catheter while flushing with fluid. In certain embodiments, a tip of the catheter can be placed into a container of fluid, such as saline, contrast media, or a mixture of saline and contrast media, during priming so that the fluid in the container, and not air, is aspirated through the tip of the catheter when the vacuum source is applied. In other embodiments, the tip of the catheter may be blocked (for example, using a plug) so that air is not aspirated from the tip of the catheter when the vacuum source is applied. In certain embodiments, the priming process may be automated such that a user can provide a single command and each catheter (and in some embodiments, each corresponding catheter hub) can be primed, sequentially (for example, as described with respect to FIGS. 20A-20C) or simultaneously.

Additional details regarding fluidics systems are disclosed in U.S. patent application Ser. No. 17/879,614, entitled Multi Catheter System With Integrated Fluidics Management, filed Aug. 2, 2022, which is hereby expressly incorporated by reference in its entirety herein.

Fluid resistance within a lumen may be greater when there is a reduction in cross sectional luminal area for flow, for example, when a second interventional device (e.g., a catheter or guidewire) extends within the lumen of a first interventional device. The amount of fluid resistance can be affected by the length of the cross sectional narrowing, for example, due to a depth of axial insertion of the second interventional device within the first interventional device. A second interventional device extending partially through the lumen of a first interventional device will provide a smaller length of cross-sectional narrowing, and accordingly may result in a lower fluid resistance within the lumen of the first catheter, than if the second interventional device were to extend entirely through the lumen of the first interventional device. Thus, fluid resistance can be lowered by at least partially decreasing a depth of axial insertion (i.e., axial overlap) of a second interventional device into the lumen through which fluid is to be injected (e.g., a length of the second interventional device into its concentrically adjacent lumen).

In some embodiments, over certain depths of insertion of a second interventional device within a first interventional device (for example, when the second interventional device is at or near a maximum insertion depth within the first interventional device), the size of the fluid channel between the devices (e.g., the annular lumen between the first interventional device and the second interventional device) can lead to higher than desirable amounts of fluid resistance during a priming procedure. In some embodiments, the depth of insertion of the second interventional device within the first interventional device can be decreased to reduce the pressure needed to prime the catheter and reduce internal interference.

In some embodiments, a catheter in the interventional device assembly can be separated from the other interventional devices for priming to reduce the pressure needed to prime the catheter and reduce internal interference. The catheter being primed may be separated from the interventional devices within the lumen of the catheter by proximally retracting the interventional devices within the lumen of the catheter. For example, the interventional devices within the lumen of the catheter being primed can be proximally retracted from the catheter being primed as far as possible while still maintaining a nested or stacked relationship (e.g., at least about 2 cm or 5 cm or more axial overlap) in order to minimize the pressure needed to prime the catheter and minimize internal interference. In other words, a catheter can be separated from more proximal interventional devices for priming while a distal tip of an adjacent proximal interventional device is still positioned within the lumen of the catheter. Maintaining at least some of the distal tip of an adjacent proximal interventional device within the lumen of the catheter may allow for easier reinsertion and advancement of the proximal interventional device after priming.

In some embodiments, the axial overlap may be between about 2 cm and about 20 cm, between about 2 cm and 10 cm, between about 2 cm and 5 cm, between about 5 cm and 20 cm, between about 5 cm and 10 cm, or any other suitable range. In some embodiments, the axial overlap may be at least about 2 cm, at least about 5 cm, at least about 10 cm, at least about 20 cm, no more than 2 cm, no more than 5 cm, no more than 10 cm, no more than 20 cm, about 2 cm, about 5 cm, about 10 cm, about 20 cm, or any other suitable amount.

In some embodiments, the robotic drive table can be programed to proximally retract the inner interventional device(s) from the catheter being primed as much as possible while still maintaining a nested or stacked relationship. In other embodiments, the robotic drive table can be programmed to separate inner devices from the catheter being primed to a distance sufficient to optimize the length of the unobstructed lumen and result in an amount of fluid resistance lower than a threshold value. After the catheter being primed is separated from the other interventional devices, the catheter can be primed by flushing the catheter with fluid, such as saline, contrast media, or a mixture of saline and contrast media.

After the catheter is primed, it may be returned to an initial position and a next catheter of the interventional device assembly can be separated from the other interventional devices within its lumen for priming. This sequence can be repeated for each catheter of the interventional device assembly. In other embodiments, after a catheter is primed, it may be advanced to a ready or drive position to begin insertion into the patient. While the foregoing describes separating catheters to be primed by retraction of inner interventional devices, an outer catheter may also be separated from inner interventional devices by distally axially advancing the outer catheter relative to the inner interventional devices. An example of a priming process is described with respect to FIGS. 20A-20C.

Figures 20A, 20B, 20C:
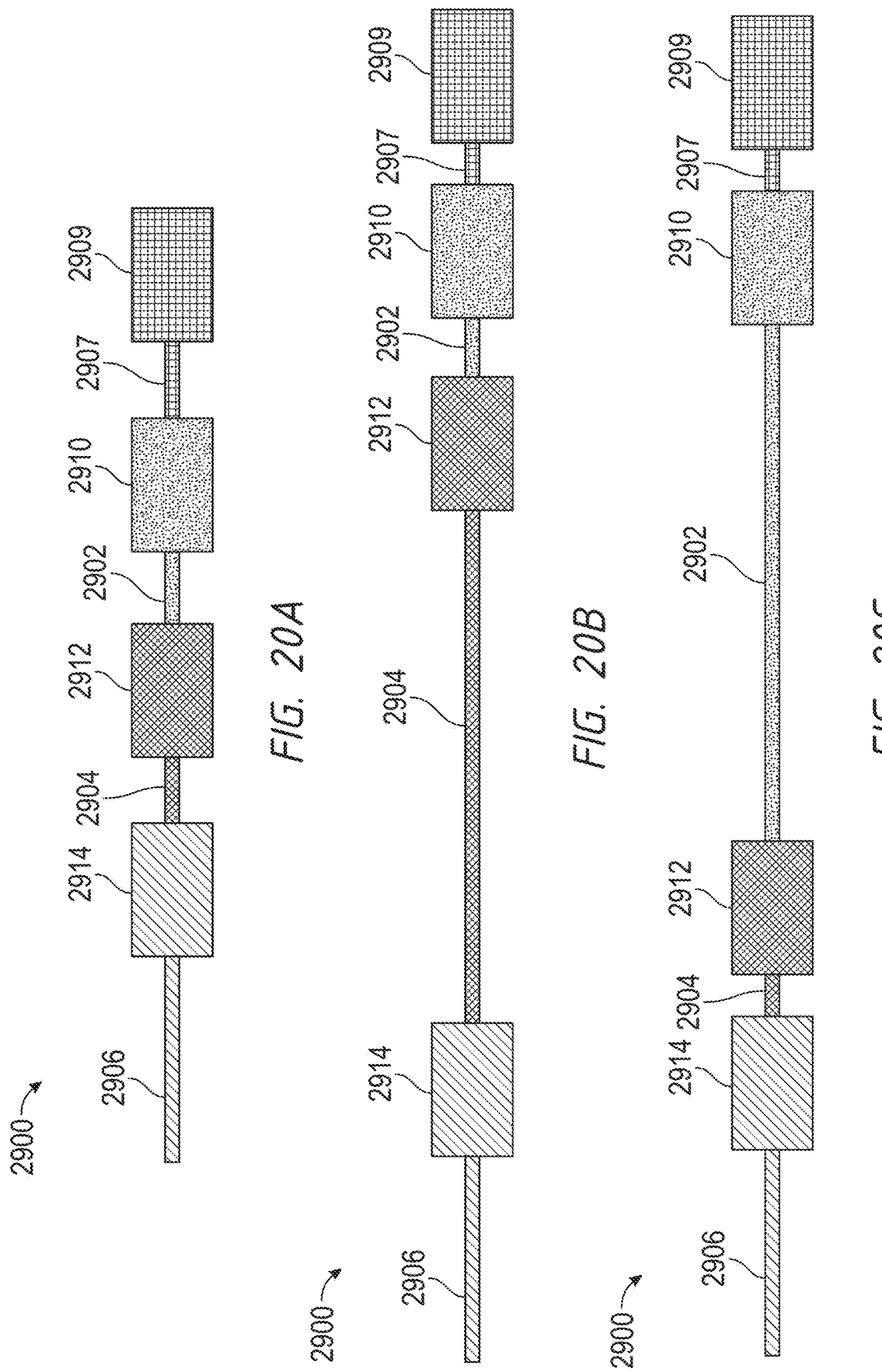
FIGS. 20A-20C depict an example sequence of steps of priming a catheter assembly in a stacked configuration.

FIG. 20A depicts the interventional device assembly 2900 assembled in a concentric stack and axially compressed configuration. As shown in FIG. 20A, the interventional devices can be fully nested within each other. This may be the configuration following unpackaging of the device assembly 2900 and placement onto the robotic drive table. A priming sequence may begin by distally axially advancing the catheter 2906 and hub 2914 relative to the catheter 2904, hub 2912, catheter 2902, hub 2910, guidewire 2907, and hub 2909, for example, as far as possible while maintaining a distal tip of the catheter 2904 within the lumen of the catheter 2906, as shown in FIG. 20B, or to a distance that will result in a desirable amount of fluid resistance for priming. In some embodiments, the catheter 2906 is advanced in response to a control signal from a control system. The catheter 2906 can then be primed by introducing priming fluid using the fluidics system. In some embodiments, priming fluid is introduced in response to a control signal from a control system. Priming the catheter 2906 can include priming the hub 2914. For example, in certain embodiments, the hub 2914 or a hemostasis valve coupled thereto can include fluidics connections to receive priming fluid from the fluidics system. After priming, the catheter 2906 can be returned to its initial position (e.g., the fully axially compressed configuration) as shown in FIG. 20A. In some embodiments, the catheter 2906 is returned to its initial position in response to a control signal from a control system.

After the catheter 2906 is primed and returned to its initial position, the catheter 2904 and hub 2912 can be distally axially advanced relative to the catheter 2902, hub 2910, guidewire 2907 and hub 2909 (also distally axially advancing the catheter 2906 and hub 2914 without changing or minimally changing their relative position with respect to catheter 2904), for example, as far as possible while maintaining a distal tip of the catheter 2902 within the lumen of the catheter 2904, as shown in FIG. 20C, or to a distance that will result in a desirable amount of fluid resistance for priming. In some embodiments, the catheter 2904 and the catheter 2906 are advanced in response to a control signal from a control system. The catheter 2904 can then be primed by introducing priming fluid using the fluidics system. In some embodiments, priming fluid is introduced in response to a control signal from a control system. Priming the catheter 2904 can include priming the hub 2912. For example, in certain embodiments, the hub 2912 or a hemostasis valve coupled thereto can include fluidics connections to receive priming fluid from the fluidics system. After priming, the catheter 2904 and catheter 2906 can be returned to their initial positions (e.g., the fully axially compressed configuration) as shown in FIG. 20A. In some embodiments, the catheter 2904 and the catheter 2906 are returned to their initial position in response to a control signal from a control system.

After the catheter 2904 is primed and returned to its initial position, the catheter 2902 and hub 2910 can be distally axially advanced relative to the guidewire 2907 and hub 2909 (also distally axially advancing the catheter 2906, hub 2914, catheter 2904, and hub 2912 without changing or minimally changing their relative positions with respect to the catheter 2902), for example, as far as possible while maintaining a distal tip of the guidewire 2907 within the lumen of the catheter 2902, or to a distance that will result in a desirable amount of fluid resistance for priming. In some embodiments, the catheter 2902, the catheter 2904, and the catheter 2906 are advanced in response to a control signal from a control system. The catheter 2902 can then be primed by introducing priming fluid using the fluidics system. In some embodiments, priming fluid is introduced in response to a control signal from a control system. Priming catheter 2902 can include priming the hub 2910. For example, in certain embodiments, the hub 2910 or a hemostasis valve coupled thereto can include fluidics connections to receive priming fluid from the fluidics system. After priming, the catheter 2902 and catheters 2904 and 2906 can be returned to their initial positions (e.g., the fully axially compressed configuration) shown in FIG. 20A. In some embodiments, the catheter 2902, the catheter 2904, and the catheter 2906 are returned to their initial position in response to a control signal from a control system.

In some embodiments, the priming procedure described with respect to FIGS. 20A-20C may be performed in response to a single control signal from a control system. In other embodiments, various steps of the priming procedure may be performed in response to unique control signals. In some embodiments, priming of each unique interventional device can be performed in response to a unique control signal.

In alternative embodiments, each of the catheters can be distally separated from one another simultaneously for priming. For example, the catheter 2902 can be distally separated from the guidewire 2907 while maintaining the distal tip of the guidewire 2907 in the lumen of the catheter 2902, the catheter 2904 can be distally separated from the catheter 2902 while maintaining the distal tip of the catheter 2902 in the lumen of the catheter 2904, and the catheter 2906 can be distally separated from the catheter 2904 while maintaining the distal tip of the catheter 2904 in the lumen of the catheter 2906 simultaneously. However, an embodiment in which only one set of adjacent hubs is separated at a time, as described with respect to FIGS. 20A-20C, can provide a smaller overall length of the assembly at any particular time, which can allow for use with a smaller robotic drive system. While separation of outer catheters from their inner interventional devices is described as distally axially advancing the catheters relative to their inner interventional devices, separation can include proximally retracting the inner interventional devices from the outer catheters.

In alternative embodiments, one or more of the catheter 2902, the catheter 2904, and the catheter 2906 can be advanced to a ready or drive position to begin insertion into the patient after priming (e.g., prior to priming a subsequent catheter). In such embodiments, the catheters may advance to the ready or drive position without returning to their initial position after priming.

As described above, in some embodiments, the catheters 2902, 2904, and 2906 may be assembled into the concentric stack orientation illustrated in FIG. 17 prior to flushing the catheters to remove air by displacing it with a fluid such as saline contrast media, or a mixture of saline and contrast media. This is preferably accomplished in each fluid lumen, such as, for example, the annular lumen between the catheter 2906 and the catheter 2904 and in between each of the additional concentric interventional devices in the concentric stack. Infusing fluid (e.g., saline, contrast media, or a mixture of saline and contrast media) under pressure may displace substantially all of the air but some small bubbles may remain, adhering to the inside wall of an outer catheter (e.g., the guide catheter 2906), the outside wall of an inner catheter (e.g., the procedure catheter 2904), or both.

While fluid is being introduced under pressure into the proximal end of the annular lumen (e.g., into a hub of the outer catheter or a hemostasis valve coupled thereto), the inner catheter may be moved with respect to the outer catheter, to disrupt the holding forces between the microbubbles and adjacent wall and allow the bubbles to be carried downstream and out through the distal opening of the lumen or removed via aspiration. The catheters may be moved axially, rotationally or both with respect to each other. In certain embodiments, the catheters may be reciprocated axially, rotationally, or both with respect to each other. In some embodiments, the catheters may be moved intermittently axially, rotationally, or both. In other embodiments, the catheters may be rotated continuously or in a constant direction. Rotational movement between catheters and/or the interventional devices described herein can include rotationally moving the catheters and/or the interventional devices through an angle with respect to each other. Such angle can be less than 360 degrees, about 360 degrees, or more than 360 degrees.

In some implementations, a first catheter is moved reciprocally with respect to an adjacent catheter or guidewire such as axially over a stroke length in a range of from about 1 mm to about 250 mm, from about 10 mm to about 250 mm, from about 5 mm to about 125 mm, from about 25 mm to about 125 mm, from about 10 mm to about 50 mm, from about 15 mm to about 30 mm, from about 5 mm to about 30 mm, from about 15 mm to about 25 mm, from about 20 mm to about 40 mm, or any other suitable range. In some implementations, a first catheter is moved reciprocally with respect to an adjacent catheter or guidewire such as axially over a stroke length of at least 5 mm, at least 10 mm, at least 15 mm, at least 20 mm, at least 25 mm, at least 30 mm, at least 50 mm, no more than 10 mm, no more than 20 mm, no more than 25 mm, no more than 30 mm, no more than 50 mm, no more than 125 mm, no more than 150 mm, about 5 mm, about 10 mm, about 15 mm, about 20 mm, about 25 mm, about 30 mm, about 50 mm, or any other suitable stroke length.

In some implementations, a first catheter is moved reciprocally with respect to an adjacent catheter or guidewire such as axially at a reciprocation frequency in a range of from about 0.5 Hz to about 1 Hz, from about 1 Hz to about 5 Hz, from about 1 Hz to about 10 Hz, from about 1 Hz to about 25 Hz, from about 5 Hz to about 10 Hz, from about 10 Hz to about 25 Hz, or any other suitable range of frequencies. In some implementations, the first catheter is moved reciprocally with respect to an adjacent catheter or guidewire such as axially at a reciprocation frequency of at least 0.5 Hz, at least 1 Hz, at least 2 Hz, at least 5 Hz, at least 10 Hz, at least 25 Hz, no more than 0.5 Hz, no more than 1 Hz, no more than 2 Hz, no more than 5 Hz, no more than 10 Hz, no more than 25 Hz, about 0.5 Hz, about 1 Hz, about 2 Hz, about 5 Hz, about 10 Hz, about 25 Hz or any other suitable frequency.

In one implementation, a first catheter is moved reciprocally with respect to the adjacent catheter or guidewire such as axially over a stroke length in a range of from about 0.5 inches to about 10 inches, or from about one inch to about 5 inches at a reciprocation frequency of no more than about 5 cycles per second or two cycles per second or less.

In some implementations, a first catheter is moved reciprocally with respect to an adjacent catheter or guidewire such as rotationally over an angle of rotation per stroke in a range of from about 5 degrees to about 180 degrees, from about 5 degrees to about 360 degrees, from about 15 degrees to about 180 degrees, from about 15 degrees to about 150 degrees, from about 15 degrees to about 120 degrees, from about 15 degrees to about 90 degrees, form about 15 degrees to about 60 degrees, from about 15 degrees to about 30 degrees, from about 30 degrees to about 180 degrees, from about 30 degrees to about 150 degrees, from about 30 degrees to about 120 degrees, from about 30 degrees to about 90 degrees, form about 30 degrees to about 60 degrees, from about 60 degrees to about 180 degrees, from about 60 degrees to about 150 degrees, from about 60 degrees to about 120 degrees, from about 60 degrees to about 90 degrees, from about 90 degrees to about 180 degrees, from about 90 degrees to about 150 degrees, from about 90 degrees to about 120 degrees, from about 120 degrees to about 180 degrees, from about 120 degrees to about 150 degrees, from about 150 degrees to about 180 degrees or any other suitable range. In some implementations, a first catheter is moved reciprocally with respect to an adjacent catheter or guidewire such as rotationally over an angle of rotation per stroke of at least 5 degrees, at least 15 degrees, at least 30 degrees, at least 60 degrees, at least 90 degrees, at least 120 degrees, at least 150 degrees, at least 180 degrees, at least 360 degrees, no more than 5 degrees, no more than 15 degrees, no more than 30 degrees, no more than 60 degrees, no more than 90 degrees, no more than 120 degrees, no more than 150 degrees, no more than 180 degrees, no more than 360 degrees, about 5 degrees, about 15 degrees, about 30 degrees, about 60 degrees, about 90 degrees, about 120 degrees, about 150 degrees, about 180 degrees, about 360 degrees, or any other suitable angle.

In some implementations, a first catheter is moved reciprocally with respect to an adjacent catheter or guidewire such as rotationally at a reciprocation frequency in a range of from about 0.5 Hz to about 1 Hz, from about 1 Hz to about 5 Hz, from about 1 Hz to about 10 Hz, from about 1 Hz to about 25 Hz, from about 5 Hz to about 10 Hz, from about 10 Hz to about 25 Hz, or any other suitable range of frequencies. In some implementations, the first catheter is moved reciprocally with respect to an adjacent catheter or guidewire such as rotationally at a reciprocation frequency of at least 0.5 Hz, at least 1 Hz, at least 2 Hz, at least 5 Hz, at least 10 Hz, at least 25 Hz, no more than 0.5 Hz, no more than 1 Hz, no more than 2 Hz, no more than 5 Hz, no more than 10 Hz, no more than 25 Hz, about 0.5 Hz, about 1 Hz, about 2 Hz, about 5 Hz, about 10 Hz, about 25 Hz or any other suitable frequency.

In some implementations, a first catheter is moved reciprocally with respect to an adjacent catheter or guidewire for a number of reciprocations between 1 and 200, between 1 and 100, between 1 and 50, between 1 and 25, between 1 and 15, between 1 and 10, between 1 and 5, between 5 and 25, between 5 and 15, between 5 and 10, or any other suitable range. In some implementations, a first catheter is moved reciprocally with respect to an adjacent catheter or guidewire for at least 1 reciprocation, at least 2 reciprocations, at least 5 reciprocations, at least 10 reciprocations, at least 15 reciprocations, at least 25 reciprocations, at least 50 reciprocations, no more than 5 reciprocations, no more than 10 reciprocations, no more than 15 reciprocations, no more than 25 reciprocations, no more 50 than reciprocations, no more than 100 reciprocations, no more than 200 reciprocations, about 1 reciprocation, about 2 reciprocations, about 5 reciprocations, about 10 reciprocations, about 25 reciprocations, about 50 reciprocations, about 100 reciprocations, about 200 reciprocations, or any other suitable number. One reciprocation can include a movement (axially or rotationally) from a first position to a second position followed by a return from the second position to the first position.

In some implementations, a first catheter is moved reciprocally with respect to an adjacent catheter or guidewire over a length of time in a range of from 1 about second to about 60 seconds, from about 1 second to about 45 seconds, from about 1 second to about 30 seconds, from about 1 second to about 20 seconds, from about 1 second to about 15 seconds, from about 1 second to about 10 seconds, from about 5 seconds to about 45 seconds, from about 5 seconds to about 30 seconds, from about 5 seconds to about 20 seconds, from about 5 seconds to about 15 seconds, from about 5 seconds to about 10 seconds, from about 10 seconds to about 30 seconds, form about 10 seconds to about 20 seconds, or any other suitable range. In some implementations, a first catheter is moved reciprocally with respect to an adjacent catheter or guidewire over a length of time of at least 1 second, at least 5 seconds, at least 10 seconds, at least 15 seconds, at least 20 seconds, at least 30 seconds, at least 45 seconds, at least 60 seconds, no more than 5 seconds, no more than 10 seconds, no more than 15 seconds, no more than 20 seconds, no more than 30 seconds, no more than 45 seconds, no more than 60 seconds, about 5 seconds, about 10 seconds, about 15 seconds, about 20 seconds, about 30 seconds, about 45 seconds, about 60 seconds, or any other suitable length of time.

Reciprocation of adjacent catheters to disrupt microbubbles may be accomplished manually by grasping the corresponding catheter hubs and manually moving the catheters axially or rotationally with respect to each other while delivering pressurized fluid (e.g., saline, contrast media, or a mixture of saline and contrast media). Alternatively, such as in a robotically driven system, a processor may be configured to robotically drive at least one of two adjacent catheter hubs (for example, at least one of hub 2914 and hub 2912) to achieve relative movement between the adjacent catheters thereby disrupting and expelling microbubbles, such as in response to user activation of a flush control. For example, in certain embodiments, two adjacent interventional devices may be moved relative to one another in response to a control signal from a control system. In certain embodiments, delivery of pressurized fluid may be performed in response to a control signal from a control system.

The reciprocation of adjacent catheters may generate shear forces that dislodge the air bubbles. For example, relative movement of the inner and outer surfaces of adjacent catheters may increase the fluid shear rate between the adjacent catheters during priming in comparison to static surfaces. In some embodiments, the shear force can be increased by increasing the flow rate of the solution (e.g., saline, contrast media, or a mixture of saline and contrast media) being provided by the fluidics system. In certain embodiments, both flow rate and relative movement between adjacent catheters are controlled to dislodge air bubbles.

In some embodiments, after each catheter is primed by the fluidics system, an ultrasound bubble detector may be used to confirm that the catheters are substantially free of air bubbles. For example, an ultrasound chip (such as mounted within a hub adjacent a catheter receiving lumen) may be run along the length of the catheters to confirm that no air bubbles remain in the system.

Figure 21A:
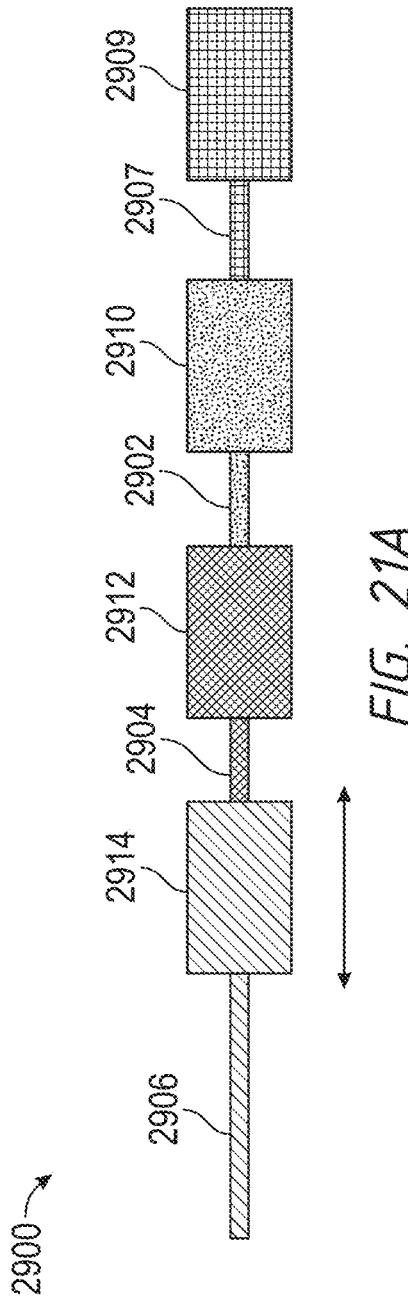
FIGS. 21A-21B depict an example sequence of steps of priming a catheter assembly in a stacked configuration.
Figure 21B:
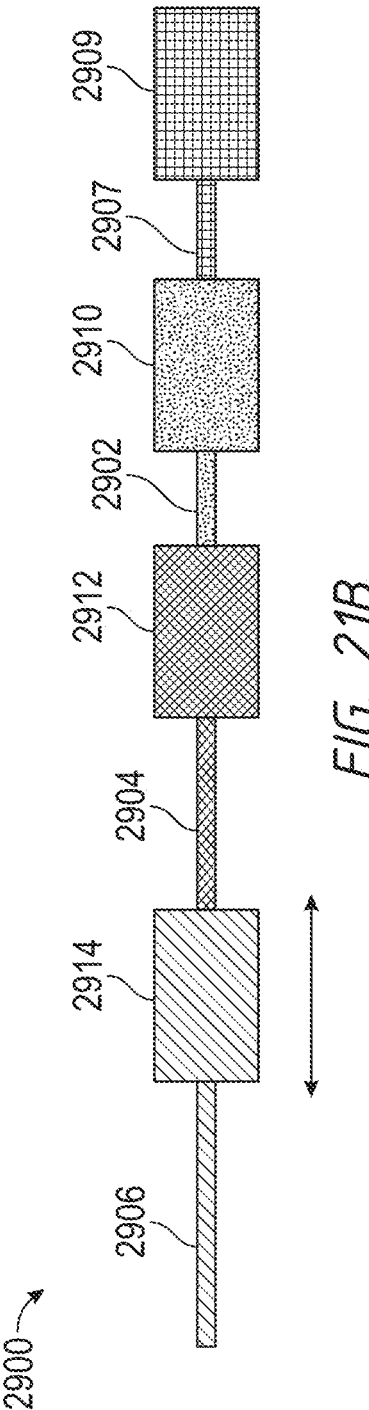

An example of a priming process including reciprocal movement of adjacent catheters is described with respect to FIGS. 21A-21B.

FIG. 21A depicts the interventional device assembly 2900 assembled in a concentric stack configuration. As shown in FIG. 21A, the interventional devices can be fully nested within each other. This may be the configuration following unpackaging of the device assembly 2900 and placement onto the robotic drive table. Alternatively, individual interventional devices of the device assembly 2900 can be assembled into the device assembly 2900 on the drive table.

A priming sequence may begin by priming the catheter 2906. In some embodiments, the catheter 2906 can be primed by introducing fluid (e.g., saline, contrast media, or a mixture of saline and contrast media) under pressure into the lumen of the catheter 2906 while generating reciprocal movement of catheter 2906 and/or hub 2914, axially, rotationally or both, relative to the catheter 2904. Priming the catheter 2906 can include priming the hub 2914. For example, in certain embodiments, the hub 2914 or a hemostasis valve coupled thereto can include fluidics connections to receive priming fluid from the fluidics system. In certain embodiments, the catheter 2906 and/or hub 2914 can be axially agitated back and forth along a longitudinal axis of the catheter 2906 (e.g., between the position of FIG. 21A and the position of FIG. 21B). Axial and/or rotational reciprocal motion of the catheter 2906 and/or hub 2914 can be performed manually or by a robotic drive table. Reciprocal movement may be generated in response to a control signal from a control system. Introducing fluid under pressure may be performed in response to a control signal from a control system.

In some embodiments, priming of the catheter 2906 may be performed by introducing fluid (e.g., saline, contrast media, or a mixture of saline and contrast media) under pressure into the lumen of the catheter 2906 while generating reciprocal movement of the catheter 2904 and/or hub 2912, axially, rotationally or both, relative to the catheter 2906. Axial and/or rotational reciprocal motion of the catheter 2904 and/or hub 2912 can be performed manually or by a robotic drive table. Reciprocal movement may be generated in response to a control signal from a control system. Introducing fluid under pressure may be performed in response to a control signal from a control system.

In some embodiments, priming of the catheter 2906 may be performed by introducing fluid (e.g., saline, contrast media, or a mixture of saline and contrast media) under pressure into the lumen of the catheter 2906 while generating reciprocal movement of both the catheter 2906 (and/or hub 2914) and the catheter 2904 (and/or hub 2912), axially, rotationally or both, relative to one another. Reciprocal movement may be generated in response to a control signal from a control system. Introducing fluid under pressure may be performed in response to a control signal from a control system.

In some embodiments, after priming the catheter 2906, the catheter 2906 can be returned to an initial position as shown in FIG. 21A. In other embodiments, after priming the catheter 2906, the catheter 2906 can be advanced to a ready or drive position to begin insertion into the patient.

In some embodiments, after the catheter 2906 is primed, the catheter 2904 can be primed. Priming the catheter 2904 can include priming the hub 2912. For example, in certain embodiments, the hub 2912 or a hemostasis valve coupled thereto can include fluidics connections to receive priming fluid from the fluidics system. In some embodiments, the catheter 2904 can be primed by introducing fluid (e.g., saline, contrast media, or a mixture of saline and contrast media) under pressure into the lumen of the catheter 2904 while generating reciprocal movement of the catheter 2904 and/or hub 2912, axially, rotationally or both, relative to the catheter 2902. Reciprocal movement may be generated in response to a control signal from a control system. Introducing fluid under pressure may be performed in response to a control signal from a control system.

In some embodiments, priming of the catheter 2904 may be performed by introducing fluid (e.g., saline, contrast media, or a mixture of saline and contrast media) under pressure into the lumen of the catheter 2904 while generating reciprocal movement of the catheter 2902 and/or hub 2910, axially, rotationally or both, relative to the catheter 2904. Axial and/or rotational reciprocal motion of the catheter 2902 and/or hub 2910 can be performed manually or by a robotic drive table. Reciprocal movement may be generated in response to a control signal from a control system. Introducing fluid under pressure may be performed in response to a control signal from a control system.

In some embodiments, priming of the catheter 2904 may be performed by introducing fluid (e.g., saline, contrast media, or a mixture of saline and contrast media) under pressure into the lumen of the catheter 2904 while generating reciprocal movement of both the catheter 2904 (and/or hub 2912) and the catheter 2902 (and/or hub 2910), axially, rotationally or both, relative to one another. Reciprocal movement may be generated in response to a control signal from a control system. Introducing fluid under pressure may be performed in response to a control signal from a control system.

In some embodiments, after priming the catheter 2904, the catheter 2904 can be returned to an initial position as shown in FIG. 21A. In some embodiments, after priming the catheter 2904, the catheter 2904 can be advanced to a ready or drive position to begin insertion into the patient.

In some embodiments, after the catheter 2904 is primed, the catheter 2902 can be primed. Priming the catheter 2902 can include priming the hub 2910. For example, in certain embodiments, the hub 2910 or a hemostasis valve coupled thereto can include fluidics connections to receive priming fluid from the fluidics system. In some embodiments, the catheter 2902 can be primed by introducing fluid (e.g., saline, contrast media, or a mixture of saline and contrast media) under pressure into the lumen of the catheter 2902 while generating reciprocal movement of the catheter 2902 and/or hub 2910, axially, rotationally or both, relative to the guidewire 2907. Reciprocal movement may be generated in response to a control signal from a control system. Introducing fluid under pressure may be performed in response to a control signal from a control system.

In some embodiments, priming of the catheter 2902 may be performed by introducing fluid (e.g., saline, contrast media, or a mixture of saline and contrast media) under pressure into the lumen of the catheter 2902 while generating reciprocal movement of the guidewire 2907 and/or hub 2909, axially, rotationally or both, relative to the catheter 2902. Axial and/or rotational reciprocal motion of the guidewire 2907 and/or hub 2909 can be performed manually or by a robotic drive table. Reciprocal movement may be generated in response to a control signal from a control system. Introducing fluid under pressure may be performed in response to a control signal from a control system.

In some embodiments, priming of the catheter 2902 may be performed by introducing fluid (e.g., saline, contrast media, or a mixture of saline and contrast media) under pressure into the lumen of the catheter 2902 while generating reciprocal movement of both the catheter 2902 (and/or hub 2910) and the guidewire 2907 (and/or hub 2909), axially, rotationally or both, relative to one another. Reciprocal movement may be generated in response to a control signal from a control system. Introducing fluid under pressure may be performed in response to a control signal from a control system.

In some embodiments, after priming the catheter 2902, the catheter 2902 can be returned to an initial position as shown in FIG. 21A. In other embodiments, after priming the catheter 2902, the catheter 2902 can be advanced to a ready or drive position to begin insertion into the patient.

In some embodiments, the priming procedure described with respect to FIGS. 21A and 21B may be performed in response to a single control signal from a control system. In other embodiments, various steps of the priming procedure may be performed in response to unique control signals. In some embodiments, priming of each unique interventional device can be performed in response to a unique control signal.

In the priming sequence described herein with respect to FIGS. 21A and 21B, the catheters are primed in order starting with the catheter 2906, followed by the catheter 2904, and then followed by the catheter 2902. However, it is contemplated that the catheters may be primed in any order. The catheters may be primed in series as described above with respect to FIGS. 21A and 21B. Alternatively, two or more of the catheters or each of the catheters may be primed in parallel.

In certain embodiments, priming the catheters can include decreasing a depth of axial insertion (i.e., axial overlap) of a second interventional device into the lumen of a first interventional device through which fluid is to be injected (e.g., a length of the second interventional device into its concentrically adjacent lumen), as described with respect. to FIGS. 20A-20C, and also generating relative reciprocal movement, axially, rotationally or both, between first interventional device and the second interventional device during priming, as discussed with respect to FIGS. 21A and 21B.

In some implementations, priming of a catheter can include vibrating at least a portion of the catheter and/or its associated hub when included. Vibration can be induced, for example, by an electric motor incorporated into a hub of the catheter, or by a separate electric motor or source of vibration put against the catheter when priming. In some implementations, at least a portion of the support table on which the catheters and/or their associated hubs are placed upon can vibrate during priming of any one or more catheters to aid in removal of air and/or microbubbles of air. Such vibration can be performed by an electric motor.

Figure 22:
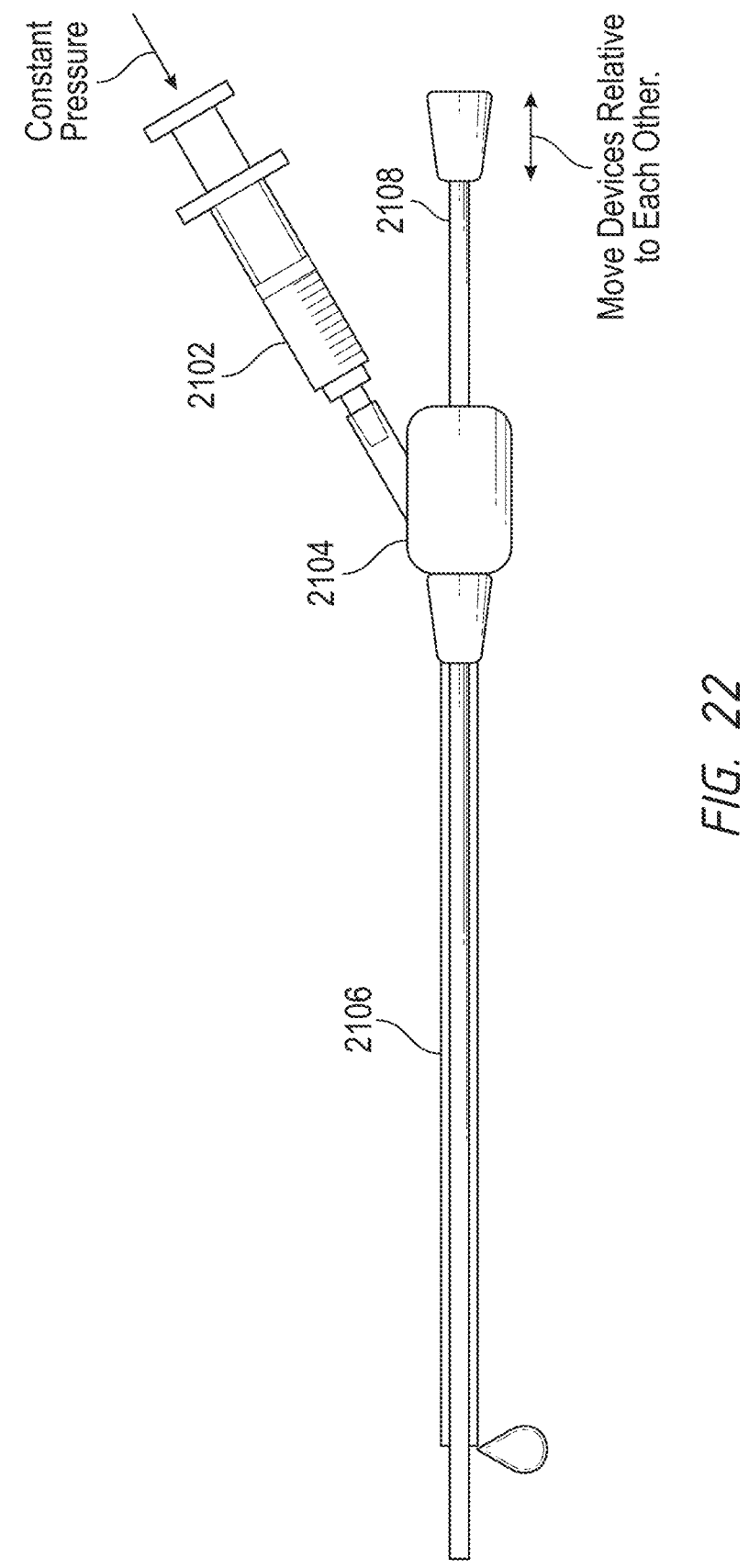
FIG. 22 depicts an example test system for the priming process depicted in FIGS. 21A-21B.
Figure 23A:
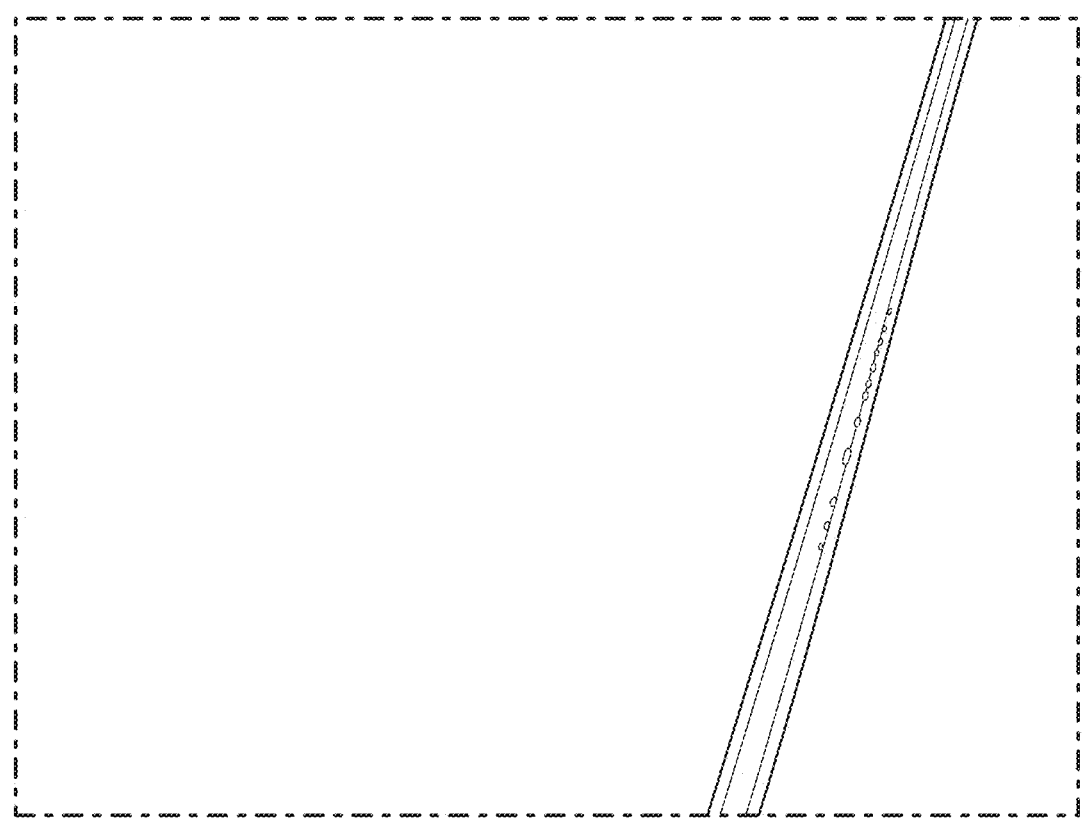
FIG. 23A shows an example of a catheter assembly.

FIG. 22 is a diagram of a test system that was used for detecting the removal of air bubbles between concentrically stacked catheters. The test system included an inner catheter 2108 positioned within an interior lumen of an outer catheter 2106 in a concentric stack. The outer catheter 2106 was coupled to a rotating hemostasis valve 2104. The hemostasis valve 2104 was coupled to a syringe 2102 so that fluid injected using the syringe would flow through the lumen between the inner catheter 2108 and the outer catheter 2016. In the test system, the inner catheter 2108 had a diameter of about 0.071 inches. The outer catheter 2106 had a diameter of about 0.088 inches. The outer catheter 2106 was transparent to permit visualization of bubbles within the lumen. A distal end of the outer catheter 2108 allowed for small volumes of fluid to exit the outer catheter. FIG. 23A is an illustration showing the catheter 2106 and catheter 2108 in a concentric stack, prior to injection of fluid.

Figure 23B:
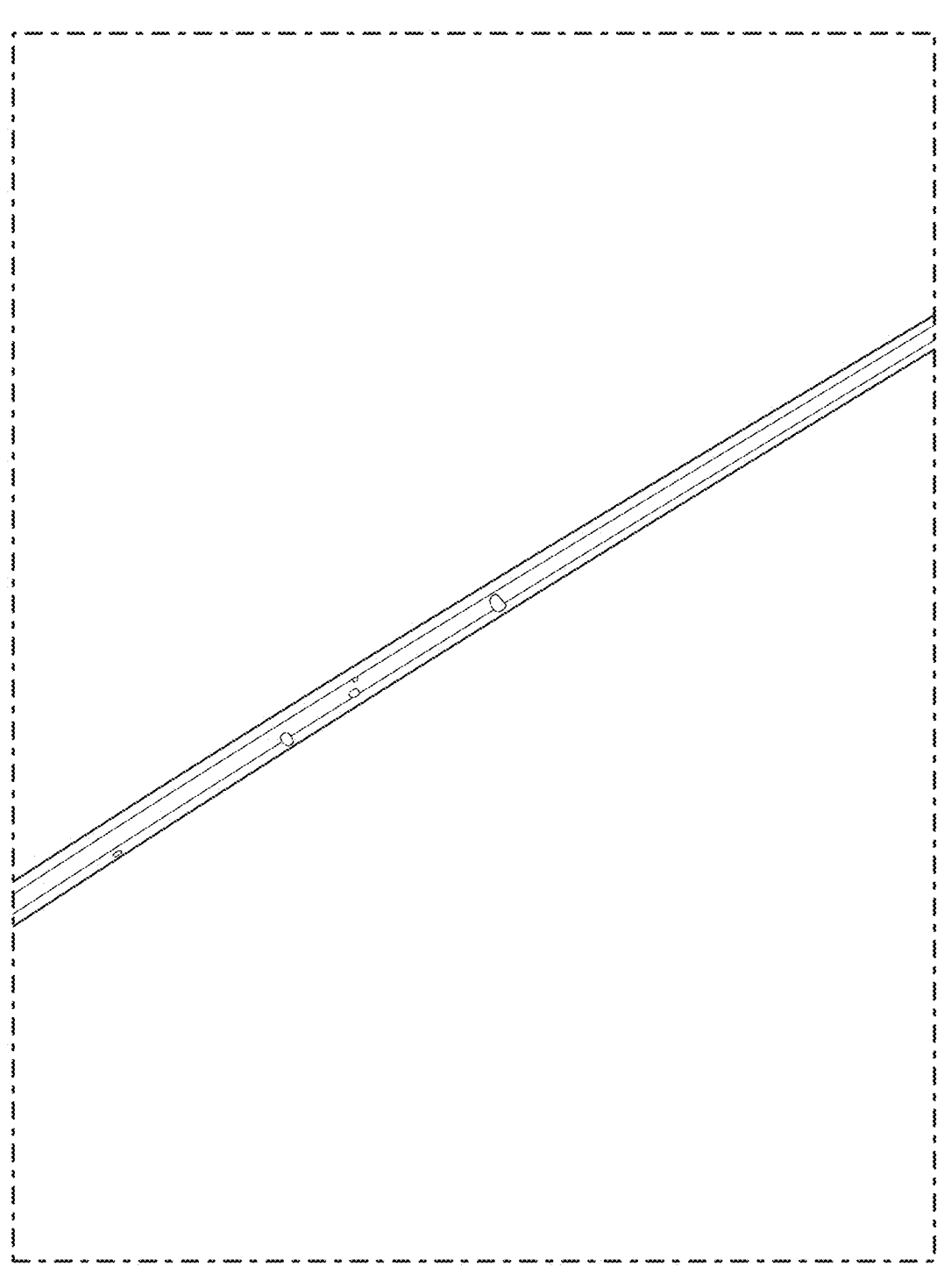
FIG. 23B shows an example of a catheter assembly after a priming procedure.

In a first example, the syringe 2102 was used to inject water at a constant pressure of about 150 psi through the hemostasis valve 2104 without moving the catheter 2106 or the catheter 2108. FIG. 23B is an illustration showing catheter 2106 and catheter 2108 following the injection of water. As shown in FIG. 23B, bubbles are present within the lumen between the catheter 2106 and the catheter 2108.

Figure 23C:
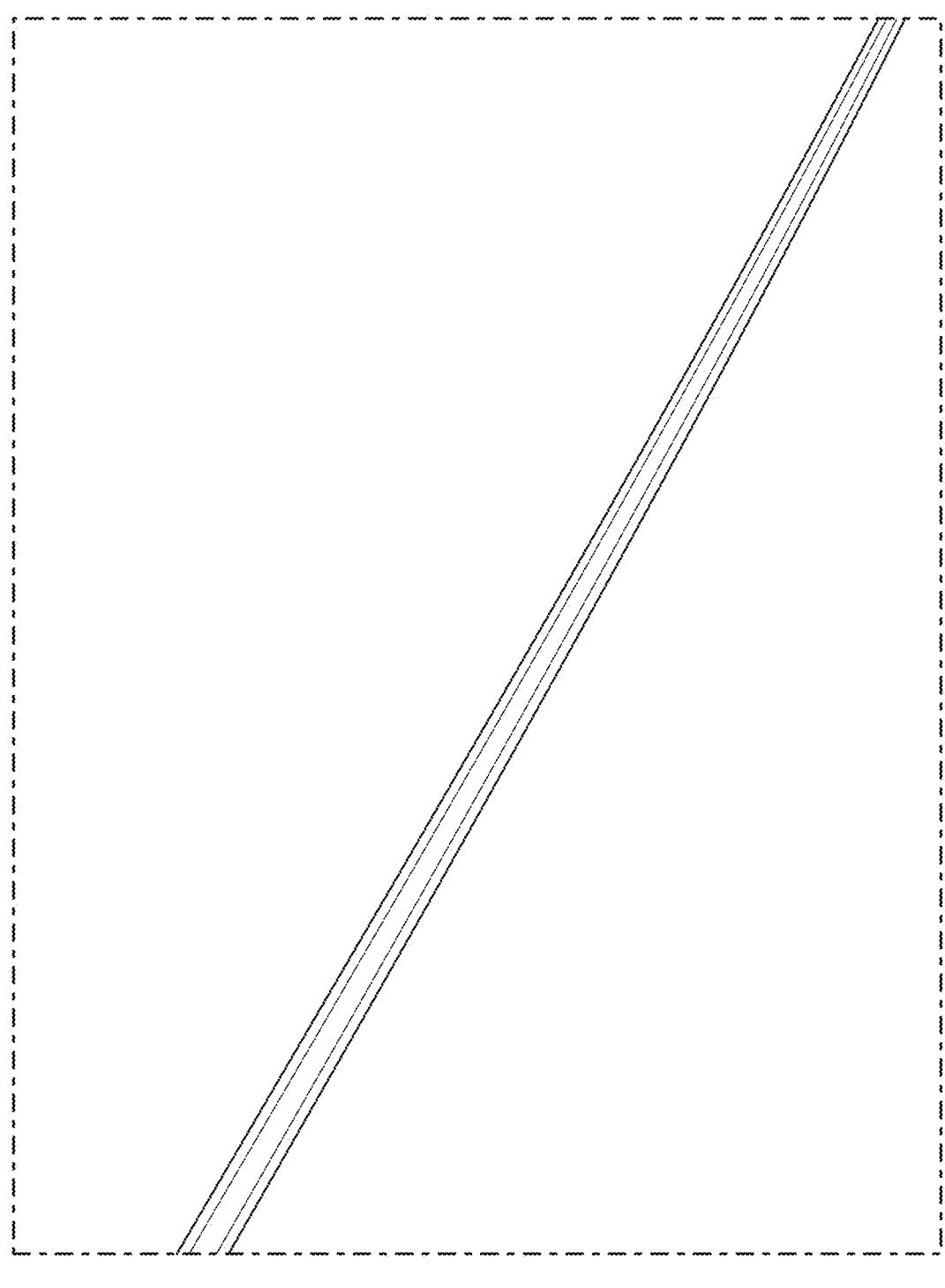
FIG. 23C shows an example of a catheter assembly after a priming procedure including relative movement between adjacent catheters.

In a second example, the syringe 2102 was used to inject water at a constant pressure of about 150 psi through the hemostasis valve 2104. Shortly after beginning to inject water, axial reciprocal movement of the inner catheter 2108 was performed for about 10 seconds. The reciprocal movement was performed at a frequency of about 1 Hz (or less) and a stroke length of about 20 mm (or more). FIG. 23C is an illustration showing the catheter 2106 and the catheter 2108 following the axial reciprocal movement. As shown in FIG. 23C, the lumen between the catheter 2106 and the catheter 2108 was substantially free of bubbles.

In a third example, an outer catheter having a diameter of about 0.071 inches and an inner catheter having a diameter of about 0.035 inches were used in the test system 2100 instead of the outer catheter 2106 and the inner catheter 2108 described with respect to Examples 1 and 2. A syringe 2102 was used to inject water at a constant pressure of about 150 psi through a hemostasis valve 2104 coupled to the outer catheter. Shortly after beginning to inject water, axial reciprocal movement of the inner catheter was performed for about 10 seconds. The reciprocal movement was performed at a frequency of about 1 Hz (or less) and a stroke length of about 20 mm (or more). Following the axial reciprocal movement, the lumen between the outer and inner catheters was found to be substantially free of bubbles by visual inspection.

FIG. 67 illustrates a schematic view of an example of a control system 4000 that may be used to electronically control the systems and components described herein and/or perform the methods described herein. The control system 4000 may be configured to automatically adjust various motors, hub adapters, hubs, interventional devices, fluidics components (e.g., valves, pumps, etc.), and/or any other components described herein in response to commands input by an operator such as a physician. In response to command inputs by an operator, the control system 4000 may cause a series of responsive events to automatically occur.

In certain embodiments, the control system 4000 can include one or more processors 4002. The one or more processors 4002 can be configured to automatically adjust the various system components described herein in response to commands input by an operator, for example, using one or more controls 4004 of the control system 4000. A single control 4004 is shown in FIG. 67. However, any suitable number of controls may be provided to correspond to various functions of the systems described herein. For example, in certain embodiments, each interventional device may have its own unique control 4004 or set of controls 4004 that can control various functions of the interventional device (e.g., axial movement, rotational movement, supply of fluids (e.g., saline, contrast, etc.), aspiration, etc.).

In certain embodiments, one or more controls 4004 may control priming functions for one or more interventional devices. For example, one or more controls 4004 can be operated to cause the interventional devices to perform a priming procedure, as described for example, with reference to FIGS. 20A-20C. For example, one or more controls 4004 can be operated to cause axial movement of one or more interventional devices relative to one or more other interventional devices (e.g., by causing axial movement of corresponding hubs and/or hub adapters). One or more controls 4004 can be operated to cause introduction of fluid into the lumen of an interventional device to prime the interventional device.

In certain embodiments, one or more controls 4004 may be operated to cause the interventional devices to perform a priming procedure, as described for example, with reference to FIGS. 21A-21B. For example, one or more controls 4004 can be operated to cause reciprocal movement (e.g., axial and/or rotational reciprocal movement) of one or more interventional devices relative to one or more other interventional devices (e.g., by causing reciprocal movement of corresponding hubs and/or hub adapters). One or more controls 4004 can be operated to cause introduction of fluid into the lumen of an interventional device to prime the interventional device (e.g., during relative reciprocal movement).

The processor 4002 may receive signals from the one or more controls 4004 and in response, initiate corresponding actions in the components of the systems described herein. For example, the processor 4002 may be configured to generate output signals that cause responsive actions to be performed by the components of the described herein.

Figure 24:
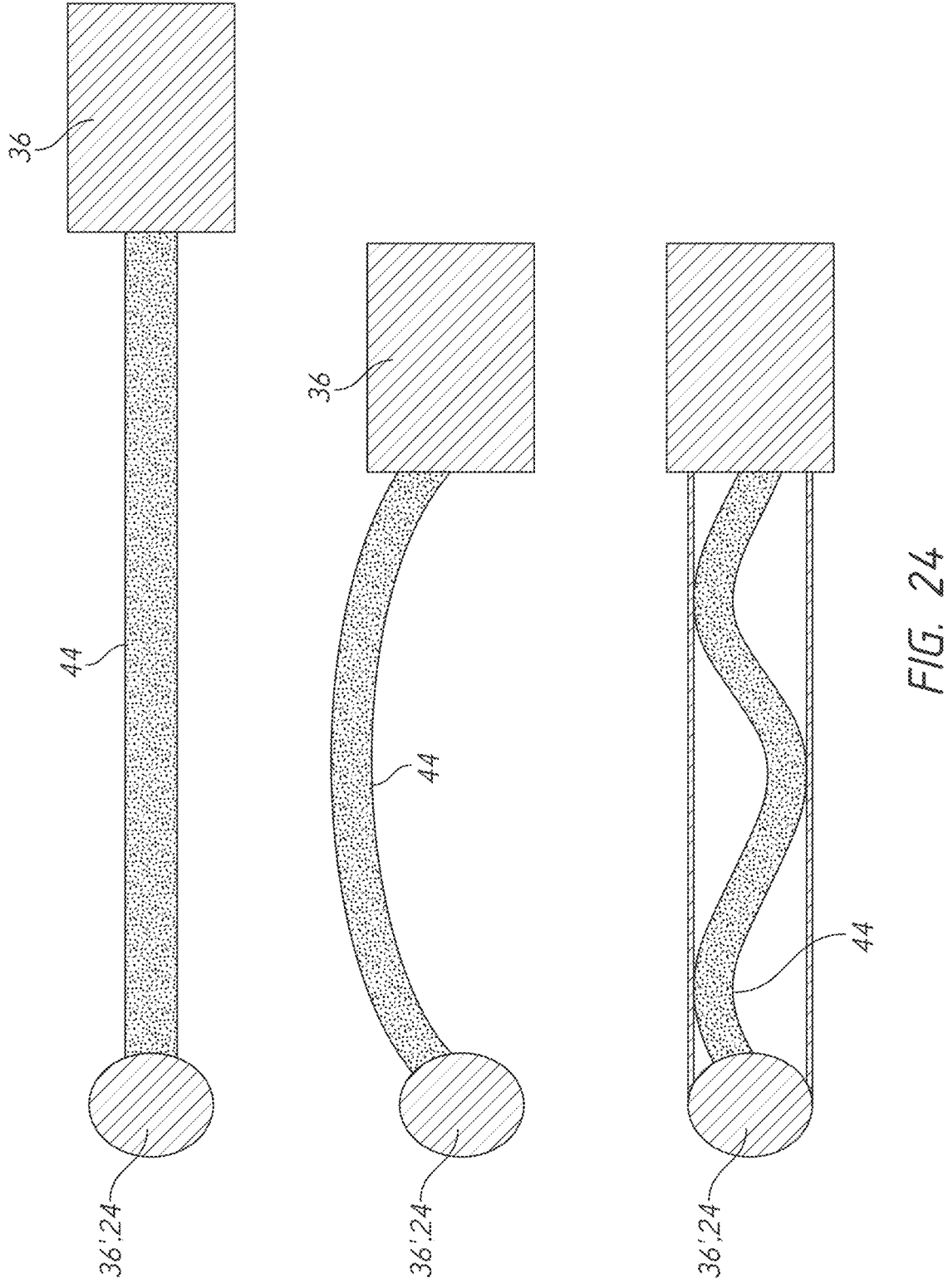
FIG. 24 depict potential scenarios of a catheter buckling between its proximal end and its distal insertion point.

FIG. 24 depicts potential scenarios of an interventional device 44 (which can be any of the interventional devices described herein) buckling between its proximal end, such as at its corresponding hub 36 (which can be any of the hubs described herein) and its distal insertion point, such as the femoral access point 24 or a distal hub 36' (which can be any of the hubs described herein). At top is the interventional device 44 prior to application of an insertion force. At middle and at bottom is the interventional device 44 after application of an insertion force (illustrated as an insertion force towards the left side of the page in FIG. 24) and buckling as a result of such applied force. Two different buckling states are shown, with the middle figure showing an unconstrained interventional device 44 buckling with a single large amplitude deflection, and the bottom figure showing a constrained interventional device 44 prevented from such large amplitude buckling and instead buckling with multiple smaller amplitude deflections along its length. Device insertion efficiency can decrease significantly because proximal input displacement is absorbed by the interventional device along the length in the formation of multiple deflections. This can result in a loss in displacement transmission at the distal tip. Further, the energy absorption along the length of the interventional device can be stored and then released spontaneously. This can result in the tips of the catheter or guidewire suddenly jumping distally uncommanded. In certain embodiments, the anti-buckling features, devices, and/or systems described herein may prevent uncommanded distal movement of a distal tip of an interventional device of more than about 1 mm, more than about 2 mm, or more than about 1 cm.

The interventional device 44 can be thought of as a beam in compression. The insertion force creates one side of the compressive force, and the reaction force can be caused by friction inside a distal interventional device 44', a distal hub 36', and/or by normal forces where the interventional device presses against vessels after going through patient access point 24. The insertion force can be as large as the reaction forces. Theoretical buckling of a beam is described by Euler's column formula:

$$F = n\pi^2 EI/L^2$$

Where: F is the critical force that the beam will buckle at; n is the factor accounting for end conditions; $\pi_2$ is a constant; E is the stiffness of the beam material; I is the moment of inertia of the beam; and L is the unsupported length of the column. In this case, n is 4 since the beam is fixed at both ends. The beam may not be perfectly rigid at both ends so the value may be lower than 4 in practice.

The moment of inertia (second moment of area) is a specific equation, since the cross section of the interventional device 44 is generally a tube:

$$I=(\pi/4)(r_2{}^4-r_1{}^4)$$

For a solid rod, for example a guidewire, the equation is the same, but the inner radius ($r_1$) is 0. Adding the foregoing into the buckling equation gives:

$$F=\pi^3 E(r_2{}^4-r_1{}^4)/L^2$$

The foregoing equation indicates there may be 5 variables related to preventing buckling: F, E, $r_2$, $r_1$, and L. The anti-buckling devices and features described herein can address one or more of such variables. For example, by supporting an interventional device over substantially its entire length, L can effectively be reduced to 0. As another example, by supporting an interventional device at or over portions of its length, L can be reduced to the distance between such supports.

One of the aforementioned variables that can be adjusted to reduce and/or prevent significant buckling of an interventional device is F. If the insertion force remains below the critical force (F), then the column may not buckle. The insertion force can be reduced by reducing the friction in a subsequent (for example, distal) catheter in a concentric stack, or whichever catheter is immediately outside of the buckling interventional device. Another source of force can be the force applied when the interventional device bumps into a vessel or is going through significant tortuosity; this may not be easily reduced, and can create a lower bound for the insertion force.

Material stiffness (E), outer radius ($r_2$), and inner radius ($r_1$), may also be controlled. These variables can have a great impact on other clinically important factors. For example, the material stiffness of an interventional device should be sufficiently low to navigate safely and effectively inside the vasculature or through an outer interventional device. An interventional device that is too stiff may not be able to navigate the curvature of the vasculature. Thus, increasing material stiffness may not be desirable. The outer diameter of an outermost interventional device should desirably be sufficiently dimensioned to safely and effectively navigate through the vasculature, and inner interventional devices should desirably be sufficiently dimensioned to traverse through outer interventional devices. Outer diameters that are too large may lead to longer recovery times and more complications, so increasing OD may not be desirable. Decreasing the ID of an interventional device may require that the outer diameters of any interventional devices that pass through that interventional device must also be smaller, which can increase the chance of the more inner devices buckling. Additionally, as described herein some interventional devices are used to perform procedures, such as aspirating (vacuum) clots. Larger IDs may be beneficial for such procedures. Furthermore, as described herein, the size of the annular lumen between adjacent interventional devices affects the fluid resistance therein. Thus, the ODs and IDs of adjacent interventional devices may be selected based to reduce fluid resistance to desirable amounts.

In some embodiments, the issues described may largely apply to the portions of the interventional devices that are advanced within the body. Opportunities are thus available to reduce or prevent buckling of portions of the interventional devices described herein that remain outside the body, such as by adjusting one or more of the material stiffness, the OD, and the ID, without changing or minimally changing the corresponding variables within the body.

Figure 25:
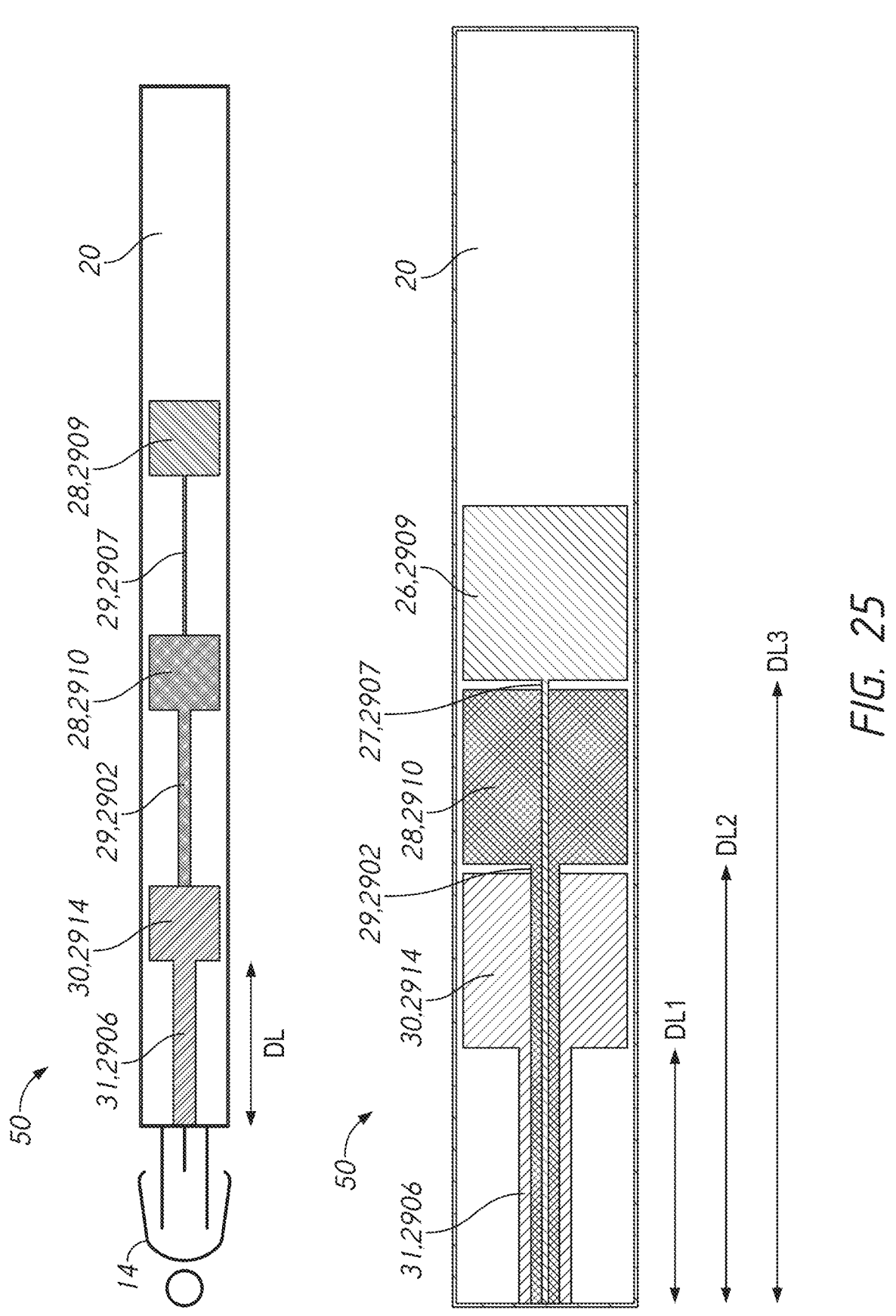
FIG. 25 depicts an example of dead lengths of an interventional device assembly.

FIG. 25 depicts an example of dead lengths of an interventional device assembly 50, which can be any of the interventional device assemblies described herein. As used herein, the term "dead length" (which can also be referred to as "DL" herein) is used to describe the portion of an interventional device, such as a catheter or guidewire, that is not intended to enter the patient 14 during a procedure. At top is a schematic of an interventional device assembly 50 on the support table 20 next to the patient 14 with the interventional devices each partially retracted from one another. As shown, the interventional device assembly 50 can include a guide catheter, a guide catheter hub, an access catheter, an access catheter hub, a guidewire, and a guidewire hub, such as the guide catheter 31 or 2906, the guide catheter hub 30 or 2914, the access catheter 29 or 2902, the access catheter hub 28 or 2910, the guidewire 27 or 2907, and the guidewire hub 26 or 2909 as described herein. At bottom is a representation of the interventional devices in a fully nested configuration and labeling the different interventional devices' dead lengths.

The guide catheter 31, 2906 can have a dead length DL1. DL1 can be greater than or equal to the minimum length of any corresponding anti-buckling device for the guide catheter 31, 2906. The access catheter 29, 2902 can have a dead length DL2. DL2 can be greater than or equal to DL1, plus the length of the guide catheter hub 30, 2914 and a minimum length of any corresponding anti-buckling device extending between the guide catheter hub 30, 2914 and the access catheter hub 28, 2910. The guidewire 27, 2907 can have a dead length DL3. DL3 can be greater than or equal to DL2, plus the length of the access catheter hub 28, 2910 and a minimum length of any corresponding anti-buckling device extending between the access catheter hub 28, 2910 and the guidewire hub 26, 2909. This pattern can continue with a 4 or 5 hub coaxial system. As the device hub gets further from the patient 14, the device has more dead length that does not enter the body.

The portion of the interventional devices in the dead length (or a portion thereof) can have significantly higher bending stiffness without affecting or minimally affecting the clinical constraints discussed above for the portions of the interventional devices positioned within the body. Any one or more of the material stiffness (E), outer radius ($r_2$), and inner radius ($r_1$) can be adjusted to maximize the critical buckling force for portions of the interventional devices that are positioned outside of the body or that may minimally enter the body.

Figures 26, 27:
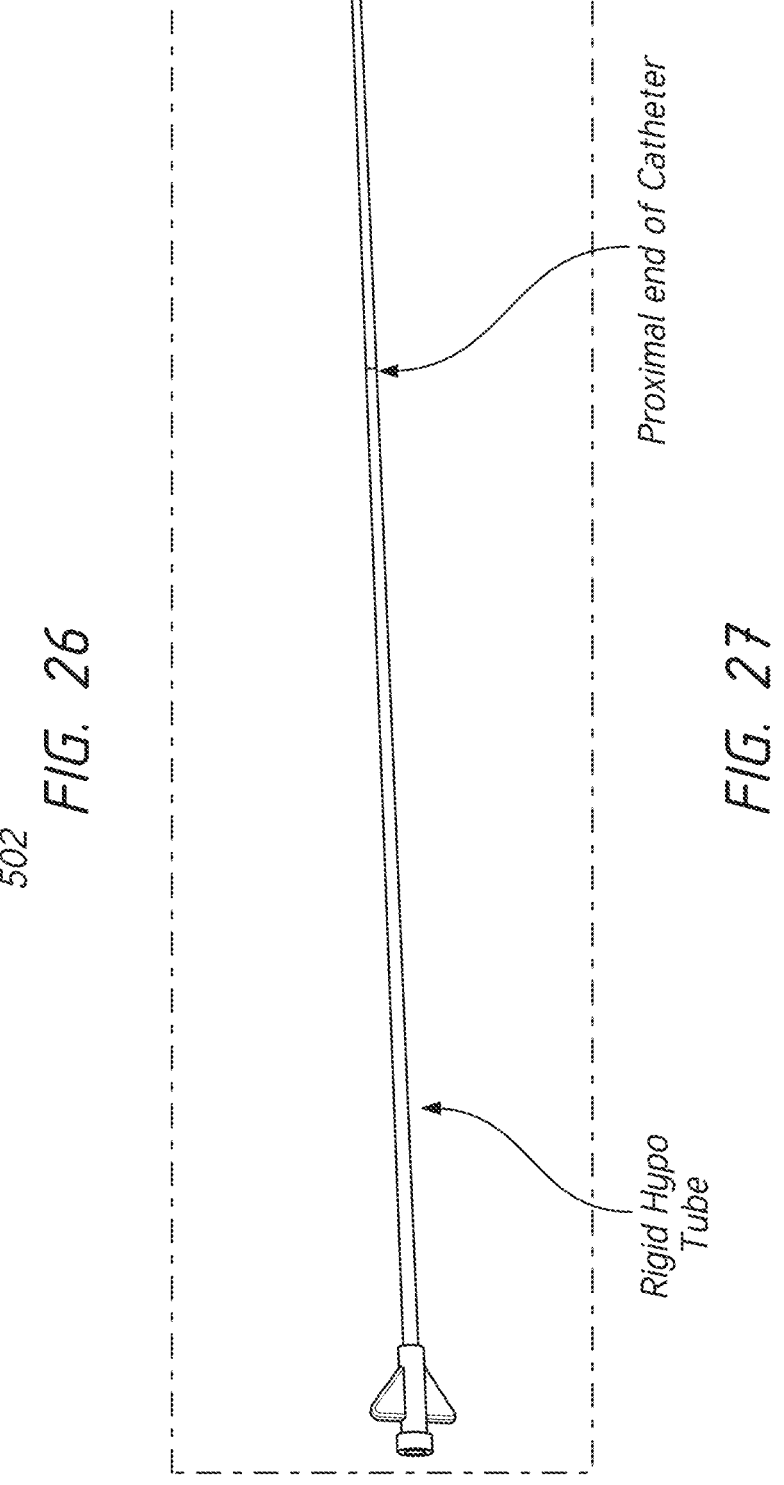
FIG. 26 depicts an example of an anti-buckling guidewire with a reinforced tube.
FIG. 27 depicts an example of an anti-buckling catheter with a stiff proximal support.

There are various ways to increase the bending stiffness of the interventional devices described herein. For example and as shown in FIG. 26, reinforcing tube 501 can be positioned over at least a portion of a guidewire (such as guidewires 31, 2906), such as, for example, over its dead length or a portion of the dead length. Standard 0.035 inch diameter (or similar) guidewires can be composed of a nitinol or stainless steel wire coated in plastic. Instead of a plastic coating, in certain embodiments, a tube 501 having a higher stiffness can be positioned over the guidewire along at least a portion of the guidewire (e.g., over its dead length of a portion of the dead length). By replacing the lower stiffness plastic with a higher stiffness tube 501, the stiffness of the guidewire can be increased, potentially without changing the OD. Such a tube 501 can be adhered to the guidewire 31, 2906 at a guidewire-to-tube interface 502 using adhesives, crimping, soldering, welding, or the like. A torsional stiffness of the guidewire 31, 2906 can be increased in addition to improving its buckling characteristics if such a tube 501 is adhered over its entire length to the guidewire 31, 2906. By way of another example, 0.014 inch (or similar) guidewires can be composed of a nitinol or stainless steel wire and can be either uncoated or coated with a thin coating. In such a case, a tube 501 can be directly adhered to such guidewires similar to as described above. Any of the tubes 501 can be made from materials that are the same as or different than a guidewire or catheter. Exemplary materials of a tube 501 for reinforcing an interventional device include hardened stainless steel, nitinol, carbon fiber, PEEK, and tungsten. By adding stiffness to the guidewire, the reinforcing tube 501 may prevent or reduce buckling of the guidewire.

Similarly, a reinforcing tube may be positioned around the exterior of at least portion of a catheter to provide increased stiffness and prevent or reduce buckling. Alternatively, at least a portion of the catheter can be stiffened by one or more of the following: integrating a stiff tube (e.g., a hypo tube) into at least a portion (e.g., a proximal end) of the catheter (e.g., without increasing or minimally increasing the OD); using different braiding material, quantity, and/or weave; and using stiffer resin.

In some embodiments, at least a portion of the catheter can be formed of or coupled to a rigid hypo tube. For example, as shown in FIG. 27, a proximal end of the catheter can be formed of a rigid hypo tube or coupled to a rigid hypo tube that extends between the catheter hub and proximal end of the catheter. The rigid hypo tube may provide a proximal stiff support to increase the load at which the catheter buckles. The rigid hypo tube may have the same ID and/or OD as the catheter or as more distal portions of the catheter to facilitate unimpeded motion of the catheter relative to other interventional devices in the interventional device assembly.

In some embodiments, if the catheter is made using a laser cut hypo tube construction, at least a portion of the catheter (e.g., the dead length portion or a portion thereof) can be manufactured without any or with minimal laser cuts to maximize stiffness. The hypo tube may be laser cut or otherwise modified towards its distal end to increase flexibility/decrease stiffness and to allow the catheter to track through more tortuous anatomy. For example, a catheter can have a hypo tube that extends from its proximal end, transitions to a braided section distally, and further distally transitions to a flexible coiled distal end. Alternatively, a hypo tube can partially or completely replace such a braided section.

A hypo tube construction without any or with minimal laser cuts can also increase torqueability of a catheter. By way of another example, a catheter can be constructed of a single hypo tube that extends the full length of the catheter, or it can be constructed of more than one hypo tube. The distal section of such a catheter can be laser cut or similarly processed to increase flexibility. In some implementations, the distal section of such a catheter can be made from nitinol tubing, laser cut to increase flexibility, and thermally set into specific standard or custom insert catheter shapes (e.g., VTK, BERN, SIM2). Transitions between a catheter constructed of multiple hypo tubes (which can be of different materials, such as nitinol and stainless steel) can be accomplished by joining hypo tube sections mechanically (e.g., interlocking), by welding, by adhesive, or similar.

Figures 28, 29:
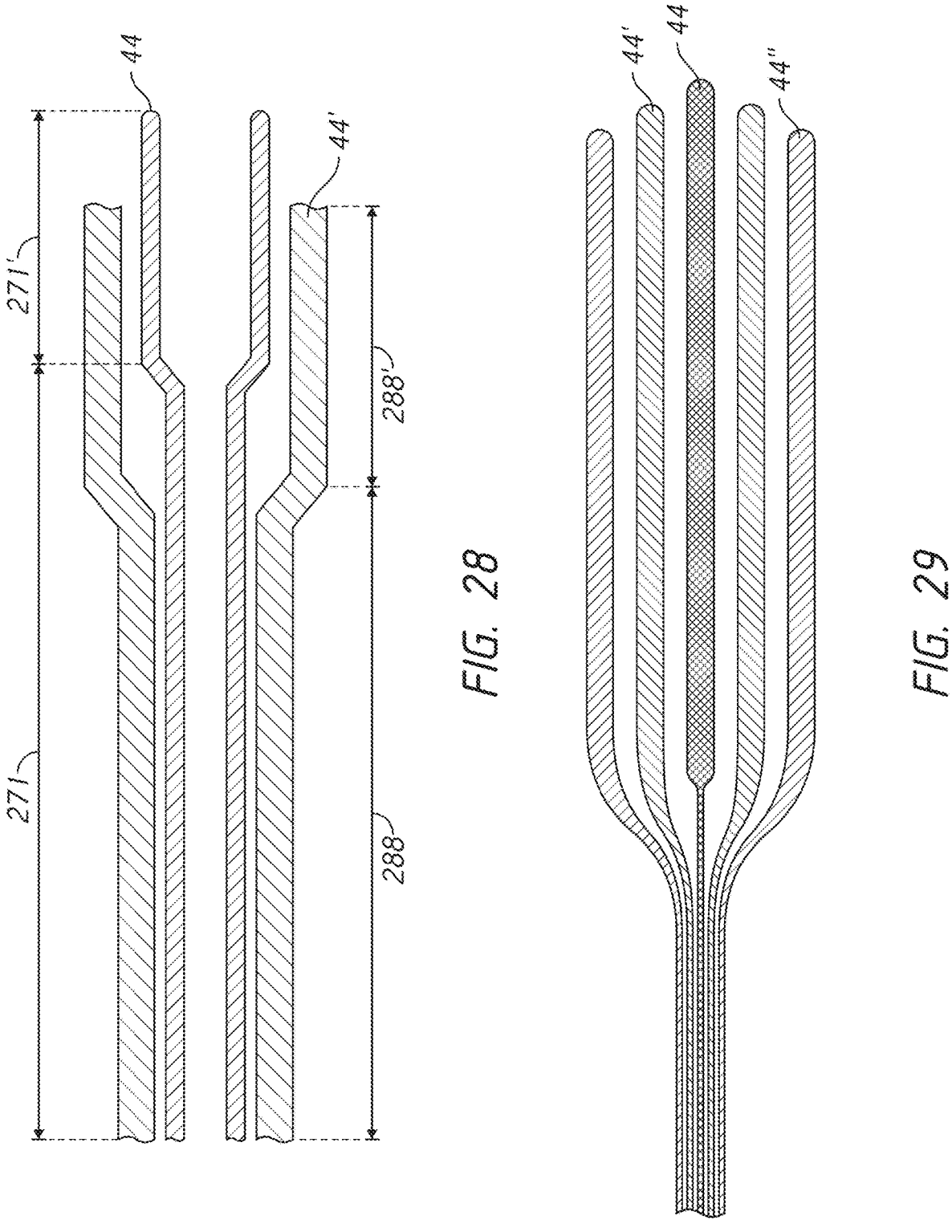
FIG. 28 depicts an example of anti-buckling catheters having increased inner and outer proximal diameters.
FIG. 29 depicts an example of anti-buckling catheters having increased inner and outer proximal diameters as well as increased proximal wall thickness.

Alternatively or in addition to increasing the material stiffness (E), the inner and outer proximal diameters (e.g., corresponding to at least a portion of their dead length) of an interventional device can be increased to prevent significant buckling during use. For example, as shown in FIG. 28, coaxially nested interventional devices (e.g., catheters) 44 and 44' can each include rigid hypo tubes at their proximal ends 271', 288' having such increased inner and outer proximal diameters relative to more distal sections 271, 288 of the interventional devices. As shown in FIG. 28, each nested interventional device can have corresponding increased ID and/or OD portions to facilitate nesting of the interventional devices.

FIG. 29 depicts an example of an anti-buckling guidewire 44 having an increased outer proximal diameter and anti-buckling catheters 44' and 44" having increased inner and outer proximal diameters as well as increased proximal wall thicknesses. For example, the catheter 44", which can be a guide catheter 31, 2906 as described herein, can have its OD and ID increased as well as its wall thickness increased (e.g., from an OD of about 0.11 inches to about 0.5 inches) at its proximal end. Further to this example, the catheter 44', which can be an access catheter 28, 2902 as described herein, can have its OD and ID increased as well as its wall thickness increased at its proximal end. This in turn allows the guidewire 44, which can be a guidewire 27,2907 as described herein, to have its OD increased at its proximal end. At distal sections of the interventional device meant to advance into the patient 14, the diameters of all interventional devices 44, 44', and 44" can narrow down to the sizes required by the clinical use case.

In some implementations, an interventional device can have a stiffened proximal portion that extends past the dead length of such device. Such stiffened proximal portion can include stiffening by any of the aforementioned configuration changes as appropriate. For example, an interventional device can be stiffened from its proximal end distally to a location where, when inserted at its full distal position relative to the patient 14, it experiences minimal tortuosity. Such a location can be at or adjacent the descending aorta with the patient access point being the femoral artery.

In some embodiments, an anti-buckling system or device can include one or more supports that can provide anti-buckling support along a length of an interventional device. In some embodiments, the support(s) can include telescoping tubes, springs, scissor mechanisms, tubes (e.g., split tubes), extendible supports, translatable supports, magnetic supports, feed rollers, grippers, channels, or any other suitable anti-buckling support mechanisms.

FIGS. 30A-30G depict an example of an anti-buckling telescoping tube 510. The telescoping tube 510 can include a plurality of concentric telescopically axially extendable and collapsible tubes or tube segments through which an interventional device 44 extends therethrough. For example and as shown, the telescoping tube 510 can include a tube 510a, a tube 510b, and a tube 510c, with the tube 510b coaxially extendable/collapsible from within tube 510a and the tube 510c coaxially extendable/collapsible from within the tube 510b. Such a pattern would repeat if the telescoping tube included more than 3 of such tubes. As further shown, the telescoping tube 510 can be secured at its proximal end by a proximal retainer 512. Similarly, however not shown, the telescoping tube can be secured at its distal end by a distal retainer. Retention of the proximal and distal ends of the telescoping tube can facilitate the extension and collapse of the tubes that make up the telescoping tube when an interventional device 44 is moved distally and proximally therethrough. For example and as shown, the proximal retainer 512 can releasably attach the proximal end of the telescoping tube 510 to a hub 511 or to a distal end of a rotating hemostatic valve 1000, which itself can be secured to the hub 511 (which can be any of the hubs described herein) of the interventional device 44. The distal retainer can releasably attach the distal end of the telescoping tube to a more distal hub or a rotating hemostatic valve coupled to a more distal hub or to an alternative distal attachment point outside of the femoral access point for a distal most interventional device (e.g., a separate structure that can be attached to the support table 20, to a separate structure that can be attached to the patient support table 12, or to an otherwise separate structure that can maintain its position relative to the patient 14). With the distal end of the telescoping tube 510 secured, when the hub 511 is moved distally across the support table 20 (as shown to the left), the telescoping tube 510 can collapse while the interventional device 44 extends therethrough. Similarly, with the distal end of the telescoping tube 510 secured, when the hub 511 is moved proximally across the support table 20 (as shown to the right), the telescoping tube 510 can extend while the interventional device 44 extends therethrough. The proximal and/or distal retainers can be configured to allow misalignment of the telescoping tube 510 therewith, for example, by allowing the tubes to angulate slightly. This may be accomplished by incorporation of a ball joint or flexible coupling.

A telescoping tube 510 can include at least two tubes, in some implementations three tubes, four tubes, or more. The greater the number of tubes that make up a telescoping tube, the shorter the overall collapsed length of such a telescoping tube can be (for example, to minimize dead length); however, the greater the number of tubes that make up a telescoping tube, the greater the diameter of the outermost tube may be to accommodate all tubes within. Generally, an innermost tube of the telescoping tube 510 has an inner diameter that can accommodate the interventional device(s) extending therethrough (e.g., an inner diameter configured to prevent significant buckling of the interventional device(s) extending therethrough). Furthermore, an inner tube has an outer diameter that is smaller than an inner diameter of an adjacent surrounding tube. For example, an inner tube can have an outer diameter that is between about 0.001" to about 0.030", between about 0.001" to about 0.020", between about 0.001" to about 0.010", between about 0.001" to about 0.0075", or between about 0.002" to about 0.005" smaller than the inner diameter of an adjacent surrounding tube. The ends of the tubes that make up the telescoping tube 510 can be flared or swaged as appropriate to ensure the ends of concentrically adjacent tubes are not extended past one another. Furthermore, one or more shims can be placed between concentrically adjacent tubes to aid in smooth operation of the telescoping tube 510 as it extends/collapses and/or to prevent the tubes from hyper-collapsing and hyper-extending. Tubes of the telescoping tube 510 can have a length such that an outer tube is shorter than a tube immediately within, or they may be about the same length.

Figure 30A:
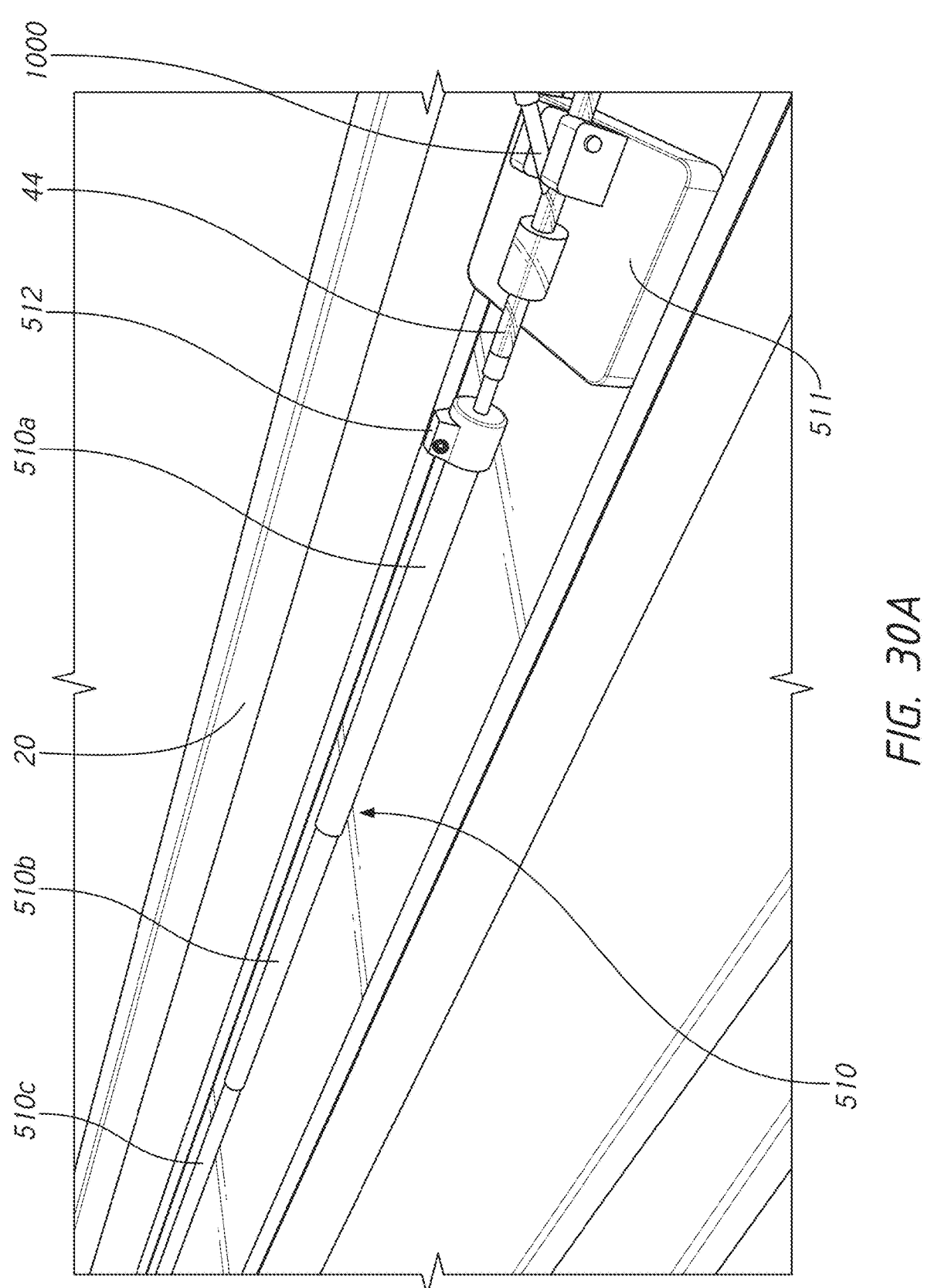
FIGS. 30A-30G depict an example of an anti-buckling telescoping tube.

With continued reference to FIG. 30A, a telescoping tube 510 can be configured to have its greatest diameter tube (e.g., its outermost tube) remain at its proximal end with successively smaller tubes extending outward axially in the distal direction as shown. In some implementations, a telescoping tube 510 can be configured to have its smallest diameter tube (e.g., its innermost tube) remain at its proximal end with successively larger tubes extending outward axially in the distal direction (the opposite of what is shown).

As mentioned above, a telescoping tube 510 can be secured at its proximal and distal ends by a proximal retainer 512 and a distal retainer. Such retainers can be attached to a rotating hemostatic valve, such as the rotating hemostatic valve 1000 shown, to an interventional device hub or a portion thereof, such as hub 511 shown, to a separate structure that can be attached to the support table 20, to a separate structure that can be attached to the patient support table 12, or to an otherwise separate structure that can maintain its position relative to the patient 14. In some implementations, the proximal and/or distal ends of a telescoping tube 510 can be directly attached or otherwise adhered to any of the aforementioned without proximal and/or distal retainers. In some implementations, a telescoping tube 510 can be integrated with or within a hub of an interventional device assembly.

Figures 30B, 30C, 30D:
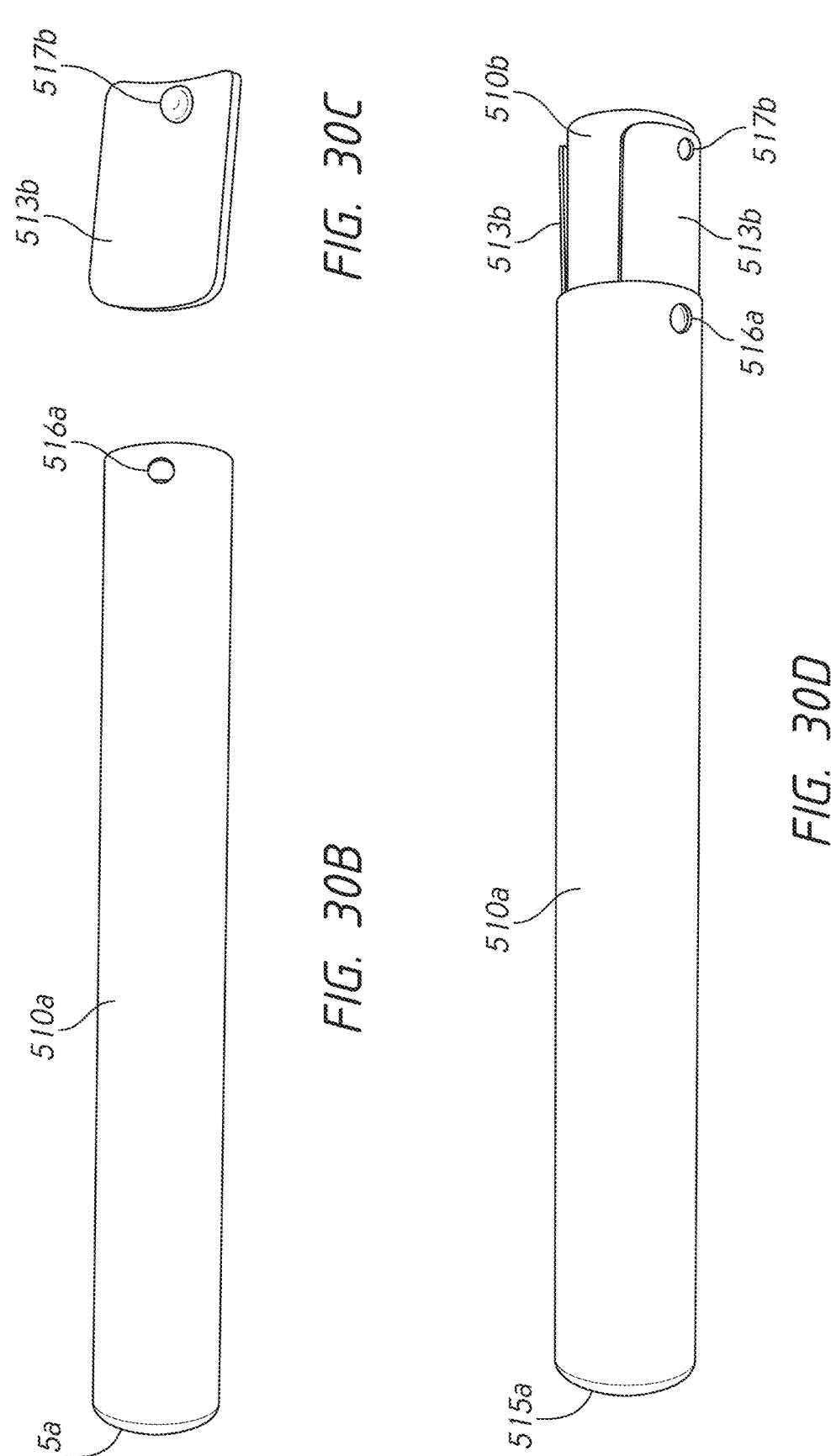

FIGS. 30B-30G show an exemplary implementation of the telescoping tube 510. FIG. 30B shows one tube of the telescoping tube 510, for example outermost tube 510a, having a swaged end 515a and a through hole 516a extending through the entirety of the tube 510a (e.g., through both sides of the tube 510a) adjacent its other end. The swaged end 515a can be configured to have a reduced inner diameter relative to the inner diameter of the rest of the tube 510a, though larger than a tube that fits within it (e.g., tube 510b). The swaged end 515a can be configured to prevent slop between the tubes 510a, 510b during use.

FIG. 30C shows an implementation of a shim that can be placed around the outer diameter of an inner tube of the telescoping tube 510, for example a shim 513b configured to be placed around tube 510b. Such a shim can be configured to fill the gap/clearance between concentrically adjacent tubes, but still allow relative axial movement of the tubes (e.g., the shim can hug the outer diameter of its associated tube and fit within the inner diameter of a tube surrounding its associated tube). Furthermore, such a shim can have a bump configured to fit within a through hole adjacent an end of its associated tube such that the bump protrudes at least partially into the inner diameter of its associated tube. For example, the shim 513b can have a bump 517b that fits within a through hole 516b of the tube 510b. In this way, the shims of a tube can be held in place adjacent the end of the tube.

FIG. 30D shows a partial assembly of tubes 510a and 510b of telescoping tube 510. As shown, tube 510b has been inserted partially into tube 510a with two shims 513b placed therebetween. Two shims can generally be used with each tube as shown, for example, one at each side of its associated tube. The bumps 517b of shims 513b are shown each disposed within a through hole of the tube 510b.

Figures 30E, 30F, 30G:
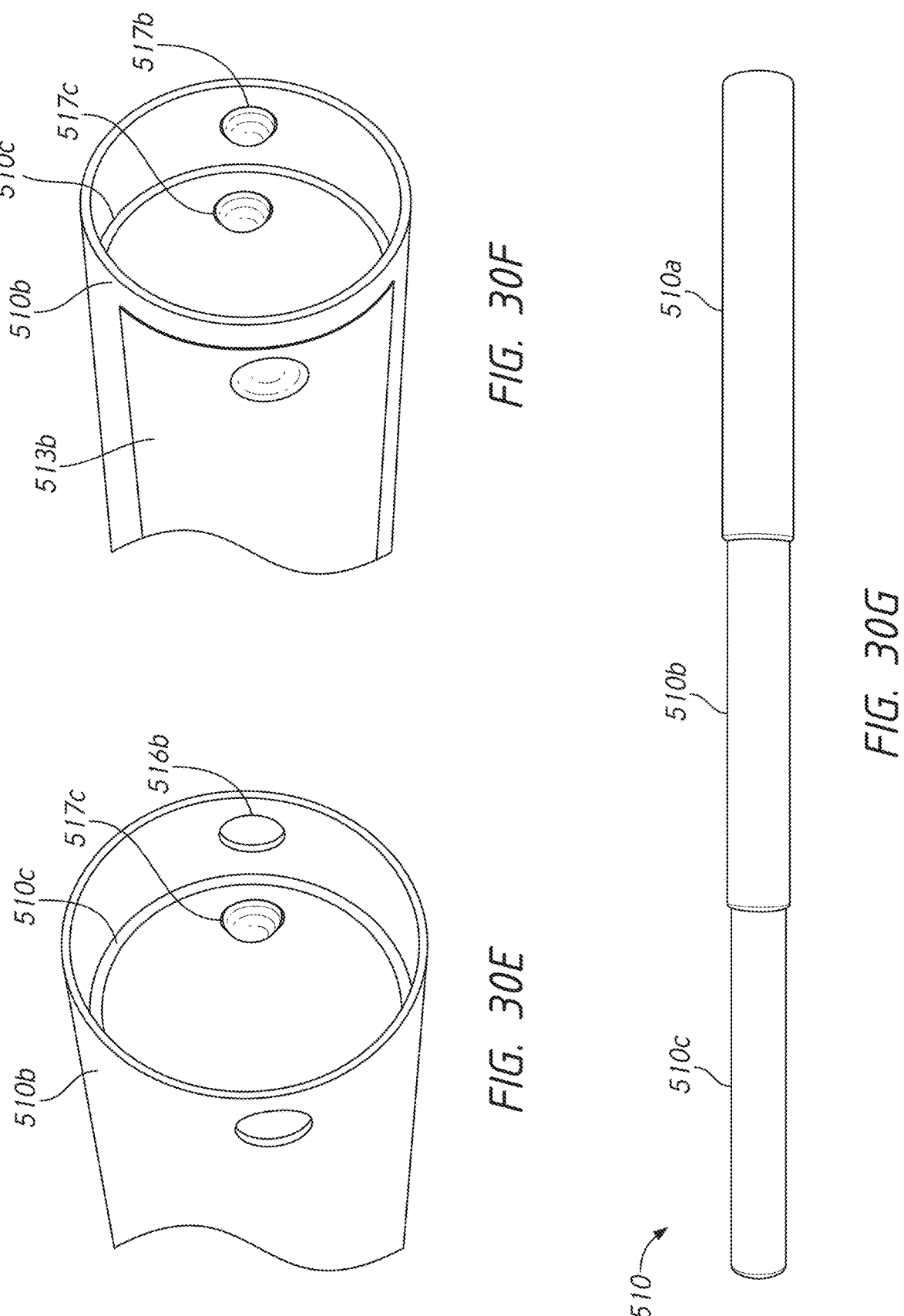

FIGS. 30E-30F show a partial assembly of tubes 510b and 510c of telescoping tube 510. FIG. 30E shows tube 510c within tube 510b with bump 517c of the shim associated with tube 510c protruding into the inner diameter of tube 510c. FIG. 30F shows the assembly of FIG. 30E but with shims 513b of tube 510b held against the outer diameter of tube 510b. As shown in FIG. 30G, the bumps 517b of the shims 513b can prevent hyper-collapsing of tube 510c within 510b. As shown, the bumps 517b can prevent the tube 510c from collapsing past the bumps 517b. In other words, the at least partial protrusion of a bump of a shim into the inner diameter of its associated tube can prevent a concentrically adjacent tube within it from collapsing past such bump. The shims can also prevent a tube from extending past a surrounding tube, for example, by catching on the swaged end (e.g., swaged end 515a) of its surrounding tube. FIG. 30G shows tubes 510a, 510b, and 510c of telescoping tube 510 assembled. Tubes of the telescoping tube 510 can be made of stainless steel, and shims of the telescoping tube 510 can be made of brass.

Figures 31A, 31B, 31C:
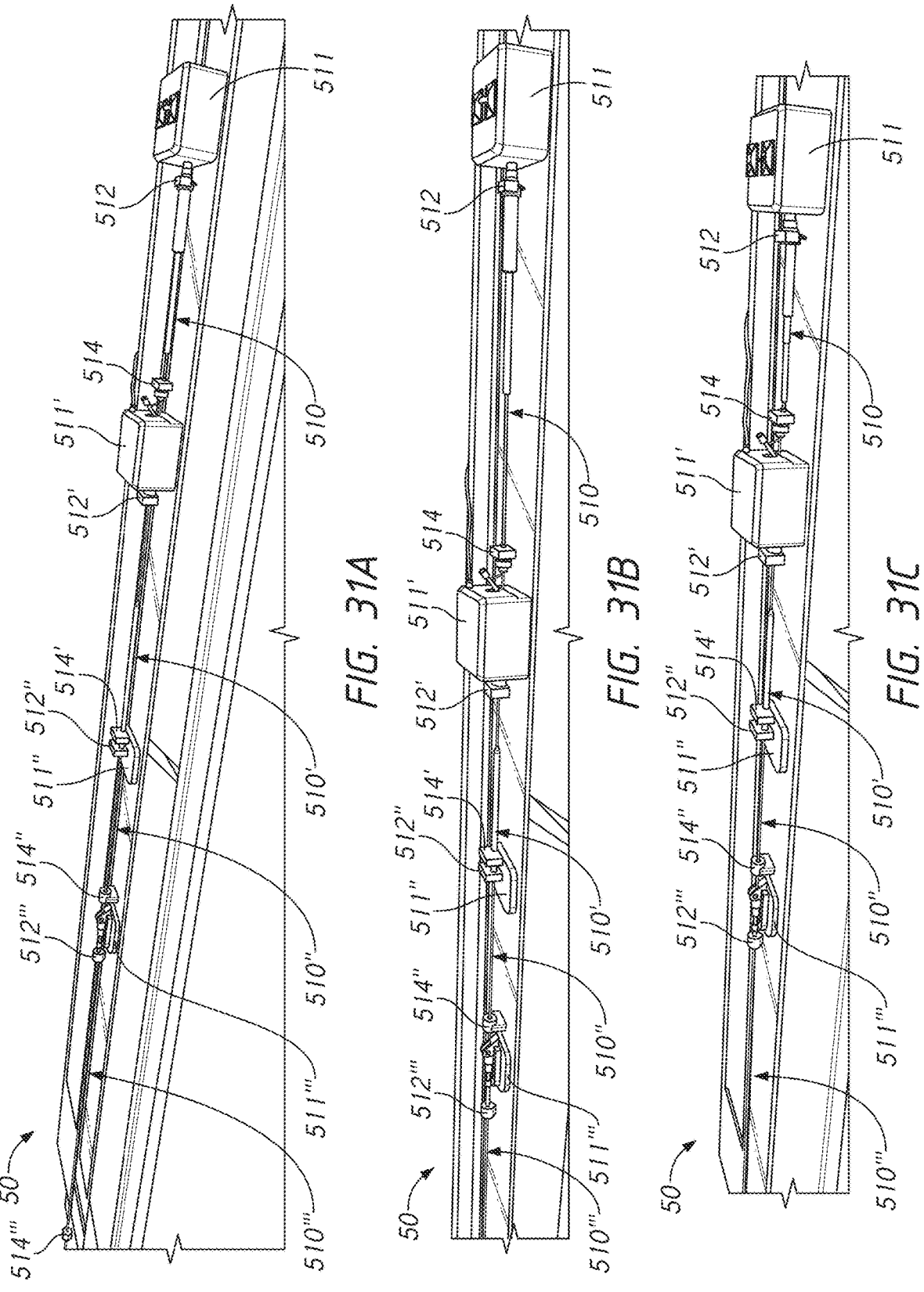
FIGS. 31A-31C depict an example of an interventional device assembly utilizing anti-buckling telescoping tubes.

FIGS. 31A-31C depict an example of an interventional device assembly 50 utilizing anti-buckling telescoping tubes 510, 510', 510", and 510'''. As shown, interventional device assembly 50 includes the hub 511, the hub 511', the hub 511", and the hub 511''' (which can be any of the hubs described herein) each driving a separate interventional device which are hidden from view within the telescoping tubes. The telescoping tube 510 extends over an interventional device between its proximal retainer 512 and its distal retainer 514 (e.g., between hub 511 and hub 511'), the telescoping tube 510' extends over an interventional device between its proximal retainer 512' and its distal retainer 514' (e.g., between the hub 511' and hub 511"), the telescoping tube 510" extends over an interventional device between its proximal retainer 512" and its distal retainer 514" (e.g., between the hub 511" and hub 511'''), and the telescoping tube 510''' extends over an interventional device between its proximal retainer 512''' and its distal retainer 514''' (e.g., between the hub 511''' and its distal retainer 514'''). The hub 511 as shown is a proximal-most hub, for example a guidewire hub. Each of the successively distally located telescoping tubes between successively distally located hubs can be configured to extend over and prevent substantial buckling of the interventional devices extending therethrough, including the interventional devices extending from hubs located more proximally. The proximal retainers 512, 512', 512", and 512''' and the distal retainers 514, 514', 514", and 514''' of the telescoping tubes 510, 510', 510", and 510''', respectively, secure the proximal and distal ends of such telescoping tubes to allow them to extend/collapse as the hubs are moved axially (e.g., proximally and distally) relative to one another. FIGS. 31A-31C show the hubs 511, 511', 511", and 511''' of the interventional device assembly 50 in such various axial and distal positions relative to one another, with the telescoping tubes 510, 510', 510", and 510''' in various extended and collapsed positions in-kind.

Also shown in FIGS. 31A-31C are the various orientations the telescoping tubes described herein can take. As described above, the telescoping tubes can have their largest diameter tube oriented proximally with at least its smallest diameter tube extending distally (such as is shown for telescoping tubes 510, 510", and 510'''), or the telescoping tubes can have their smallest diameter tube oriented proximally with at least its largest diameter tube extending distally (such as is shown for telescoping tube 510').

In some implementations, a telescoping tube can be housed at least partially within its corresponding hub to minimize a dead length of the interventional device(s) disposed therein. For example, a telescoping tube can be housed completely or nearly completely within its corresponding hub. In such example, all but a connector portion of the telescoping tube may be housed within the hub while such connector portion extends outside the hub or adjacent an end of the hub for accessing such connector portion.

In some implementations, a telescoping tube can be configured to allow rotation thereof, for example, when connected to a rotating hemostatic valve as described herein and upon rotation of such a hemostatic valve. In some implementations, a telescoping tube can be configured to remain substantially rotationally stationary and not substantially rotate upon rotation of a connected rotating hemostatic valve.

Figure 32:
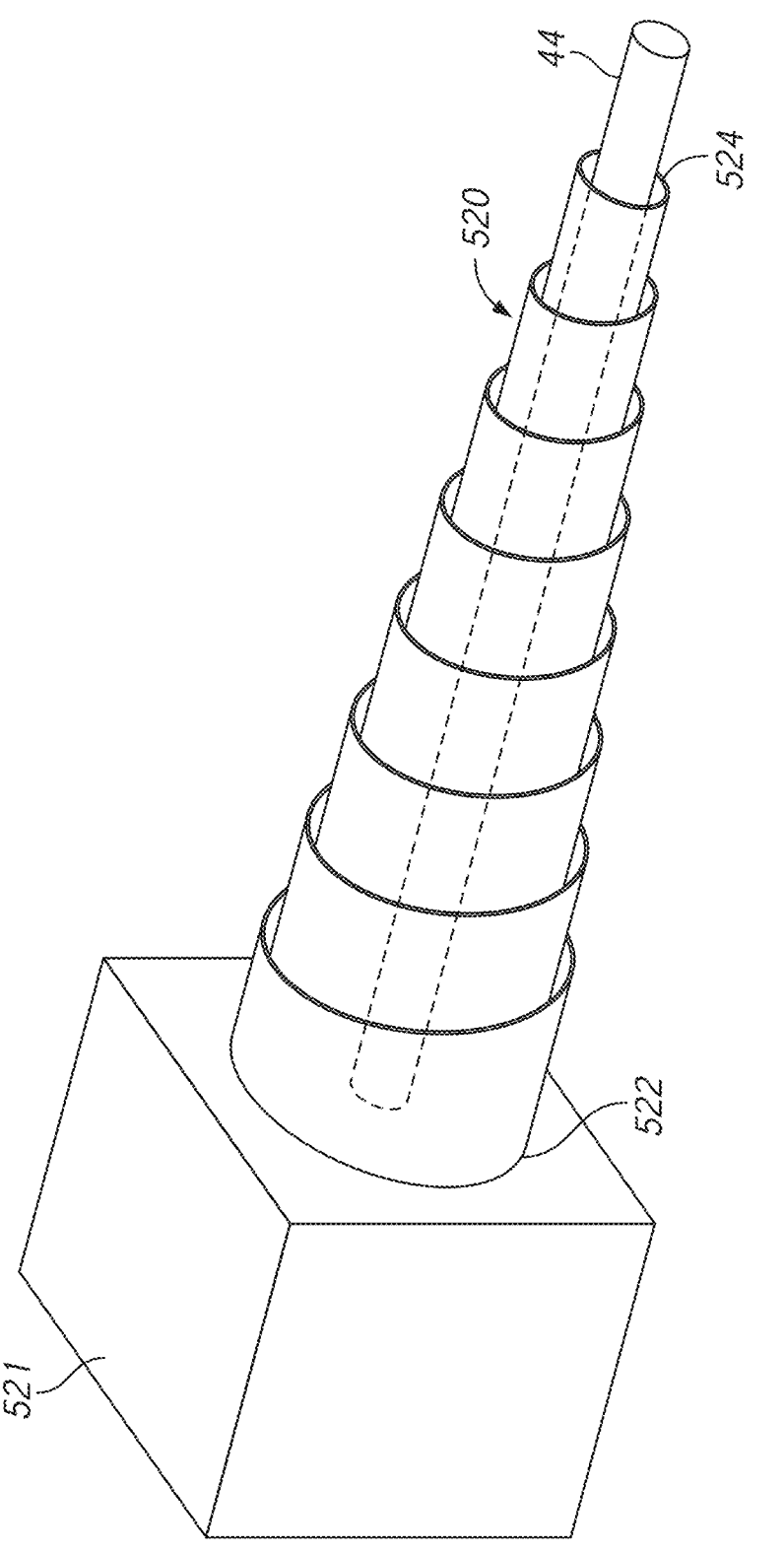
FIG. 32 depicts an example of an anti-buckling telescoping spring.

FIG. 32 depicts an example of an anti-buckling telescoping spring 520. Similar to the telescoping tubes described herein, the telescoping spring 520 can be configured to extend and collapse axially about an interventional device 44 (or more) extending therethrough. Also similar to the telescoping tubes described herein, the telescoping spring 520 can have a proximal retainer 522 and/or a distal retainer 524 to secure its proximal and distal ends, respectively. As shown, the telescoping spring 520 has a proximal retainer 522 configured to attach its proximal end to a hub 521 (which can be any of the hubs described herein). The distal retainer 524 may be configured to attach to a distal hub or a separate structure that can be attached to the support table 20, to a separate structure that can be attached to the patient support table 12, or to an otherwise separate structure. The telescoping spring 520 can be configured to nest upon itself, or in other words coil within itself, as shown to minimize the dead length in a state when the telescoping spring 520 is fully collapsed. The telescoping spring 520 can provide a rigid surface that prevents substantial buckling of an interventional device 44 extending therethrough. The telescoping spring 520 can be a constant force wound spring that biases to a collapsed position, a fully extended position, or any position therebetween. In some implementations, the telescoping spring 520 can be a variable force wound spring that biases to a collapsed position, a fully extended position, or any position therebetween.

Figure 33:
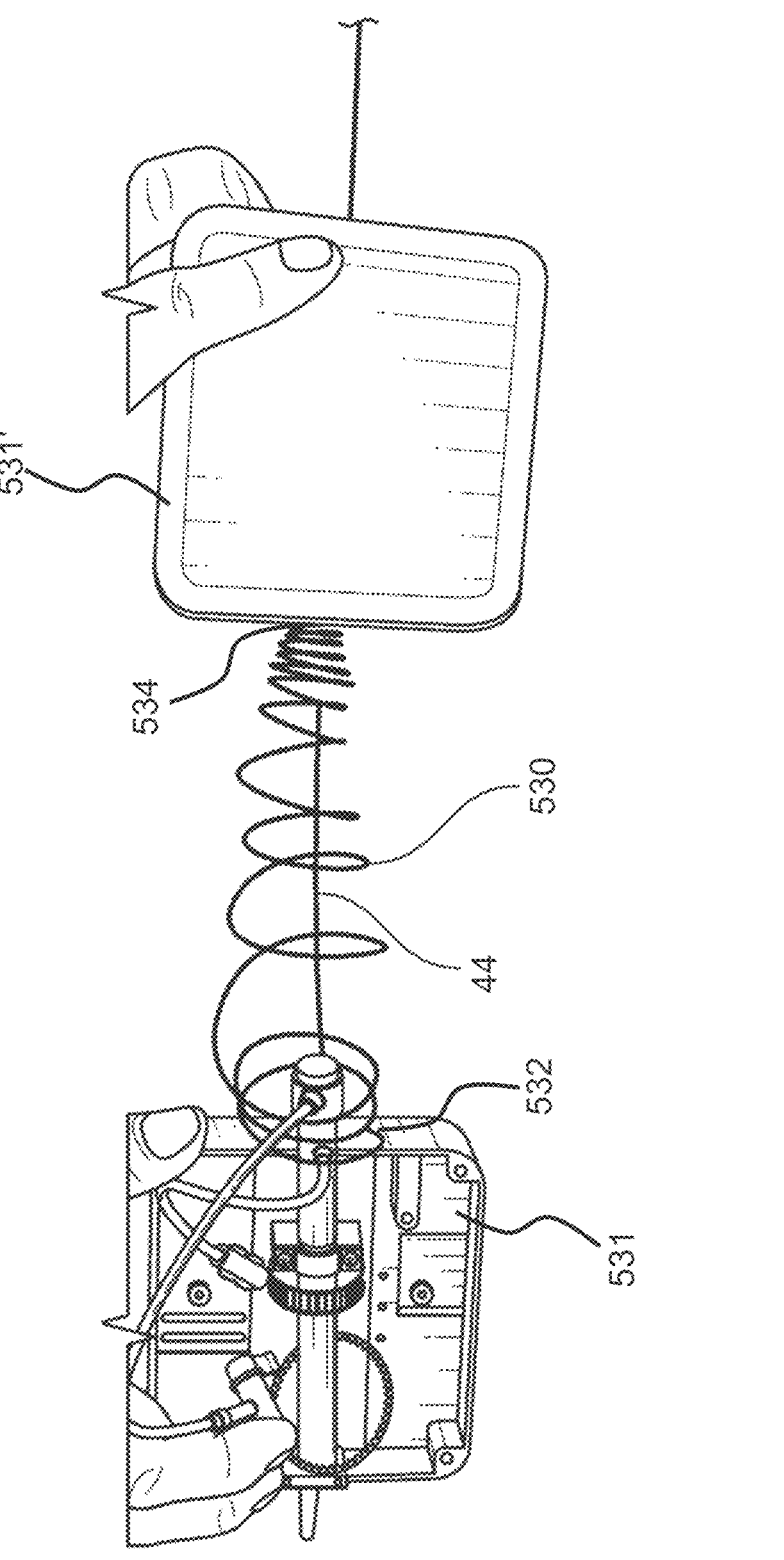
FIG. 33 depicts an example of an anti-buckling spring.

FIG. 33 depicts an example of an anti-buckling spring 530. Similar to the telescoping tubes and telescoping spring described herein, the spring 530 can be configured to extend and collapse axially about an interventional device 44 (or more) extending therethrough. Also similar to the telescoping tubes and telescoping spring described herein, the spring 530 can have a proximal retainer 532 and/or a distal retainer 534 to secure its proximal and distal ends, respectively, and/or it can be attached directly to hubs at its proximal and distal ends (e.g., hubs 531 and 531' as shown, which can be any of the hubs described herein). The spring 530 can be configured to nest within itself to reduce its dead length when fully collapsed, and as such can have a variable outer diameter along its length as shown. In some implementations, the spring 530 can have a substantially constant outer diameter and stacks upon itself when collapsed. The spring 530 can provide an outer structure that prevents substantial buckling of an interventional device 44 extending therethrough.

Figure 34A:
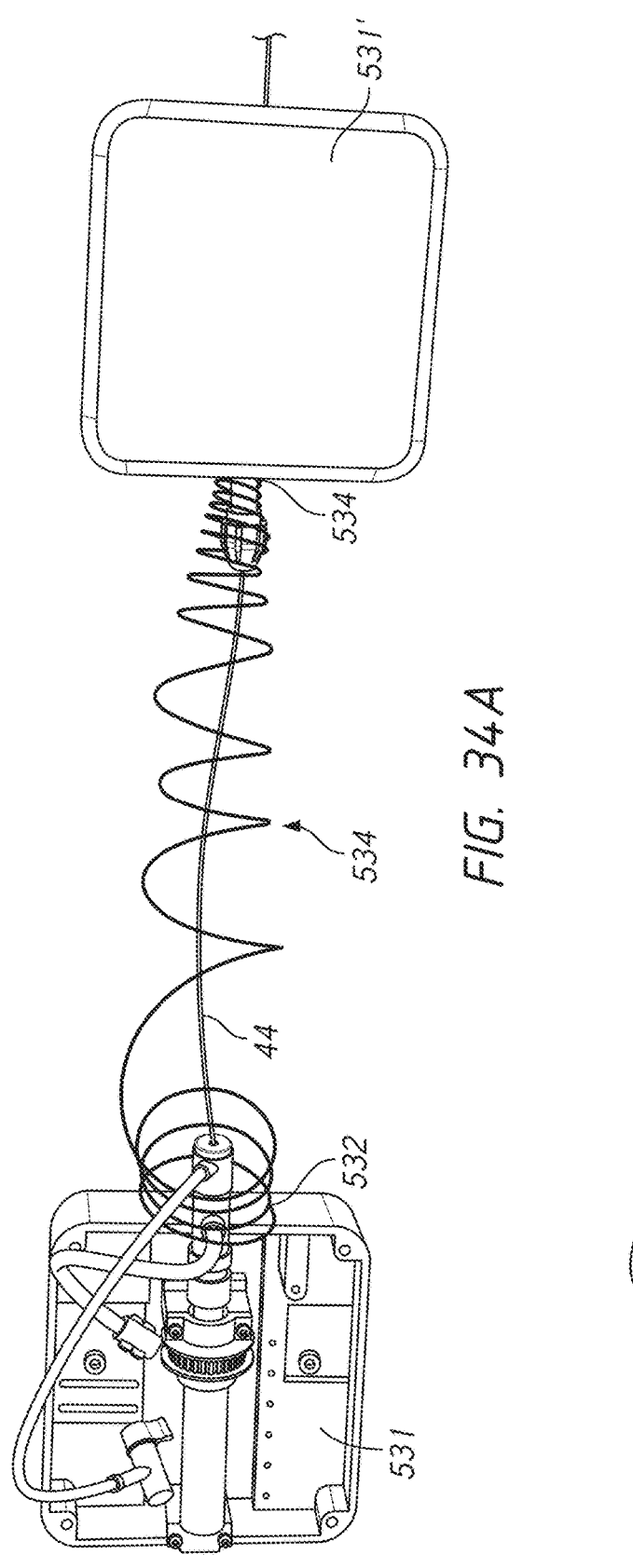
FIGS. 34A-34B depict an example of interventional devices utilizing an anti-buckling spring.
Figure 34B:
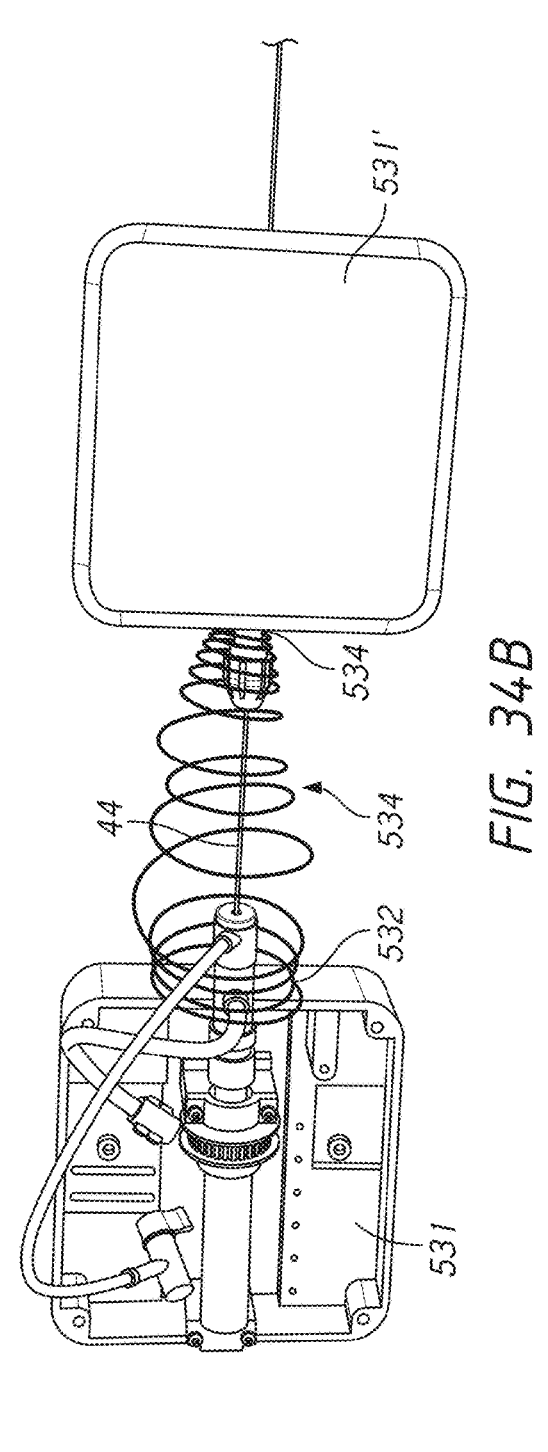

FIGS. 34A-34B depict an example of an interventional device 44 utilizing the anti-buckling spring 530 described with respect to FIG. 33 having a variable diameter. Shown is the spring 530 in a relatively extended position (FIG. 34A) and a relatively collapsed position (FIG. 34B).

Figures 35A, 35B, 35C:
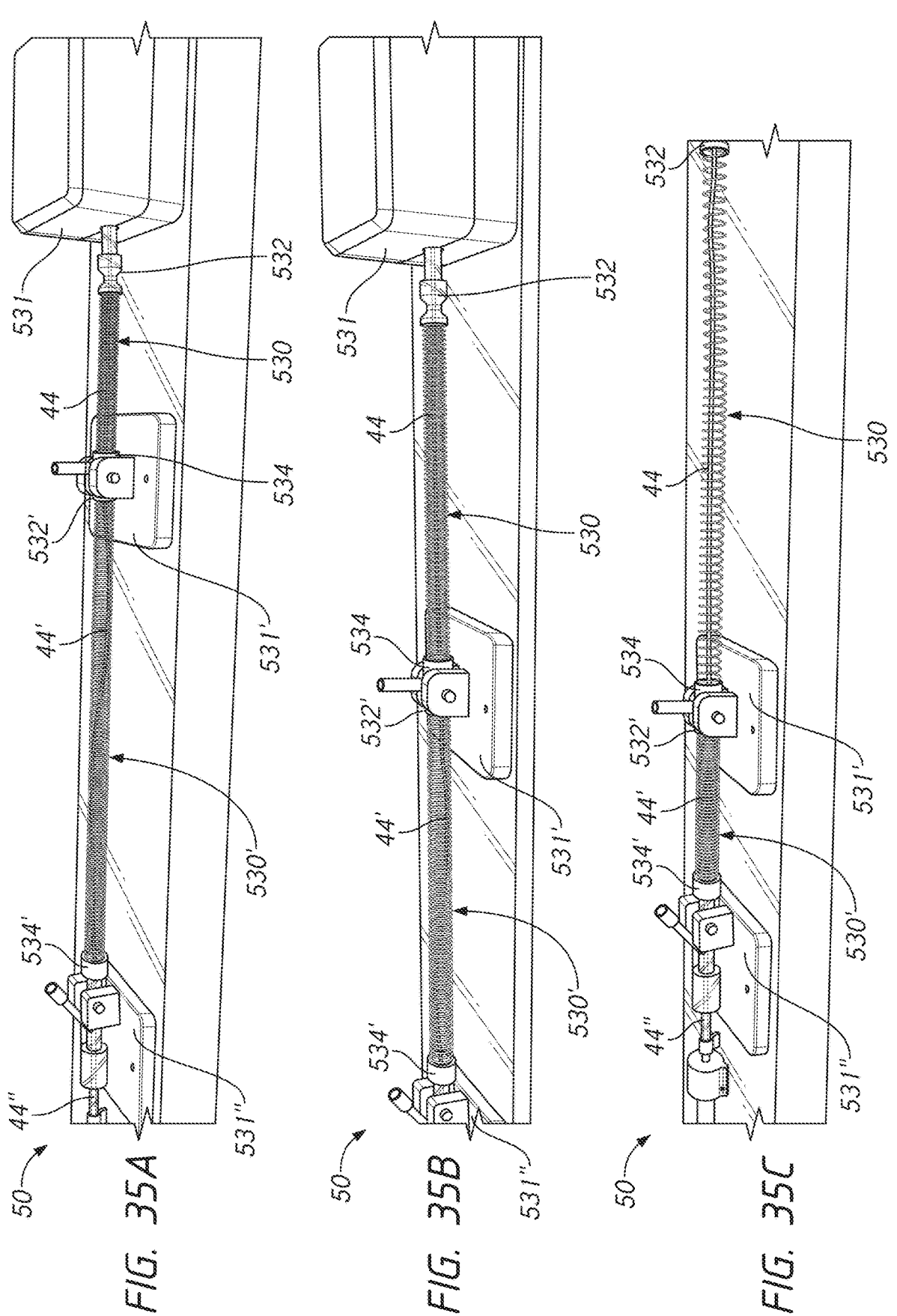
FIGS. 35A-35C depict an example of interventional devices utilizing anti-buckling springs.

FIGS. 35A-35C depict an example of an interventional device assembly 50 utilizing anti-buckling springs 530 and 530' each having substantially constant diameters. As shown, interventional device assembly 50 includes the hub 531, the hub 531', and the hub 531" (which can be any of the hubs described herein) each driving separate interventional devices 44, 44', and 44" that are located within the springs. The spring 530 extends over the interventional device 44 between its proximal retainer 532 and its distal retainer 534 (e.g., between hub 531 and hub 531') and the spring 530' extends over the interventional device 44' between its proximal retainer 532' and its distal retainer 534' (e.g., between the hub 531' and hub 531"). The hub 531 as shown is a proximal-most hub, for example a guidewire hub. Each of the successively distally located springs between successively distally located hubs can be configured to extend over and prevent substantial buckling of the interventional devices extending therethrough, including the interventional devices extending from hubs located more proximally. The proximal retainers 532 and 532' and the distal retainers 534 and 534' of the springs 530 and 530', respectively, secure the proximal and distal ends of such springs to allow them to extend/collapse as the hubs are moved axially (e.g., proximally and distally) relative to one another. FIGS. 31A-31C show the hubs 531, 531', and 531" of the interventional device assembly 50 in such various axial and distal positions relative to one another, with the springs 530 and 530' in various extended and collapsed positions in-kind.

Figures 36A, 36B, 36C:
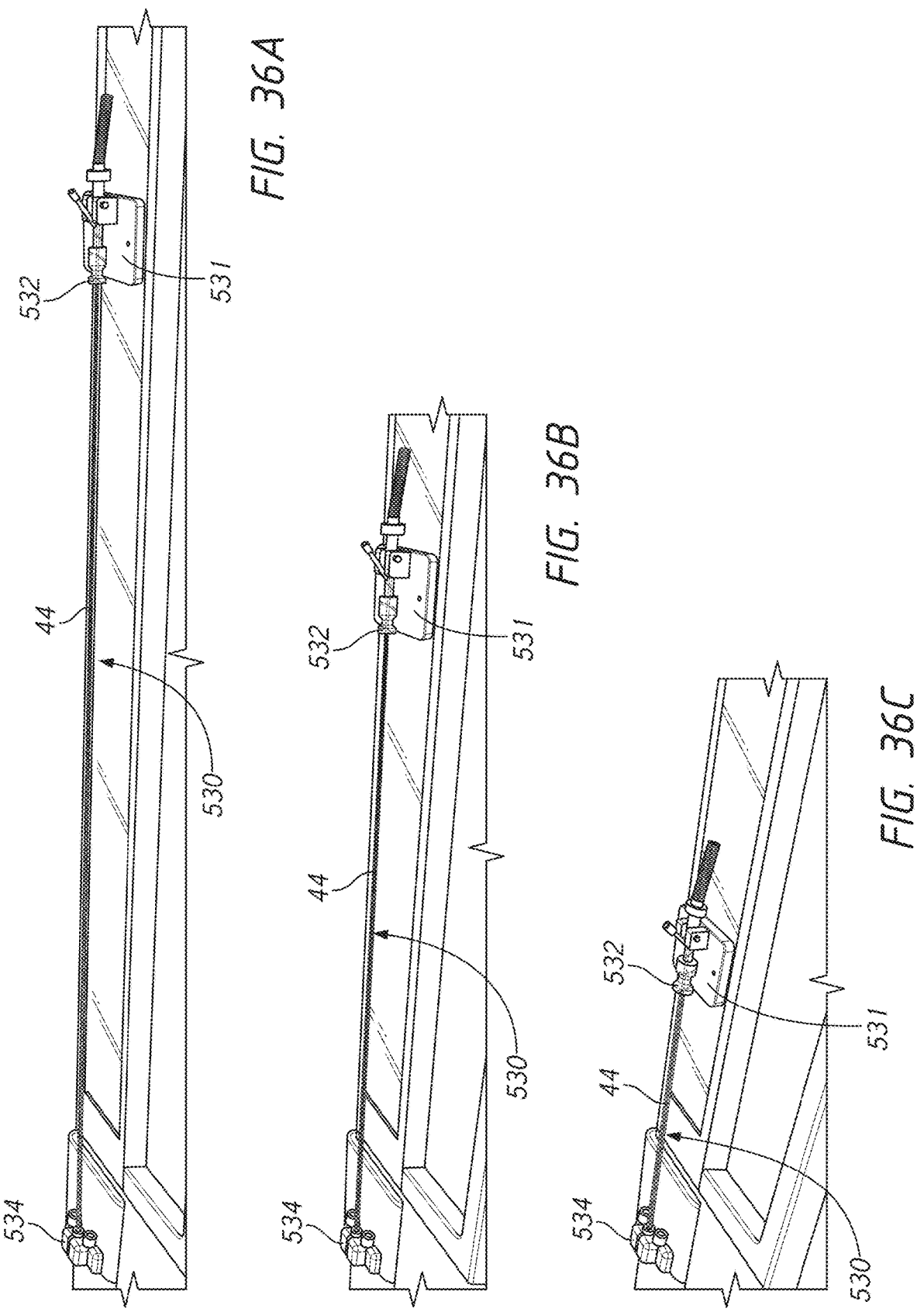
FIGS. 36A-36C depict an example of an interventional device utilizing an anti-buckling spring.

FIGS. 36A-36C depict an example of an interventional device 44 utilizing an anti-buckling spring 530 having a substantially constant diameter. Shown is the spring 530 in an extended position (FIG. 36A) a mid-extended position (FIG. 36B) and a collapsed position (FIG. 36C) between its proximal retainer 532 and its distal retainer 534.

Figure 37:
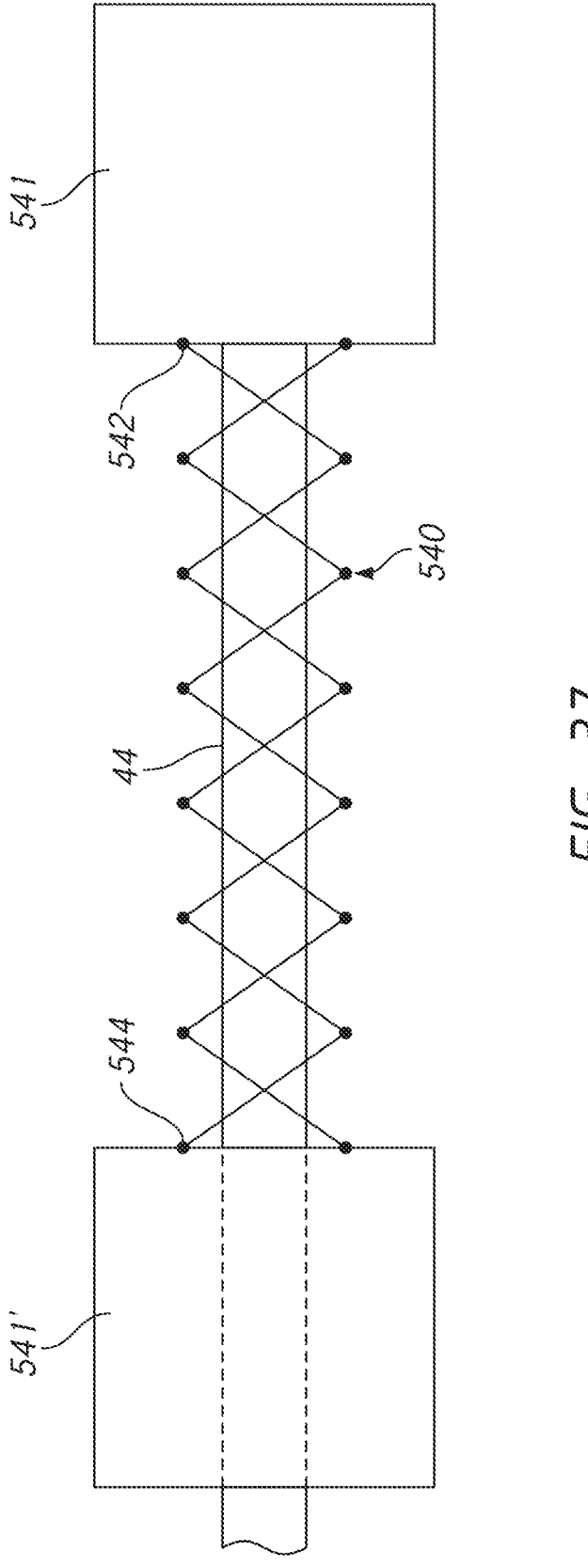
FIG. 37 depicts an example of an anti-buckling scissor mechanism.

FIG. 37 depicts an example of an interventional device 44 utilizing an anti-buckling scissor mechanism 540. Similar to the telescoping tubes, telescoping springs, and springs described herein, the scissor mechanism 540 can be configured to extend and collapse axially about an interventional device 44 (or more) extending therethrough. Also similar to the telescoping tubes, telescoping springs, and springs described herein, the scissor mechanism 540 can have a proximal retainer 542 and/or a distal retainer 544 to secure its proximal and distal ends, respectively, and/or it can be attached directly to hubs at its proximal and distal ends (e.g., hubs 541 and 541' as shown, which can be any of the hubs described herein). The scissor mechanism 540 can be configured to operate similar to a scissor lift, such that it can expand and collapse axially. The scissor mechanism 540 can provide an outer structure that prevents substantial buckling of an interventional device 44 extending therethrough.

Figures 38, 39A:
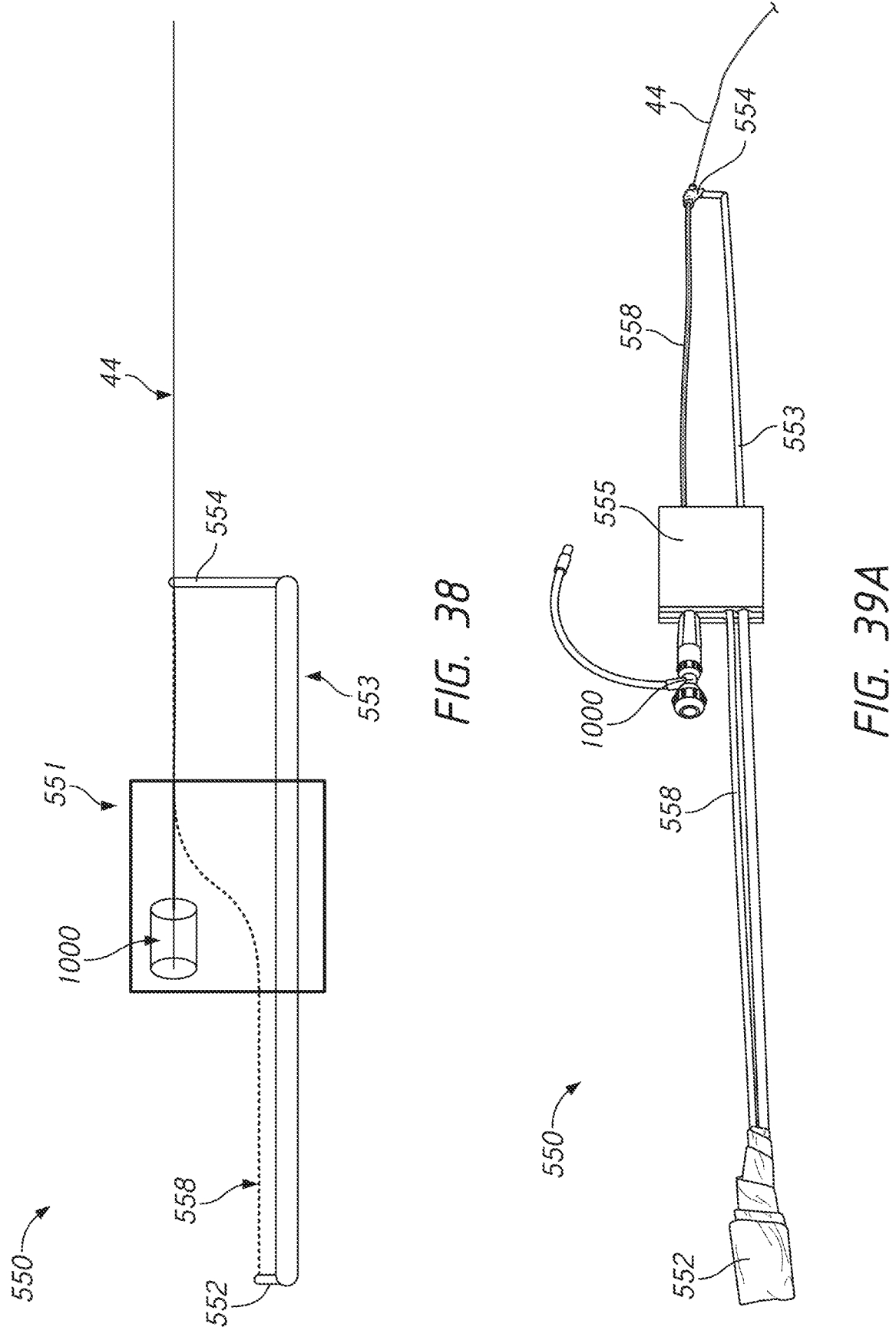
FIG. 38 depicts an example of an anti-buckling split tube with support rod.
FIGS. 39A-39E depict an example of an anti-buckling split tube with support rod.

FIG. 38 depicts an example of an anti-buckling split tube with a support rod 550. The split tube with support rod 550 can include a split tube 558 secured at its proximal end to a rod 553 with a proximal retainer 552 and at its distal end to the rod 553 with a distal retainer 554. A split in the split tube 558 can extend through a sidewall of the split tube 558 and can be, for example, a continuous longitudinal split. As shown, the split tube 558 can be routed through at least a portion of a hub 551 (which can be the same or similar to any of the hubs described herein) or through a hub interface configured to position the split tube 558 such that the interventional device 44 can extend therethrough (e.g., such that the interventional device 44 can enter a lumen of the split tube via the split in the split tube 558). For this, the split tube 558 can be made of a pliable material (e.g., silicone) such that it can travel through the hub 551 or the hub interface along a bent path. Furthermore, being of a pliable material, the split of the split tube 558 can generally close upon itself except for where the interventional device 44 traverses the split, which can advantageously provide support to the interventional device 44 along at least a portion of its length (e.g., at least some of its dead length) to prevent substantial buckling of the interventional device 44. The split of the split tube 558 can be positioned at least partially within the hub 551. The interventional device can enter the split tube within the hub 551. By positioning at least a portion of the interventional device and the split tube within the hub 551, dead length can be reduced.

As shown in FIG. 38, the interventional device 44 can extend (e.g., distally) from a position within the hub 551 (e.g., a rotating hemostatic valve 1000, which can be affixed to or relative to the hub 551), enter the split tube 558 through its split, and exit the split tube 558 out its distal end adjacent the distal retainer 554. As shown, the proximal end of the interventional device 44 can be formed of or coupled to a hypo tube. While not shown, the distal retainer 554 can be configured to attach (e.g., releasably attach) to a hub or other structure distal to the hub 551. In this way, when the hub 551 moves distally or proximally relative to the distal retainer 554, the interventional device 44 can be continuously routed through the split tube 558 that provides anti-buckling support. In some implementations, the rod 553 can provide tension to the split tube 558, however tension may not be required for function in some embodiments. Tension may assist in maintaining the tube in a relatively straight configuration so as to provide anti-buckling support. For example, tension may increase lateral stiffness and/or resistance to bending or buckling of an otherwise flexible tube.

Figures 39B, 39C, 39D, 39E:
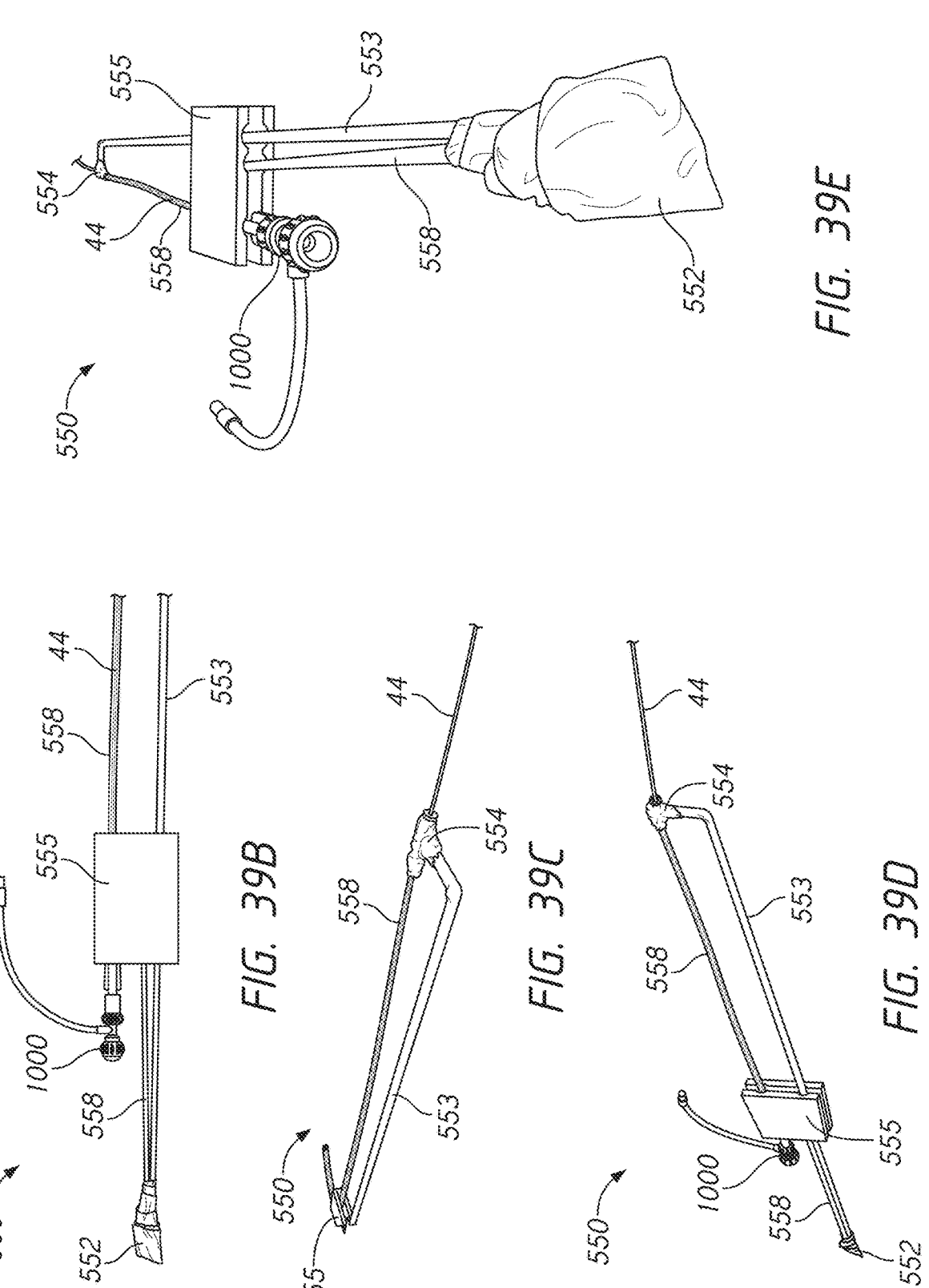

FIGS. 39A-39E depict an example of the anti-buckling split tube with support rod 550 described with respect to FIG. 38. FIG. 39A shows a top view of the split tube with support rod 550. FIG. 39B shows a close-up top view of a proximal end of the split tube with support rod 550. FIGS. 39C-39D show perspective views of the split tube with support rod 550. As shown in FIGS. 39A-39E, the split tube 558 is routed through a hub interface 555, which can be configured to releasably attach to a hub (such as hub 551 of FIG. 38).

Figures 40A, 40B:
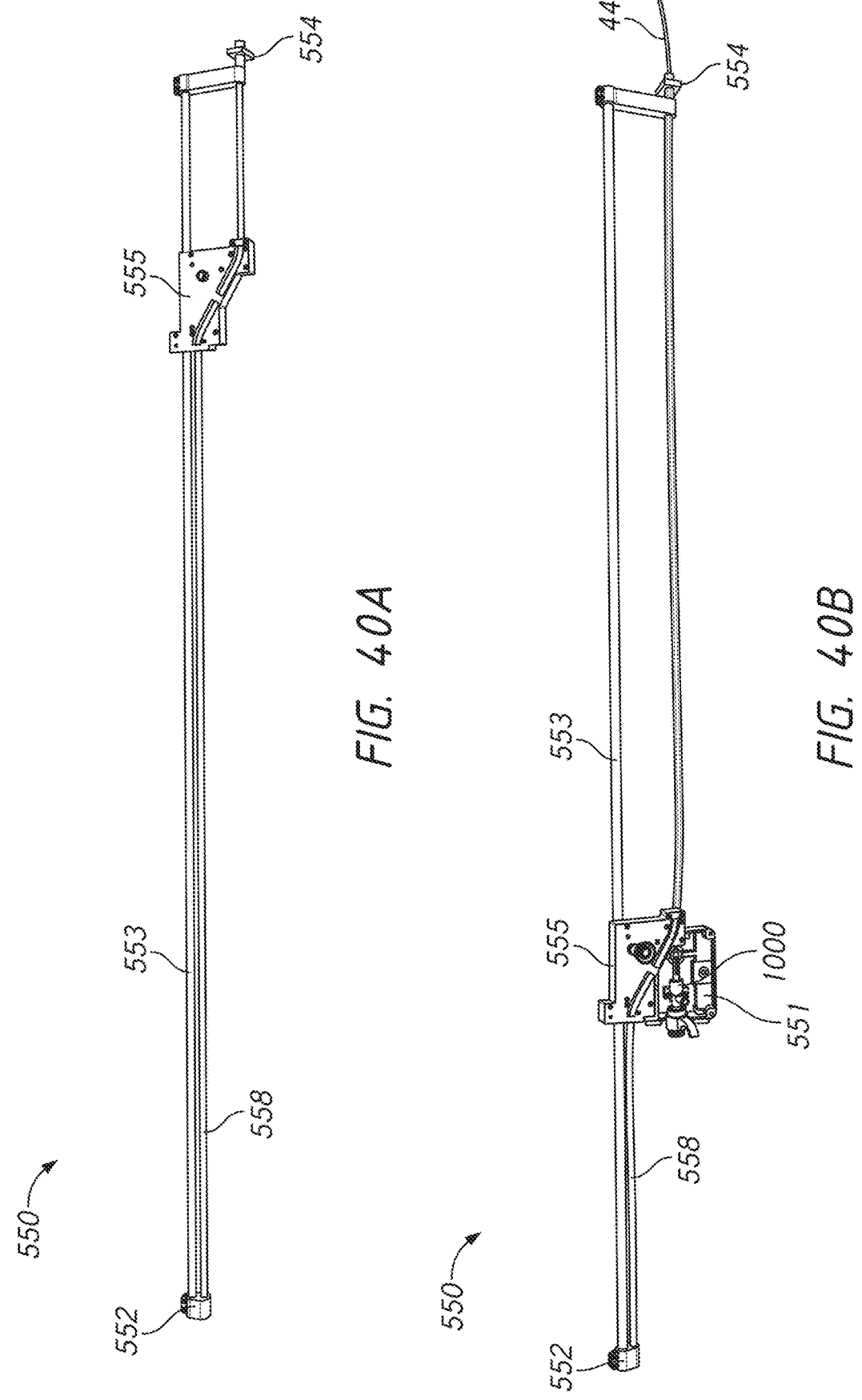
FIGS. 40A-40E depict an example of an anti-buckling split tube with support rod.

FIGS. 40A-40B depict another example of the anti-buckling split tube with support rod 550 described with respect to FIG. 38. FIG. 40A shows a top view of the split tube with support rod 550 without an interventional device 44 therethrough and with the split tube 558 routing through a hub interface 555. FIG. 40B shows a top view of the split tube with support rod 550 with the split tube 558 routing through a hub interface 555 and the hub interface 555 connected to the hub 551.

Figure 40C:
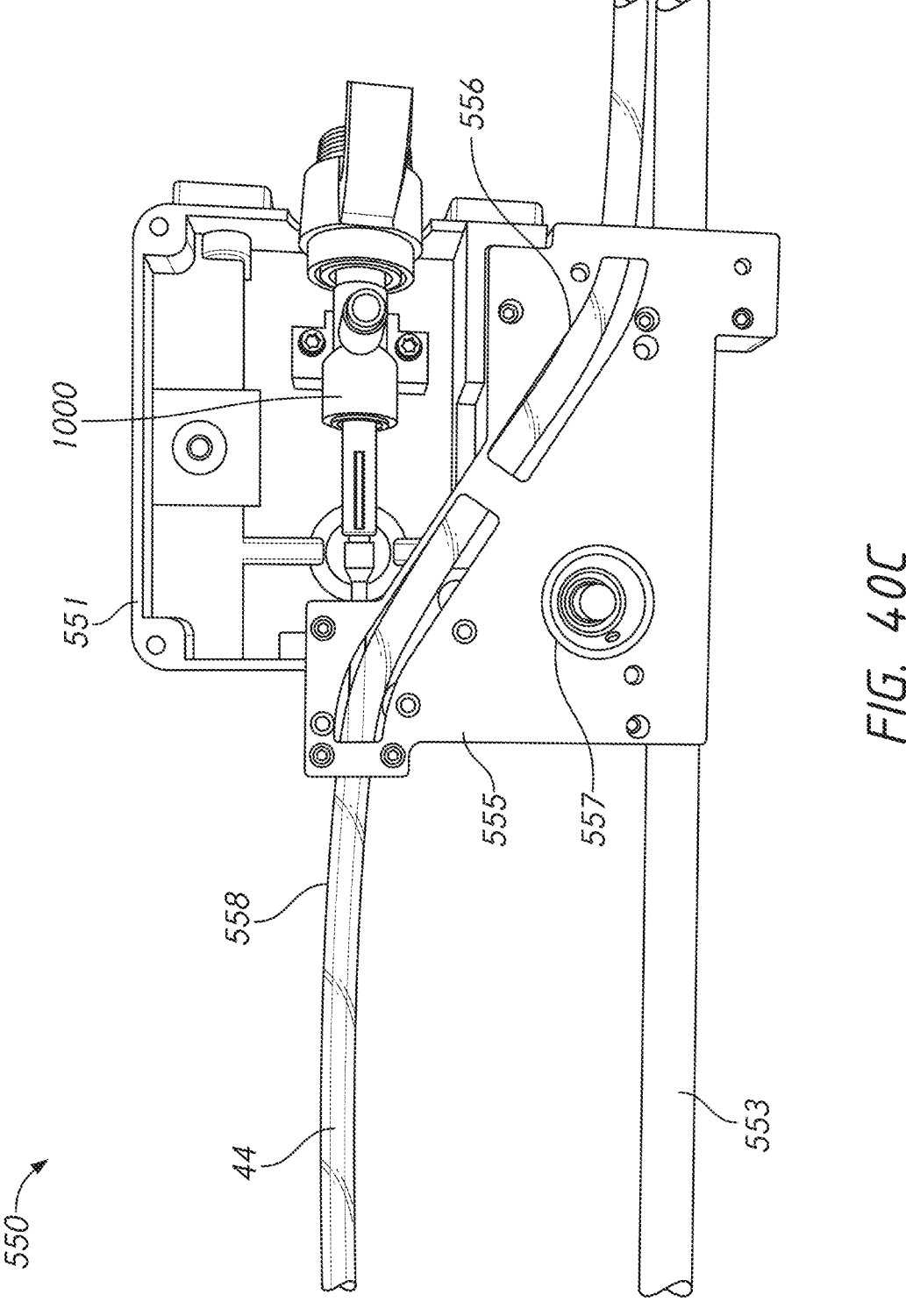
Figure 40D:
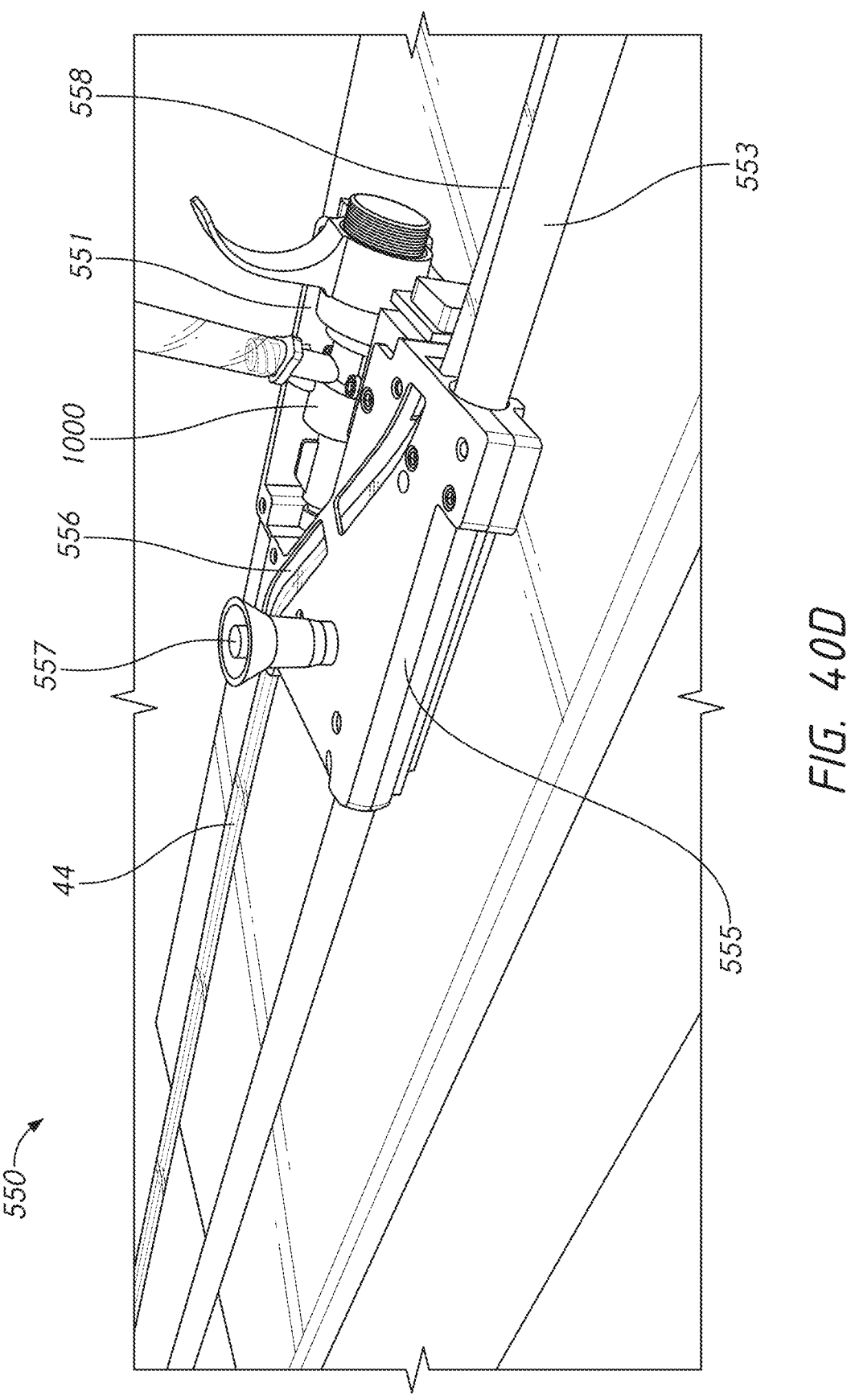
Figure 40E:
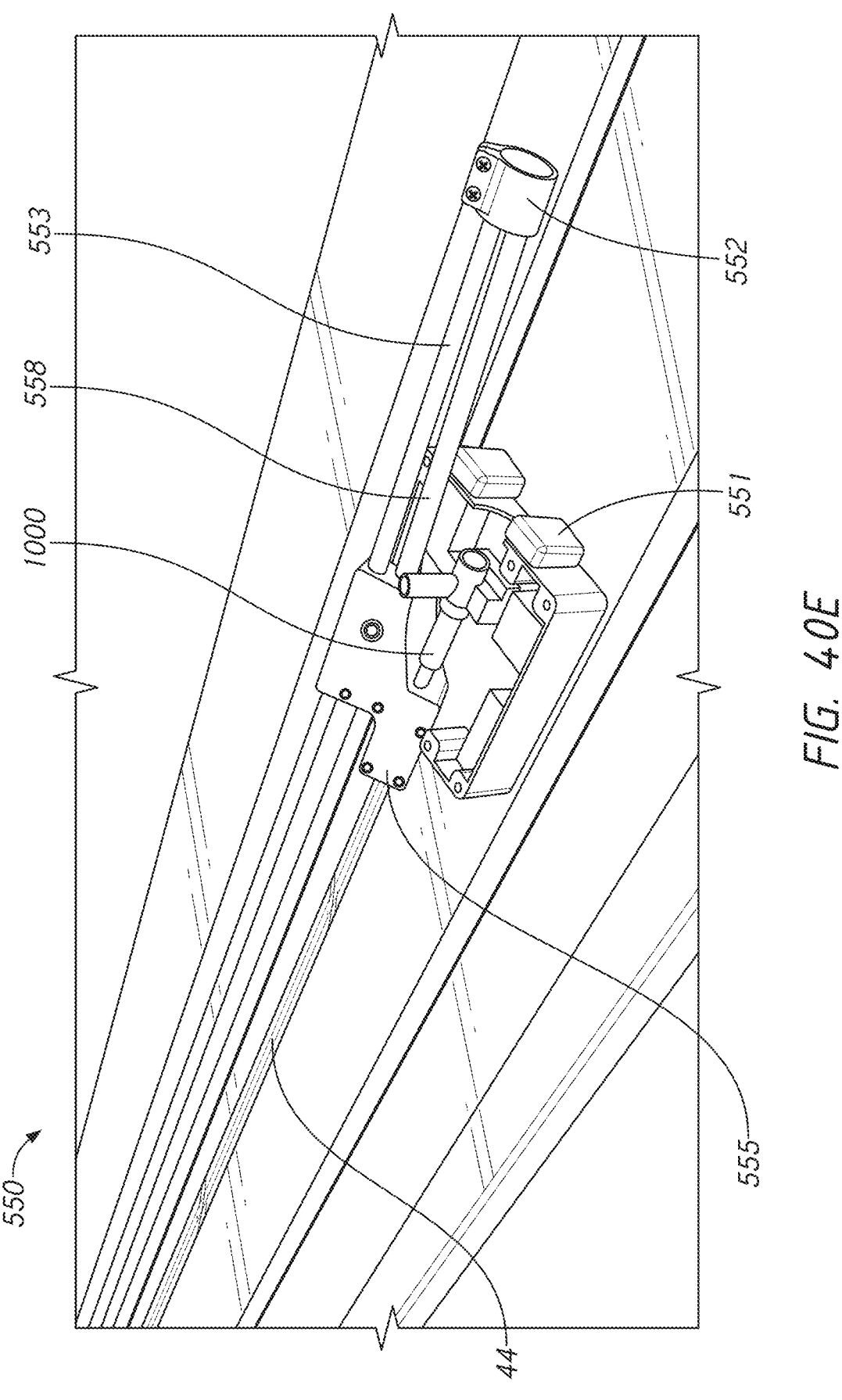

FIG. 40C shows a close up view of the split tube 558 routing through the hub interface 555 and the hub interface 555 connected to the hub 551. FIG. 40D shows a perspective view of the split tube 558 routing through the hub interface 555 and the hub interface 555 connected to the hub 551. FIG. 40E shows a perspective view of the split tube 558 routing through the hub interface 555 and the hub interface 555 connected to the hub 551 in another configuration. As shown in FIGS. 40A-40D, the split tube interface 555 can include a channel or track 556 configured to route the split tube 558 therethrough and position the split tube 558 to receive the interventional device 44. As shown in FIGS. 40B-40D, the hub interface 555 can include a pin 557 configured to releasably connect the hub interface 555 to the hub 551. As shown in FIG. 40E, the hub interface 555 can be connected to the hub 551 in various ways and at various positions and/or angles relative to the hub 551. Such variations can advantageously allow multiple split tube with support rods 550 to be used in an interventional device assembly without them interfering with one another.

Figure 41:
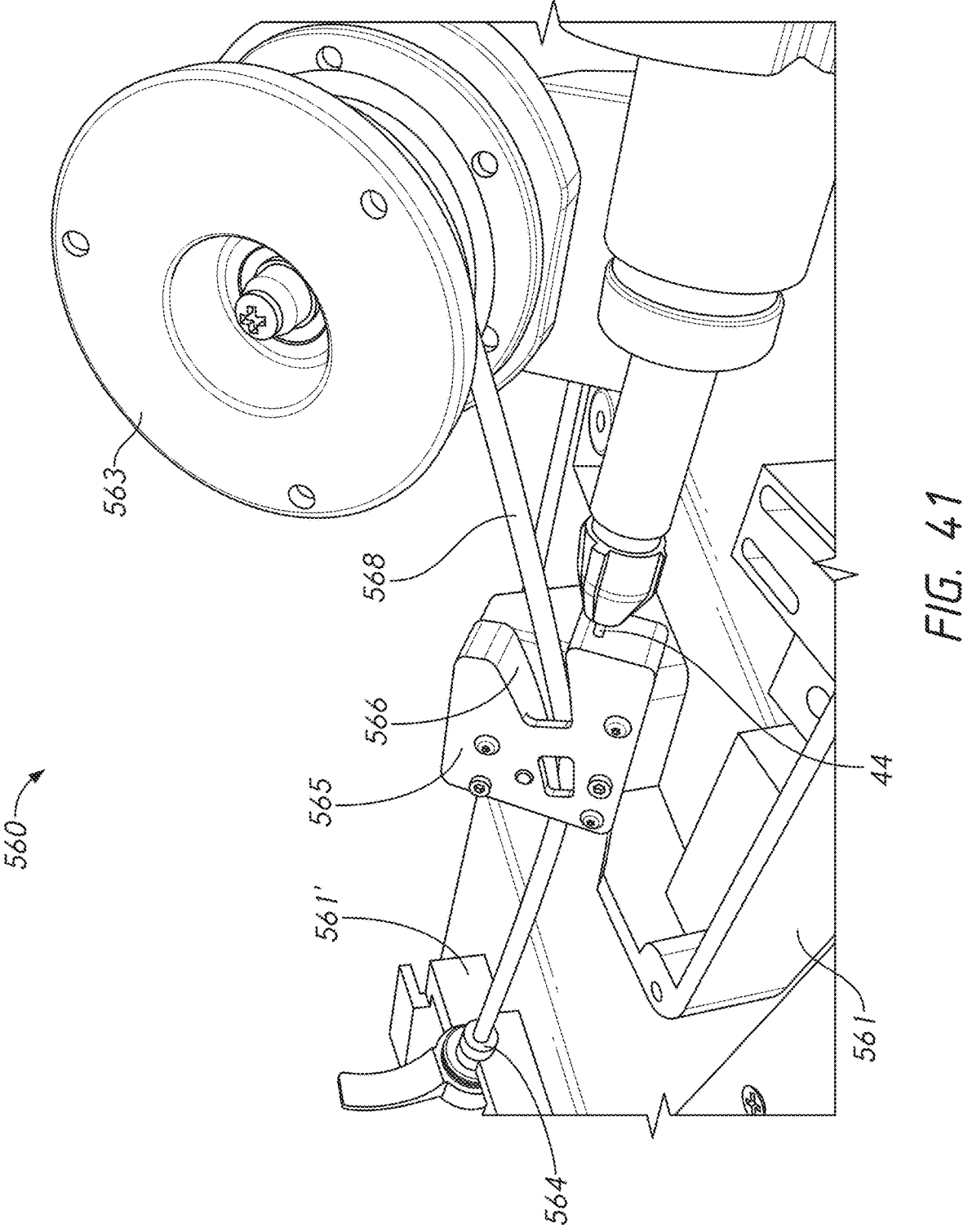
FIG. 41 depicts an example of an anti-buckling split tube with reel.

FIG. 41 depicts an example of an anti-buckling split tube with reel 560. The split tube with reel 560 can include a split tube 568 secured at its proximal end to a portion of a reel 563 at a proximal attachment (hidden from view) and at its distal end to a distal attachment 564. Similar to the split tube 558, a split in the split tube 568 can extend through a sidewall of the split tube 568 and can be, for example, a continuous longitudinal split. As shown, the split tube 568 can be routed through a hub interface 565 that releasably connects to hub 561 (which can be the same or similar to any of the hubs described herein) or through at least a portion of the hub 561 for similar positioning. The hub interface 565 and/or the hub 561 can be configured to position the split tube 568 such that the interventional device 44 can extend therethrough (e.g., such that the interventional device 44 can enter a lumen of the split tube via the split in the split tube 568). For example, the hub interface 565 can include a track 566 configured to route the split tube 558 therethrough and position the split tube 558 to receive the interventional device 44. The split tube 568 can be made of a pliable material (e.g., silicone) such that it can travel through the hub 561 or the hub interface 565 along a bent or curved path. Furthermore, being of a pliable material, the split of the split tube 568 can generally close upon itself except for where the interventional device 44 traverses the split, which can advantageously provide support to the interventional device 44 along at least a portion of its length (e.g., at least some of its dead length) to prevent substantial buckling of the interventional device 44. The interventional device 44 can extend (e.g., distally) from a rotating hemostatic valve 1000, which can be affixed to or relative to the hub 561, and enter the split tube 568 through its split. Not shown, the interventional device 44 can exit the split tube 568 out its distal end adjacent the distal attachment 564. the distal attachment 564 can be configured to attach (e.g., releasably attach) to a hub or other structure distal to the hub 561, such as hub 561' (which can be the same or similar to any of the hubs described herein). Furthermore, the reel 563 can be spring loaded (e.g., via a torsion spring) or motor operated such that the split tube 568 winds about and unwinds from the reel 563 in use. For example, the split tube 568 can wind about the reel 563 when the hub 561 moves distally and unwind from the reel 563 when the hub 561 moved proximally. In this way, when the hub 561 moves distally or proximally relative to the distal attachment 564, the interventional device 44 can be continuously routed through the split tube 568 that provides anti-buckling support. In some implementations, the reel 563 can provide tension to the split tube 568 (e.g., via the torsion spring or motor). Tension may increase lateral stiffness and/or resistance to bending or buckling of an otherwise flexible tube. The split tube with reel 560 can advantageously provide a space efficient anti-buckling solution.

FIGS. 42A-42D depict an example of an anti-buckling split tube with reel 570. The split tube with reel 570 can be similar to the split tube with reel 560 in some or many respects. For example, the split tube with reel 570 can have a split tube 578, a reel 573, a proximal attachment 572, a distal attachment 574, a hub interface 575, a hub 571, and a rotating hemostatic valve 1000 that are the same or similar and can have any of the functionality and features of the split tube 568, the reel 563, the proximal attachment, the distal attachment 564, the hub interface 565, the hub 561, and the rotating hemostatic valve 1000 of the split tube with reel 560 described with respect to FIG. 41. FIGS. 42A-42D show various perspective views of the split tube with reel 570 without the split tube 578, although if shown it would attach at its proximal end to proximal attachment 572 of the reel 573, wind about the reel 573, extend from the reel 573 through the track 576 of the hub interface 575 where it receives the interventional device 44, and attach at its distal end to distal attachment 574.

Different than the split tube with reel 560, the split tube with reel 570 has a safety mechanism to prevent undesirable distal advancement of the interventional device 44 (e.g., the reel 573 can put tension on the split tube 578 if spring loaded such as by torsion spring 588 as shown, which could pull the hub 571 and thus the interventional device 44 distally). The safety mechanism can include a spring 581, a rack 582, a gear 583, a shaft 584, a cam 585, a spring-loaded pawl 586, and a rachet wheel 587. As shown though FIGS. 42A-42D, the rack 582 can be biased in a downward position (e.g., towards the support table 20 upon which the hub 571 rests such that it extends below the bottom of the hub 571) by the spring 581. The gear 583 can mesh with the rack 582 such that movement of the rack 582 (e.g., up or down) rotates the gear 583, which in turn rotates the shaft 584 attached thereto. The cam 585, also attached to the shaft 584, thus also rotates upon movement of the rack 582. The cam 585 can interact with the spring-loaded pawl 586 to either cause the pawl 586 to contact the rachet wheel 587 and prevent rotation thereof in at least one rotational direction (e.g., clockwise as shown), or to cause the pawl 586 to not contact the rachet wheel 587 and allow free rotation thereof. When the hub 571 is pulled away from the support table 20, the rack 582 is biased downward by the spring 581 as described above, which through interactions between the rack 582, the gear 583, the shaft 584, and the cam 585 causes the spring-loaded pawl 586 to contact the rachet wheel 587 and prevent rotation thereof in the at least one rotational direction. This can be considered the safety or safety on position. Conversely, when the hub 571 is set against the support table 20, the downward bias of the rack 582 by the spring 581 is overcome and the rack 582 is moved upward, which through interactions between the rack 582, the gear 583, the shaft 584, and the cam 585 causes the spring-loaded pawl 586 to pull away from and not contact the rachet wheel 587 and allow rotation thereof. This can be considered the safety off position.

With continued reference to FIGS. 42A-42D, the distal attachment 574 can include a structure having one or more magnets 579 configured to releasably attach to a distal hub (not shown). This effectively allows the split tube 578 to extend from hub 571/hub interface 575 in the distal direction to provide anti-buckling support to the interventional device 44. The hub 571 can include one or more magnets (e.g., at a proximal end thereof) 577 configured to releasably attach to a distal attachment of a proximal hub configured the same or similar to the distal attachment 574.

Figures 42A, 42B:
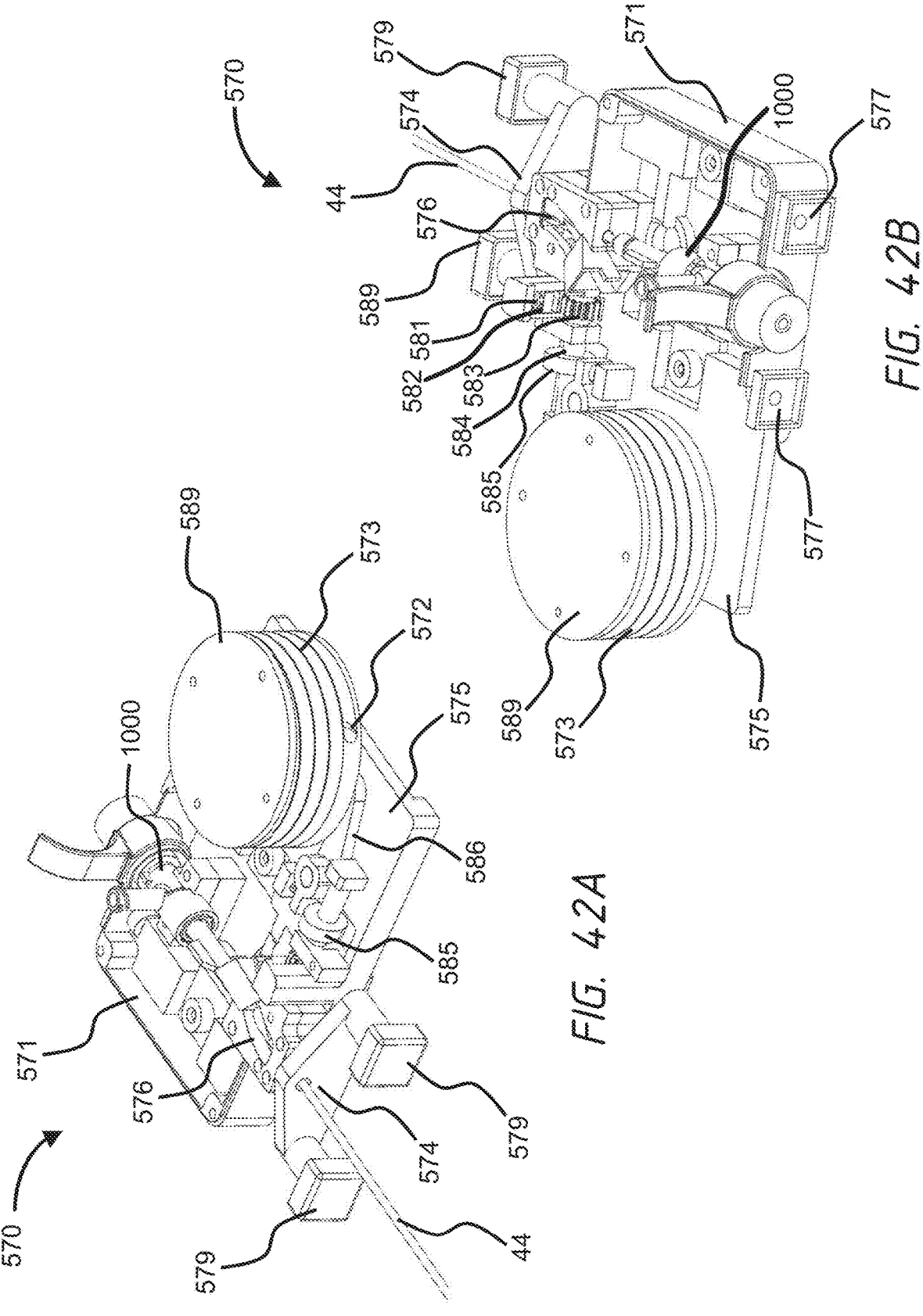
FIGS. 42A-42D depict an example of an anti-buckling split tube with reel.
Figures 42C, 42D:
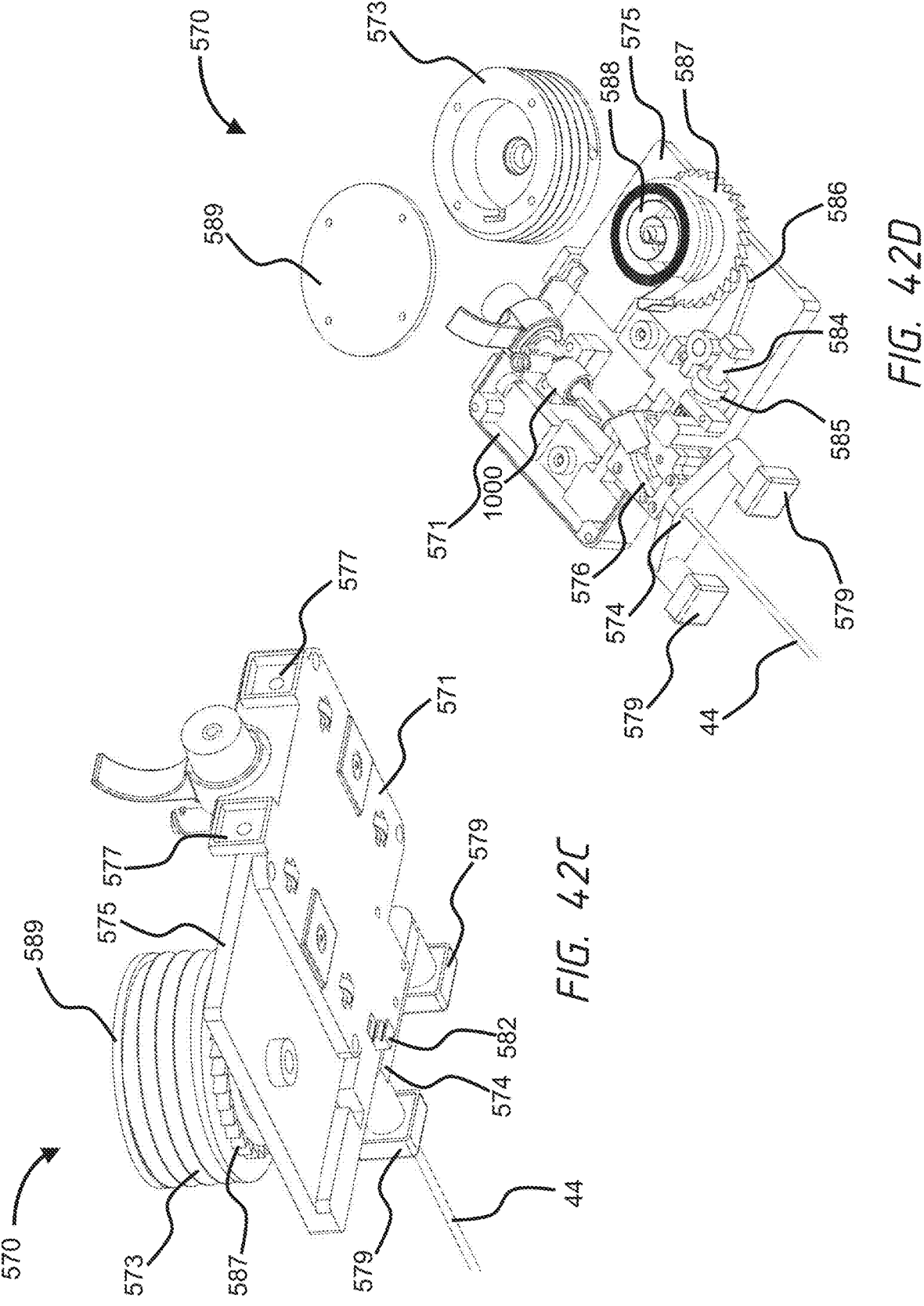

The bottom perspective view of FIG. 42C shows the rack 582 extending below the bottom of the hub 571 in the safety position. Also shown in FIG. 42C are one or more driven magnets (two as shown) and one or more rollers (four as shown) as described herein. The partial exploded view of FIG. 42D shows the reel 573 removed from the rachet wheel 587 and the torsion spring 588 it is connected thereto, along with a cover 589 of the reel 573 removed.

Figure 43:
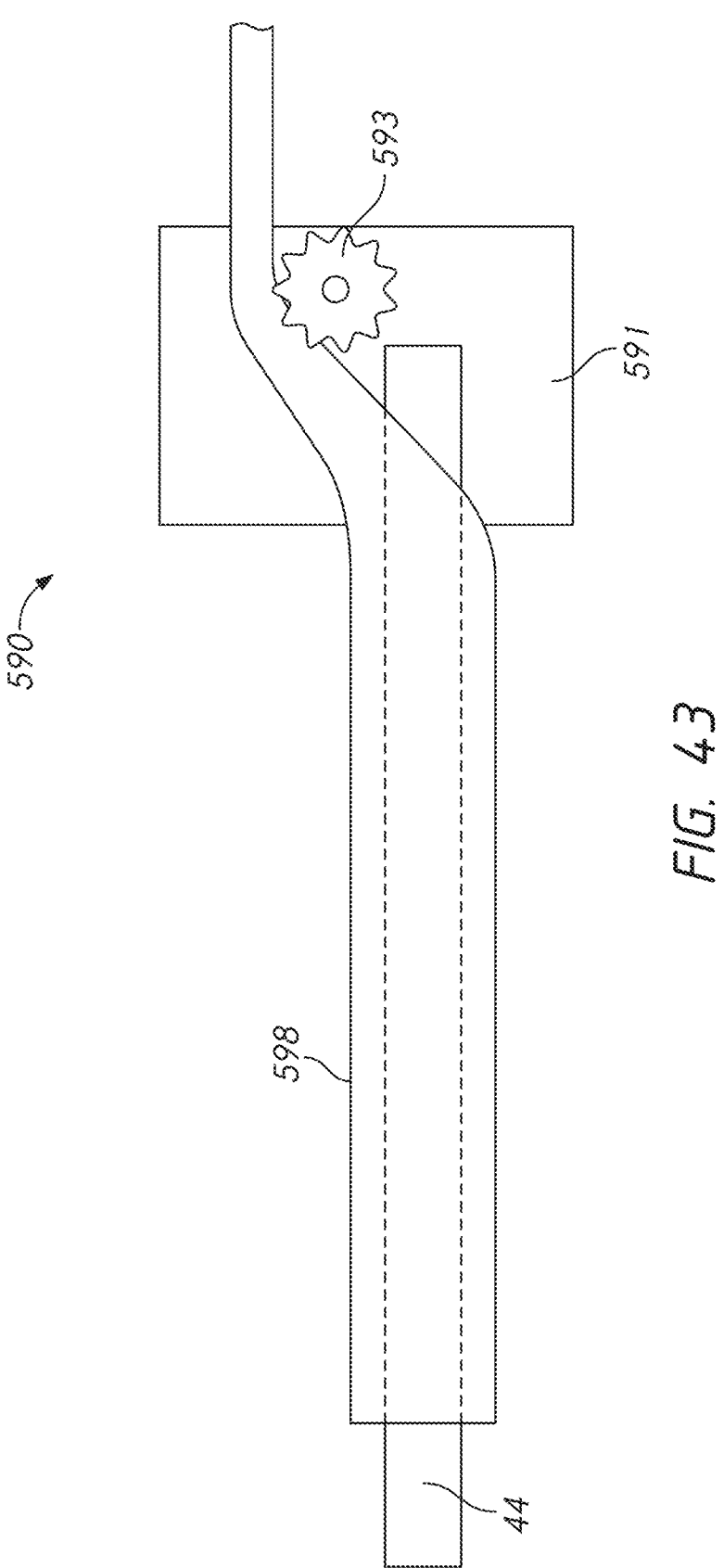
FIG. 43 depicts an example of an anti-buckling split tube with sprocket.

FIG. 43 depicts an example of an anti-buckling split tube with sprocket 590. The split tube with sprocket 590 can be similar to the split tube with rod support 550, the split tube with reel 560, and the split tube with reel 570 in some or many respects. For example, the split tube with sprocket 590 can have a split tube 598 and a hub 591 that are the same or similar and can have any of the functionality and features of the split tubes 558, 568, and 578 and the hubs 551, 561, and 571 described herein. Different than the other split tube based anti-buckling embodiments, the split tube with sprocket 590 can include a split tube 598 that interfaces with a sprocket 593 that can hold tension on the split tube 598 as the hub 591 and interventional device 44 move proximally and distally (e.g., as the interventional device 44 moves inside the split tube 598). Tension may increase lateral stiffness and/or resistance to bending or buckling of an otherwise flexible tube. The sprocket 593 can attach directly to the hub 591 or to the hub via a hub interface (not shown) and can be configured to hold and apply such tension on the split tube 598 by a torsion spring or motor. The proximal end of the split tube 598 can extend proximally past the hub 591 as shown, and can be, as examples, connected to a proximal attachment that interfaces with a hub located proximal to the hub 591 or connected to a proximal attachment that interfaces with a support rod. In some implementations, the proximal end of the split tube 598 can connect to a reel attached to the hub 591 or a hub interface attached to the hub 591 as described herein, and the split tube 598 can wind about such reel (e.g., the sprocket 593 can wind or unwind the split tube 598 about the reel). The distal end of the split tube 598 can extend distally so that the split tube 598 provides anti-buckling support to the interventional device 44, and can be, for example, connected to a distal attachment or retainer as described herein. Furthermore, the split tube with sprocket 590 can include a track configured to route the split tube 598 therethrough and position the split tube 598 to receive the interventional device 44 as described herein.

Figure 44:
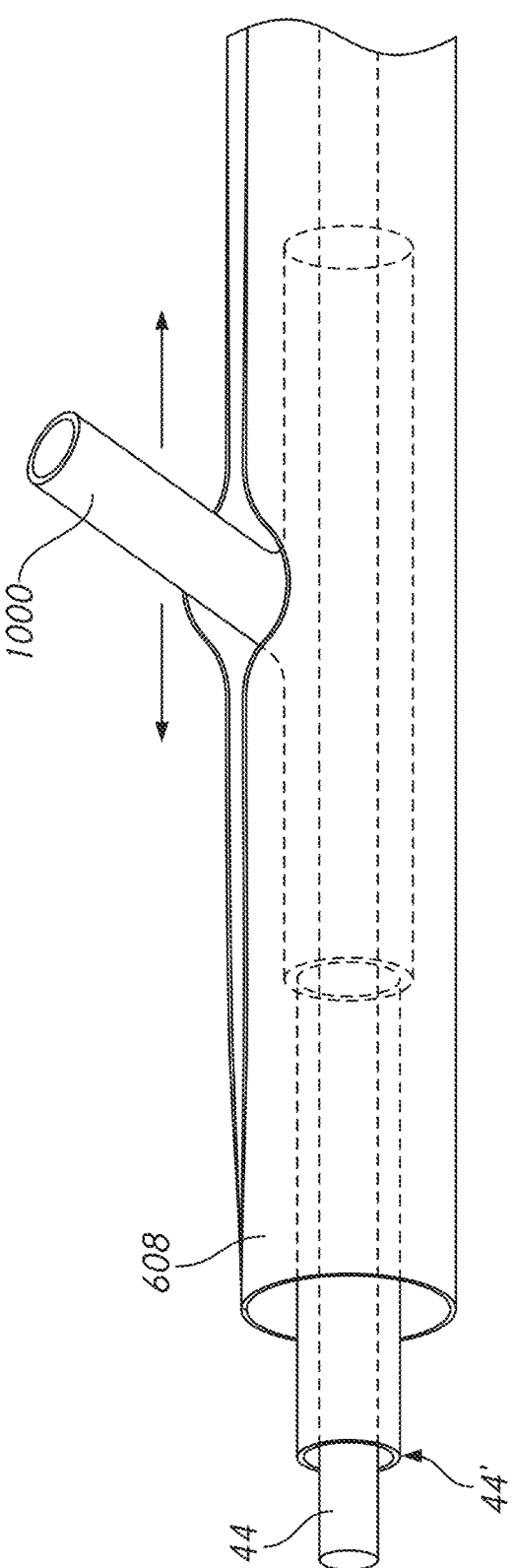
FIG. 44 depicts an example of an anti-buckling split tube.

FIG. 44 depicts an example of an anti-buckling split tube 608. The split tube 608 can be similar to the split tubes 558, 568, 578, and 598 in some or many respects. The split tube 608 can provide a channel, via its lumen, for interventional devices, such as interventional devices 44 and 44' as shown, to be contained within. In this way the split tube 608 provides anti-buckling support. Different than the other split tubes described herein, the split tube 608 can be configured to house at least a portion of the rotating hemostatic valve(s) 1000 the interventional devices routed therethrough attach to. Furthermore, the split tube 608 can be configured to allow such rotating hemostatic valve(s) 1000 to move distally and proximally therethrough along with the interventional device(s) they attach to. In some implementations without rotating hemostatic valve(s) 1000, the split tube 608 can be configured to allow movement of at least a portion of the hubs the interventional device(s) attach to therethrough. The split tube 608, like other split tubes described herein, can be made of a pliable material. In some implementations, the split tube 608 can be made of a semi-rigid material or a rigid material (e.g., sufficient to maintain the split tube 608 in a straight or relatively straight configuration without the application of additional tension to the split tube 608). In some embodiments, the split tube 608 may not house a portion of the rotating hemostatic valve 1000. Such embodiments may allow for a smaller split tube 608.

Figure 45A:
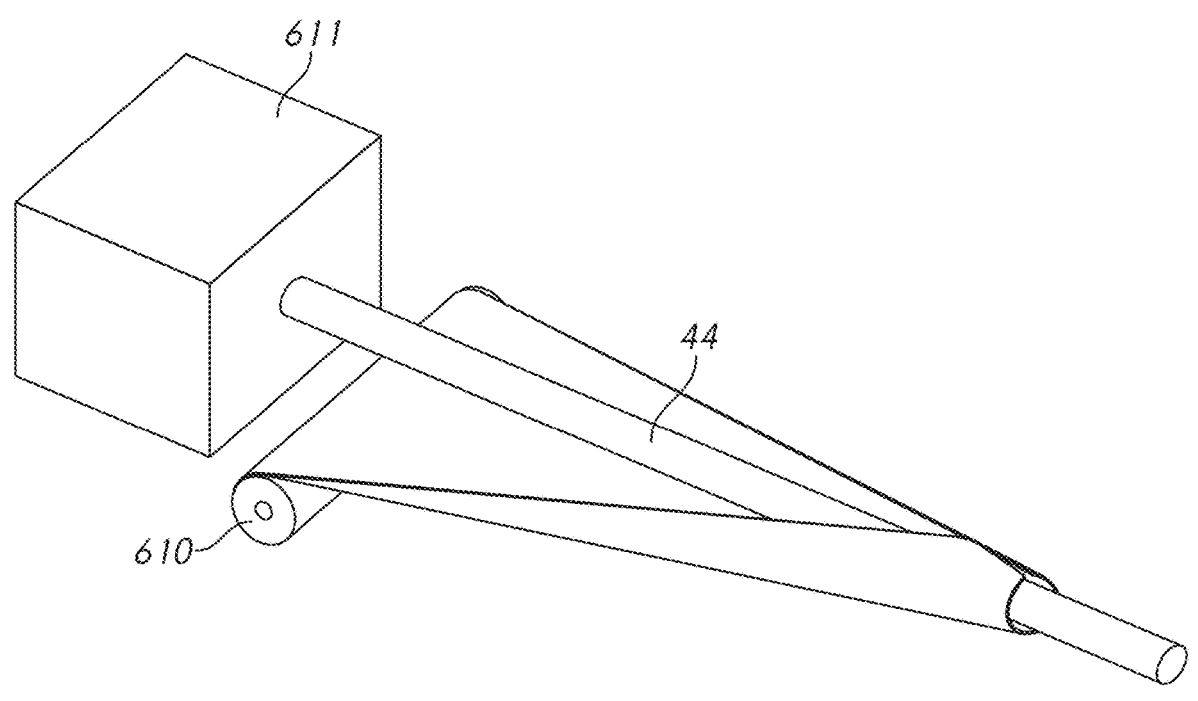
FIGS. 45A-45B depict examples of anti-buckling storable extendible supports.
Figure 45B:
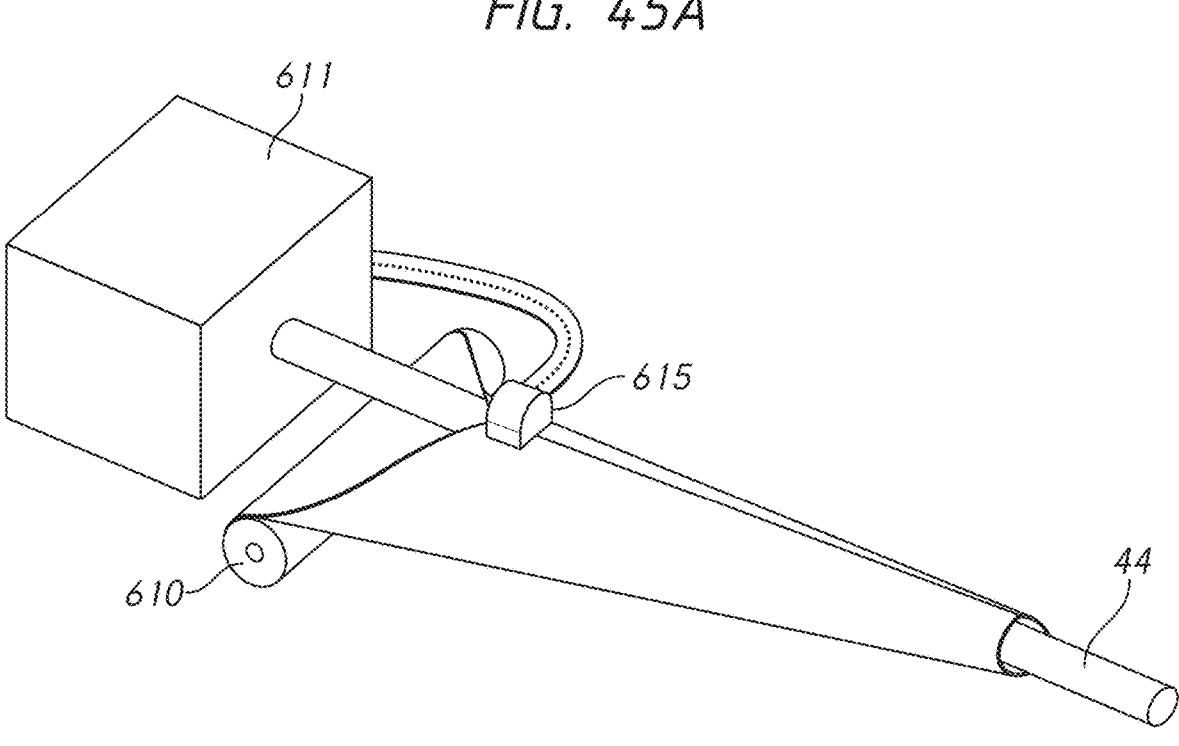

FIGS. 45A-45B depict examples of anti-buckling storable extendible supports 610. As shown in FIG. 45A, the storable extendible support 610 can be configured to roll or otherwise collapse upon itself distally adjacent to where interventional device 44 extends from its hub 611. The storable extendible support 610 can unroll to provide anti-buckling support to the interventional device 44 (e.g., in response to movement of the hub 611. For example and as shown, the storable extendible support 610 can unroll and at least partially enclose the interventional device 44 (e.g., by forming a partial tube around the interventional device 44 through which the interventional device 44 can travel proximally and distally). For this, the storable extendible support 610 can have a shape memory and/or be made of a shape memory material. In some embodiments, the distal end of the storable extendible support 610 can be attached to a distal attachment that attaches to a distally located hub or attachment site, such that upon relative movement between such distal attachment and the hub 611 the storable extendible support 610 extends and retracts to provide anti-buckling support to the interventional device 44 spanning such distance. As shown in FIG. 45B, a zipper 615 can be configured to enclose the storable extendible support 610 about the interventional device 44 adjacent to where the storable extendible support 610 extends from its storage location. Such a zipper 615 can attach to the hub 611 or a component thereof as shown. This configuration of the storable extendible support 610 with zipper 615 can advantageously provide for greater enclosure of the interventional device 44 and thus improved anti-buckling support. Furthermore, such a configuration can allow the storable extendible support 610 to be made from a material other than a shape memory material or from having a shape memory.

Figures 46A, 46B:
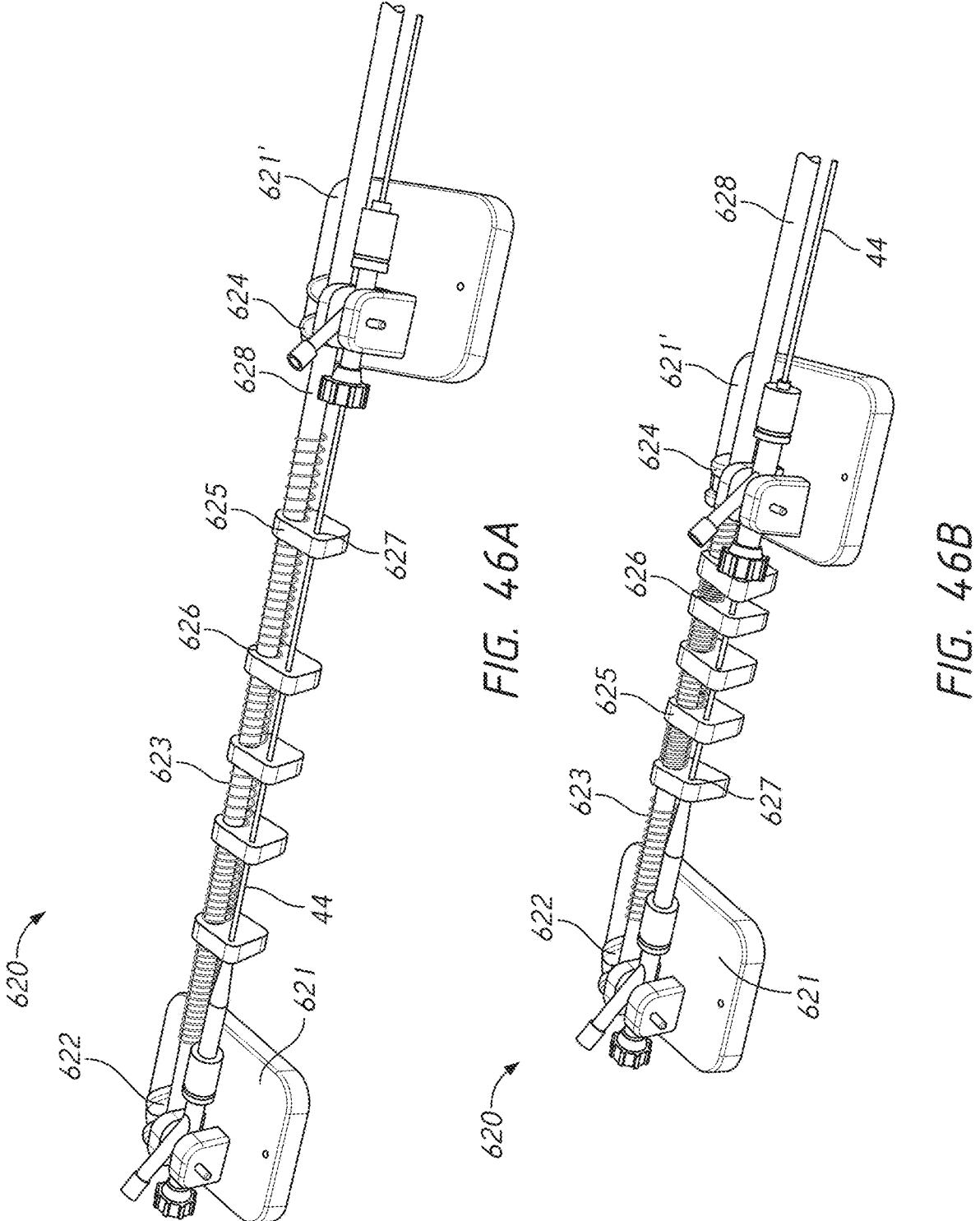
FIGS. 46A-46B depict an example of anti-buckling supports.

FIGS. 46A-46B depict an example of anti-buckling supports 620. The anti-buckling supports 620 can include a rod 628 and supports 625 configured to extend between hubs, a hub and an attachment point, or two attachment points and provide anti-buckling support to an interventional device 44 spanning therebetween. The anti-buckling supports 620 can also include springs 623 as shown configured to distribute/ space (e.g., evenly space) the supports 625 between such span. As shown, the rod 628 can be attached to hub 621 and to hub 621' located distal to the hub 621 (both of which can be the same or similar to any of the hubs described herein). One of such attachments to the hubs can be a fixed attachment (e.g., proximal attachment 622), while the other can be an attachment that allows translation of the rod 628 therethrough (e.g., distal attachment 624). Further as shown, the supports 625 can be configured to slide along the rod 628, such as via a through hole 626 in each support 625. The springs 623, when included, can be disposed over the rod 628 between each support 625 and between attachment points 622, 624 and supports 625. Each support 625 can also be configured to surround at least a part of the interventional device 44 to provide anti-buckling support thereto. For example and as shown, each support 625 can have a through hole 627 configured to receive therethrough at least a portion of the interventional device 44. In some implementations, the supports 625 can instead be rings or other enclosed shape. FIG. 46A shows the anti-buckling supports 620 in a relatively expanded configuration, while FIG. 46B shows the anti-buckling supports 620 in a relatively collapsed configuration.

Figures 47A, 47B:
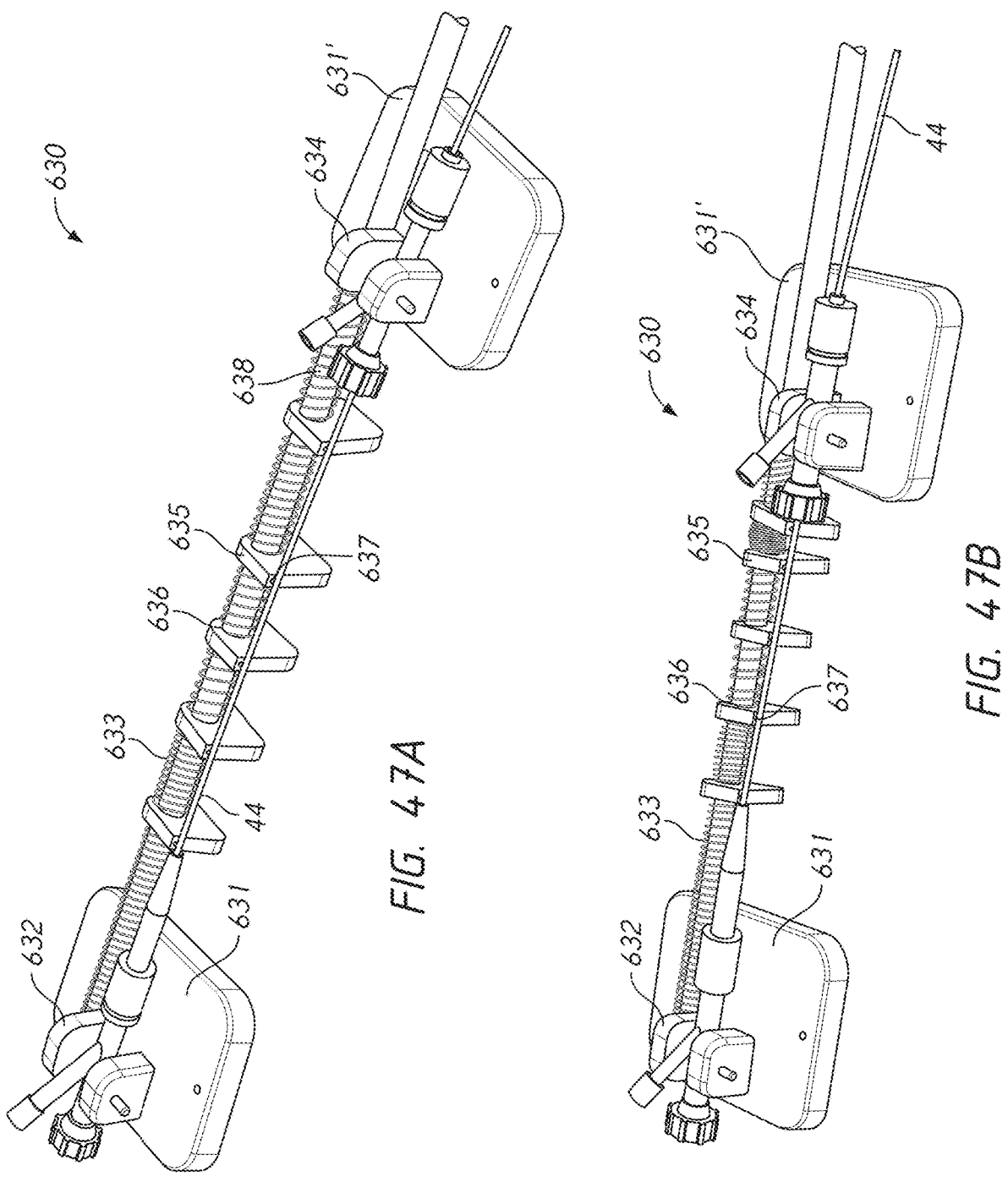
FIGS. 47A-47B depict an example of magnet-based anti-buckling supports.

FIGS. 47A-47B depict an example of magnet-based anti-buckling supports 630. The magnet-based anti-buckling supports 630 can be similar to the anti-buckling supports 620 in some or many respects. For example, the magnet-based anti-buckling supports 630 can include a rod 638, supports 635 with through holes 636, springs 633, proximal attachment 632, and distal attachment 634 that are the same or similar or can have any of the functionality and/or features of the rod 628, supports 625 with through holes 626, springs 623, proximal attachment 622, and distal attachment 624 described with respect to the anti-buckling supports 620. For example, in some embodiments, the rod 638 can couple to the hub 631 and the hub 631'. Different than the anti-buckling supports 620, the supports 635 of the magnet-based anti-buckling supports 630 can each have a magnet 637 instead of a through hole 627, the magnets 637 configured to attract at least a portion of the interventional device 44 and thus provide anti-buckling support to the interventional device 44 as it extends therealong. FIG. 47A shows the magnet-based anti-buckling supports 630 in a relatively expanded configuration, while FIG. 47B shows the magnet-based anti-buckling supports 630 in a relatively collapsed configuration. In some implementations, one or more of the supports 635 of the magnet-based anti-buckling supports 630 can include a through hole or other feature that at least partially surrounds at least a portion of the interventional device 44, such through hole or feature configured to work in combination with the magnet 635 to attract and/or support the interventional device 44 and prevent substantial buckling thereof.

Figure 48:
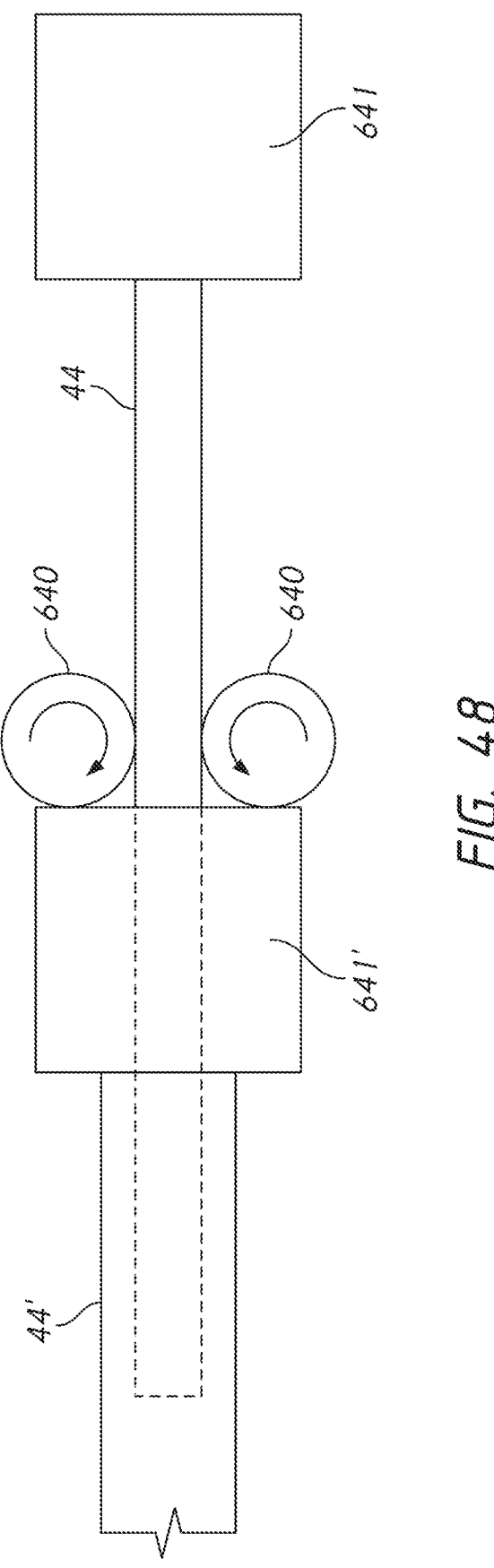
FIG. 48 depicts an example of anti-buckling feed rollers.

FIG. 48 depicts an example of anti-buckling feed rollers 640. The feed rollers 640 can include one or more rollers (two are shown) configured to feed an interventional device 44 into another interventional device 44' located distally. As shown, the feed rollers 640 can be positioned proximal to hub 641' to feed the interventional device 44 extending from hub 641 through the interventional device 44'. The feed rollers 640 may be coupled to the proximal end of the hub 641'. By feeding the interventional device 44 distally from such location, the load on the unsupported portion of such device can be reduced, thus reducing and/or preventing buckling thereof. One or more of the feed rollers 640 can be driven so as to feed the interventional device 44, such as by a motor or torsion spring (which can be operated in combination with a brake on the feed roller 640 being driven). The feed rollers 640 can feed an interventional device into a distal hub to reduce the possibility of buckling due to loads inside the vasculature.

Figure 49:
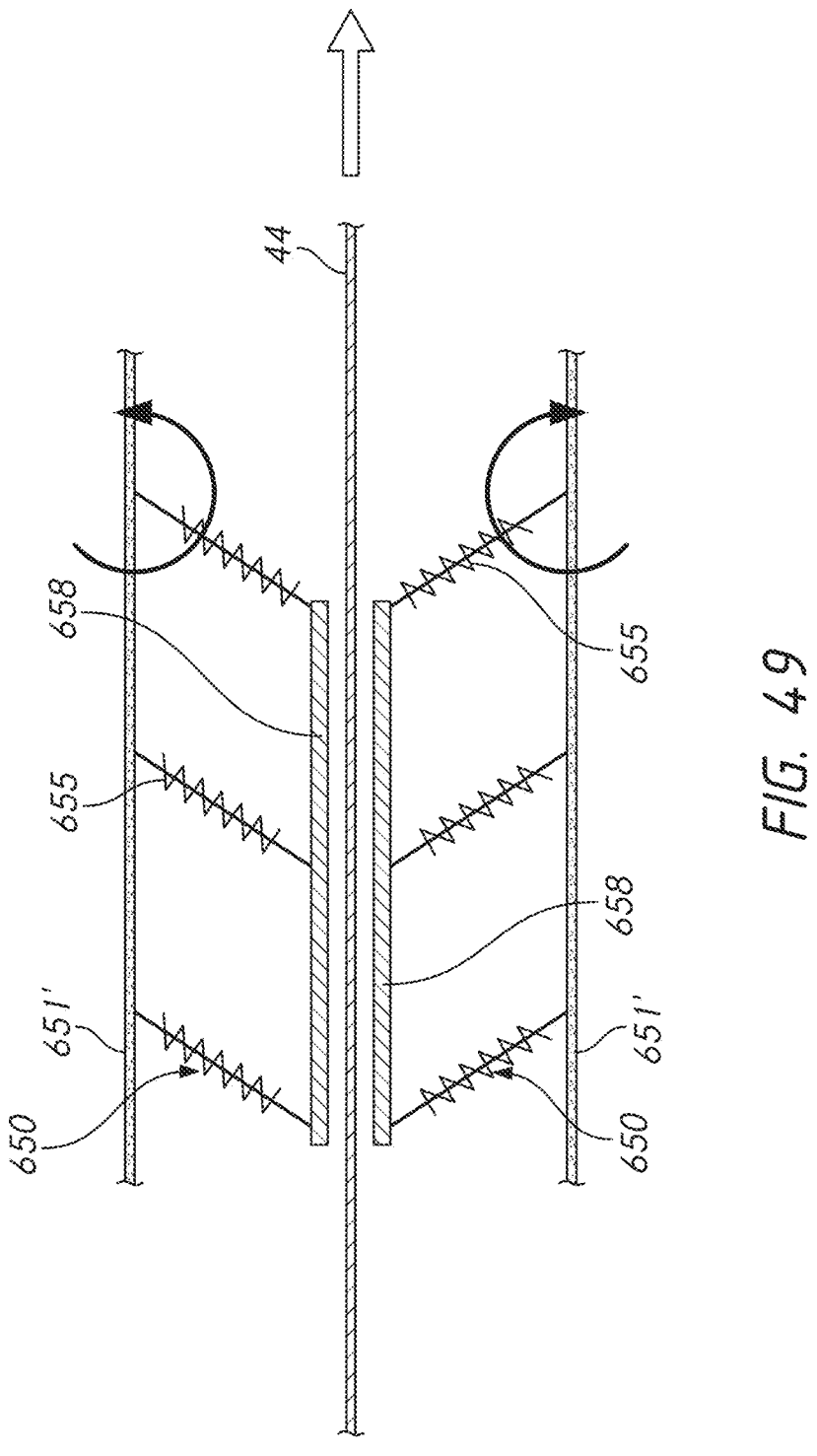
FIG. 49 depicts an example of anti-buckling grippers.

FIG. 49 depicts an example of anti-buckling grippers 650. Similar to the feed rollers 640, the grippers 650 can be configured to contact at least a portion of an interventional device 44 and feed it into another interventional device located distally. The grippers 650 can include linking portions 655 and contact portions 658, the linking portions 655 configured to attach the contact portions 658 to a hub 651' of the distally located interventional device. By feeding the interventional device 44 distally from such location, the load on the unsupported portion of such device can be reduced, thus reducing and/or preventing buckling thereof. The grippers 650 including the contact portions 658 and linking portions 655 can comprise a set of four bar linkages, one on either side of the interventional device 44 being fed, that can come together to contact and feed such interventional device 44. Furthermore, the grippers 650 can be driven (e.g., rotated) by a motor of the hub 651'. The grippers 650 can provide a large contact/friction patch and thus a high grip force on the interventional device 44 being fed. Furthermore, the grippers 650 (e.g., the linking portions 655) can be at least somewhat flexible or spring-like and provide the normal force to grip the interventional device 44. The grippers 650 may pull an interventional device into a distal hub to reduce the possibility of buckling due to loads inside the vasculature.

Figure 50:
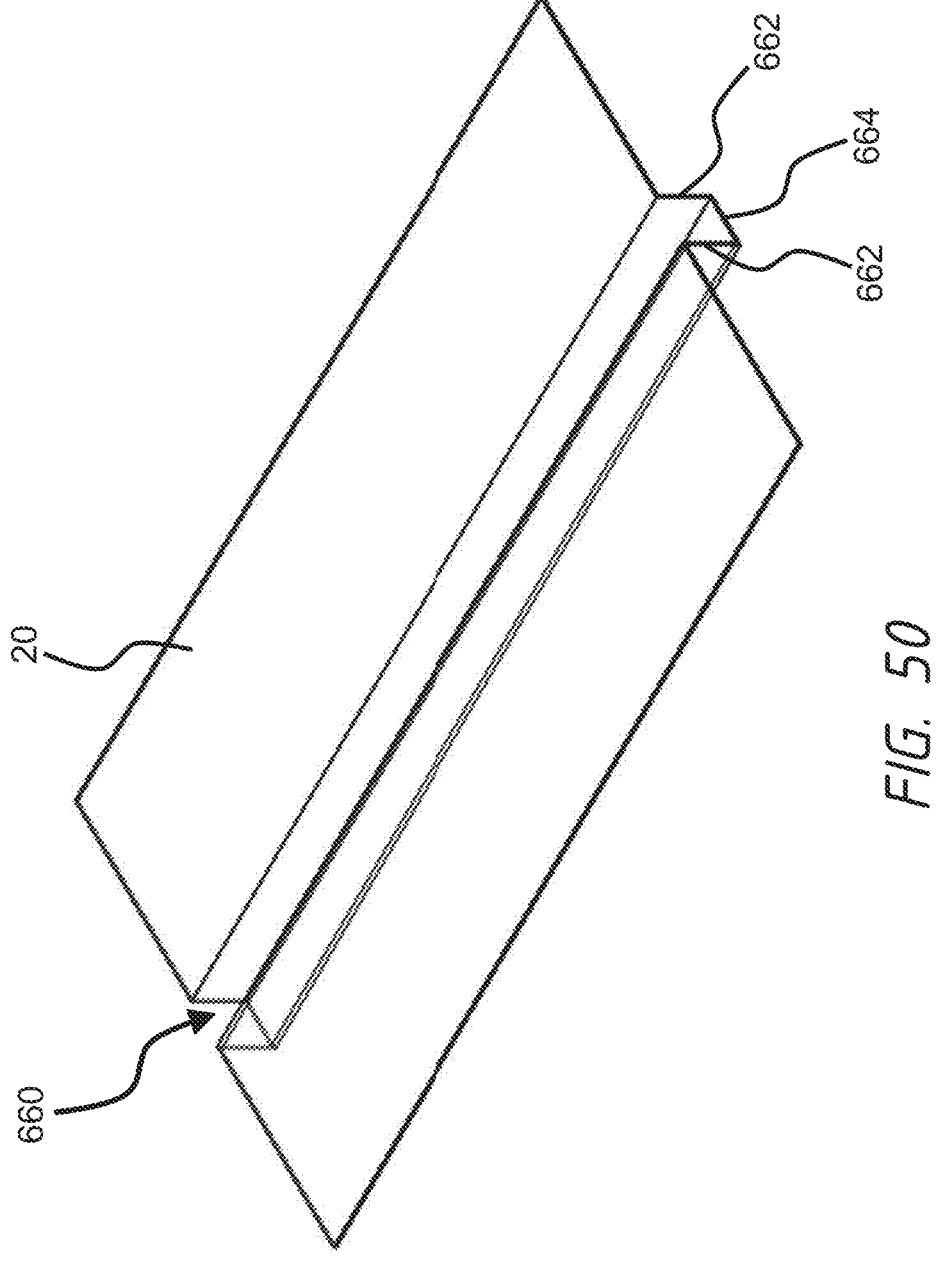
FIG. 50 depicts an example of an anti-buckling channel.

FIG. 50 depicts an example of an anti-buckling channel 660. The channel 660 can be configured to control, limit, reduce, or prevent buckling of an interventional device 44 extending therethrough. Furthermore, the channel 660 can be configured to redirect the longitudinal force applied to an interventional device 44 extending therethrough to advance such device into a distal interventional device. The channel 660 can be formed in the support table 20 and/or in the sterile barrier tray described herein. The channel 660 can have sidewalls 662 that extend generally downward below the surface of the support table 20 and/or sterile barrier tray and a bottom 664 that is below and generally parallel with the surface of the support table 20 and/or sterile barrier tray. The channel 660 can be the same or similar and/or include any one or more features of the channels described herein, such as channels 106, 112, 205, 206, and/or 207. The channel 660 can extend in a generally longitudinal/linear direction and have a rectangular cross-sectional shape as shown, although as described elsewhere herein, the channel 660 can have other cross-sectional shapes and configurations.

FIGS. 51A-51E depict example configurations of the anti-buckling channel 660 described with respect to FIG. 50, in particular configurations of the cross-sectional shape of such channel 660 that can encourage an interventional device 44 to stay within the channel 660. FIG. 51A shows a channel 660a having a generally rectangular cross-section formed by the sidewalls 662a and bottom 664a. FIG. 51B shows a channel 660b having a generally trapezoidal cross-section formed by the sidewalls 662b and bottom 664b, with the sidewalls 662b tilted towards a centerline 665b of the channel 660b as they extend upward from the bottom 664b. FIG. 51C shows a channel 660c having a generally trapezoidal cross-section similar to that of the channel 660b but with the addition of retaining features 663c that extend away from a centerline 665c of the channel 660c where the sidewalls 662c meet the bottom 664c. As shown, the retaining features 663c can be rounded, semi-circle-like extensions. In addition to the trapezoidal like cross-section of the channel 660c, the retaining features 663c can aid in encouraging an interventional device 44 to stay within the channel 660c. FIG. 51D shows a channel 660d having a generally rectangular cross-section similar to that of the channel 660a but with the addition of one or more constraining elements 661d located where the sidewalls 660d meet the surface of the support table 20 and/or sterile barrier tray. The channel includes sidewalls 662d and a bottom 664d. As shown, the channel 660d includes constraining elements 661d at either side thereof, however in some implementations such constraining elements 661d may extend from only one side. FIG. 51E shows a dual channel configuration comprising two channels 660a adjacent one another and separated by at least a portion of the surface of the support table 20 and/or sterile barrier tray, however a dual channel configuration can comprise a mix or match of any of the channel cross-sections described herein. A dual channel configuration can allow for multiple interventional device assemblies to be prepared and used either serially or simultaneously during a patient procedure. A channel 660 can comprise any one or more of the features, elements, and or shapes of the channels 660a, 660b, 660c, and 660d.

Figures 52, 53:
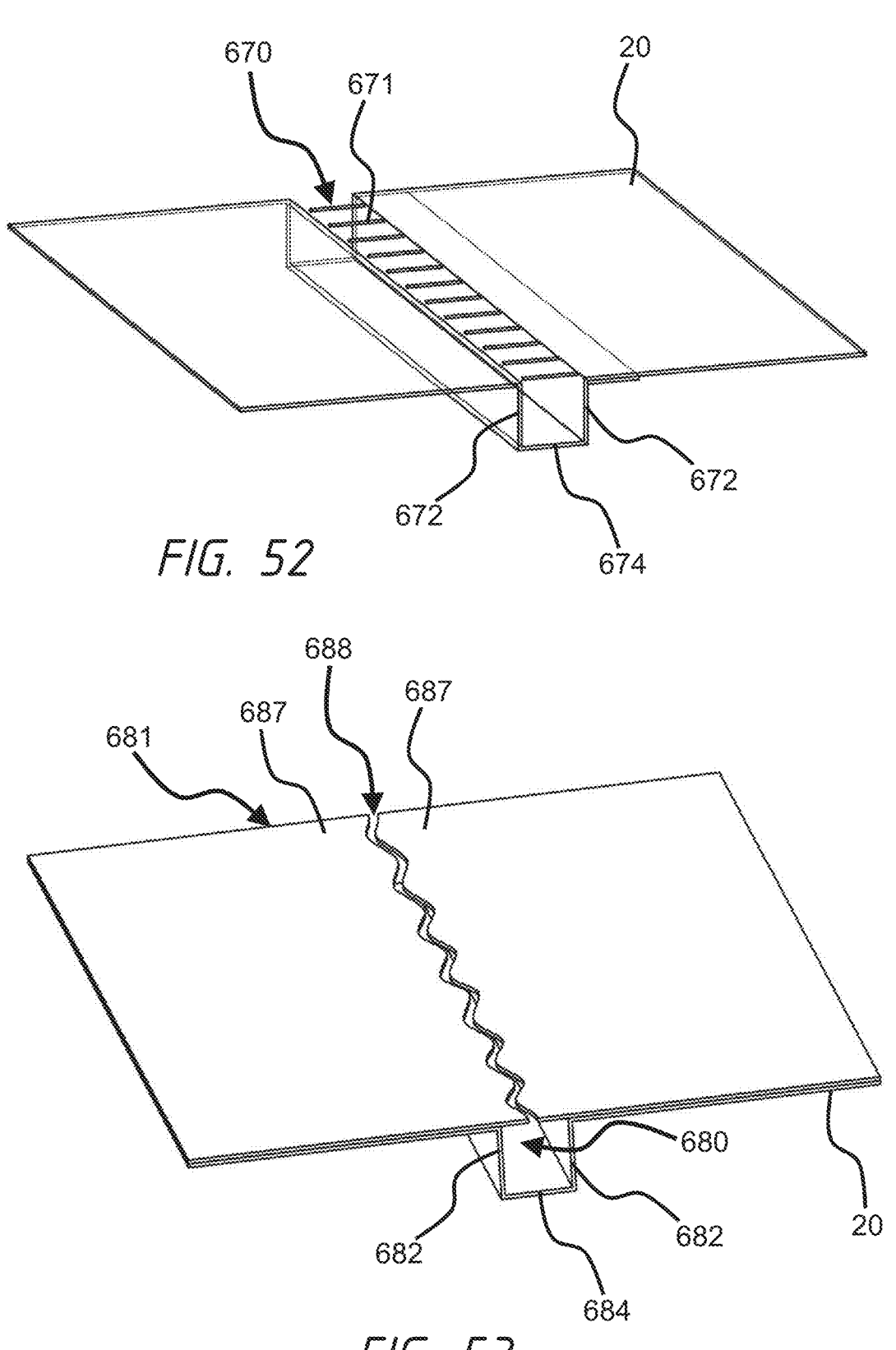
FIG. 52 depicts an example of an anti-buckling channel.
FIG. 53 depicts an example of an anti-buckling channel.

FIG. 52 depicts an example of an anti-buckling channel 670 having constraining elements 671. The channel 670 can be the same or similar to the channel 660 in some or many respects. For example, the channel 670 can include sidewalls 672 and a bottom 674 the same or similar to the sidewalls 662 and the bottom 664 of the channel 660. Furthermore, the constraining elements 671 can be the same or similar to the constraining elements 661d described with respect to FIG. 51D. As shown in FIG. 52, the constraining elements 671 can include one or more generally linear extensions from a side of the channel 670 that extend substantially over the opening of the channel 670. Such constraining elements 671 can be similar to a comb or brush and be configured to redirect any buckling of an interventional device extending through the channel 670 back into the channel 670. Furthermore, the constraining elements 671 can be made of a resilient and flexible material that can deflect to allow components of an interventional device/assembly to travel through and along the channel while retaining the interventional device therein. In some implementations, such constraining elements 671 can extend from both sides of the channel 670; in such a configuration, the constraining elements 671 may extend at a minimum past a centerline of the channel 670. While the constraining elements 671 are shown to extend substantially across the channel 670 in a direction generally planar with the surface of the support table 20 and/or sterile barrier tray, in some implementations the constraining elements 671 can extend at an angle thereto. For example, the constraining elements 671 can be configured to extend across the channel 670 and downward towards the bottom 674 at an angle of less than about 45 degrees relative to the surface. Such downward orientation can aid in retaining an interventional device within the channel 670. The channel 670 can have any of the cross-sectional shapes and/or features described with respect to FIGS. 51A-51D and/or any of the channels described herein.

FIG. 53 depicts an example of an anti-buckling channel 680 having a constraining element 681. The channel 680 can be the same or similar to the channels 660 and 670 in some or many respects. For example, the channel 680 can include sidewalls 682 and a bottom 684 the same or similar to the sidewalls 662, 672 and the bottoms 664, 674 of the channels 660, 670. Furthermore, the constraining element 681 can be similar to the constraining elements 661d and/or 671 described with respect to FIG. 51D and FIG. 52. As shown in FIG. 53, the constraining element 681 can include a flexible membrane 687 having a zig-zag like cut 688 positioned adjacent a top of the channel 680. Such a configuration of the constraining element 681 can deflect to allow components of an interventional device/assembly to travel through and along the channel while retaining the interventional device therein. While the constraining element 681 is shown in FIG. 53 as extending over the channel 680 from both sides, in some implementations the constraining element 681 can extend from only one side of the channel 680. The channel 680 can have any of the cross-sectional shapes and/or features described with respect to FIGS. 51A-51D and/or any of the channels described herein.

Figures 54A, 54B:
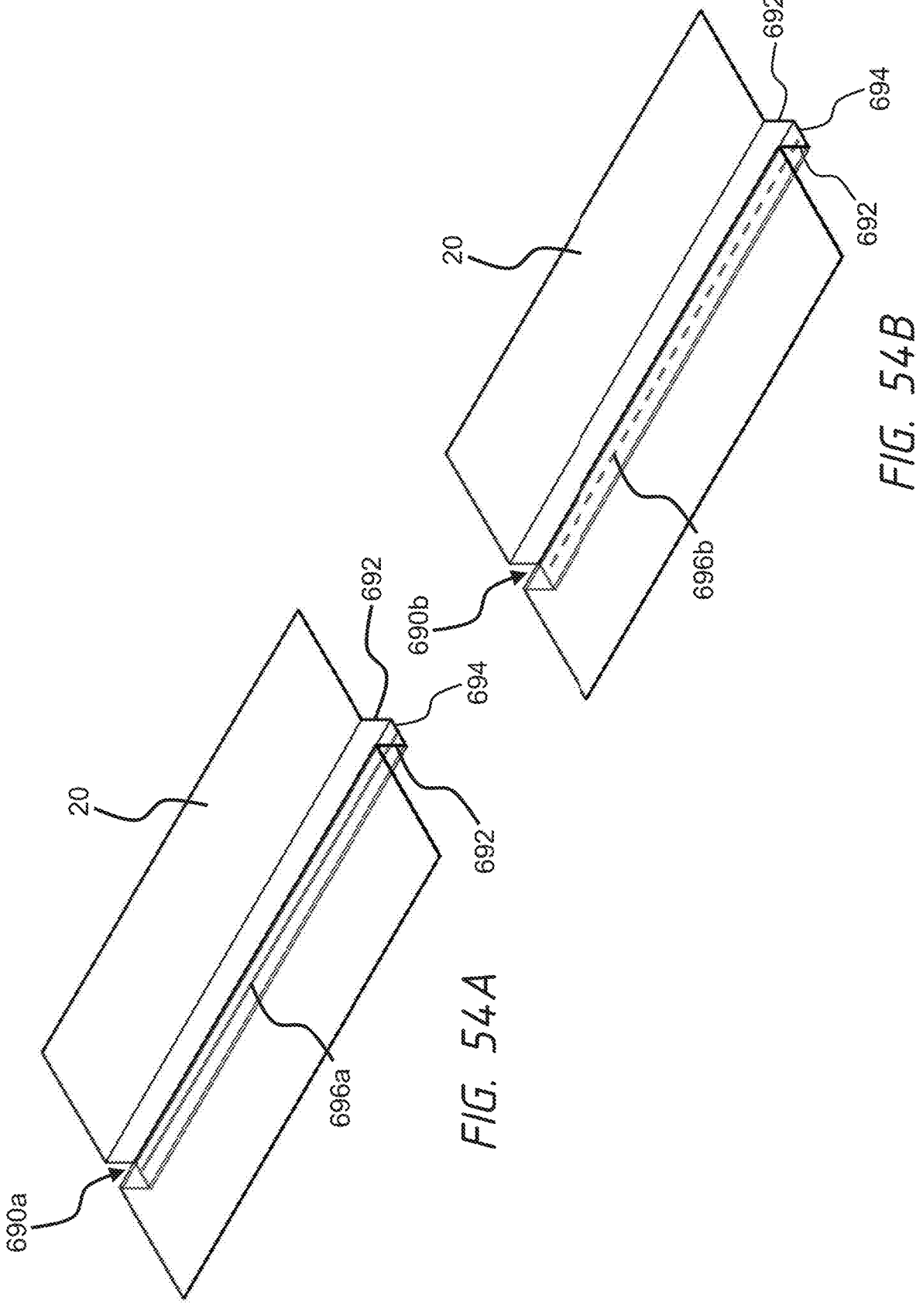
FIGS. 54A-54B depict examples of anti-buckling channel with magnet(s).

FIGS. 54A-54B depict examples of anti-buckling channels 690a, 690b having one or more magnets 696a, 696b therein, respectively. The channels 690a, 690b can be the same or similar to the channel 660 in some or many respects. For example, the channels 690a, 690b can include sidewalls 692 and a bottom 694 the same or similar to the sidewalls 662 and the bottom 664 of the channel 660. Different than the channel 660, the channels 690a, 690b can include one or more magnets 696a, 696b positioned along the bottom 694 configured to aid in retaining an interventional device within the channels 690a, 690b. For example, the one or more magnets 696a, 696b can attract at least a portion of an interventional device to aid in keeping such device within the channels 690a, 690b. FIG. 54A shows a configuration of channel 690a including a strip magnet 696a that extends along the bottom 694, while FIG. 54B shows a configuration of channel 690b including multiple magnets 696b dispersed and extending along the bottom 694. The channels 690a, 690b can have any of the cross-sectional shapes and/or features described with respect to FIGS. 51A-51D and/or any of the channels described herein, and/or any of the constraining elements described herein.

Figure 55A:
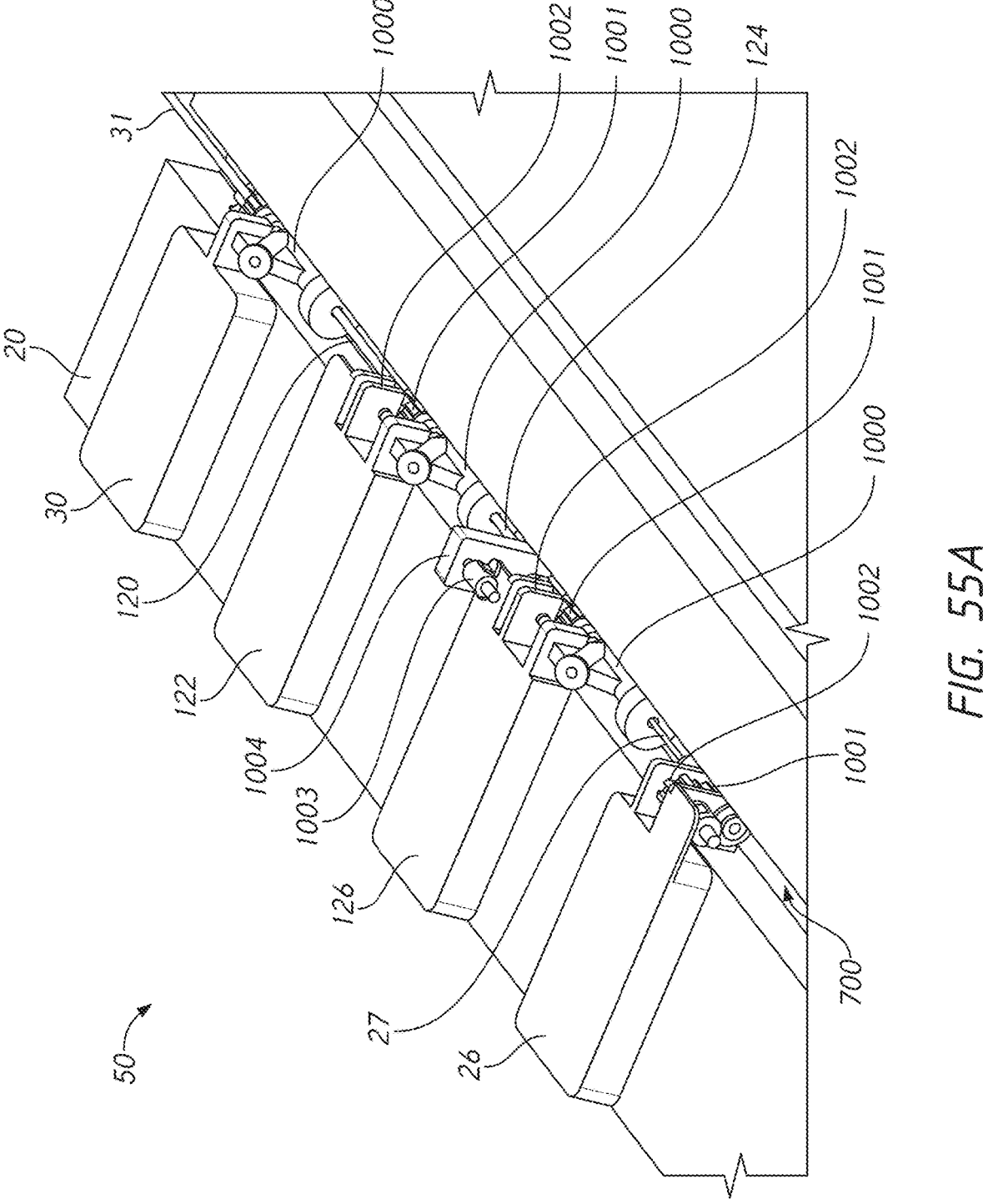
FIGS. 55A-55D depict an example of an interventional device assembly utilizing an anti-buckling channel.
Figures 55B, 55C, 55D:
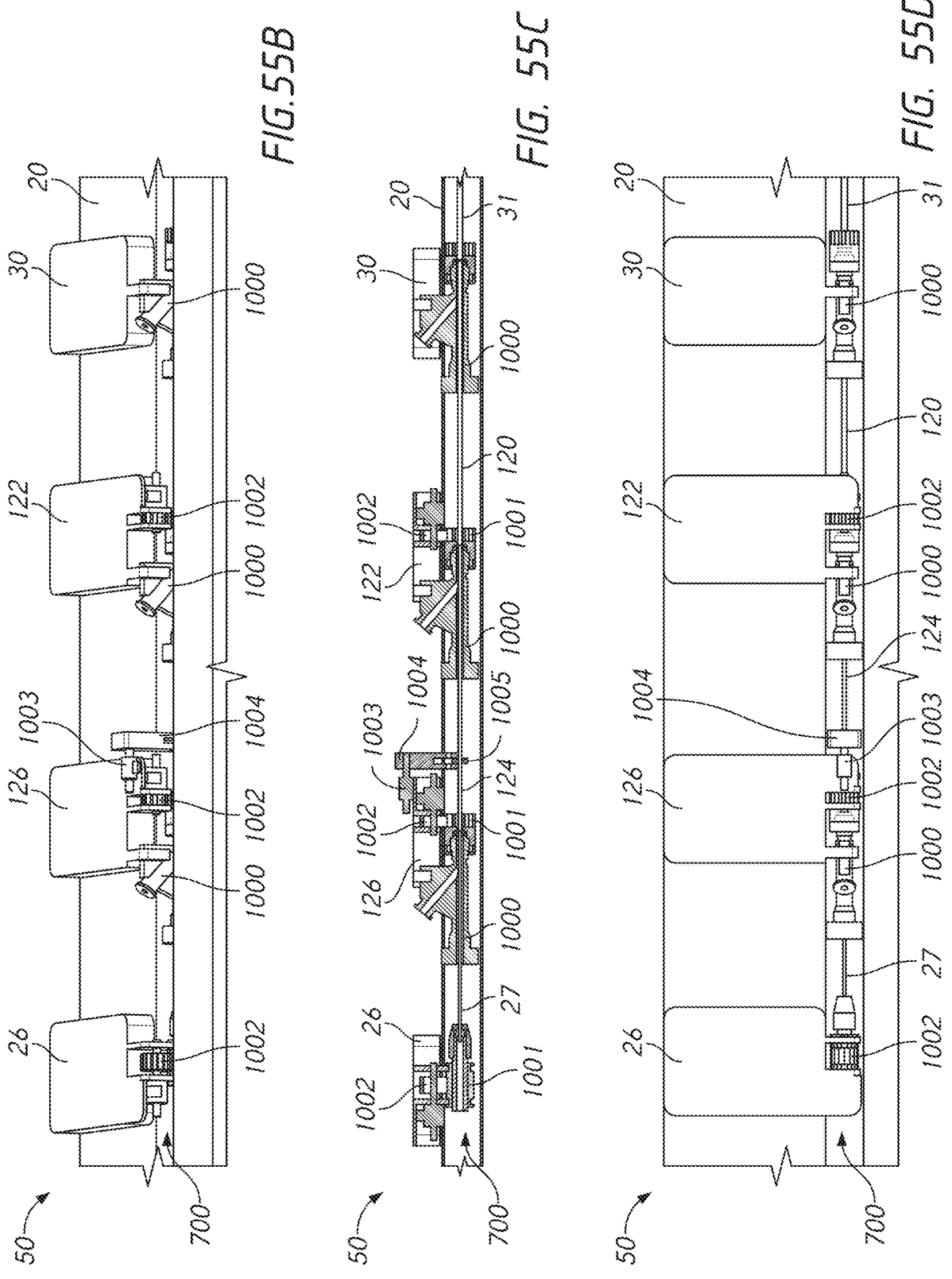

FIGS. 55A-55D depict an example of an interventional device assembly 50 utilizing an anti-buckling channel 700. FIGS. 55A-55B show perspective views, FIG. 55C shows a side cross-sectional view, and FIG. 55D shows a top view of the interventional device assembly 50 stack. The interventional device assembly 50 can be the same or similar to any of the interventional device assemblies described herein. For example, the interventional device assembly can include the guide catheter hub 30 with guide catheter 31 extending distally therefrom, the first procedure catheter hub 122 with the first procedure catheter 120 extending distally therefrom, the second procedure catheter or access catheter hub 126 with the second procedure catheter or access catheter 124 extending distally therefrom, and the guidewire hub 26 with the guidewire 27 extending distally therefrom. As shown, each catheter of the interventional device assembly 50 can have a rotating hemostatic valve 1000 connected to their respective proximal end. Further as shown, the interventional device assembly 50 can be configured such that a centerline of the interventional device assembly 50 is within the anti-buckling channel 700. The anti-buckling channel

700 can be the same or similar to and include any of the features and/or functionality of any of the channels described herein. While the guide catheter hub 30, guide catheter 31, first procedure catheter hub 122, first procedure catheter 120, second procedure catheter or access catheter hub 126, second procedure catheter or access catheter 124, guidewire hub 26, and guidewire 27 are shown in FIGS. 55A-55D, it would be understood by one of skill in the art that any combination of interventional devices and interventional device hubs described herein can be employed in the embodiment of FIGS. 55A-55D.

Each of the hubs of the interventional device assembly 50 can be configured to interact with their respective interventional device (e.g., catheter or guidewire) by snapping down on top of their respective rotating hemostatic valve when included. Such configuration can advantageously provide enhanced system flexibility. Each of the hubs can be configured to be re-sterilizable after use and/or otherwise be reusable. In some implementations, the hubs can be integral with their respective interventional device. Rotation of an interventional device of the interventional device assembly 50, such as of the guidewire 27, the second procedure catheter or access catheter 124, and/or the first procedure catheter 120, can be accomplished by a gear 1001 on the rotating part of the guidewire or rotating hemostatic valve that engages with a motor driven gear 1002 on a respective hub. Articulation of an interventional device of the interventional device assembly 50, such as of the second procedure catheter or access catheter 124, can be accomplished by a linear actuator 1003 that drives a tang 1004 that can engage with a circular flange 1005 fixed to the outer shaft of such articulating interventional device.

Figures 56, 57:
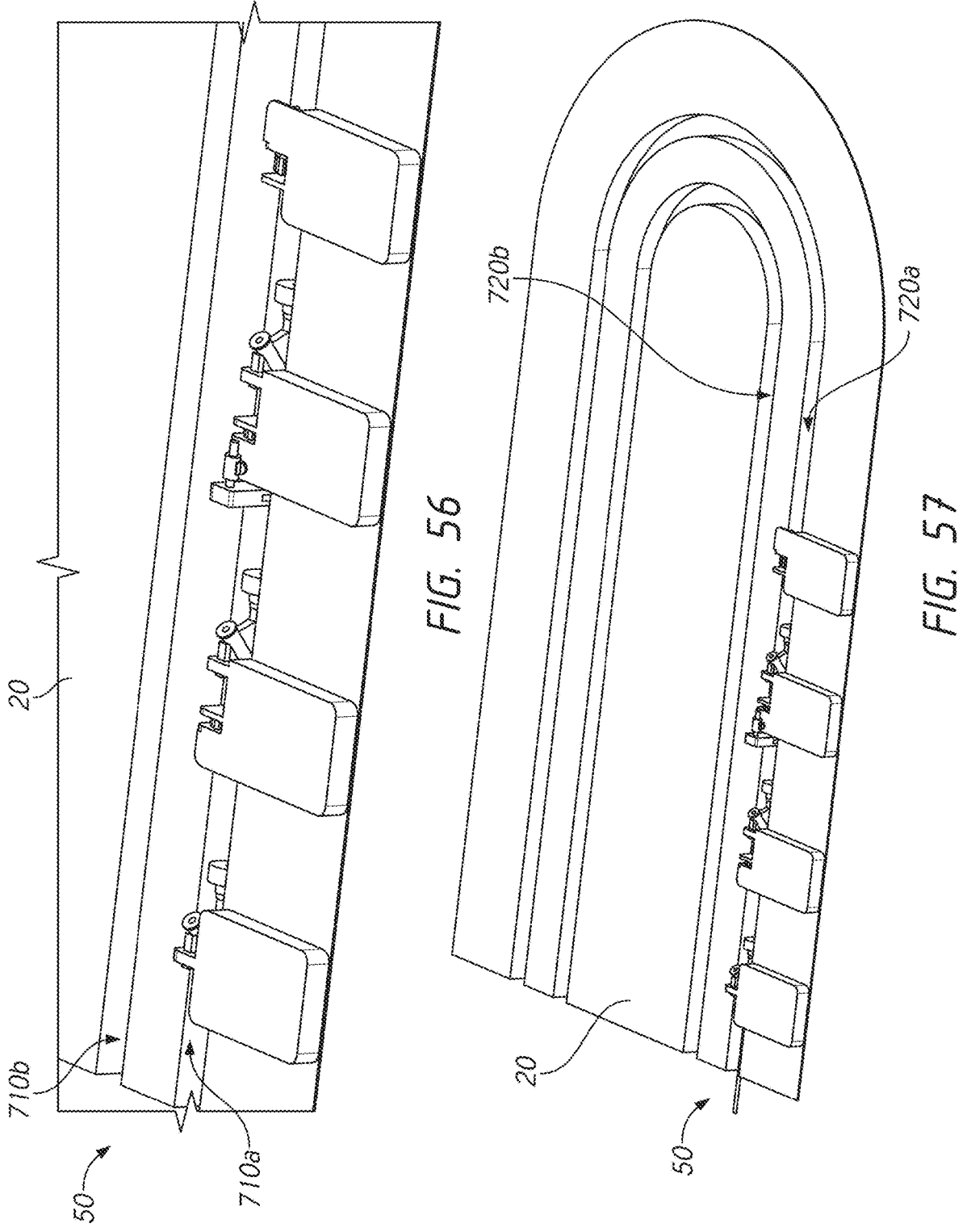
FIG. 56 depicts an example of an interventional device assembly utilizing anti-buckling channel(s).
FIG. 57 depicts an example of an interventional device assembly utilizing curved anti-buckling channel(s).

FIG. 56 depicts an example of an interventional device assembly 50 utilizing anti-buckling channels 710a, 710b. The interventional device assembly 50 can be the same as or similar to any of the interventional device assemblies described herein. Furthermore, the anti-buckling channels 710a, 710b can be the same or similar to any of the channels described herein. A dual channel configuration can allow for multiple interventional device assemblies to be prepared and used either serially or simultaneously during a patient procedure. Such configuration can advantageously shorten the time required to perform a patient procedure.

FIG. 57 depicts an example of an interventional device assembly 50 utilizing curved anti-buckling channels 720a, 720b. The interventional device assembly 50 can be the same as or similar to any of the interventional device assemblies described herein. Furthermore, the anti-buckling channels 720a, 720b can be the same as or similar to any of the channels described herein but with a curve each as shown. A curved dual channel configuration can allow for multiple interventional device assemblies to be prepared and used either serially or simultaneously during a patient procedure. Such configuration can advantageously shorten the time required to perform a patient procedure. Furthermore, a curved dual channel configuration can advantageously reduce the overall length of the support table 20 and/or sterile barrier tray.

Figures 58A, 58B, 58C:
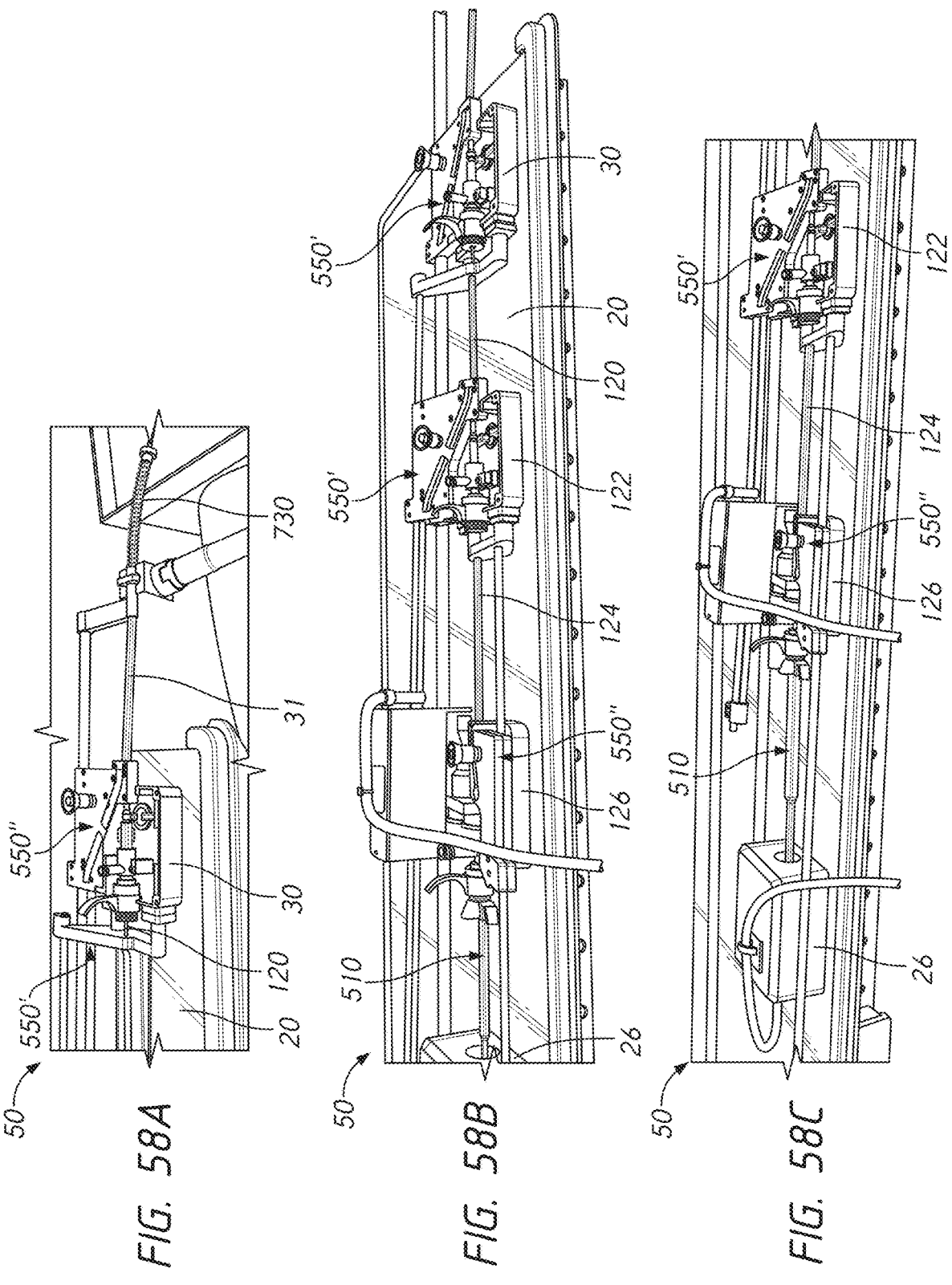
FIGS. 58A-58C depict an example of an interventional device assembly utilizing various anti-buckling solutions.

FIGS. 58A-58C depict an example of an interventional device assembly 50 utilizing various anti-buckling devices/solutions. The interventional device assembly 50 can be the same as or similar to any of the interventional device assemblies described herein. For example and as shown, the interventional device assembly 50 can include the guide catheter hub 30 with guide catheter 31 extending distally therefrom, the first procedure catheter hub 122 with the first procedure catheter 120 extending distally therefrom, the second procedure catheter or access catheter hub 126 with the second procedure catheter or access catheter 124 extending distally therefrom, and the guidewire hub 26 with the guidewire 27 extending distally therefrom. The guidewire hub 26 with the guidewire 27 is shown utilizing an anti-buckling telescoping tube 510 as described herein. The second procedure catheter hub 126 with the second procedure catheter 124 is shown utilizing a split tube with support rod 550 as described herein. The first procedure catheter hub 122 with the first procedure catheter 120 is shown utilizing another split tube with support rod 550' as described herein that is at a different angle relative to the support table 20 than the split tube with support rod 550 in order to clear the other anti-buckling devices of the interventional device assembly 50. The guide catheter hub 30 with guide catheter 31 is shown utilizing another split tube with support rod 550'' as described herein that is similarly at a different angle relative to the support table 20 than the split tubes with support rods 550, 550' to clear such anti-buckling devices. Also shown in FIGS. 58A-58C is an anti-buckling tubular attachment 730 that will be described with respect to FIGS. 59A-59C. While the guide catheter hub 30, guide catheter 31, first procedure catheter hub 122, first procedure catheter 120, second procedure catheter or access catheter hub 126, second procedure catheter or access catheter 124, and guidewire hub 26 are shown in FIGS. 58-58C, it would be understood by one of skill in the art that any combination of interventional devices and interventional device hubs described herein can be employed in the embodiment of FIGS. 58A-58C.

FIGS. 59A-59C depict an example of an anti-buckling tubular attachment 730. FIGS. 59A-59B show perspective views of the tubular attachment 730, and FIG. 59C shows a side view of the tubular attachment 730. The tubular attachment 730 can be configured to span between a distal attachment of any of the anti-buckling devices or assemblies described herein and an insertion sheath or other patient vascular interface and provide anti-buckling support to the interventional devices disposed therethrough. For this, the tubular attachment can have a distal end 734 and a proximal end 732 with a generally tubular body 731 spanning therebetween defining a lumen 736 configured to receive the interventional devices of an interventional device assembly (such as any of those described herein). The tubular attachment 730 can be configured to allow for an angle between an end of the support table 20 and/or a distal attachment of any of the anti-buckling devices or assemblies described herein and an insertion sheath or other patient vascular interface. For example, the tubular body 731 can have a plurality of circumferential cuts 735 to provide the tubular attachment 730 with flexibility. The tubular attachment 730 can be formed or molded out of a resilient and/or flexible material. In some implementations, the tubular attachment 730 can be made at least in part out of a laser cut hypo tube. The tubular attachment 730 can have a proximal attachment portion 733 at its proximal end 732 configured to attach to a clip or otherwise with a distal attachment of any of the anti-buckling devices or assemblies described herein. For example, the proximal attachment portion 733 can comprise one or more circumferential rings that extend outward from the tubular body 731. The tubular attachment 730 can have a distal attachment portion 737 at its distal end 734 configured to attach to an insertion sheath or other patient vascular interface. For example, the distal attachment portion 737 can comprise a castle-like structure with internal radially oriented clips that extend distally from the tubular body 731.

In some embodiments, a laser cut or machined flexible coupling tube, such as tubular body 731 can be incorporated into a telescoping tube, for example, as an inner most and/or outer most tube segment. In some embodiments, each tubular segment of a telescoping tube can be machined to provide selective flexibility (e.g., laterally for bending and/or axially for longitudinal elasticity).

FIGS. 60A-60E show another implementation of a telescoping tube 810. The telescoping tube 810 can be similar to the telescoping tube 510 in some or many respects and/or include any or all of the functionality of the telescoping tube 510 described herein. For example and similar to the telescoping tube 510, the telescoping tube 810 can be configured to extend and collapse axially about an interventional device 44 (or more) extending therethrough. Furthermore, the telescoping tube 810 can be configured to prevent hyper-collapsing, hyper-extension, and/or excessive slop between tubes that make up the telescoping tube 810. Differences between the telescoping tube 510 and the telescoping tube 810 can confer certain advantages to the telescoping tube 810. For example, the telescoping tube 810 can advantageously have less friction when extending/collapsing and be more space efficient (e.g., have less dead length) than the telescoping tube 510.

FIG. 60A shows a perspective view of the telescoping tube 810 in a fully collapsed position. As shown, the telescoping tube 810 can have a first end 822 and a second end 824. The telescoping tube 810 can attach to a proximal retainer 812 at its first end 822, for example, via an innermost tube. The telescoping tube 810 can attach to a distal retainer 814 at its second end 824, for example, via an outermost tube. In this way, when the proximal retainer 812 and distal retainer 814 are moved distally/proximally relative to one another, the telescoping tube 810 can extend/collapse. The proximal retainer 812 and the distal retainer 814 can have various features that facilitate their attachment (e.g., releasable attachment) to various other components of an interventional device assembly. For example and as will be described in more detail with respect to FIGS. 61A-61E, the distal retainer 814 can include one or more tabs 825 configured to releasably attach the second end 824 of the telescoping tube 810 to other components of an interventional device assembly.

FIG. 60B shows two cross-sectional views through the telescoping tube 810, with the left side of FIG. 60B showing the first end 822 and the right side of FIG. 60B showing the second end 824. As shown, the telescoping tube 810 can include a plurality of concentric telescopically axially extendable and collapsible tubes or tube segments through which one or more interventional device(s) can extend therethrough. For example and as shown, the telescoping tube 810 can include a tube 810a, a tube 810b, a tube 810c, and more up to a tube 810n, with the tube 810b coaxially extendable/collapsible from within tube 810a, the tube 810c coaxially extendable/collapsible from within the tube 810b, and so on for all tubes up to tube 810n (n is not meant to limit the number of tubes, but to instead be an open-ended number greater than one). Each of the tubes that make up the telescoping tube 810, except for the outermost tube 810a, can have a shim associated therewith. For example, the tube 810b can have a shim 813b, the tube 810c can have a shim 813c, and so on through tube 810n. Such shims can be attached to an outer diameter of its associated tube adjacent their second end 824. Furthermore, each of the tubes that make up the telescoping tube 810, except for the innermost tube 810n, can have a stop associated therewith. The stop may be in the form of a cap, one or more protrusions, and/or any suitable structures. For example, the tube 810a can have a cap 815a, the tube 810b can have a cap 815b, and so on through tube 810n-1 (with 810n-1 indicating a tube that directly surrounds a tube 810n). Such caps can be attached to an end of their respective tube at their first end 822. The telescoping tube 810 is shown with its outermost tube (e.g., tube 810a) attached to the distal retainer 814 and its innermost tube (e.g., tube 810n) attached to the proximal retainer 812. In such implementations, the first end 822 can be considered the proximal end of the telescoping tube 810 and the second end 824 can be considered the distal end of the telescoping tube 810. In some implementations, the telescoping tube 810 can be configured in a reversed manner (e.g., outermost tube 810a attached to the proximal retainer 812, and innermost tube 810n attached to the distal retainer 814).

As described herein, the distal retainer 814 can be positioned closer to the access point of the patient than the proximal retainer 812. Embodiments in which the outermost tube 810a is attached to the distal retainer 814 can provide the benefit of preventing an interventional device from catching on an edge of a tube or tube segment of the telescoping tube 810 during distal advancement of the interventional device (e.g., advancement into the patient) through the telescoping tube 810, for example, when replacing interventional devices in an interventional device assembly or otherwise inserting an interventional device through the telescoping tube 810. For example, as shown in FIG. 60D, the tube 810b includes an edge 807. In certain embodiments, if the tube 810b is positioned distal to the tube 810a, there may be a risk that an interventional device advancing distally through the tube 810a and into the tube 810b will catch on the edge 807. In certain embodiments in which the tube 810a is positioned distal to the tube 810b, an interventional device may be advanced distally through the tube 810b and into the tube 810a without a risk of catching on the edge 807 or an edge of the tube 810a.

The telescoping tube 810 can be configured to have a clearance between adjacent concentric tubes (e.g., between an outer diameter of an inner tube and an inner diameter of an outer tube) of between about 0.001" and about 0.010", such as about 0.002", about 0.003", about 0.004", or about 0.005". Furthermore, each of the tubes that make up the telescoping tube 810 can be cut to length and thereafter unmodified (e.g., no swaging required), simplifying manufacturing. As shown in FIG. 60B, an outer tube can be shorter than a tube directly concentrically adjacent within it. For example, an outer tube can be about 0.020" shorter or less, such as about 0.010" shorter, than a tube directly concentrically adjacent within it. In some implementations, an outer tube and a tube directly concentrically adjacent within it can be about the same length.

FIG. 60C shows an exemplary tube, in this case a tube 810b, of the telescoping tube 810. As shown, the tube 810b has a shim 813b attached around its outer diameter adjacent its second end 824. Shims of the tubes (which can also be referred to herein as "tube segments") of the telescoping tube 810 can comprise a polyimide tape (e.g., Kapton tape) wrapped and adhered around the outer diameter of the tube (e.g., such that the shim does not slide relative to the tube). For example, the shim 813b can be a 1 cm wide piece of Kapton tape with a thickness of 0.0025" (including its adhesive) adhered and wrapped around the outer diameter of the tube 810b. Shims of the telescoping tubes can be made with such polyimide tape and be sized as necessary for the particular use case and configuration. A wrappable shim can extend less than 360 degrees around a tube, about 360 degrees around a tube, or more than 360 degrees around a tube. For example, the number of turns of a wrappable shim around a tube can be custom tailored to each tube to minimize clearance between tubes without binding of relative axial movement between one another. In some implementations, shims of the tubes of the telescoping tube 810 can comprise a heat shrink material. A telescoping tube 810 can require less force to extend/collapse than a telescoping tube 510 in part due to the configuration of the shim(s) (e.g., due to difference in clearance, difference in coefficient of friction, or both). In some implementations, the surfaces of the tubes of a telescoping tube can be machined, polished, and/or honed to minimize friction therebetween.

FIG. 60C also shows the cap 815b of tube 810b prior to attachment of the cap 815b to the first end 822 thereof. Caps of the tubes of the telescoping tube 810 can have a ring-like configuration, with an inner diameter that is less than an inner diameter of its associated tube, and an outer diameter that is greater than an outer diameter of its associated tube. The tubes of the telescoping tube 810 can be made of stainless steel (e.g., 304 stainless steel). The caps of the tubes can similarly be made of stainless steel (e.g., 304 stainless steel), to facilitate joining (e.g., laser welding) of a cap to its respective tube. To prevent the caps from misforming during such joining procedure, the caps can be between about 0.003" to about 0.015" thick, such as between about 0.007" and about 0.010" thick, and/or annealed and/or tempered. To ensure a cap is attached concentrically about its respective tube, the cap can be attached (e.g., laser welded) with an inner tube extending therethrough (e.g., fully extended therethrough).

FIG. 60D shows an inner tube, in this example 810b, of a telescoping tube fully extended relative to its outer tube, 810a. As shown, hyper-extension of the inner tube 810b can be prevented by the interaction between the shim 813b of the tube 810b and the cap 815a of the tube 810a. Specifically, hyper-extension of the inner tube 810b can be prevented by an end of the shim 813b, which has a greater outer diameter than the outer diameter of the tube 810b, hitting against a portion of the cap 815a that extends inwards of the inner diameter of the tube 810a. In other words, the cap 815a can act as a stop that prevents the shim 813b, and thus the tube 810b, from extending further out of the tube 810a. This interaction between the cap 815a and shim 813b can be similar to the interaction between a swaged end 515a and a shim 513b of a telescoping tube 510, however in a more space efficient manner as the cap can be shorter in axial length than a swage.

FIG. 60E shows tubes 810a through 810e of a telescoping tube near fully collapsed upon one another. As shown, hyper-collapsing of the tubes can be prevented via the interaction between the outer diameter portion of a cap, for example cap 815b, interacting with the inner diameter portion of the next larger cap, in this example 815a. Specifically, hyper-collapsing of an inner tube can be prevented by the outer diameter portion of the inner tube's cap hitting against the inner diameter portion of the outer tube's cap. In other words, a cap of an outer tube can act as a stop that prevents a cap of an inner tube, and thus the inner tube, from collapsing further inward. Such interaction can be similar for each inner/outer tube pair. Also shown in FIG. 60E, the tubes that make up a telescoping tube can have wall thicknesses that differ from one another. In some implementations, the tubes that make up a telescoping tube can have substantially the same wall thickness.

FIGS. 60F-60G depict an alternative embodiment of a tube, such as tube 810b, in which a section of the tube has a larger outer diameter than the rest of the tube instead of a shim 813b. As shown in FIGS. 60F-60G, the tube 810b can include a first tube section 833 having a first outer diameter and a second tube section 837 having a second outer diameter. In some embodiments, the tube 810b can include a tapered section 836 between the first tube section 833 and the second tube section 837. As shown, the tube 810b can include a uniform inner diameter.

The first tube section 833 can have a larger outer diameter than the second tube section 837. The first tube section 833 can be dimensioned to contact the cap 815a of the tube 810a (for example, in a similar manner as the shim 813b in FIG. 60D) to prevent hyper-extension of the tube 810b. Specifically, hyper-extension of the inner tube 810b can be prevented by an end 838 of the first tube section 833, which has a greater outer diameter than the outer diameter of the second tube section 837, hitting against a portion of the cap 815a that extends inwards of the inner diameter of the tube 810a. In other words, the cap 815a can act as a stop that prevents the first tube section 833 from extending further out of the tube 810a.

In certain embodiments, a tube, such as tube 810b, having a uniform outer diameter can be ground along a portion of the length (e.g., by plunge grinding) to form the second tube section 837.

As an example, in certain embodiments, the first tube section 833 can have a wall thickness of between about 0.005" and about 0.020", and the second tube section 837 can have a wall thickness of between about 0.003" and about 0.014" (e.g., due to grinding along the second tube section 837). In some embodiments, the first tube section 833 can have a wall thickness of between about 0.007" and 0.008". In some embodiments, the second tube section 837 can have a wall thickness of about 0.0035". In some embodiments, the first tube section 833 can have a wall thickness of about 0.0160" and the second tube section 837 can have a wall thickness of about 0.0136". In some embodiments, the first tube section 833 can have a wall thickness of about 0.0065" and the second tube section 837 can have a wall thickness of about 0.0041".

In some embodiments, the first tube section 833 can have a wall thickness of about 0.0070" and the second tube section 837 can have a wall thickness of about 0.0046". In some embodiments, the first tube section 833 can have a wall thickness of about 0.0075" and the second tube section 837 can have a wall thickness of about 0.0051". In some embodiments, the first tube section 833 can have a wall thickness of about 0.008" and the second tube section 837 can have a wall thickness of about 0.0056".

Due to the different wall thicknesses, the first tube section 833 and the second tube section 837 have different outer diameters. The different outer diameters of the first tube section 833 and the second tube section 837 may provide a shoulder of several thousandths of an inch (e.g., a shoulder of between about 0.002" and about 0.004"). In some embodiments, the shoulder may be between 0.002" and 0.017", between 0.0035" and 0.005", or any other suitable size in width. In some embodiments, outer diameters along portions of the tube 810 can range between about 0.06 inches and about 0.5 inches.

In some embodiments, the transition between the outer diameter of the first tube section 833 and the outer diameter of the second tube section 837 may be a gradual (e.g., tapered transition). In some embodiments, transition may extend along a length (e.g., a length of the shoulder) less than or at most 0.020".

In some implementations, any one or more of the tubes of a telescoping tube (e.g., an inner tube, an outer tube, or any of the tubes) can incorporate one or more cuts similar to or the same as those of the tubular body 731 shown in FIGS. 59A-59C. Such cuts can provide flexibility to one or more of the tubes, for example in bending, and/or longitudinal elasticity. In some implementations, such configuration can allow a telescoping tube to tolerate misalignment in the interventional device assembly.

FIGS. 60H-60J show alternative implementations of the telescoping tube 810 having an inner diameter reducing feature configured to advantageously reduce the unsupported free length of interventional device(s) extending through the telescoping tube 810. As shown, the telescoping tube 810 can include caps 817 (which can also be referred to herein as "restrictor plates") at the second end 824. FIG. 60H shows a perspective view of the telescoping tube 810 of these alternative implementations in a fully collapsed position, and FIGS. 60I-60J show perspective cross-sectional views through the telescoping tubes 810 of these alternative implementations with tubes 810a through 810c each in a partially extended position. Different than the implementation of FIGS. 60A-60G, each of the tubes that make up the telescoping 810 of these alternative implementations (e.g., tubes 810a through 810n) can have a cap 817 attached to their second end 824. For example, the tube 810a can have a cap 817a, the tube 810b can have a cap 817b, the tube 810c can have a cap 817c, and so on through tube 810n. As shown in FIG. 60I, the telescoping tube 810 can include caps 817 in addition to shims 813 as described with respect to FIGS. 60B-60D. As shown in FIG. 60J, the telescoping tube 810 can include caps 817 in addition to the tubes having first and second tube sections 833, 837 as described with respect to FIGS. 60F-60G. In some implementations, the telescoping tube 810 can include caps 817 instead of the shims 813 as shown in FIGS. 60B-60D or the first and second tube sections 833, 837 as shown in FIGS. 60F-60G.

As shown in FIGS. 60H-60J, a cap 817 can have a disc-like configuration. The cap 817 can have a through hole 819 extending through its axial width. In some embodiments, the cap 817 can have an outer diameter that is the same as or generally the same as the outer diameter of its associated tube. In some embodiments, the cap 817 can be attached to the second end 824 of its associated tube concentrically with respect to the outer diameter of its associated tube.

In some embodiments, the through hole 819 of the cap 817 can be centered with respect to the cap 817 and/or centered with respect to the inner diameter of its associated tube. The diameter of the through hole can be smaller than the diameter of the associated tube of the cap 817. The through hole 819 can be sized and shaped to accommodate (e.g., with clearance) the interventional device(s) extending through the telescoping tube 810. Advantageously, the cap 817, via the through hole 819, can reduce the unsupported free length of the interventional device(s) extending through the telescoping tub 810. Reducing the unsupported free length of the interventional device(s) can in turn reduce or prevent buckling of the interventional device(s). In some embodiments, buckling of an interventional device may be characterized by a sinusoidal wave shape that may become a helical shape. Reducing the unsupported free length of the interventional device(s), for example, via caps 817, can reduce or prevent such buckling of the interventional device(s) and/or increase the force required to cause such buckling. Reducing the unsupported free length of the interventional device(s) can also advantageously provide a substantially linear relationship between the force input at the proximal end of the interventional device used to advance the interventional device in a distal direction and distal travel of the distal end of the interventional device. A telescoping tube 810 with caps 817 can be used with an interventional device comprising a guidewire as described herein.

The caps 817 can be made of stainless steel (e.g., 304 stainless steel), to facilitate joining (e.g., laser welding) of a cap to its respective tube. In some embodiments, the caps can be between about 0.003" to about 0.012" thick, such as between about 0.005" thick and about 0.010" thick, about 0.005" thick, about 0.006" thick, about 0.007" thick, about 0.008" thick, about 0.009" thick, about 0.01" thick, or any other suitable thickness. In some embodiments, the thickness of the caps 817 can be selected to prevent the caps from mis-forming during the joining procedure. The caps 817 may also be annealed and/or tempered to prevent mis-forming. In some embodiments, the cumulative thicknesses of the caps 817 in the axial direction may define a minimum axial length of the collapsed telescoping tube 810a.

A telescoping tube 810 having an inner diameter reducing feature, such as caps 817, can advantageously have tubes 810a-810n of a larger diameter than a telescoping tube 810 without such inner diameter reducing feature. Tubes of a larger diameter can advantageously be more resistant to bending or buckling than tubes of a smaller diameter. Thus, a telescoping tube 810 with an inner diameter reducing feature and larger diameter tubes 810a-810n can be more resistant to bending or buckling in use than a telescoping tube 810 having smaller diameter tubes 810a-810n without such inner diameter reducing feature. A telescoping tube 810 with an inner diameter reducing feature may provide for larger diameter tubes 810a-810n that may be more resistant to bending or buckling in use than a telescoping tube 810 having smaller diameter tubes 810a-810n while the inner diameter reducing feature provides for a smaller inner diameter about the interventional device(s) due to the through-holes in the caps that can reduce bending or buckling of the interventional device(s) in comparison to a larger inner diameter.

In some embodiments, the cap 817 can have an outer diameter larger than the outer diameter of its associated tube. In this way, the cap 817 can function similarly to the shim 813 or first tube section 833 by spacing an inner tube of the telescoping tube 810 from a concentrically adjacent outer tube (e.g., spacing the outer diameter of the inner tube from the inner diameter of the concentrically adjacent outer tube) and providing a surface which the concentrically adjacent tubes can slide upon. Furthermore, with such configuration of the cap 817, the cap 817 can prevent hyper-extension of an inner tube out of its concentrically adjacent outer tube by the interaction between the cap 817 of the inner tube and the cap 815 of the outer tube. For example, hyper-extension of the inner tube 810b can be prevented by the interaction between cap 817b of the tube 810b and the cap 815a of the outer tube 810a. Specifically, hyper-extension of the inner tube 810b can be prevented by an end of the cap 817b, which has a greater outer diameter than the outer diameter of the tube 810b, hitting against a portion of the cap 815a that extends inwards of the inner diameter of the tube 810a. In other words, the cap 815a can act as a stop that prevents the cap 817b, and thus the tube 810b, from extending further out of the tube 810a. In some embodiments, this interaction between the cap 815a and the cap 817b can be similar to the interaction between a cap 815a and a shim 813b, a cap 815a and a first tube section 833a, or the interaction between swaged end 515a and a shim 513b, however in a more space efficient manner as the caps can be shorter in axial length than a cap and shim or a swage.

In some implementations, tubes of the telescoping tube 810 can have a cap 817 and a shim 813 (such as shown in FIG. 60I). In some implementations, tubes of the telescoping tube 810 can have a cap 817 and first and second tube section 833, 837 (such as shown in FIG. 60J). In such implementations, the cap 817 can have an outer diameter about the same as the outer diameter of its associated tube, or it can have an outer diameter that is greater than the outer diameter of its associated tube. In some implementations, tubes of a telescoping tube 810 can have a shim 813, a cap 817, or both at their second end 824.

In some implementations, a cap 817 can have a cup-like configuration that can receive the second end 824 of its associated tube. In such configuration, the cup-like cap 817 can function similar to the disc-like cap 817 and have a through-hole 819, but provide an extended longitudinal outer surface similar to the shim 813 or first tube section 833. Such cup-like cap 817 can be joined to its associated tube in a variety of ways including press-fit, welded, glued, or otherwise adhered.

In some implementations, an inner diameter reducing feature of the telescoping tube 810 can have a different configuration than the disc-like or cup-like cap 817. For example, the second end 824 of a tube can be bent inward to effectively reduce its inner diameter. Furthermore, an inner diameter reducing feature may be centered or off-centered with respect to the inner diameter of its associated tube. In some implementations, the cap 817 can comprise a funnel-like shape having a taper that narrows in the distal direction (e.g., to facilitate distal extension of an interventional device therethrough without catching on an edge). In some implementations, the through hole 819 of a cap 817 can comprise a chamfered or angled opening.

Figure 61A:
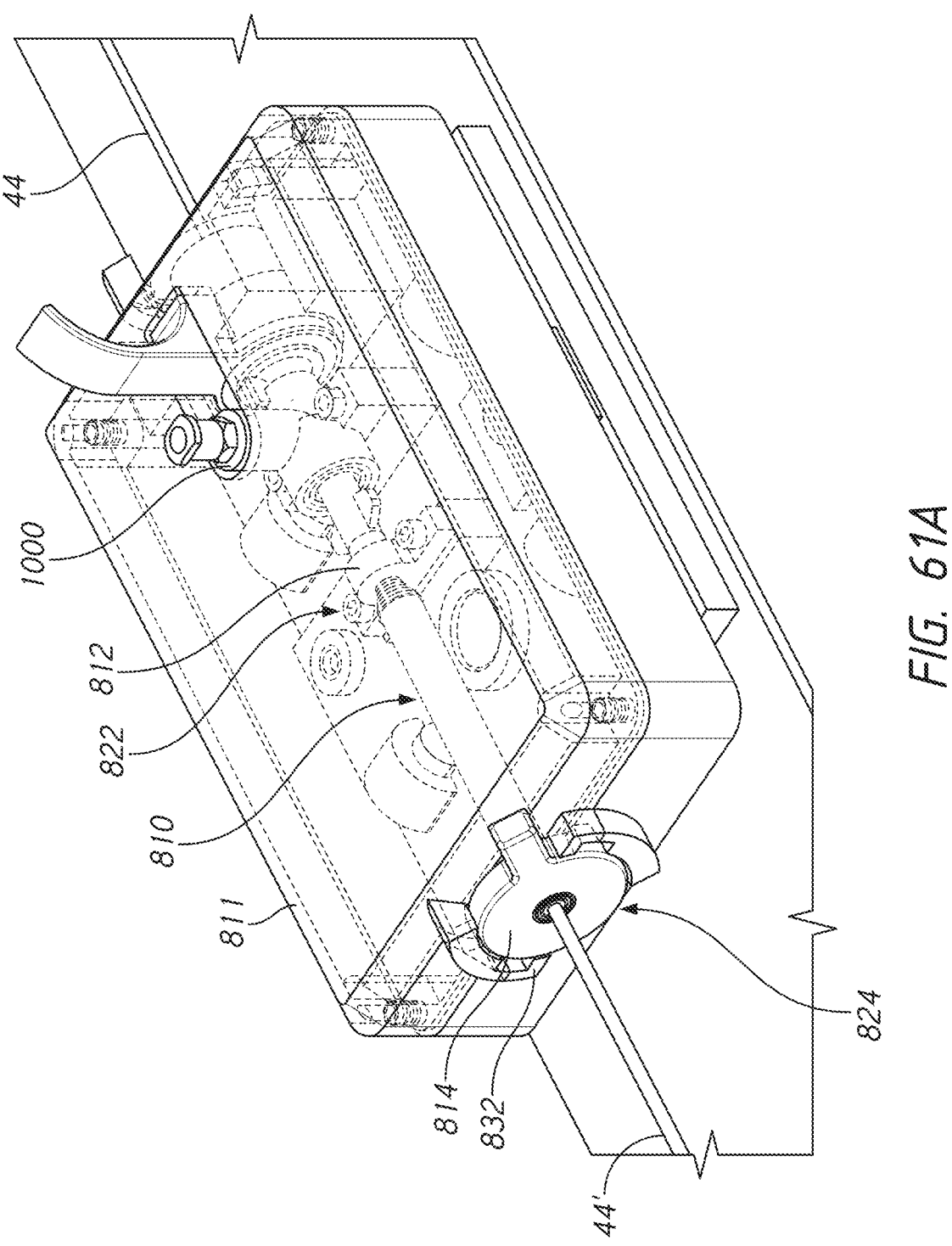

FIGS. 61A-61E show an example of an interventional device assembly utilizing an anti-buckling telescoping tube 810. FIG. 61A shows a hub 811 (which can be similar or the same as any of the hubs described herein) with an interventional device 44 entering the hub 811 at its proximal end and an interventional device 44' (in which the interventional device 44 can extend at least partially therethrough) extending distally from the hub 811 through the telescoping tube 810 (e.g., extending distally from hemostatic valve 1000 of the hub 811 through the telescoping tube 810).

Figure 61B:
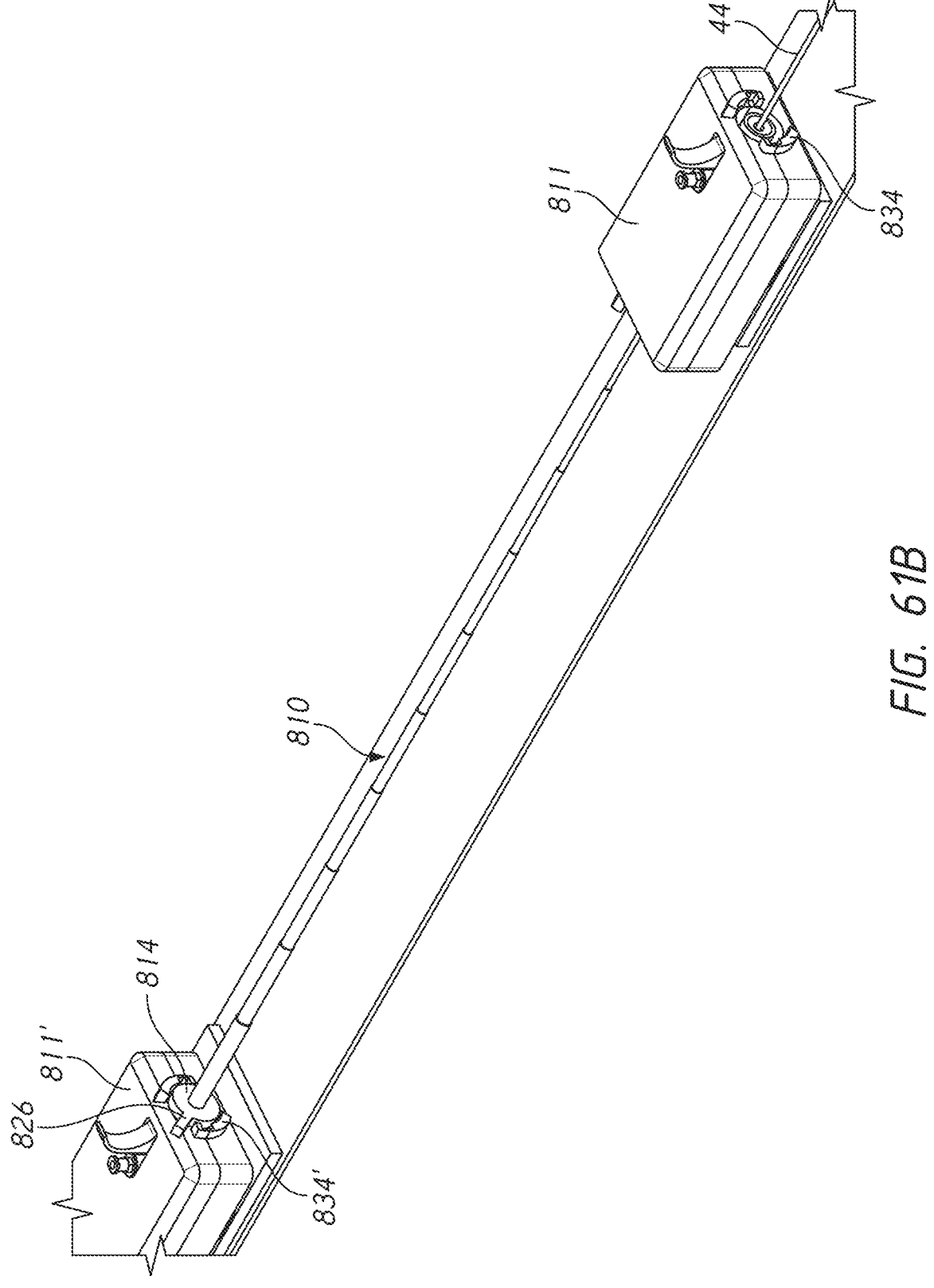

As shown in FIG. 61A, the telescoping tube 810 is in its fully collapsed configuration. One end, such as the first end 822, of the telescoping tube 810 can attach to the hub 811 via the proximal retainer 812. The proximal retainer 812 can attach to the hub 811 such that the first end 822 of the telescoping tube 810 moves with the hub 811 as it moves. The other end, such as the second end 824, of the telescoping tube 810 can be configured to releasably attach to a distal end of the hub 811 via the interaction between the distal retainer 814 and a distal hub attachment 832. For example, the second end 824 of the telescoping tube 810 can releasably lock to the hub 811 via the interaction between the distal retainer 814 of the hub 810 and the distal hub attachment 832 of the hub 811. A user can unlock the distal retainer 814 from the distal hub attachment 832 and extend the distal retainer 814 distally for attaching it to another hub or attachment point, such as shown in FIG. 61B. In some embodiments, a user may manually attach and/or detach the telescoping tube 810 (and/or any of the other anti-buckling systems described herein) to a hub.

As also shown in FIG. 61A, in some implementations, a telescoping tube, such as the telescoping tube 810, can be nearly fully or fully contained or substantially integrated with or within a hub of the interventional device assembly.

Such a configuration can advantageously minimize dead length(s) of the interventional devices that extend therethrough. Such a configuration can also facilitate handling and setup/teardown of the interventional device assembly and its components.

As described herein, hubs may desirably have a length of about 10 cm or less. Accordingly, a telescoping tube configured to be fully contained or nearly fully contained within a hub may need a large number of segments in order to fit within the hub while being able to expand over a significantly larger distance between adjacent hubs during movement of the hubs (e.g., greater than about 25 cm, greater than about 50 cm, greater than about 75 cm, greater than about 100 cm, greater than about 125 cm, greater than about 150 cm, greater than about 175 cm, or greater than about 200 cm). Larger inner diameters of tube segments of the telescoping tube may allow for larger deflections of the interventional device within the tube segments. It may be desirable to balance the number of tube segments against the increase in inner diameter required by additional tube segments. Therefore, it may be desirable to maximize an expansion or lengthening ratio, which may be a ratio between a fully expanded length of the telescoping tube and a largest inner diameter of the outer most telescoping tube segment. It may be desirable to minimize tube segment wall thickness and/or clearance between the inner surface of one tube segment and the outer surface of the tube segment that extends through it. Additional parameters that may affect the amount of deflection of the interventional device may include the overall stroke length of the interventional device that the anti-buckling system will support, the diameter and flexibility of the interventional device, and/or the amount of friction that the anti-buckling system adds to shaft insertion and/or withdrawal forces.

FIG. 61B shows two hubs of an interventional device assembly, in this case the hub 811 and a hub 811' disposed distal to hub 811, with the telescoping tube 810 extending therebetween. The distal retainer 814 is shown attached to (e.g., releasably locked to) a proximal hub attachment 834' disposed at a proximal end of the hub 811' (as shown, the hub 811 can also have a proximal hub attachment 834 for receiving an end of a telescoping tube if one were to be positioned proximal to the hub 811). With the ends of the telescoping tube 810 secured to the hubs 811 and 811' as shown, when the hubs move closer to one another the telescoping tube 810 can correspondingly collapse, and when the hubs move farther apart from one another the telescoping tube 810 can correspondingly expand. Positioned as shown, the telescoping tube 810 can provide anti-buckling support to interventional device(s) extending therethrough, such as interventional device 44 shown entering the proximal end of hub 811 and interventional device 44'.

Figures 61C, 61D, 61E:
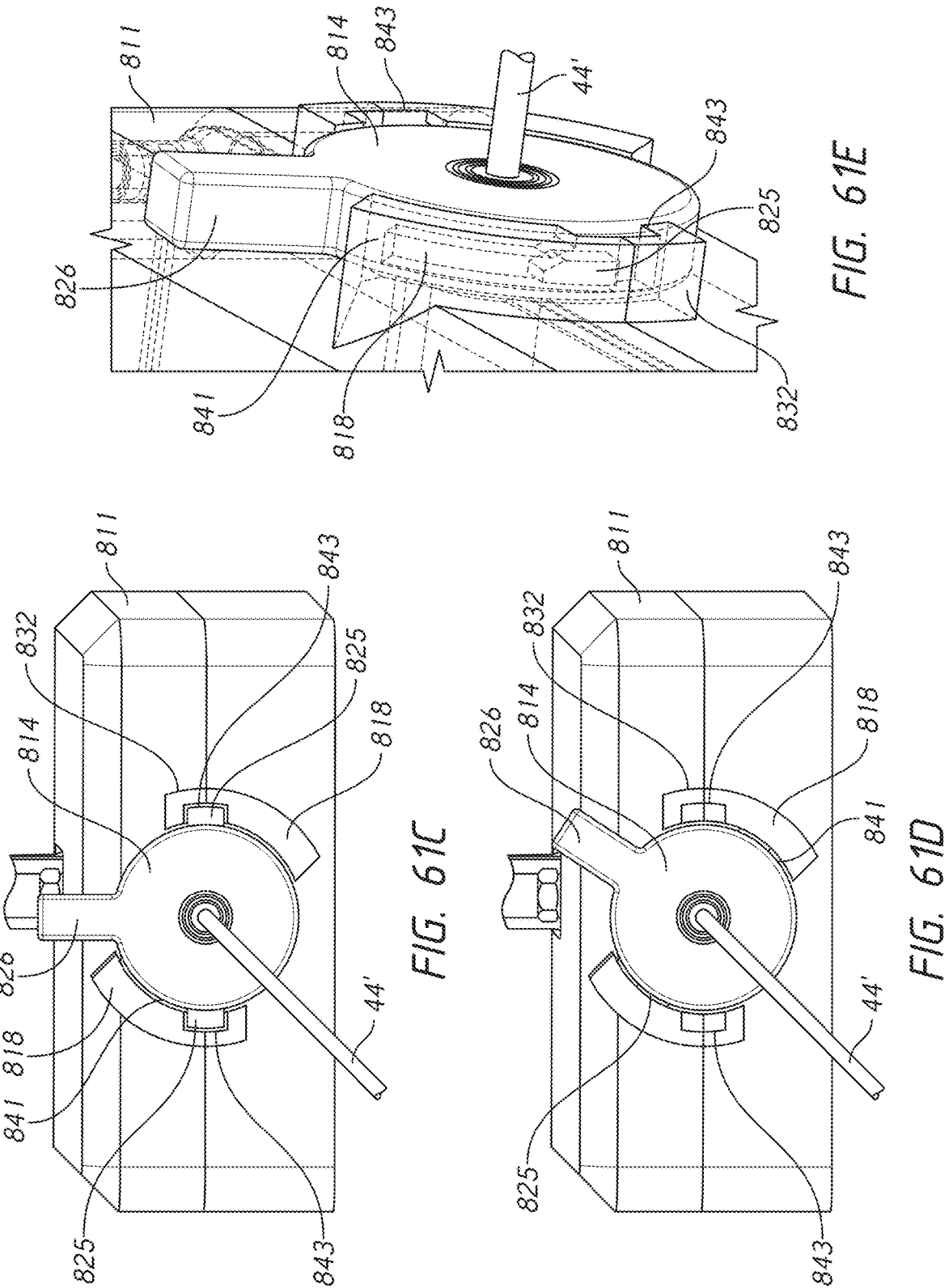

FIGS. 61C-61E show details of the releasable attachment between the distal retainer 814 of the telescoping tube 810 and the distal hub attachment 832 of the hub 811, which can correspond to the position of the two shown in FIG. 61A. The shape and features of the distal retainer 814 can releasably lock with corresponding shape and features of the distal hub attachment 832.

As shown in FIG. 61C, the distal retainer 814 can have a body with one or more tabs 825 extending radially outward therefrom. The distal hub attachment 832 can have a corresponding recess 841 configured to receive the body of the distal retainer 814 and one or more slots 818 configured to releasably receive and lock with the one or more tabs 825. For example and as shown, the body of the distal retainer 814 can have a circular shape, and the recess 841 of the distal hub attachment 832 can have a corresponding circular shape. Furthermore and as shown, the distal retainer 814 can have two tabs 825, and the distal hub attachment 832 can have two slots 818. The releasable locking connection between the distal retainer 814 and the distal hub attachment 832 can be achieved by positioning the two components as shown in FIG. 61C, with the tabs 825 aligned with cutout portions 843 of the slots 818 so that the distal retainer 814 can be seated fully into the distal hub attachment 832.

To lock the distal retainer 814 with the distal hub attachment 832, the distal retainer 814 can be rotated relative to the distal hub attachment 832 as shown in FIGS. 61D-61E such that the tabs 825 engage with the slots 818 (e.g., rotated about a quarter of a turn). To aid in the engagement of the tabs 825 with the slots 818, the tabs 825 can have a tapered leading edge as shown, and/or the slots 818 can have a taper (e.g., an internal taper). In some implementations, a detent can be incorporated into the tabs 825 and/or slots 818 to aid in the releasable attachment/locking therebetween. To facilitate handling and the releasable attachment of the distal retainer 814 with the distal hub attachment 832, the distal retainer 814 can include an arm 826 extending therefrom. The arm 826 can be configured to be manipulated by a user to rotate the distal retainer 814. The arm 826 can also be configured to be manipulated by a user to extend/collapse the telescoping tube 810 and/or to seat/unseat the distal retainer 814 with the distal hub attachment 832.

Unlocking the distal retainer 814 from the distal hub attachment 832 can be accomplished by reversing the locking process (e.g., rotating the distal retainer 814 in the reverse direction and separating from the distal hub attachment 832). While the releasable attachment between the distal retainer 814 and the distal hub attachment 832 has been described above, such releasable attachment can be the same or similar between the distal retainer 814 and other attachment points, such as a proximal hub attachment (e.g., proximal hub attachment 834' of hub 811' or proximal hub attachment 834 of hub 811 shown in FIG. 61B) and/or a distal attachment 860 described in FIGS. 63A-64B.

FIG. 62A shows an anti-buckling telescoping tube 810 attached to a variant of the anti-buckling tubular attachment 730 described with respect to FIGS. 59A-59C, and FIG. 62B shows this assembly attached to a hub 811'. The variant of the tubular attachment 730 shown in FIGS. 62A-62B is the same as and/or similar to the tubular attachment 730 shown and described with respect to FIGS. 59A-59C and includes any and/or all of the functionality of the tubular attachment 730. As shown in FIGS. 62A-62B, this variant of the tubular attachment 730 is configured to attach to the second end 824 of the telescoping tube 810. For example, the proximal end 732 of the tubular attachment 730 can attach to the distal retainer 814 (e.g., to a distal end of the distal retainer 814) of the telescoping tube 810. The tubular attachment 730 can be attached to the telescoping tube 810 such that an interventional device extending within the telescoping tube 810 can axially extend distally therefrom and into the tubular attachment 730 (e.g., such as shown in FIG. 62B with interventional device 44' extending through both while attached to hub 811'). This assembly can attach to the hub 811' or any of the hubs described herein that are located at a distal end of an interventional device assembly.

FIGS. 63A-63B show a distal attachment 860 of an interventional device assembly. The distal attachment 860 (which can also be referred to herein as a "distal lock") can be configured to releasably attach to a distal retainer 814 of any of the telescoping tubes 810 described herein at a distal end of the interventional device assembly. For this, the distal attachment 860 can include any one or more of the features of the proximal and/or distal hub attachments 834, 832 described herein. The distal attachment 860 can include a recess 861 and one or more slots 868 configured to receive the body and one or more tabs 835 of the distal retainer 814 of the telescoping tube 810 and releasably lock therewith. For example and as shown, the distal attachment 860 can have a circular recess 861 and two slots 868 configured to releasably lock with the a distal retainer 814 having a circular body and two tabs 835. Similar to the cutout portions 843 of the proximal and/or distal hub attachments 834, 832 described herein, the distal attachment 860 can include cutout portions 863 so that the distal retainer 814 can be seated into the distal attachment 860. The distal attachment 860 can also include an open-ended through hole 865 configured to receive any portion of the interventional device assembly that may extend distal of the distal retainer 814 of a telescoping tube 810 attached thereto. For example, and as shown in FIGS. 64A-64B, the distal attachment 860 can be configured to receive an anti-buckling telescoping tube 810 attached to an anti-buckling tubular attachment 730. Further as shown in FIGS. 64A-64B, the distal attachment 860 can be configured to attach to a support table 20 adjacent a distal end thereof or another structure attached to the support table 20. In other embodiments, the distal attachment 860 can coupled to support separate from the support table 20.

In other embodiments, the distal retainer 814 can include a magnet (e.g., in the form of a magnetic ring) that can be magnetically secured to a position along the drive table. For example, the magnetic distal retainer 814 can attach to a distal attachment 860 in the form of a metallic bent shim attached to the drive table (e.g., attached to a sterile barrier of the drive table).

To lock a distal retainer 814 of a telescoping tube 810 with the distal attachment 860 as shown in FIGS. 64A-64B, the distal retainer 814 can be rotated relative to the distal attachment 860 such that the tabs of the distal retainer 814 engage with the slots 868 (e.g., rotated about a quarter of a turn). To aid in the engagement of the tabs of the distal retainer 814 with the slots 868, the slots 868 can have a taper (e.g., an internal taper) as shown in FIGS. 63A-63B. In some implementations, a detent can be incorporated into the slots 868 to aid in the releasable attachment/locking therebetween.

Also shown in FIGS. 64A-64B, in some implementations an anti-buckling tubular attachment 730 can be without the circumferential cuts 735 described with respect to at least FIGS. 59A-59C. In such implementations, the tubular attachment 730 can comprise a flexible material and not require such circumferential cuts 735 to bend between its attachment to the distal attachment 860 and insertion sheath 900 as shown. In some implementations, the tubular attachment 730 depicted in FIGS. 64A-64B can include circumferential cuts 735 and or be the same as or similar to the tubular attachment 730 described with respect to FIGS. 59A-59C and/or FIGS. 62A-62B.

Figures 65A, 65B, 65C, 65D, 65E, 65F:
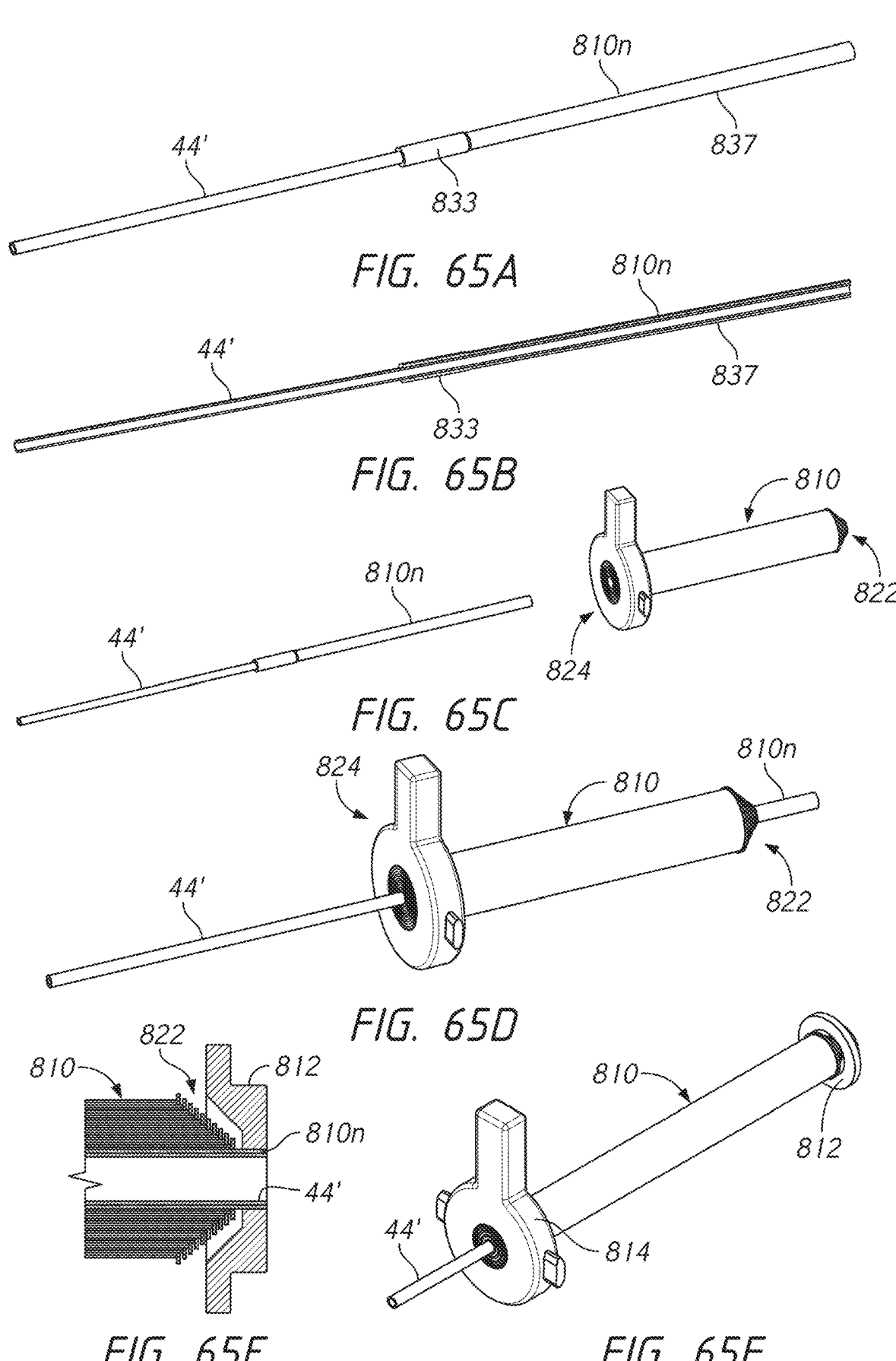

FIGS. 65A-65F show an implementation of an anti-buckling telescoping tube 810 attached to an interventional device 44' and the assembly thereof. FIG. 65A shows a perspective view and FIG. 65B shows a cross-sectional perspective view of an innermost tube segment 810n of a telescoping tube 810 with the interventional device 44' attached thereto. In this example, the telescoping tube 810 comprises tube segments having first and second tube sections 833, 837, however in some implementations the telescoping tube 810 can instead include tube segments having shims 813 as described herein. As shown in FIGS. 65A-65B, the interventional device 44' can attach to an inner portion of the innermost tube segment 810n. In some implementations and as shown, the innermost tube segment 810n can have an inner diameter that is substantially similar to or the same as an outer diameter of the interventional device 44' attached thereto. The interventional device 44' can insert fully or nearly fully within the tube segment 810n such that proximal ends of each substantially align (e.g., as shown in FIG. 65E). Further as shown, the interventional device 44' can attach to the tube segment 810n such that the first tube section 833 is positioned distal to the proximal end of the interventional device 44'. In some implementations, the interventional device 44' can be bonded to the tube segment 810n.

After the interventional device 44' is attached to the innermost tube segment 810n, the proximal end thereof (e.g., the second tube section 837) can be inserted into the second end 824 (e.g., distal end) of the remainder of the telescoping tube 810. FIG. 65C shows before and FIG. 65D shows after such insertion. As shown in FIG. 65D, the proximal end of the innermost tube 810n can extend proximally past the rest of the telescoping tube 810 for attachment to an interventional device termination (which can also be referred to as a "catheter termination") within a hub of the interventional device assembly. Such an interventional device termination can include and/or be coupled to a gear train for rotating the interventional device 44'. In some implementations, such an interventional device termination can include and/or be coupled to fluidics. In some implementations, such an interventional device termination can include a proximal retainer 812 as shown in the cross section of FIG. 65E and perspective view of FIG. 65F.

The proximal retainer 812 shown in FIGS. 65E-65F can be similar to and/or incorporate any of the features of the proximal retainers 812 described herein. In the example shown in FIGS. 65E-65F, the proximal retainer 812 can be configured to receive and attach to the innermost tube segment 810n. Further as shown, the proximal retainer 812 can comprise a circular shape with a recess configured to receive at least a portion of the first end 822 of the telescoping tube therewithin. Such configuration can advantageously reduce the dead length of the telescoping tube assembly. The proximal retainer 812 can be coupled to or part of a chassis in a hub of an interventional device assembly as described herein.

In some implementations, an interventional device (e.g., 44, 44' or others described herein) can be loaded into a telescoping tube 810 by fully collapsing the telescoping tube 810 and then inserting the interventional device therethrough. In some implementations, a telescoping tube 810 and/or one or more of the tube segments thereof can be sized in length and/or diameter based on a buckling characteristic of an interventional device extending therethrough. A buckling characteristic can include a periodicity of buckling of the interventional device, which can vary along the length of the interventional device. For instance, the period of buckling of an interventional device may be shorter at its proximal end than its distal end, therefore a telescoping tube (or any of the anti-buckling devices described herein) can be configured to provide more radial restriction at/adjacent the proximal end/portion of the interventional device than at the distal end/portion thereof. A telescoping tube 810 having an innermost tube positioned at its proximal end and an outermost tube positioned at its distal end can provide such differential radial restriction. In some implementations, a ratio between an inner diameter of an outermost tube of a telescoping tube 810 and an outer diameter of an interventional device extending within the telescoping tube 810 can be between about 2 and about 50, such as between about 4 and about 25, between about 2 and about 10, between about 2 and about 6, between about 10 and about 20, between about 20 and about 30, between about 30 and about 40, between about 40 and about 50, between about 2 and about 20, between about 5 and about 15, between about 25 and about 50, or any other suitable ratio.

FIG. 66A shows a distal retainer 814 that is a variant of the distal retainer 814 for attaching a telescoping tube 810 to another component of an interventional device assembly. As shown, the distal retainer 814 can be configured similar to a lens cap of a camera and have the telescoping tube 810 attach to a face thereof. The distal retainer 814 can have spring loaded tabs 825 that can be biased radially outward. To attach the distal retainer 814 to a corresponding attachment, such as to another hub or attachment point of an interventional device assembly, the tabs 825 of the distal retainer 814 can configured to move radially inward and then release back to their biased radially outward position into locking engagement with such corresponding attachment. To unlock the distal retainer 814, the tabs 825 can be moved radially inward (as indicated by the arrows) to release the tabs 825 from the corresponding attachment.

FIG. 66B shows an attachment between a distal retainer and another component of an interventional device assembly that is a variant of how the distal retainer 814 attaches to another component of an interventional device assembly. As shown, the distal retainer and its corresponding attachment can be configured similar to a trocar cap. For example, the distal retainer can be configured as component 844 shown and have snap barbs 845 configured to push into corresponding snap barb receptacles 855 of corresponding attachment configured as component 854. Upon pushing the snap barbs 845 into the snap barb receptacles 855, a lock release lever 856 of component 854 can rotate, thus locking the snap barbs 845 in place and the two components 854, 855 together. To unlock the components 844 and 854 from one another, the lock release lever 856 of component 854 can be rotated and the components 844, 854 separated to release them from one another. As another example, the distal retainer can instead be configured as component 854 and its corresponding attachment can be configured as component 855, with similar locking/unlocking therebetween as described above.

While the foregoing describes robotically driven interventional devices and manually driven interventional devices, the devices may be manually driven, robotically driven, or any combination of manually and robotically driven interventional devices, as will be appreciated by those of skill in the art in view of the disclosure herein.

The foregoing represents one specific implementation of a robotic control system. A wide variety of different robotic control system constructions can be made, for supporting and axially advancing and retracting two or three or four or more assemblies to robotically drive interventional devices, as will be appreciated by those of skill in the art in view of the disclosure herein.

While the foregoing describes interventional devices that are driven by a drive table, other suitable robotic drive systems or mechanisms may be used to drive the interventional devices, as will be appreciated by those of skill in the art in view of the disclosure herein.

The anti-buckling devices described herein can be integrated or pre-installed with their associated hub(s), or they can be configured to be installed by a user. Furthermore, the interventional device(s) described herein can be pre-installed with their associated hub(s) and/or anti-buckling device(s), or they can be configured to be installed by a user.

Various systems and methods are described herein primarily in the context of a neurovascular access or procedure (e.g., neurothrombectomy). However, the catheters, systems (e.g., drive systems), and methods disclosed herein can be readily adapted for any of a wide variety of other diagnostic and therapeutic applications throughout the body, including particularly intravascular procedures such as in the peripheral vasculature (e.g., deep venous thrombosis), central vasculature (pulmonary embolism), and coronary vasculature, as well as procedures in other hollow organs or tubular structures in the body.

The foregoing description and examples has been set forth merely to illustrate the disclosure and are not intended as being limiting. Each of the disclosed aspects and embodiments of the present disclosure may be considered individually or in combination with other aspects, embodiments, and variations of the disclosure. In addition, unless otherwise specified, none of the steps of the methods of the present disclosure are confined to any particular order of performance. Modifications of the disclosed embodiments incorporating the spirit and substance of the disclosure may occur to persons skilled in the art and such modifications are within the scope of the present disclosure.

Terms of orientation used herein, such as "top," "bottom," "horizontal," "vertical," "longitudinal," "lateral," and "end" are used in the context of the illustrated embodiment. However, the present disclosure should not be limited to the illustrated orientation. Indeed, other orientations are possible and are within the scope of this disclosure. Terms relating to circular shapes as used herein, such as diameter or radius, should be understood not to require perfect circular structures, but rather should be applied to any suitable structure with a cross-sectional region that can be measured from side-to-side. Terms relating to shapes generally, such as "circular" or "cylindrical" or "semi-circular" or "semi-cylindrical" or any related or similar terms, are not required to conform strictly to the mathematical definitions of circles or cylinders or other structures, but can encompass structures that are reasonably close approximations.

Conditional language used herein, such as, among others, "can," "might," "may," "e.g.," and the like, unless specifically stated otherwise, or otherwise understood within the context as used, is generally intended to convey that some embodiments include, while other embodiments do not include, certain features, elements, and/or states. Thus, such conditional language is not generally intended to imply that features, elements, blocks, and/or states are in any way required for one or more embodiments or that one or more embodiments necessarily include logic for deciding, with or without author input or prompting, whether these features, elements and/or states are included or are to be performed in any particular embodiment.

Conjunctive language, such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

The terms "approximately," "about," and "substantially" as used herein represent an amount close to the stated amount that still performs a desired function or achieves a desired result. For example, in some embodiments, as the context may dictate, the terms "approximately", "about", and "substantially" may refer to an amount that is within less than or equal to 10% of the stated amount. The term "generally" as used herein represents a value, amount, or characteristic that predominantly includes or tends toward a particular value, amount, or characteristic. As an example, in certain embodiments, as the context may dictate, the term "generally parallel" can refer to something that departs from exactly parallel by less than or equal to 20 degrees.

Where term "about" is utilized before a range of two numerical values, this is intended to include a range between about the first value and about the second value, as well as a range from the first value specified to the second value specified.

Unless otherwise explicitly stated, articles such as "a" or "an" should generally be interpreted to include one or more described items. Accordingly, phrases such as "a device configured to" are intended to include one or more recited devices. Such one or more recited devices can be collectively configured to carry out the stated recitations. For example, "a processor configured to carry out recitations A, B, and C" can include a first processor configured to carry out recitation A working in conjunction with a second processor configured to carry out recitations B and C.

The terms "comprising," "including," "having," and the like are synonymous and are used inclusively, in an open-ended fashion, and do not exclude additional elements, features, acts, operations, and so forth. Likewise, the terms "some," "certain," and the like are synonymous and are used in an open-ended fashion. Also, the term "or" is used in its inclusive sense (and not in its exclusive sense) so that when used, for example, to connect a list of elements, the term "or" means one, some, or all of the elements in the list.

Overall, the language of the claims is to be interpreted broadly based on the language employed in the claims. The language of the claims is not to be limited to the non-exclusive embodiments and examples that are illustrated and described in this disclosure, or that are discussed during the prosecution of the application.

Although systems, devices, and methods for endovascular implants and accurate placement thereof have been disclosed in the context of certain embodiments and examples, this disclosure extends beyond the specifically disclosed embodiments to other alternative embodiments and/or uses of the embodiments and certain modifications and equivalents thereof. Various features and aspects of the disclosed embodiments can be combined with or substituted for one another in order to form varying modes of systems, devices and methods for endovascular implants and accurate placement thereof. The scope of this disclosure should not be limited by the particular disclosed embodiments described herein.

Certain features that are described in this disclosure in the context of separate implementations can be implemented in combination in a single implementation. Conversely, various features that are described in the context of a single implementation can be implemented in multiple implementations separately or in any suitable subcombination. Although features may be described herein as acting in certain combinations, one or more features from a claimed combination can, in some cases, be excised from the combination, and the combination may be claimed as any subcombination or variation of any subcombination.

While the methods and devices described herein may be susceptible to various modifications and alternative forms, specific examples thereof have been shown in the drawings and are herein described in detail. It should be understood, however, that the invention is not to be limited to the particular forms or methods disclosed, but, to the contrary, the invention is to cover all modifications, equivalents, and alternatives falling within the spirit and scope of the various embodiments described and the appended claims. Further, the disclosure herein of any particular feature, aspect, method, property, characteristic, quality, attribute, element, or the like in connection with an embodiment can be used in all other embodiments set forth herein. Any methods disclosed herein need not be performed in the order recited. Depending on the embodiment, one or more acts, events, or functions of any of the algorithms, methods, or processes described herein can be performed in a different sequence, can be added, merged, or left out altogether (e.g., not all described acts or events are necessary for the practice of the algorithm). In some embodiments, acts or events can be performed concurrently, e.g., through multi-threaded processing, interrupt processing, or multiple processors or processor cores or on other parallel architectures, rather than sequentially. Further, no element, feature, block, or step, or group of elements, features, blocks, or steps, are necessary or indispensable to each embodiment. Additionally, all possible combinations, subcombinations, and rearrangements of systems, methods, features, elements, modules, blocks, and so forth are within the scope of this disclosure. The use of sequential, or time-ordered language, such as "then," "next," "after," "subsequently," and the like, unless specifically stated otherwise, or otherwise understood within the context as used, is generally intended to facilitate the flow of the text and is not intended to limit the sequence of operations performed. Thus, some embodiments may be performed using the sequence of operations described herein, while other embodiments may be performed following a different sequence of operations.

Moreover, while operations may be depicted in the drawings or described in the specification in a particular order, such operations need not be performed in the particular order shown or in sequential order, and all operations need not be performed, to achieve the desirable results. Other operations that are not depicted or described can be incorporated in the example methods and processes. For example, one or more additional operations can be performed before, after, simultaneously, or between any of the described operations. Further, the operations may be rearranged or reordered in other implementations. Also, the separation of various system components in the implementations described herein should not be understood as requiring such separation in all implementations, and it should be understood that the described components and systems can generally be integrated together in a single product or packaged into multiple products. Additionally, other implementations are within the scope of this disclosure.

Some embodiments have been described in connection with the accompanying figures. Certain figures are drawn and/or shown to scale, but such scale should not be limiting, since dimensions and proportions other than what are shown are contemplated and are within the scope of the embodiments disclosed herein. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various embodiments can be used in all other embodiments set forth herein. Additionally, any methods described herein may be practiced using any device suitable for performing the recited steps.

The methods disclosed herein may include certain actions taken by a practitioner; however, the methods can also include any third-party instruction of those actions, either expressly or by implication. For example, actions such as "positioning an electrode" include "instructing positioning of an electrode."

The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers and should be interpreted based on the circumstances (e.g., as accurate as reasonably possible under the circumstances, for example ±5%, ±10%, ±15%, etc.). For example, "about 1 V" includes "1 V." Phrases preceded by a term such as "substantially" include the recited phrase and should be interpreted based on the circumstances (e.g., as much as reasonably possible under the circumstances). For example, "substantially perpendicular" includes "perpendicular." Unless stated otherwise, all measurements are at standard conditions including temperature and pressure.

What is claimed is:

1. An interventional device assembly, comprising:
a first hub positioned along a drive table, the first hub comprising a proximal end and a distal end;
an interventional device coupled to the first hub and extending distally therefrom; and
a telescoping tube comprising a proximal end and a distal end, the proximal end of the telescoping tube being secured within an interior of the first hub between the proximal end of the first hub and the distal end of the first hub, the distal end of the telescoping tube being configured to secure to a second hub positioned along the drive table or a distal attachment coupled to the drive table;
wherein at least a portion of the interventional device extends through the telescoping tube; and
wherein the telescoping tube is contained by the first hub when detached from the second hub or the distal attachment and fully axially collapsed.

2. The interventional device assembly of claim 1, wherein the telescoping tube comprises a plurality of concentric telescopically axially extendable and collapsible tube segments.

3. The interventional device assembly of claim 2, wherein the plurality of tube segments comprise an outermost tube segment attached to a distal retainer.

4. The interventional device assembly of claim 3, wherein the distal retainer is configured to releasably attach to the second hub or the distal attachment.

5. An interventional device assembly, comprising:
a first hub positioned along a drive table, the first hub comprising a proximal end and a distal end;
an interventional device coupled to the first hub and extending distally therefrom; and
a telescoping tube comprising a proximal end and a distal end, the proximal end of the telescoping tube being secured within an interior of the first hub between the proximal end of the first hub and the distal end of the first hub, the distal end of the telescoping tube being configured to secure to a second hub positioned along the drive table or a distal attachment coupled to the drive table;
wherein at least a portion of the interventional device extends through the telescoping tube;

wherein the telescoping tube comprises a plurality of concentric telescopically axially extendable and collapsible tube segments;
wherein the plurality of tube segments comprise an outermost tube segment attached to a distal retainer;
wherein the distal retainer is configured to releasably attach to the second hub or the distal attachment; and
wherein the distal retainer is further configured to releasably attach to the first hub when the telescoping tube is detached from the second hub and is fully axially collapsed.

6. An interventional device assembly, comprising:
a first hub positioned along a drive table, the first hub comprising a proximal end and a distal end;
an interventional device coupled to the first hub and extending distally therefrom; and
a telescoping tube comprising a proximal end and a distal end, the proximal end of the telescoping tube being secured within an interior of the first hub between the proximal end of the first hub and the distal end of the first hub, the distal end of the telescoping tube being configured to secure to a second hub positioned along the drive table;
wherein at least a portion of the interventional device extends through the telescoping tube;
wherein the telescoping tube comprises a plurality of concentric telescopically axially extendable and collapsible tube segments;
wherein the plurality of tube segments comprise an outermost tube segment attached to a distal retainer;
wherein the distal retainer is configured to releasably attach to the second hub;
wherein the distal retainer comprises a body with one or more tabs extending radially outward therefrom;
wherein the second hub comprises a proximal hub attachment comprising a recess and one or more slots configured to receive the body and one or more tabs of the distal retainer, respectively; and
wherein the distal retainer is configured to be rotated relative to the proximal hub attachment when received within the proximal hub attachment to releasably attach the distal retainer to the proximal hub attachment.

7. An interventional device assembly, comprising:
a first hub positioned along a drive table, the first hub comprising a proximal end and a distal end;
an interventional device coupled to the first hub and extending distally therefrom; and
a telescoping tube comprising a proximal end and a distal end, the proximal end of the telescoping tube being secured within an interior of the first hub between the proximal end of the first hub and the distal end of the first hub, the distal end of the telescoping tube being configured to secure to a distal attachment coupled to the drive table;
wherein at least a portion of the interventional device extends through the telescoping tube;
wherein the telescoping tube comprises a plurality of concentric telescopically axially extendable and collapsible tube segments;
wherein the plurality of tube segments comprise an outermost tube segment attached to a distal retainer;
wherein the distal retainer is configured to releasably attach to the distal attachment;
wherein the distal retainer comprises a body with one or more tabs extending radially outward therefrom;

wherein the distal attachment comprises a recess and one or more slots configured to receive the body and one or more tabs of the distal retainer, respectively; and wherein the distal retainer is configured to be rotated relative to the distal attachment when received within the distal attachment to releasably attach the distal retainer to the distal attachment.

8. The interventional device assembly of claim 3, further comprising an anti-buckling tubular attachment comprising a proximal end and a distal end and a tubular body extending therebetween, the proximal end attached to and extending distally from the distal retainer and the distal end configured to releasably attach to an insertion sheath.

9. An interventional device assembly, comprising:

a first hub positioned along a drive table, the first hub comprising a proximal end and a distal end;

an interventional device coupled to the first hub and extending distally therefrom; and a telescoping tube comprising a proximal end and a distal end, the proximal end of the telescoping tube being secured within an interior of the first hub between the proximal end of the first hub and the distal end of the first hub, the distal end of the telescoping tube being configured to secure to a second hub positioned along the drive table or a distal attachment coupled to the drive table;

wherein at least a portion of the interventional device extends through the telescoping tube;

wherein the telescoping tube comprises a plurality of concentric telescopically axially extendable and collapsible tube segments;

wherein the plurality of tube segments comprise an outermost tube segment attached to a distal retainer;

wherein the interventional device assembly further comprises an anti-buckling tubular attachment comprising a proximal end and a distal end and a tubular body extending therebetween, the proximal end attached to and extending distally from the distal retainer and the distal end configured to releasably attach to an insertion sheath; and wherein the tubular body of the anti-buckling tubular attachment comprises a plurality of circumferential cuts to provide the tubular attachment with flexibility.

10. The interventional device assembly of claim 2, wherein the plurality of tube segments comprises an innermost tube segment and one or more outer tube segments, wherein each of the one or more outer tube segments is coupled to a cap at its proximal end, the cap having a through hole configured to receive the interventional device therethrough.

11. The interventional device assembly of claim 10, wherein the cap has an outer diameter greater than an outer diameter of the tube segment to which the cap is coupled.

12. The interventional device assembly of claim 10, wherein the through hole of the cap has a diameter smaller than an inner diameter of the tube segment to which the cap is coupled.

13. The interventional device assembly of claim 2, wherein the plurality of tube segments comprises an outermost tube segment and one or more inner tube segments, wherein each of the one or more inner tube segments comprises a shim attached around a portion of its outer diameter.

14. The interventional device assembly of claim 2, wherein the plurality of tube segments comprises an outermost tube segment and one or more inner tube segments, wherein each of the one or more inner tube segments comprises a first tube section having a first outer diameter and a second tube section having a second outer diameter.

15. The interventional device assembly of claim 2, wherein each of the plurality of tube segments comprises an inner diameter reducing feature configured to reduce an unsupported free length of the interventional device when the interventional device extends through the telescoping tube.

16. The interventional device assembly of claim 2, wherein a clearance between adjacent concentric tube segments of the plurality of tube segments is between about 0.001 inches and about 0.010 inches.

17. The interventional device assembly of claim 2, wherein each of the plurality of tube segments has a wall thickness that is substantially the same.

18. The interventional device assembly of claim 2, wherein an innermost tube segment of the plurality of tube segments is attached to the interventional device.

19. The interventional device assembly of claim 18, wherein the innermost tube segment of the plurality of tube segments is bonded to the interventional device.

20. The interventional device assembly of claim 4, wherein the plurality of tube segments comprise and an innermost tube segment attached to a proximal retainer, wherein the proximal retainer is configured to attach within the interior of the first hub.

* * * * *